United States Patent
Shluzas et al.

(10) Patent No.: US 10,173,010 B2
(45) Date of Patent: *Jan. 8, 2019

(54) SYSTEM AND METHOD FOR SAFETY SYRINGE

(71) Applicant: Credence Medsystems, Inc., Menlo Park, CA (US)

(72) Inventors: Alan E. Shluzas, San Carlos, CA (US); Stephen H. Diaz, Palo Alto, CA (US); John F. Shanley, Emerald Hills, CA (US); Jeff Tillack, Foster City, CA (US); Dan Thayer, Tustin, CA (US); Gary Steese-Bradley, San Jose, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 272 days.

This patent is subject to a terminal disclaimer.

(21) Appl. No.: 14/956,282

(22) Filed: Dec. 1, 2015

(65) Prior Publication Data
US 2016/0279333 A1    Sep. 29, 2016

Related U.S. Application Data

(63) Continuation of application No. 14/696,342, filed on Apr. 24, 2015, now Pat. No. 10,010,677.
(Continued)

(51) Int. Cl.
*A61M 5/315* (2006.01)
*A61M 5/32* (2006.01)
(Continued)

(52) U.S. Cl.
CPC ........ *A61M 5/31501* (2013.01); *A61J 1/2096* (2013.01); *A61M 5/2033* (2013.01);
(Continued)

(58) Field of Classification Search
CPC ............... A61M 5/3234; A61M 5/508; A61M 2005/3231; A61M 2005/3239;
(Continued)

(56) References Cited

U.S. PATENT DOCUMENTS 4,874,381 A   10/1989 Vetter
4,908,022 A   3/1990 Haber
(Continued)

FOREIGN PATENT DOCUMENTS

EP   2022521 A1   2/2009
JP   05500621     2/1993
(Continued)

OTHER PUBLICATIONS

Amendment and Response to Non-Final Office Action dated Jul. 18, 2017 for U.S. Appl. No. 14/321,713, filed Oct. 13, 2017.
(Continued)

*Primary Examiner* — Emily Schmidt
(74) *Attorney, Agent, or Firm* — Vista IP Law Group LLP

(57) ABSTRACT

One embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends, the proximal end comprising an anchoring geometry configured to be at least partially inserted into the stopper member such that upon retraction of the stopper member, the needle is pulled proximally along with the stopper to be at least partially contained within the interior medicine chamber.

22 Claims, 161 Drawing Sheets

Related U.S. Application Data

(60) Provisional application No. 61/984,033, filed on Apr. 24, 2014, provisional application No. 62/014,035, filed on Jun. 18, 2014, provisional application No. 62/059,110, filed on Oct. 2, 2014, provisional application No. 62/105,717, filed on Jan. 20, 2015, provisional application No. 62/117,672, filed on Feb. 18, 2015, provisional application No. 62/150,761, filed on Apr. 21, 2015.

(51) Int. Cl.
*A61J 1/20* (2006.01)
*A61M 5/50* (2006.01)
*A61M 5/20* (2006.01)
*A61M 5/34* (2006.01)
*A61M 5/31* (2006.01)

(52) U.S. Cl.
CPC ........ *A61M 5/3137* (2013.01); *A61M 5/3148* (2013.01); *A61M 5/31513* (2013.01); *A61M 5/31515* (2013.01); *A61M 5/3232* (2013.01); *A61M 5/3234* (2013.01); *A61M 5/3276* (2013.01); *A61M 5/3293* (2013.01); *A61M 5/348* (2013.01); *A61M 5/508* (2013.01); *A61M 5/5066* (2013.01); *A61J 1/201* (2015.05); *A61J 1/2065* (2015.05); *A61M 5/31505* (2013.01); *A61M 5/31596* (2013.01); *A61M 5/3202* (2013.01); *A61M 5/329* (2013.01); *A61M 5/344* (2013.01); *A61M 2005/3103* (2013.01); *A61M 2005/3128* (2013.01); *A61M 2005/3131* (2013.01); *A61M 2005/3139* (2013.01); *A61M 2005/31508* (2013.01); *A61M 2005/3226* (2013.01); *A61M 2005/3231* (2013.01); *A61M 2005/3241* (2013.01)

(58) Field of Classification Search
CPC .......... A61M 2005/3241; A61M 5/322; A61M 2005/3235; A61M 5/3232
See application file for complete search history.

(56) References Cited

U.S. PATENT DOCUMENTS

| | | | |
|---|---|---|---|
| 4,927,414 A | 5/1990 | Kulli | |
| 4,944,723 A | 7/1990 | Haber et al. | |
| 5,002,536 A | 3/1991 | Thompson et al. | |
| 5,053,010 A | 10/1991 | McGary | |
| 5,112,316 A | 5/1992 | Venturini | |
| 5,211,628 A | 5/1993 | Marshall | |
| 5,215,533 A | 6/1993 | Robb | |
| 5,330,430 A | 7/1994 | Sullivan | |
| 5,342,310 A | 8/1994 | Ueyama et al. | |
| 5,403,288 A | 4/1995 | Stanners | |
| 5,615,772 A | 4/1997 | Naganuma | |
| 5,669,887 A | 9/1997 | Cooper | |
| 5,676,346 A | 10/1997 | Leinsing | |
| 5,681,292 A | 10/1997 | Tober et al. | |
| 5,792,107 A | 8/1998 | Petrocelli | |
| 5,993,418 A | 11/1999 | Alexander | |
| 6,010,486 A * | 1/2000 | Carter ................. | A61M 5/3234 604/110 |
| 6,090,081 A | 7/2000 | Sudo et al. | |
| 6,183,440 B1 | 2/2001 | Bell | |
| 6,413,237 B1 | 7/2002 | Caizza et al. | |
| 6,585,700 B1 | 7/2003 | Trocki et al. | |
| 6,709,019 B2 | 3/2004 | Parker et al. | |
| 7,500,964 B2 | 3/2009 | Shaw et al. | |
| 8,088,104 B2 | 1/2012 | Smith | |
| 8,167,837 B2 | 5/2012 | Judd | |
| 9,919,110 B2 | 3/2018 | Diaz et al. | |
| 10,010,677 B2 | 7/2018 | Shluzas et al. | |
| 2003/0004468 A1 * | 1/2003 | Righi ................. | A61M 5/3234 604/243 |
| 2004/0215150 A1 | 10/2004 | Shue et al. | |
| 2006/0253074 A1 | 11/2006 | Thayer | |
| 2006/0258984 A1 * | 11/2006 | Kiehne ............... | A61M 5/3234 604/110 |
| 2007/0129675 A1 * | 6/2007 | Summerville ...... | A61M 5/3234 604/110 |
| 2008/0027381 A1 | 1/2008 | Smith et al. | |
| 2008/0269690 A1 | 10/2008 | Felix-Faure | |
| 2009/0018503 A1 | 1/2009 | Walton et al. | |
| 2009/0259195 A1 | 10/2009 | Lin Lee | |
| 2010/0010450 A1 | 1/2010 | Runfola et al. | |
| 2010/0256560 A1 | 10/2010 | Li | |
| 2010/0262119 A1 | 10/2010 | Schraga | |
| 2010/0286609 A1 | 11/2010 | Mahurkar | |
| 2013/0030382 A1 | 1/2013 | Sudo | |
| 2013/0060191 A1 | 3/2013 | Thorley et al. | |
| 2013/0079716 A1 * | 3/2013 | Thorley ............. | A61M 5/31511 604/110 |
| 2015/0073344 A1 | 3/2015 | Van Damme et al. | |
| 2018/0296770 A1 | 10/2018 | Diaz et al. | |

FOREIGN PATENT DOCUMENTS

| | | |
|---|---|---|
| JP | 2007514486 | 6/2007 |
| JP | 2008-535589 | 9/2008 |
| JP | 2009540875 | 11/2009 |
| JP | 2011509810 | 3/2011 |
| JP | 2012519511 | 8/2012 |
| KR | 20130000843 U | 2/2013 |
| WO | WO 90/06146 | 6/1990 |
| WO | WO 91/04065 | 4/1991 |
| WO | WO 93/18808 A1 | 9/1993 |
| WO | 2003/039634 A1 | 5/2003 |
| WO | WO 2005058398 A1 | 6/2005 |
| WO | WO 2005058399 A1 | 6/2005 |
| WO | WO 2006/108243 | 10/2006 |
| WO | WO 2007/130388 | 11/2007 |
| WO | WO 2009/094345 | 11/2009 |
| WO | WO 2010065375 A1 | 6/2010 |
| WO | WO 2010/100241 A1 | 9/2010 |
| WO | WO 2010/100243 | 9/2010 |
| WO | WO 2010/100244 A1 | 9/2010 |
| WO | WO 2011/075760 A1 | 6/2011 |
| WO | WO 2012038959 A2 | 3/2012 |
| WO | WO 2012/073035 A1 | 6/2012 |
| WO | WO 2012151314 A2 | 8/2012 |
| WO | WO 2015/003016 A3 | 1/2015 |

OTHER PUBLICATIONS

Amendment Response to Non-Final Office Action dated Aug. 2, 2017 for U.S. Appl. No. 14/321,735.
Final Office Action dated Aug. 4, 2017 for U.S. Appl. No. 14/696,342.
Notice of Allowance dated Aug. 24, 2017 for U.S. Appl. No. 14/321,706.
Amendment Response to Non-Final Office Action dated Aug. 25, 2017 for U.S. Appl. No. 14/321,721.
Amendment Response to Non-Final Office Action dated Aug. 25, 2017 for U.S. Appl. No. 14/321,729.
Notice of Allowance dated Aug. 31, 2017 for U.S. Appl. No. 14/321,735.
Amendment Response to Final Office Action filed Sep. 11, 2017 for U.S. Appl. No. 14/543,787.
Notice of Allowance dated Sep. 22, 2017 for U.S. Appl. No. 14/321,721.
Notice of Allowance dated Sep. 22, 2017 for U.S. Appl. No. 14/321,729.
Notice of Allowance dated Nov. 8, 2017 for U.S. Appl. No. 14/321,713.
Amendment and Response to Final Office Action dated Aug. 4, 2017 for U.S. Appl. No. 14/696,342, filed Nov. 6, 2017.
Non-Final Office Action dated Nov. 27, 2017 for U.S. Appl. No. 14/543,787.

(56) References Cited

OTHER PUBLICATIONS

Notice of Allowance dated Dec. 12, 2017 for U.S. Appl. No. 14/696,342.
International Search Report and Written Opinion dated Nov. 19, 2015, International Application No. PCT/US2015/027670 with International Filing Date of Apr. 24, 2015, (18 pages).
Non-Final Office Action dated May 3, 2017 for U.S. Appl. No. 14/321,706.
Non-Final Office Action dated May 3, 2017 for U.S. Appl. No. 14/321,735.
European Extended Search Report dated Feb. 21, 2017 for EP Appln. No. 14819246.1.
International Search Report and Written Opinion dated Jan. 6, 2015, International Patent Application No. PCT/US14/45160 with International Filing Date of Jul. 1, 2014, (14 pages).
Non-Final Office Action dated May 26, 2017 for U.S. Appl. No. 14/321,729.
Non-Final Office Action dated May 30, 2017 for U.S. Appl. No. 14/321,721.
Non-Final Office Action dated Jul. 18, 2017 for U.S. Appl. No. 14/321,713.
International Search Report and Written Opinion dated Apr. 8, 2015, International Patent Application No. PCT/US14/65998 with International Filing Date of Nov. 17, 2014, (12 pages).
Non-Final Office Action dated Nov. 30, 2016 for U.S. Appl. No. 14/543,787.
Final Office Action dated Jun. 12, 2017 for U.S. Appl. No. 14/543,787.
Non-Final Office Action dated Apr. 14, 2017 for U.S. Appl. No. 14/696,342.
Amendment Response to Non-Final Office Action for U.S. Appl. No. 14/696,342, dated Jul. 14, 2017.
Amendment Response to Non-Final Office Action for U.S. Appl. No. 14/543,787, dated Feb. 28, 2017.
Extended European Search Report dated Jun. 23, 2017 for EP Application No. 14862453.9, Credence Medsystems, Inc.
Response to Extended European Search Report and Rule 70(2) filed Sep. 20, 2017 for EP application No. 14819246.1, Credence Medsystems Inc.
Response to Extended European Search Report and Rule 70(2) filed Jan. 19, 2018 for EP application No. 14862453.9, Credence Medsystems Inc.
First Examination Report dated Feb. 21, 2018 for Australian application No. 2014284373, Credence MedSystems Inc.
Amendment and Response to Non-Final Office Action for U.S. Appl. No. 14/543,787, filed Feb. 27, 2018.
Extended European Search Report dated Feb. 5, 2018 for EP Application No. 15782398.0, Credence Medsystems, Inc.
Voluntary Amendments filed Jan. 6, 2017 for EP application No. 14862453.9, Credence MedSystems Inc.
Official Action dated Mar. 2, 2018 for Japanese Application No. 2016-524332, Credence MedSystems Inc.
Notice of Allowance and Issue Fee due for U.S. Appl. No. 14/696,342 dated Apr. 20, 2018.
Final Office Action for U.S. Appl. No. 14/543,787 dated Apr. 9, 2018.
Amendment and Response filed Jun. 4, 2018 for Japanese Patent Application No. 2016-524332 (23 pages).
First Examination Report dated Jun. 4, 2018 for Chinese application No. 2014800480204, Credence MedSystems Inc.
First Examination Report dated Jul. 25, 2018 for Australian application No. 2014348292, Credence Medsystems Inc.
Notice of Appeal and Pre-Appeal Brief filed Jul. 9, 2018 for U.S. Appl. No. 14/543,787.
Official Action dated Sep. 12, 2018 for Japanese Patent Application No. 2016531649, Credence Medsystems Inc.
Examination Response to an Examiner's Report dated Oct. 10, 2018 for Australian application No. 2014284373, Credence Medsystems Inc.
Notice of Acceptance dated Oct. 24, 2018 for Australian Patent Application No. 2014284373, Credence Medsystems Inc.
Notice of Allowance and Fee(s) Due dated Oct. 31, 2018 for U.S. Appl. No. 14/543,787, filed Nov. 17, 2014.
Notice of Allowance dated Nov. 2, 2018 for Japanese Patent Application No. 2016-524332, Credence Medsystems Inc.
Response to European search report dated Aug. 28, 2018 for European Patent Application No. 15782398, Credence Medsystems Inc.

\* cited by examiner

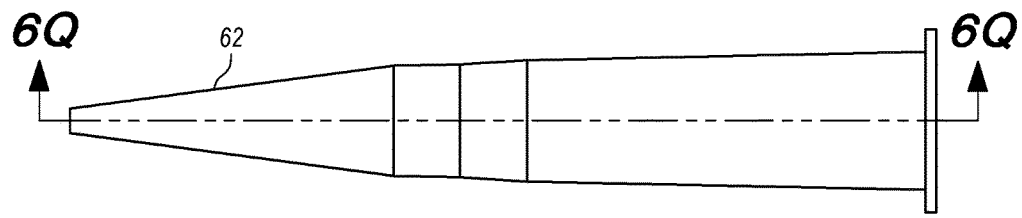
FIG. 6P
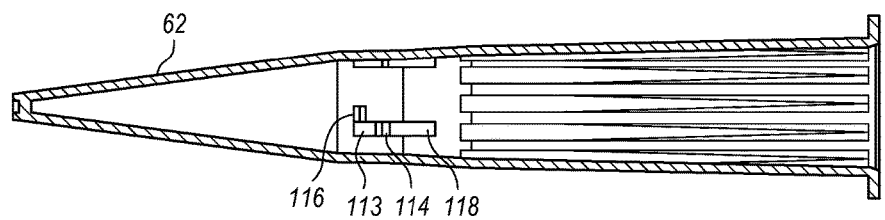
FIG. 6Q
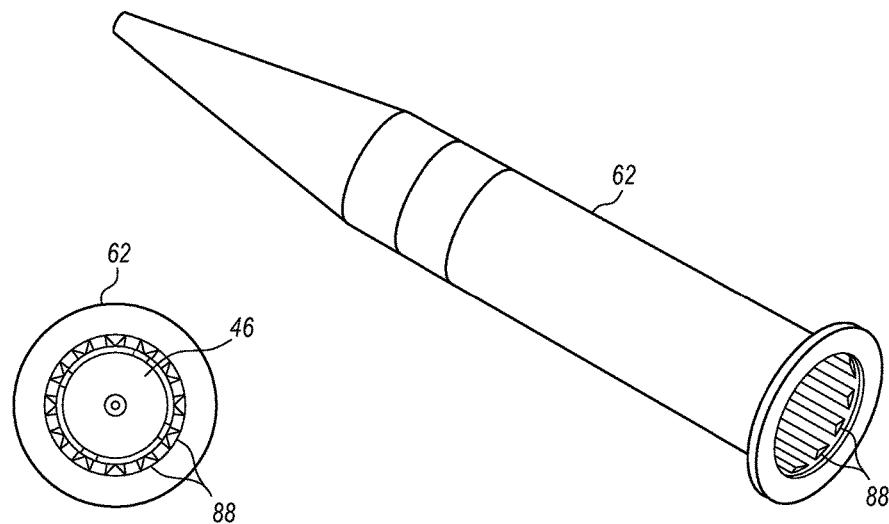
FIG. 6S
FIG. 6R

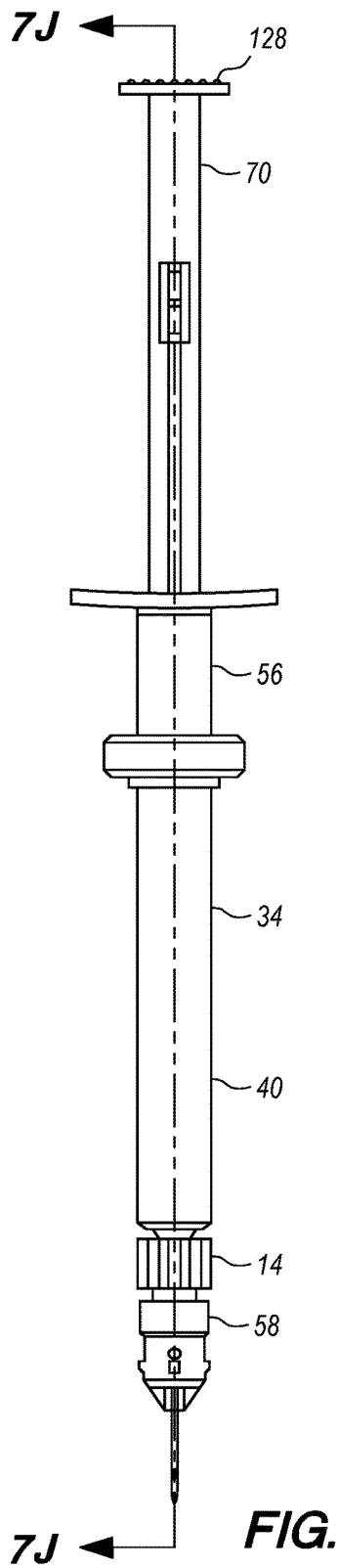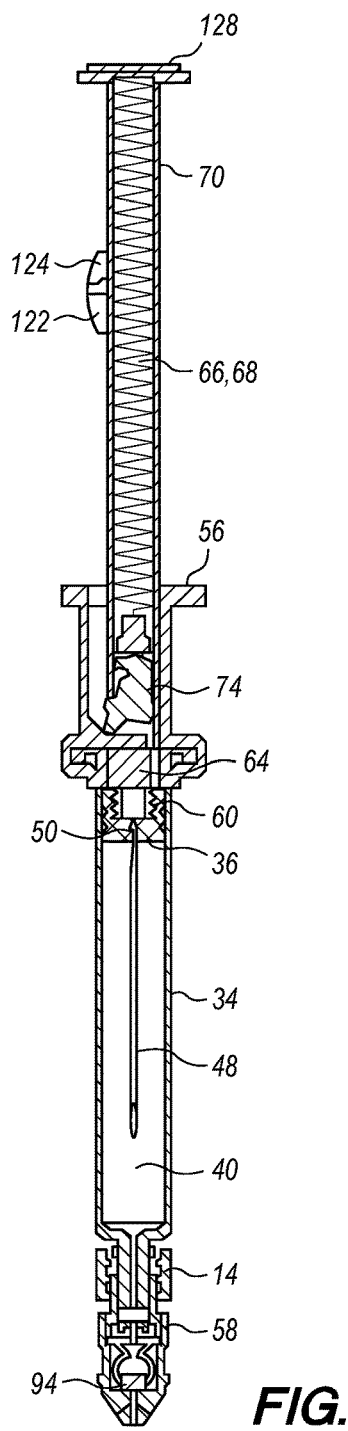
FIG. 7I
FIG. 7J

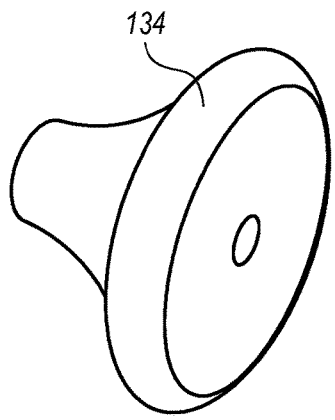
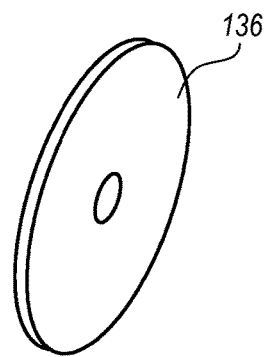
FIG. 8D   FIG. 8E
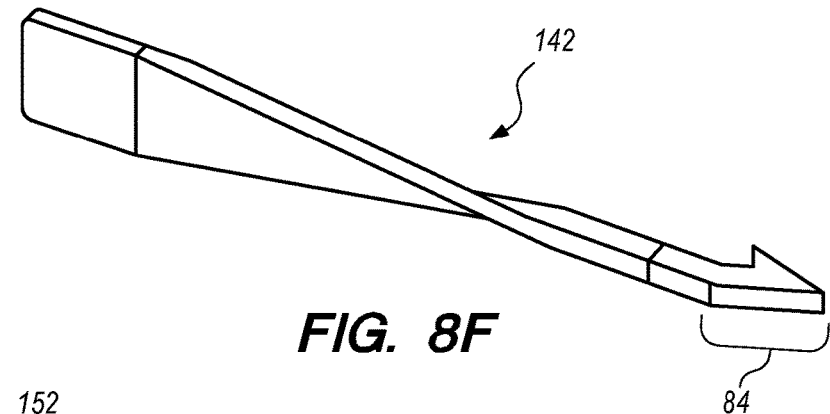
FIG. 8F
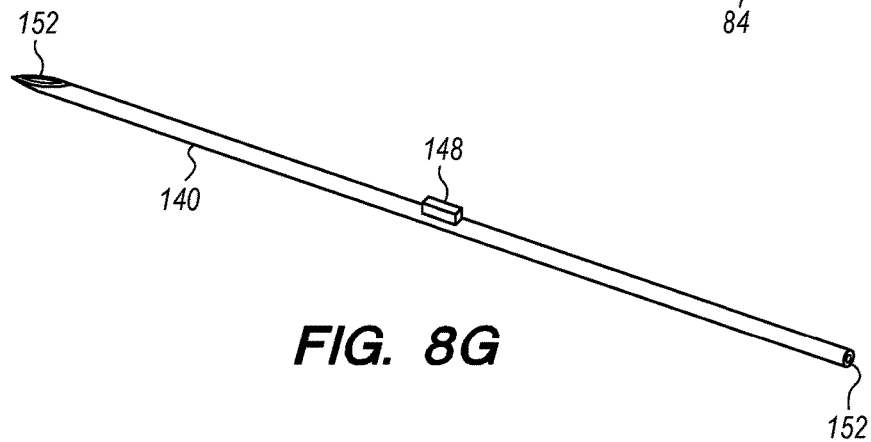
FIG. 8G

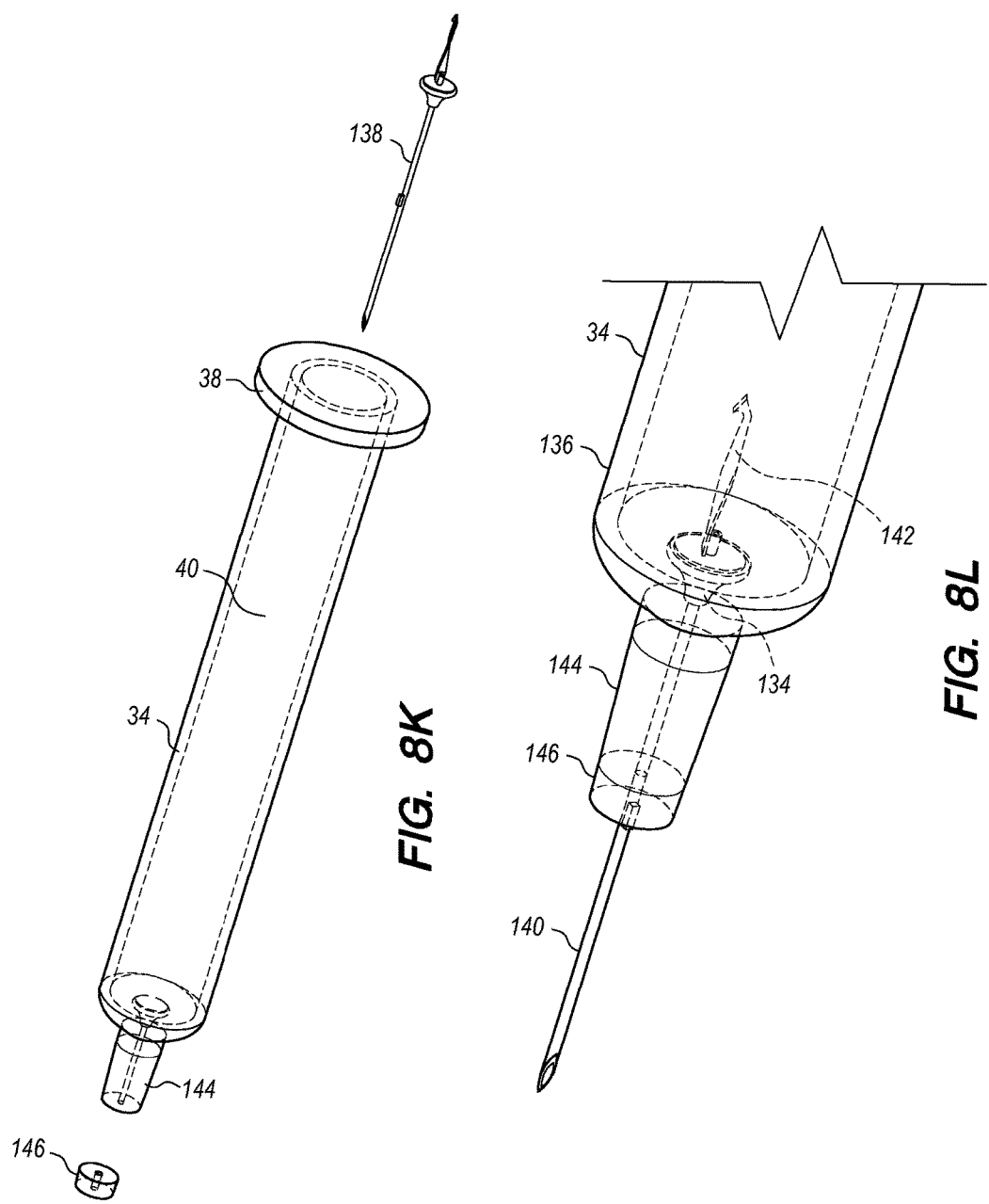

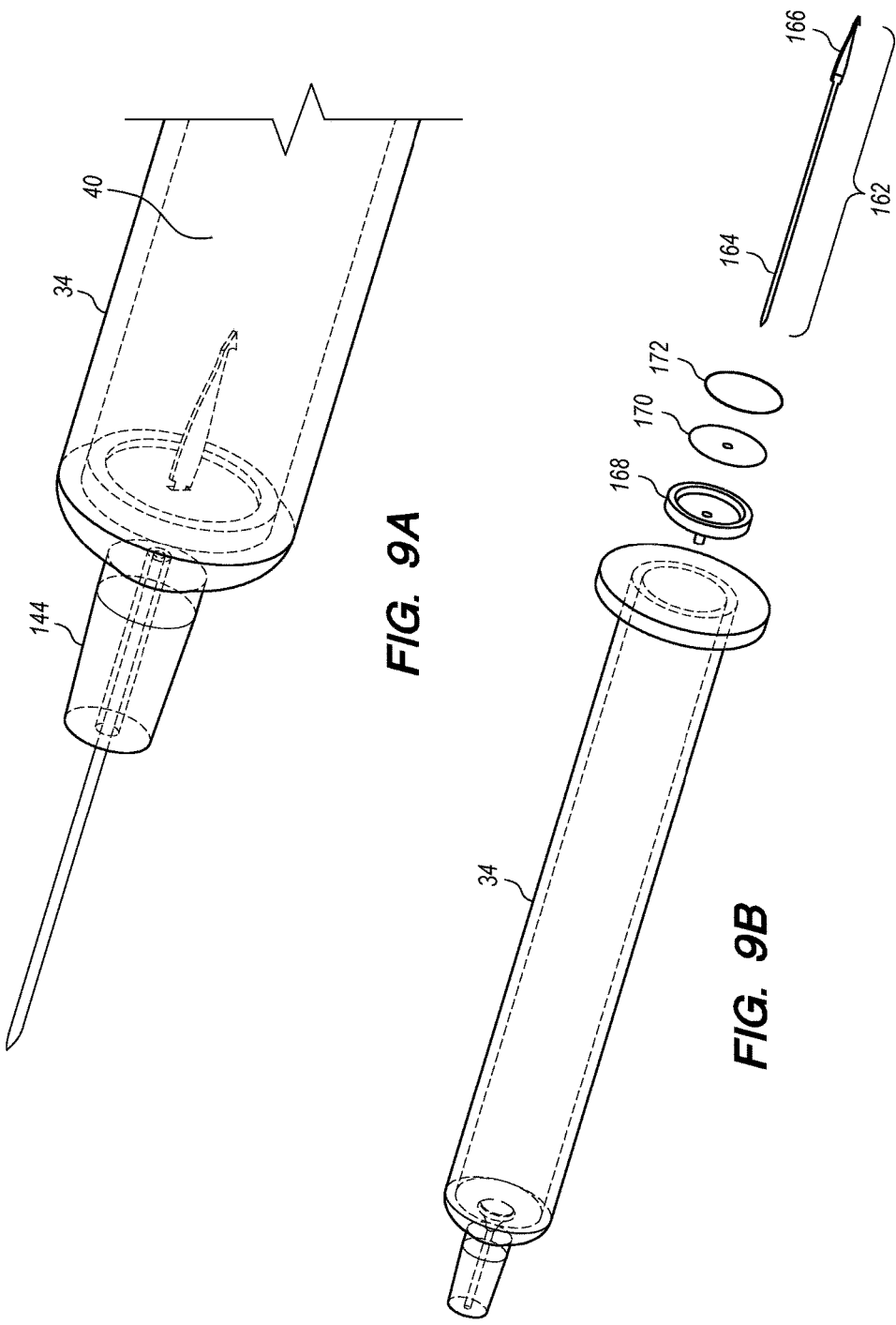

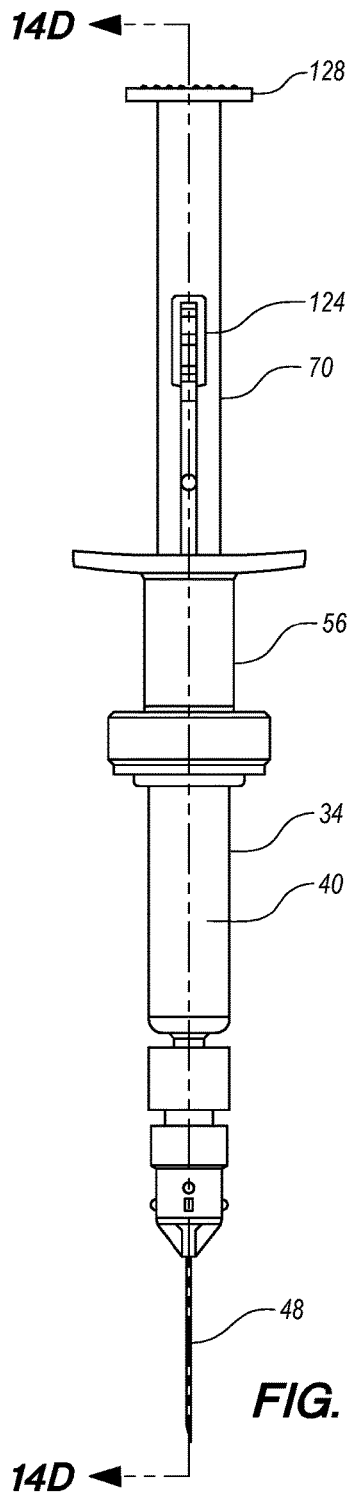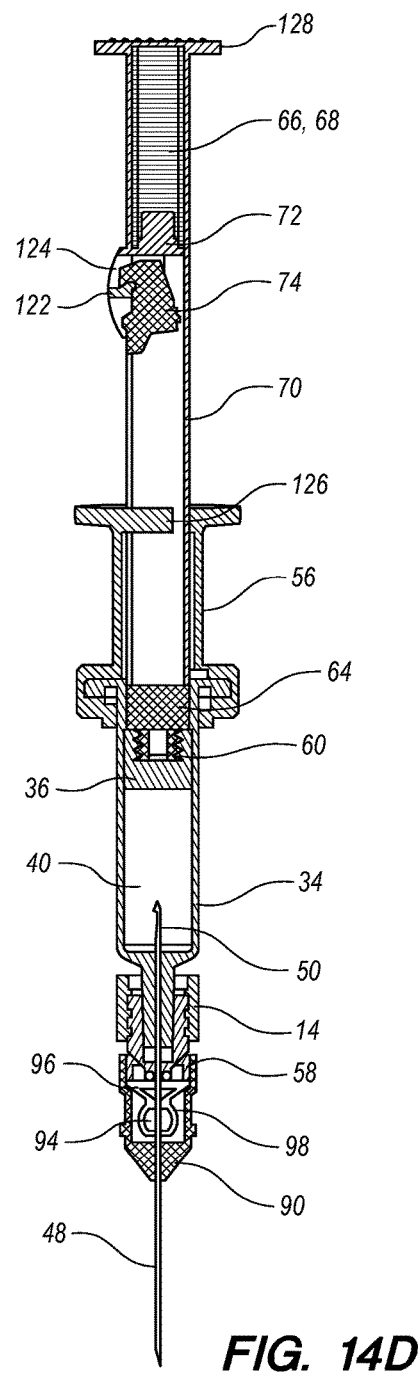
FIG. 14C
FIG. 14D

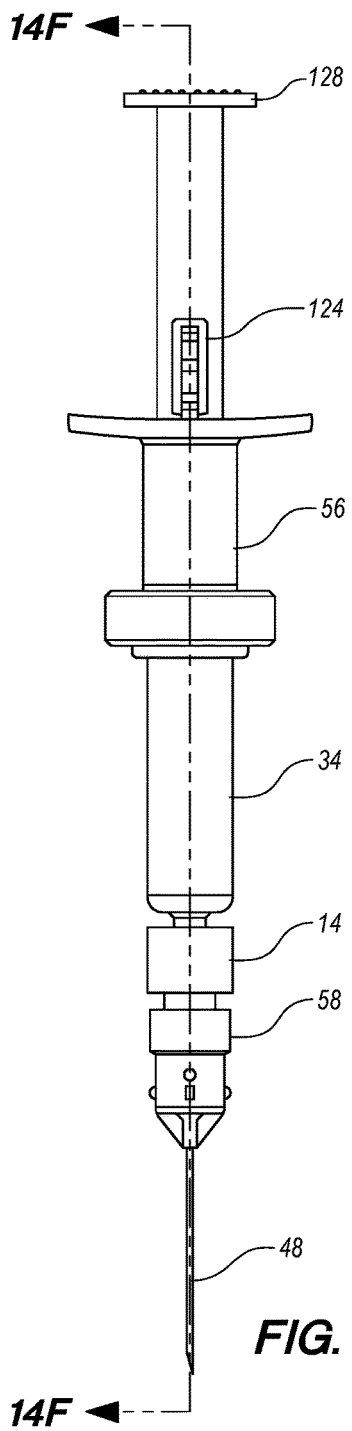
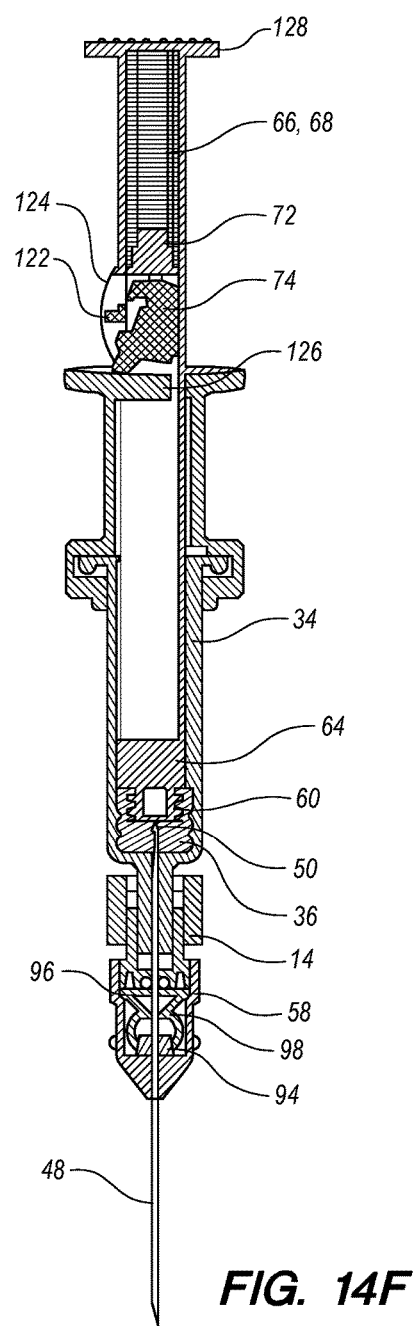
FIG. 14E
FIG. 14F

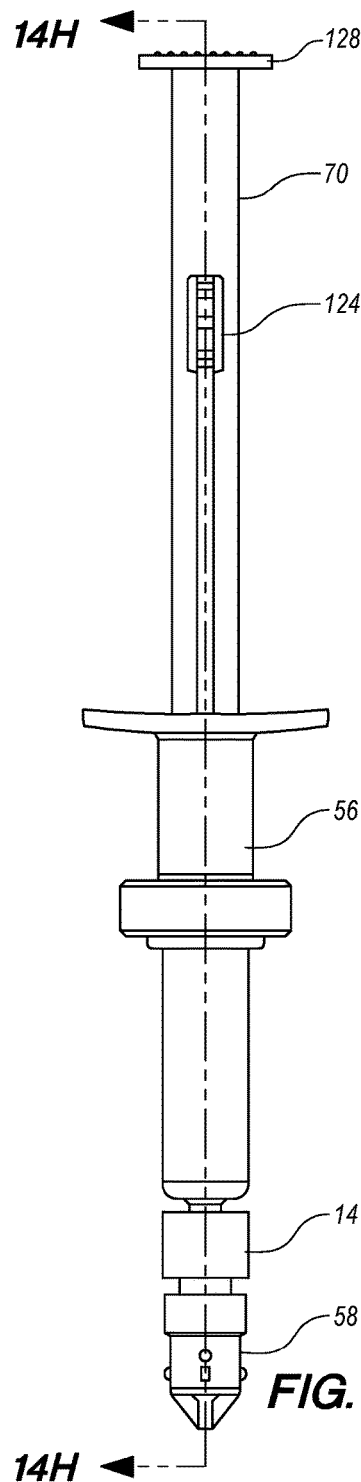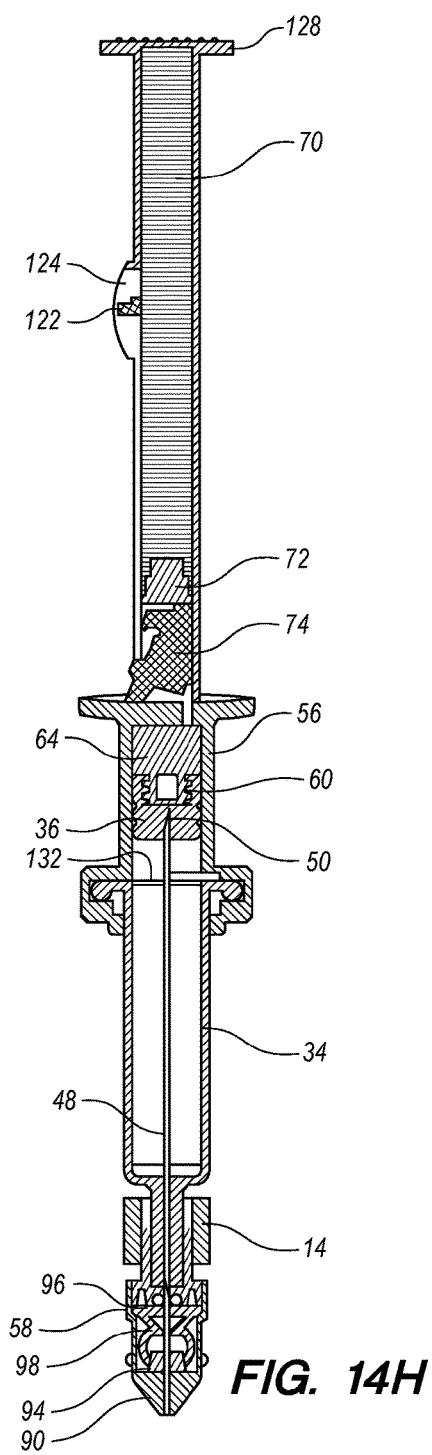

```
┌─────────────────────────────────────────────────────────────┐
│  Providing an injecting assembly comprising a syringe body  │
│  defining an interior medicine chamber and a distal needle  │
│  interface; a stopper member configured to be inserted into │
│  the interior medicine chamber to contain medicine within   │
│  the medicine chamber; a plunger member configured to be    │
│  manually manipulated to insert the stopper member          │──312
│  relative to the syringe body; and a needle having proximal │
│  and distal ends, the proximal end configured to be coupled │
│  to the stopper member upon insertion of the stopper member │
│  to a fully-inserted position, such that upon retraction    │
│  of the stopper member, the needle is pulled proximally     │
│  along with the stopper to be contained within the          │
│  interior medicine chamber                                  │
└─────────────────────────────────────────────────────────────┘
                              │
                              ▼
┌─────────────────────────────────────────────────────────────┐
│  Upon retraction of the needle into the interior medicine   │
│  chamber to a position wherein the distal end of the needle │
│  is contained within the interior medicine chamber,         │──314
│  misaligning the needle with a longitudinal axis of the     │
│  syringe body such that it is prevented from being          │
│  reinserted out of the interior medicine chamber            │
└─────────────────────────────────────────────────────────────┘
                              │
                              ▼
┌─────────────────────────────────────────────────────────────┐
│  Configuring the needle to plastically deform (such as by   │
│  bending of at least one portion of the needle) upon        │
│  attempt to re-insert the needle relative to the syringe    │──316
│  body after the needle becomes misalgined with a            │
│  longitudinal axis of the syringe body                      │
└─────────────────────────────────────────────────────────────┘
```

*FIG. 17*

```
┌─────────────────────────────────────────────────────────────────┐
│ Providing an injecting assembly comprising a syringe body       │
│ defininging an interior medicine chamber; a stopper member      │
│ configured to be inserted into the interior medicine chamber    │
│ to contain medicine within the medicine chamber; a plunger      │──318
│ member configured to be manually manipulated to insert the      │
│ stopper member relative to the syringe body; a needle having    │
│ sharpened distal end; and a needle door member movably          │
│ coupled the syringe body                                        │
└─────────────────────────────────────────────────────────────────┘
                                │
                                ▼
┌─────────────────────────────────────────────────────────────────┐
│ Moving the needle door member from a first state wherein the    │
│ needle door member facilitates insertion of the needle relative │
│ to the syringe body, to a second state wherein the needle door  │──320
│ member prevents insertion of the needle relative to the         │
│ syringe body                                                    │
└─────────────────────────────────────────────────────────────────┘
                                │
                                ▼
┌─────────────────────────────────────────────────────────────────┐
│ Slidably moving the needle door member in a plane relative to   │
│ the longitudinal axis of the needle (such as a plane that is    │──322
│ substantially perpendicular relative to the longitudinal axis   │
│ of the needle)                                                  │
└─────────────────────────────────────────────────────────────────┘
```

FIG. 18A

| Providing an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end coupled to a distal end of the syringe body; and a needle sheath operativley coupled to the syringe body and defining a lumen through which at least the distal end of the needle may be passed, the needle sheath configured to have a first state, wherein the needle sheath is compressed toward the proximal end of the needle to expose the distal end of the needle for injecting, and a second state, wherein the needle sheath is advanced forward over the needle distal end to substantially cover the needle and prevent contact with the distal end of the needle; wherein in the first state, an energy storage member (such as a spring) is compressed to bias the needle sheath to spring forward into the second state but for a sheath retention element which retains the needle sheath in the first position until the stopper member has been advanced to a predetermined position relative to the syringe body 9 such as one wherein the stopper member has been advanced to a maximum advancment position relative to the syringe body; at the predetermined position, the plunger may apply a load against the needle, which may release the sheath retention element) | ─364 |
|---|---|

↓

| Advancing the stopper member into the predetermined position relative to the syringe body to cause the needle sheath to be advanced forward over the needle distal end | ─366 |
|---|---|

↓

| Using a sheath-limiting member to restrain the needle sheath from advancing in the second state past a predetermined axial extention position relative to the syringe body | ─368 |
|---|---|

*FIG. 25*

```
┌─────────────────────────────────────────────────────────────────────┐
│   Providing an injecting assembly comprising a syringe body defining an interior  │
│  medicine chamber; a stopper member configured to be inserted into the interior    │
│  medicine chamber to contain medicine within the medicine chamber; a plunger       │
│     member configured to be manually manipulated to insert the stopper member      │
│ relative to the syringe body; a needle having proximal and distal ends, the proximal│
│  end coupled to a distal end of the syringe body; and a telescoping needle sheath  │
│ operatively coupled to the syringe body and defining a lumen through which at least│
│      the distal end of the needle may be passed, the needle sheath configured to have a│
│         first state, wherein the telescoping needle sheath is telescopically compressed │──370
│    toward the proximal end of the needle to expose the distal end of the needle for│
│ injecting, and a second state, wherein the needle sheath is telescopically advanced│
│       forward over the needle distal end to substantially cover the needle and prevent│
│ contact with the distal end of the needle; wherein in the first state, an energy storage│
│       member (such as a spring) is compressed to bias the needle sheath to spring  │
│     forward into the second state but for a sheath retention element which retains the│
│ needle sheath in the first position until the stopper member has been advanced to a│
│         predetermined position relative to the syringe body (such as one wherein the│
│    stopper member has been advanced to a maximum advancement position relative     │
│     to the syringe body; at the predetermined position, the plunger may apply a load│
│         against the needle, which may release the sheath retention element)        │
└─────────────────────────────────────────────────────────────────────┘
                                      │
                                      ▼
┌─────────────────────────────────────────────────────────────────────┐
│    Advancing the stopper member into the predetermined position relative to the syringe│──372
│     body to cause the needle sheath to be telescopically advanced forward over the needle│
│                                    distal end                                       │
└─────────────────────────────────────────────────────────────────────┘
                                      │
                                      ▼
┌─────────────────────────────────────────────────────────────────────┐
│    Using a sheath-limiting member to restrain the needle sheath from advancing in the│──374
│   second state past a predetermined axial extension position relative to the syringe body│
└─────────────────────────────────────────────────────────────────────┘
```

*FIG. 26*

Providing an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having proximal and distal ends, the proximal end being removably coupled to the distal needle interface of the syringe body and at least partially retractable into the interior medicine chamber ⟶ 394 manipulating the plunger member relative to the syringe body to transform a plunger latching member from a latched state to an unlatched state, the plunger latching member intercoupled between the syringe body and the plunger member, wherein the plunger latching member is substantially disposed within a lumen defined by the plunger member ⟶ 396

*FIG. 30*

| Providing an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having proximal and distal ends, the proximal end being removably coupled to the distal needle interface of the syringe body and at least partially retractable into the interior medicine chamber | ─398 |

| Manipulating the plunger member relative to the syringe body to transform a plunger latching member from a latched state to an unlatched state, the plunger latching member slidably and rotatably intercoupled between the syringe body and the plunger member such that upon substantially full insertion of the plunger member relative to the syringe member, the plunger latch member is axially moved and also rotated to convert from the latched state to the unlatched state, and also to allow the plunger member to insert the stopper member to a full insertion position wherein substantially all of the contents of the interior medicine chamber may be expelled out of the needle | ─400 |

*FIG. 31*

Providing an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body using a proximal manipulation interface; a spring member disposed within a lumen defined through the plunger member; a needle having proximal and distal ends, the proximal end being removably coupled to the distal needle interface of the syringe body and at least partially retractable into the interior medicine chamber ⟶ 402

Manipulating the plunger member relative to the syringe body to transform a plunger latching member from a latched state to an unlatched state, the plunger latching member intercoupled between the syringe body and the plunger member; wherein the plunger latching member is substantially disposed within the plunger member lumen and coupled to the spring member such that the spring member is compressed more in the latched state than it is in the unlatched state; and wherein the proximal manipulation interface is configured to facilitate manual engagement to control a rate of plunger member retraction in the unlatched state ⟶ 404

*FIG. 32*

Providing an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having a proximal end and a sharpened distal end, the proximal end being removably coupled to the distal needle interface of the syringe body and at least partially retractable into the interior medicine chamber ⟶ 406

Manipulating the plunger member relative to the syringe body to transform a plunger latching member from a latched state to an unlatched state, the plunger latching member intercoupled between the syringe body and the plunger member; wherein the plunger latching member is substantially disposed within a lumen defined by the plunger member; and wherein in the unlatched state, the plunger member is at least partially prevented from being reinserted relative to the syringe body by one or more toothlike structures comprising the plunger latching member which are configured to prevent movement of the plunger member syringe body ⟶ 408

*FIG. 33*

Providing an injecting assembly comprising a syringe body defining an interior medicine chamber; a stopper member configured to be inserted into the interior medicine chamber to contain medicine within the medicine chamber; a plunger member configured to be coupled to the stopper member, and to insert the stopper member relative to the syringe body; and a needle having proximal and distal ends, the proximal end comprising an anchoring geometry configured to be at least partially inserted into the stopper member ⟶ 410

Retracting the stopper member to pull the needle proximally along with the stopper to be at least partially contained within the interior medicine chamber; wherein the stopper member defines a threaded proximal interface, and wherein the plunger member has a distal threaded interface configured to be helically coupled into the threaded proximal interface of the stopper member, the distal threaded interface being purposely undersized relative to the threaded proximal interface of the stopper member, such that upon such helical coupling, an outer geometry of the stopper member is not substantially increased by virtue of the helical intercoupling between the stopper member and plunger member distal threaded interface ⟶ 412

*FIG. 34*

Providing an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end comprising an anchoring geometry configured to be at least partially inserted into the stopper member such that upon retraction of the stopper member, the needle is pulled proximally along with the stopper to be at least partially contained within the interior medicine chamber; a first imaging marker (such as a metallic bead, metallic ring, or a radiation-emitting beacon) coupled to a first known location on the needle; and a second imaging marker (such as a metallic bead, metallic ring, or a radiationemitting beacon) coupled to a second known location on the needle ⟶ 420

Utilizing an imaging system to detect the positions of the first and second imaging markers such that the orientation of the needle may be determined relative to a global coordinate system ⟶ 422

FIG. 36

```
┌─────────────────────────────────────────────────────────────────────┐
│ Providing an injecting assembly comprising a syringe body having proximal and distal ends │
│ and defining an interior medicine chamber; a stopper member configured to be inserted into │
│ the interior medicine chamber to contain medicine within the medicine chamber, the stopper │
│   member comprising a distal surface configured to be directly interfaced with the medicine │
│ within the medicine chamber; a plunger member comprising a proximal interface configured │
│    to be manually manipulated to move the stopper member relative to the syringe body; a │──424
│   needle having a sharpened distal end; and an extension member coupled to the proximal │
│   end of the syringe body, the extension member operatively coupled to the plunger member │
│  and configured to contain the stopper member if the stopper is withdrawn to such an extent │
│              that it at least partially exits the interior medicine chamber │
└─────────────────────────────────────────────────────────────────────┘
                                    │
                                    ▼
┌─────────────────────────────────────────────────────────────────────┐
│         Withdrawing at least a portion of the stopper member into the              │──426
│                              extension member                                      │
└─────────────────────────────────────────────────────────────────────┘
                                    │
                                    ▼
┌─────────────────────────────────────────────────────────────────────┐
│ Containing residual droplets of medicine which may remain coupled to the distal surface of │
│   the stopper member until they become contained by a fluid containment surface (such as │
│    one that defines one or more fluted geometries configured to retain the residual droplets │
│         and/or defines one or more perforations configured to retain the residual droplets) │──428
│ positioned immediately adjacent the distal surface upon withdrawal of the stopper member │
│      into the extension chamber; an absorbant member may be fluidly coupled to the fluid │
│       containment surface, the absorbant member configured to absorb and retain the residual │
│                                     droplets │
└─────────────────────────────────────────────────────────────────────┘
```

FIG. 37

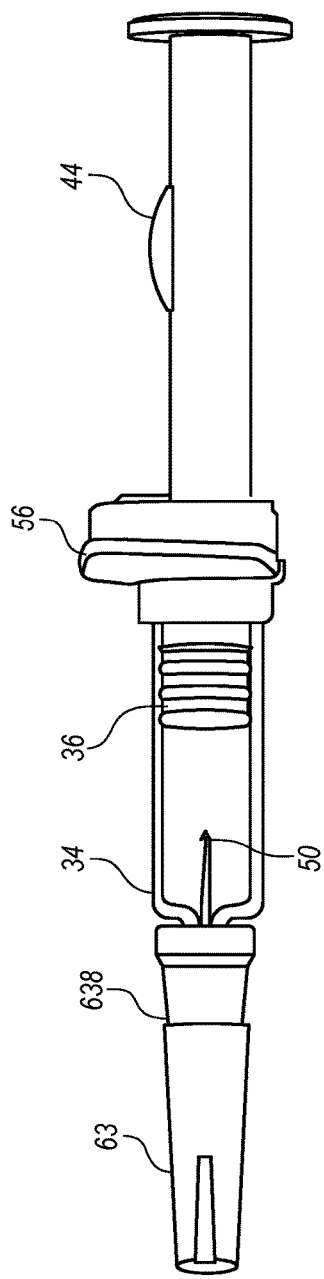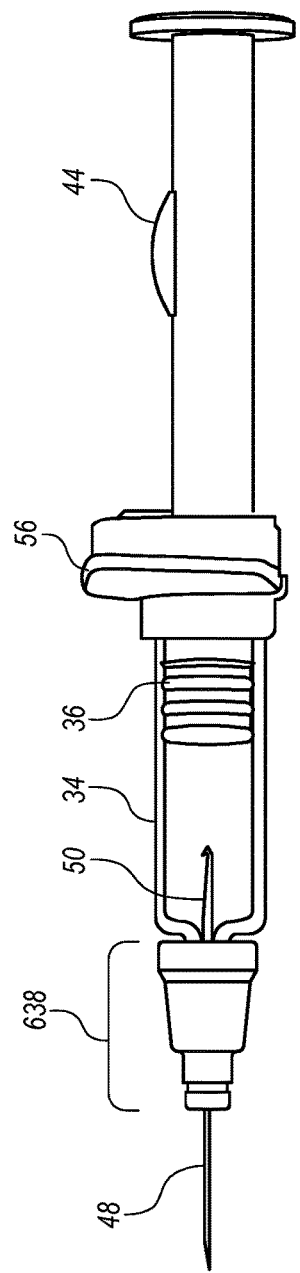
FIG. 50A
FIG. 50B

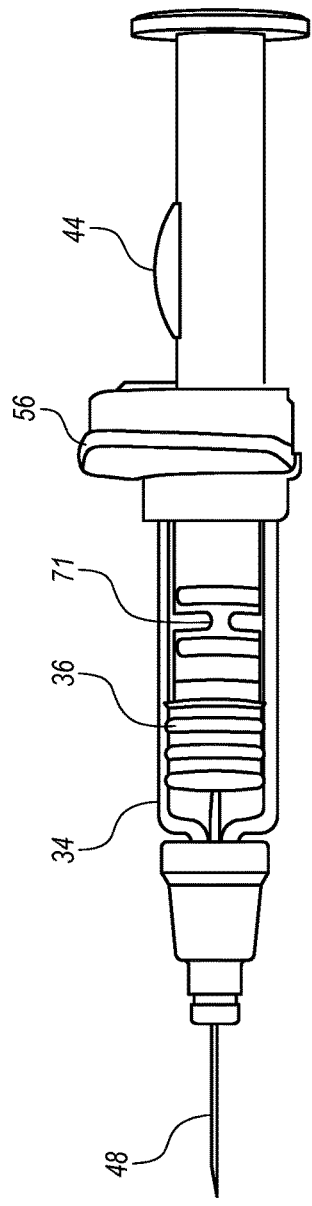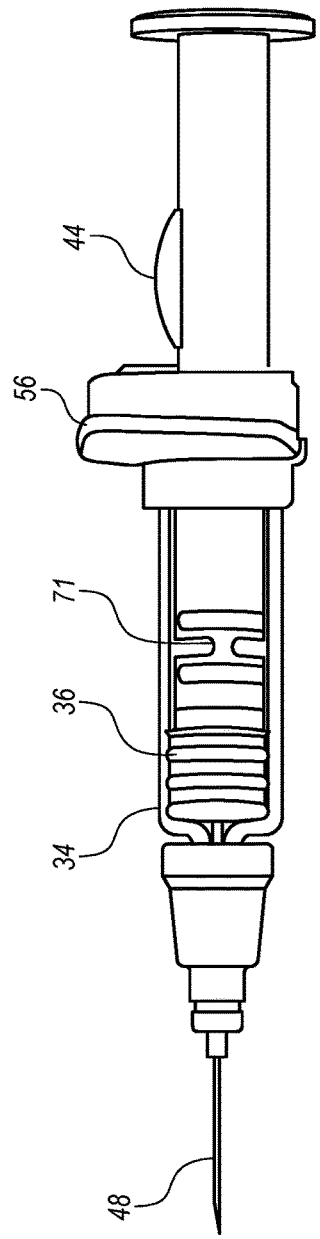

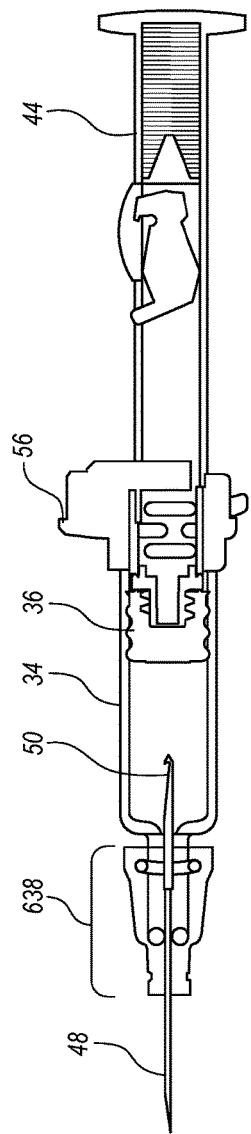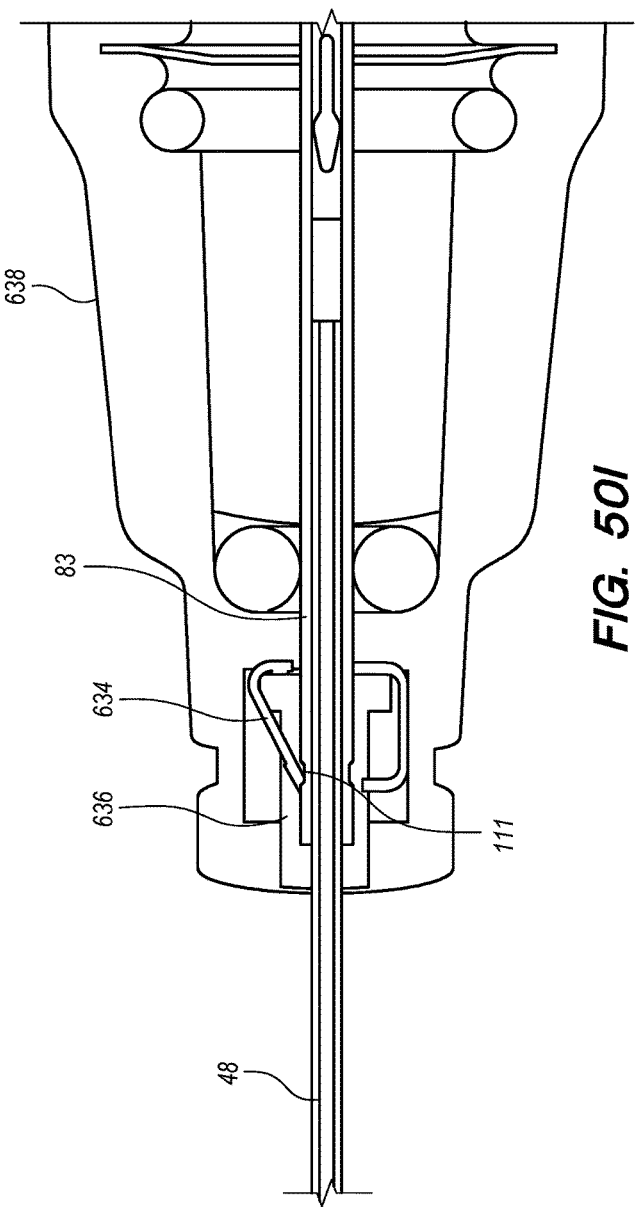

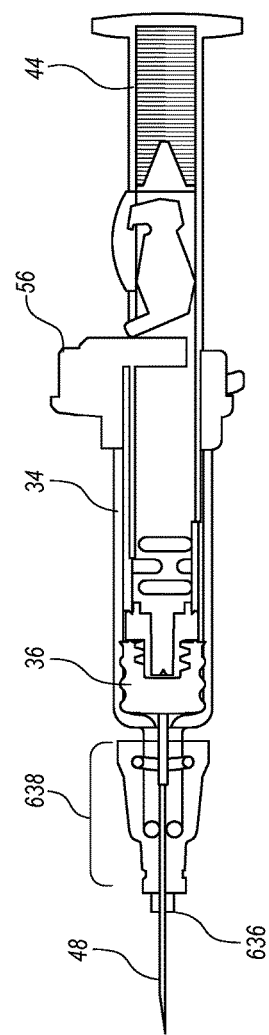
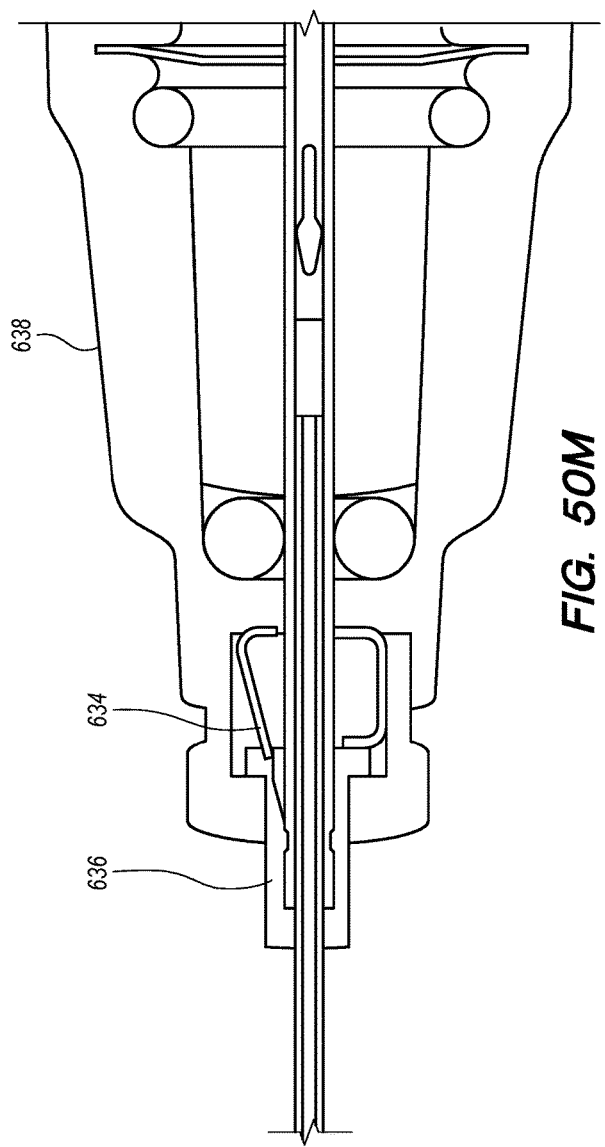
FIG. 50L
FIG. 50M

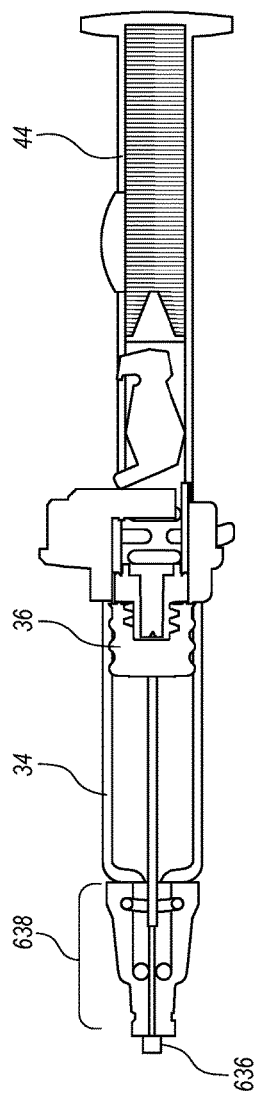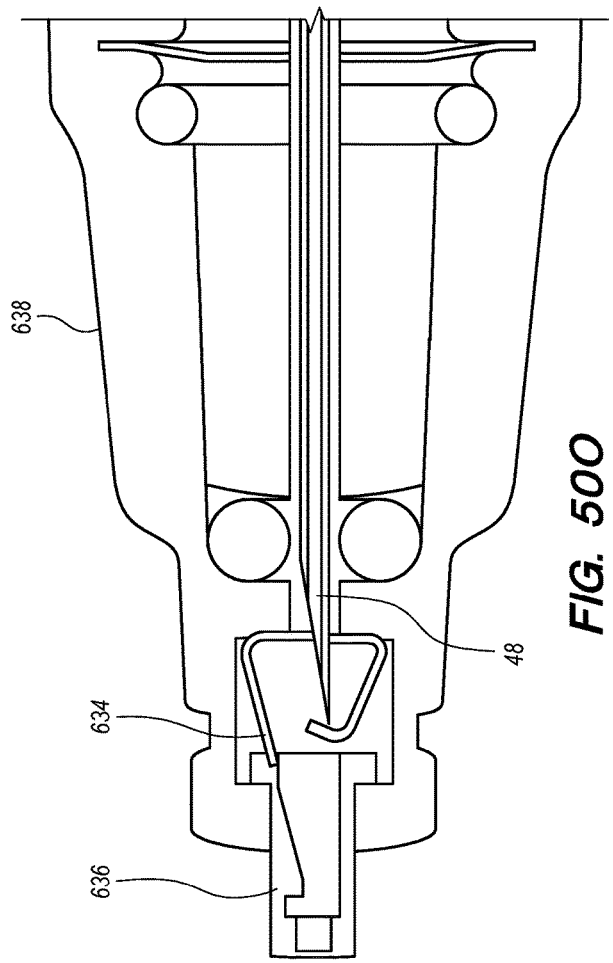
FIG. 50N
FIG. 50O

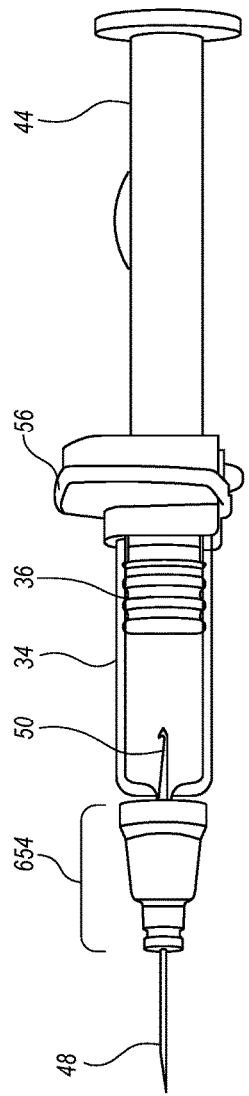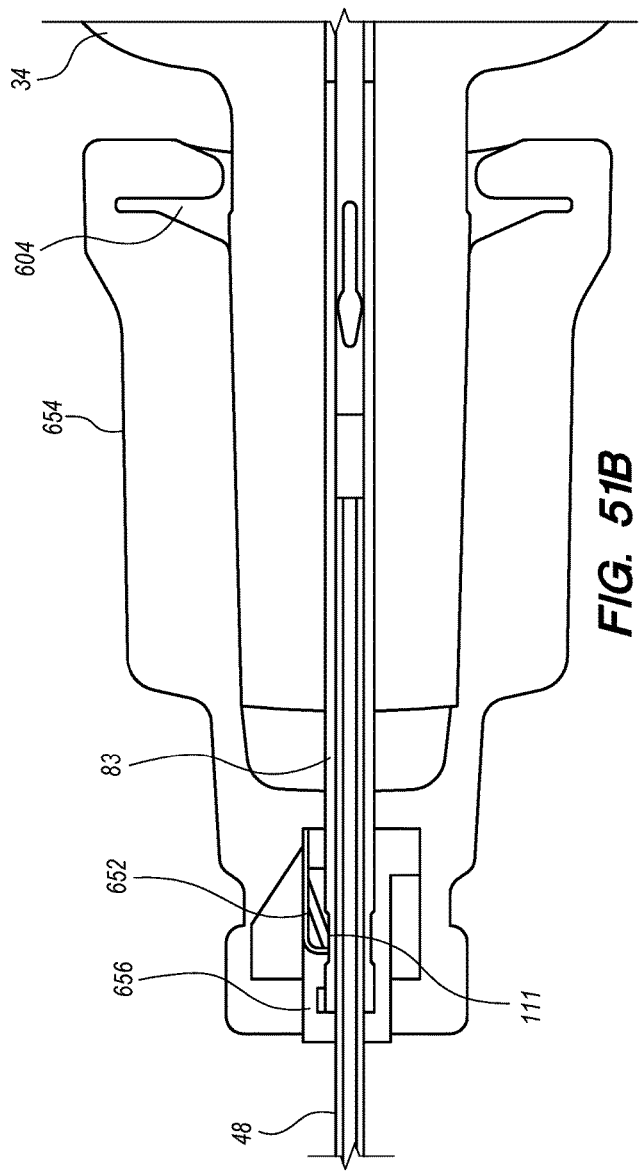
FIG. 51A
FIG. 51B

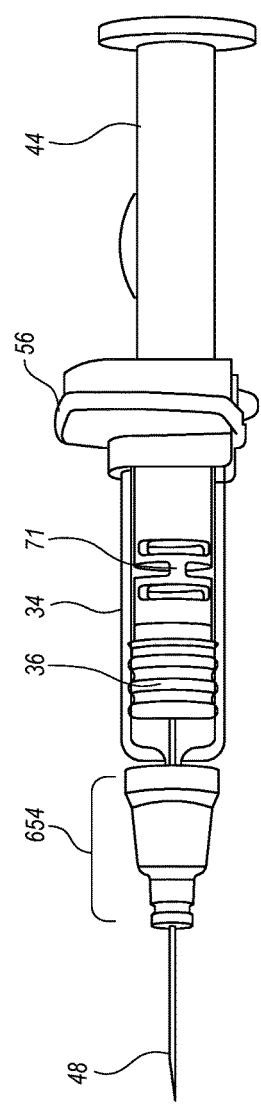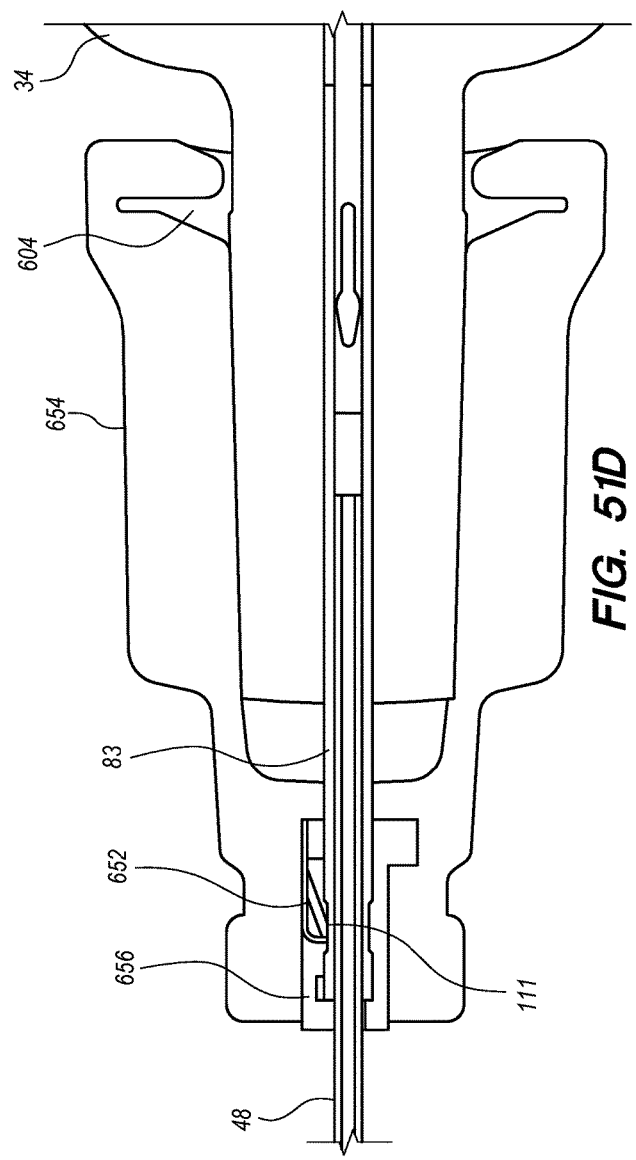
FIG. 51C
FIG. 51D

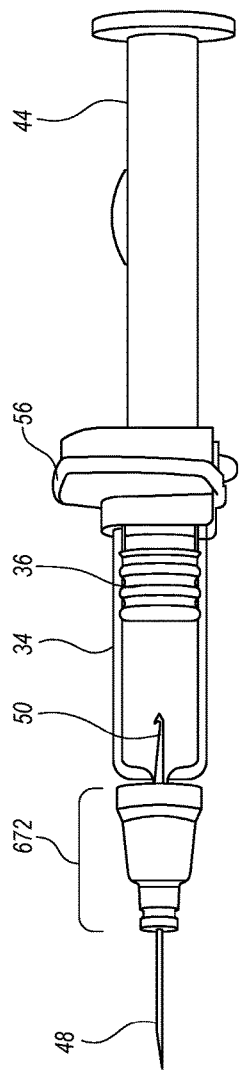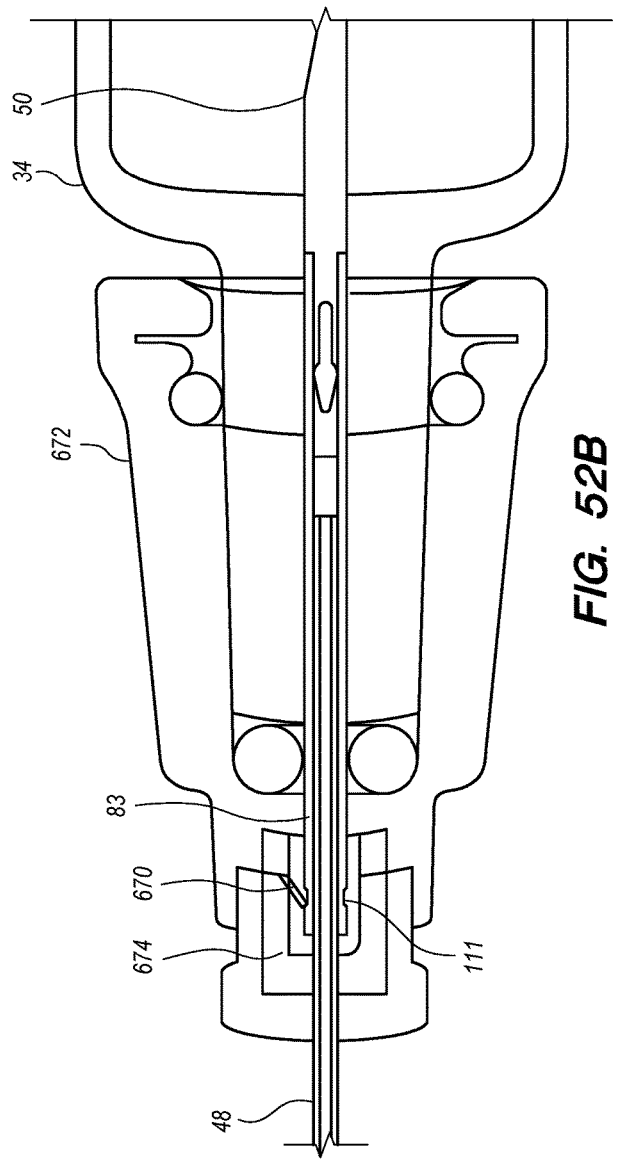
FIG. 52A
FIG. 52B

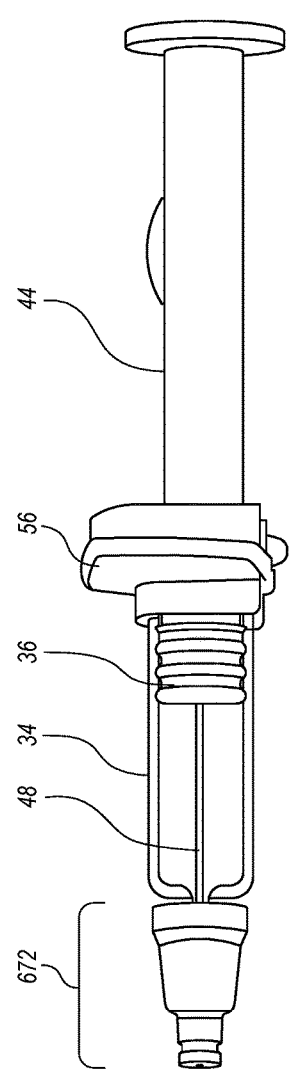
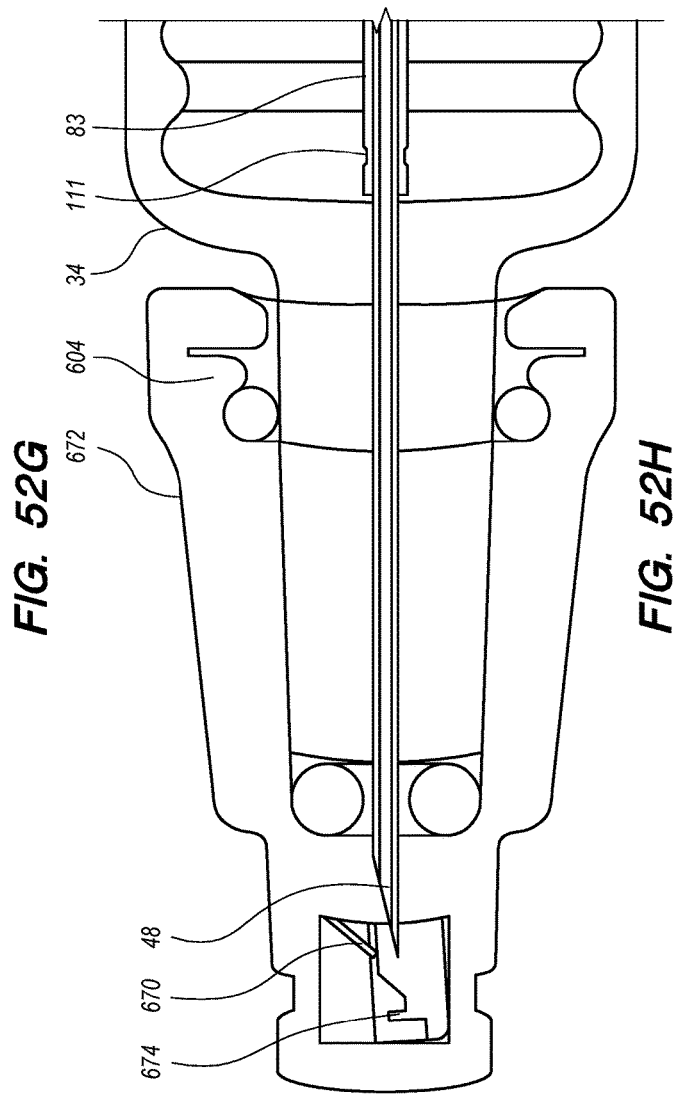
FIG. 52G
FIG. 52H

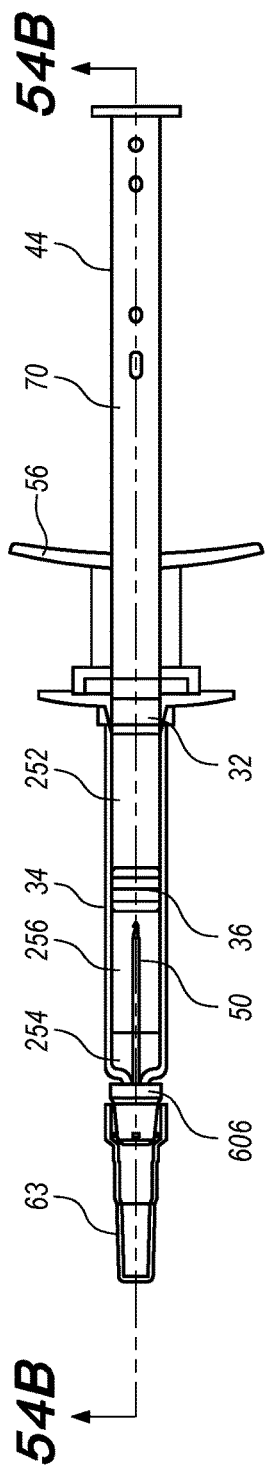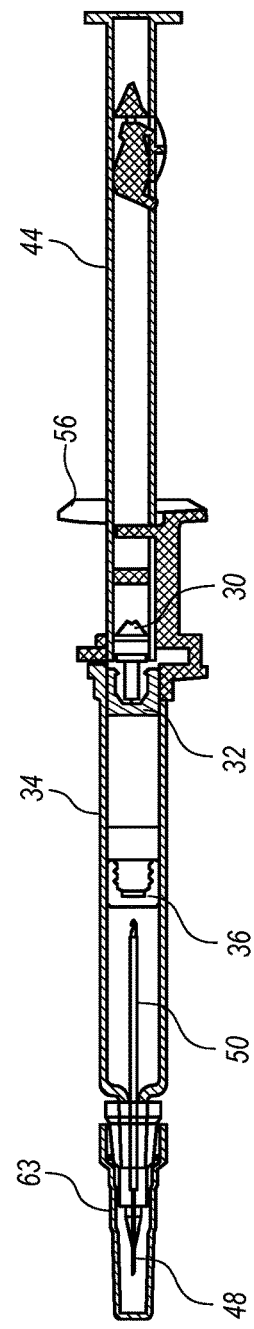
FIG. 54A
FIG. 54B

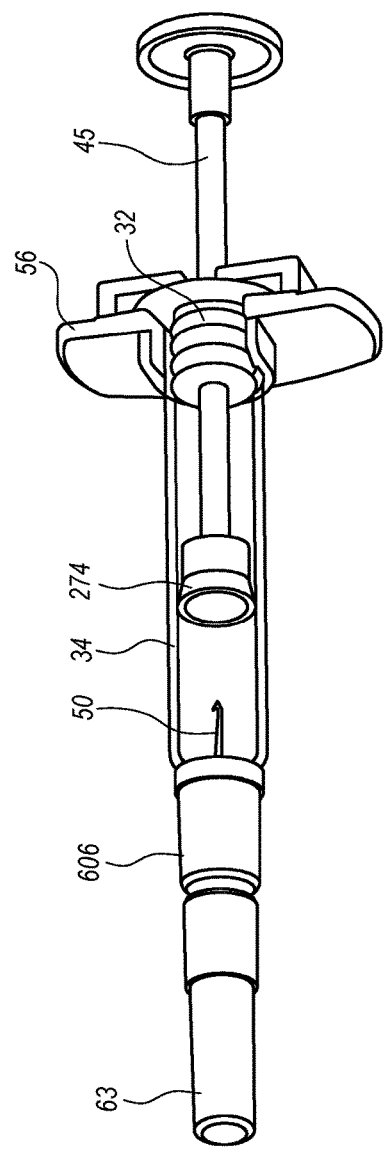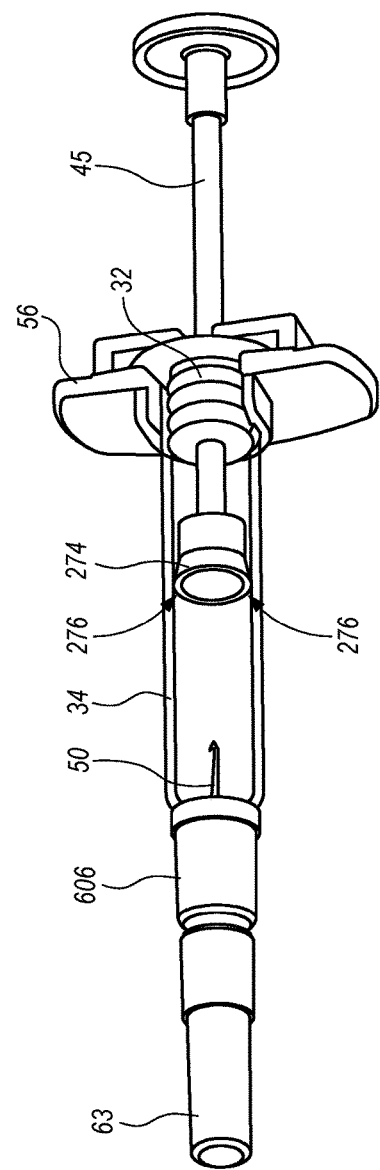

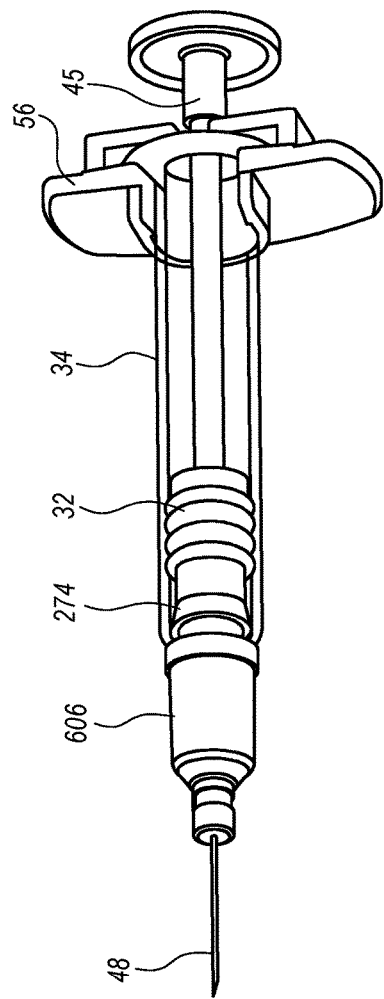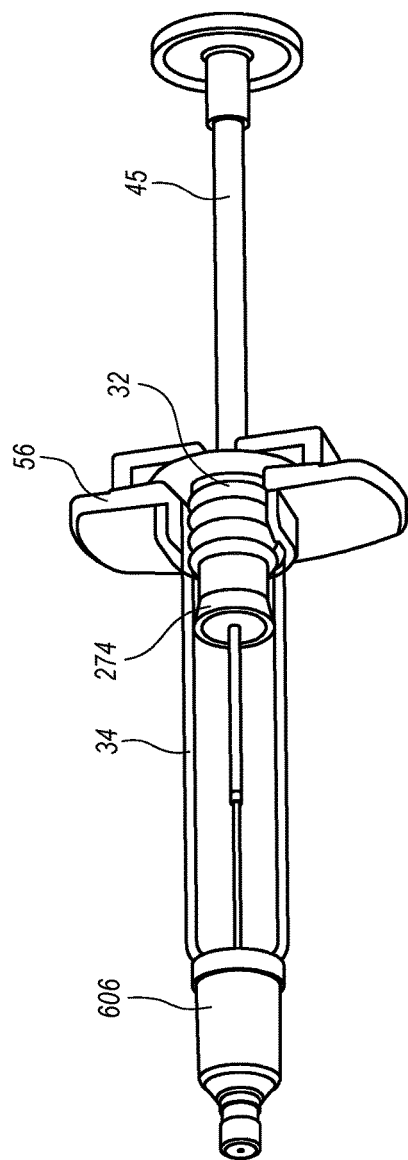

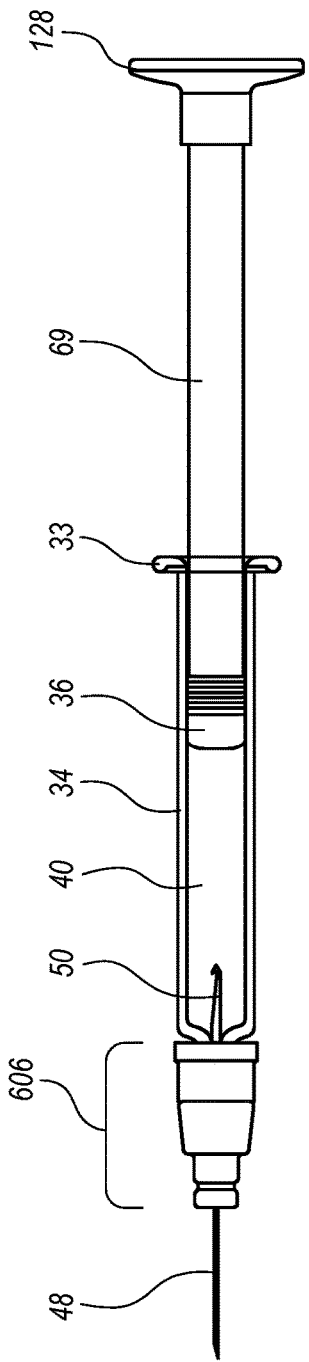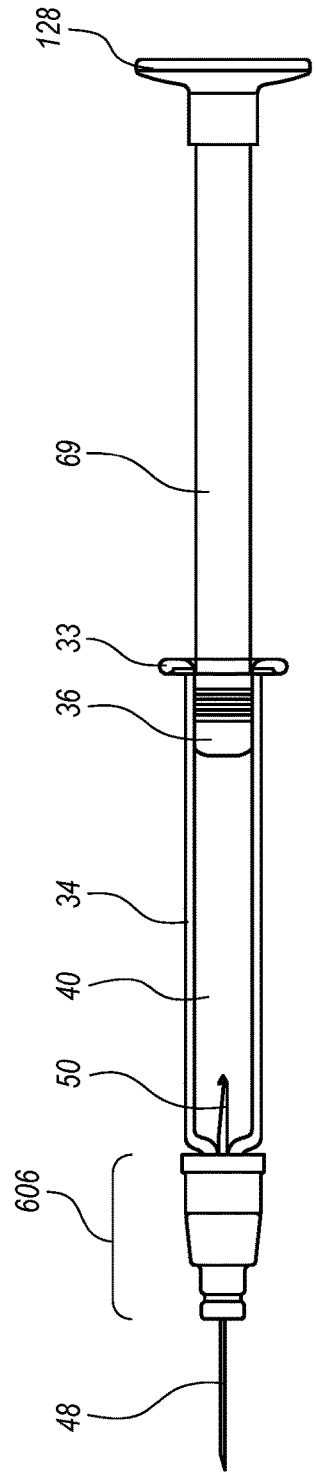

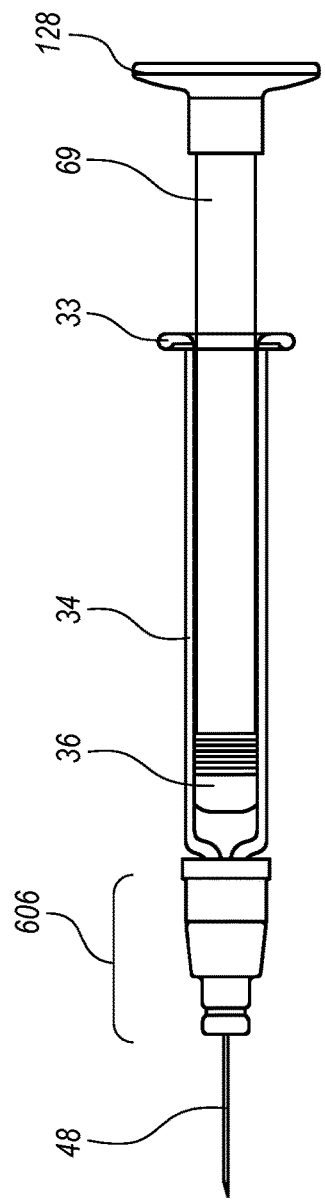
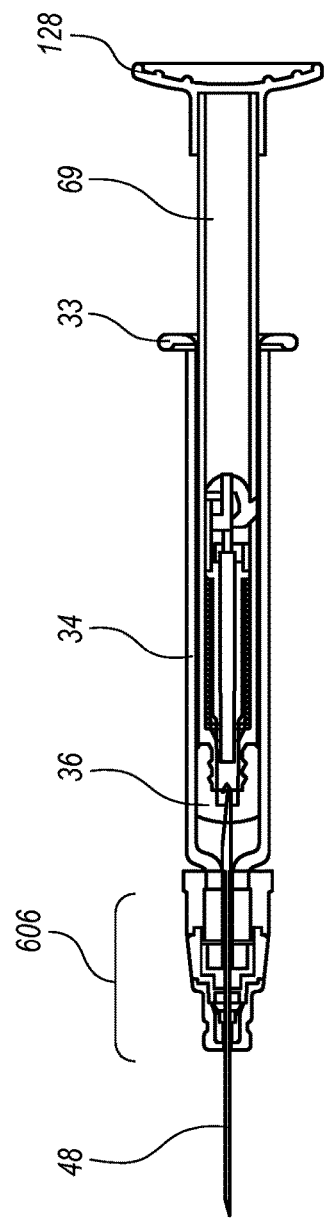
FIG. 59E
FIG. 59F

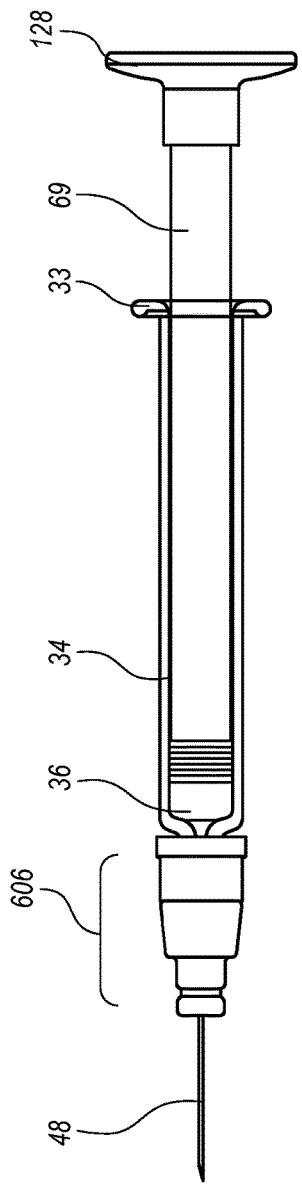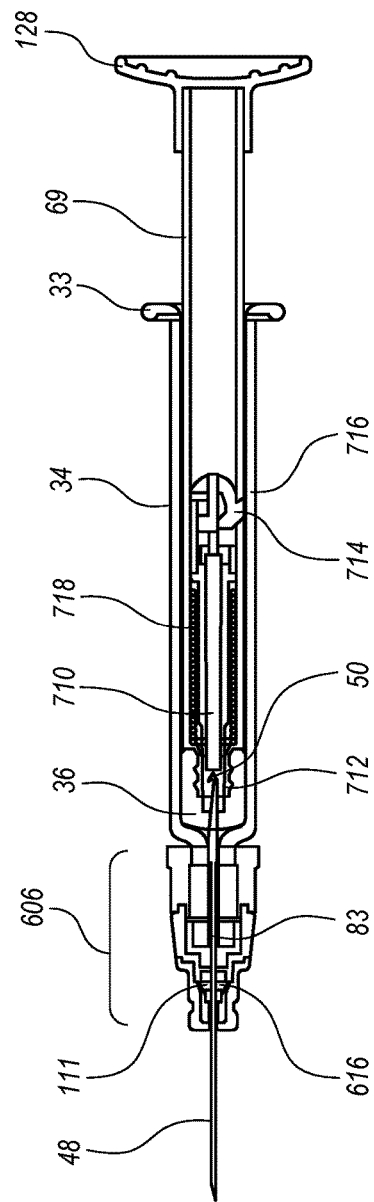

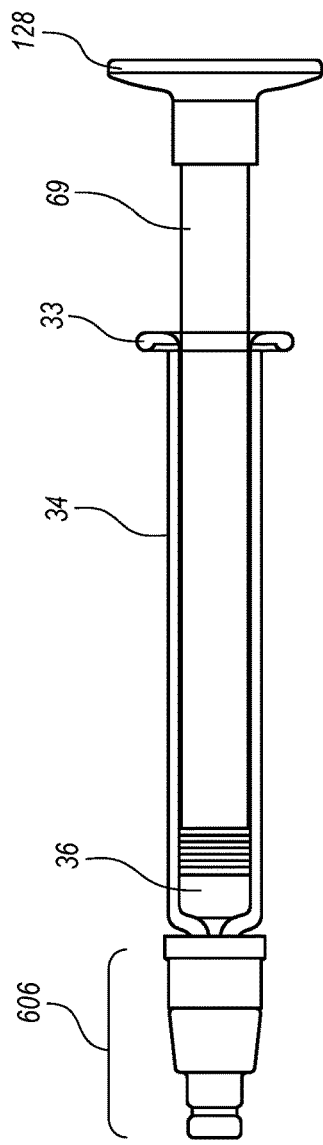
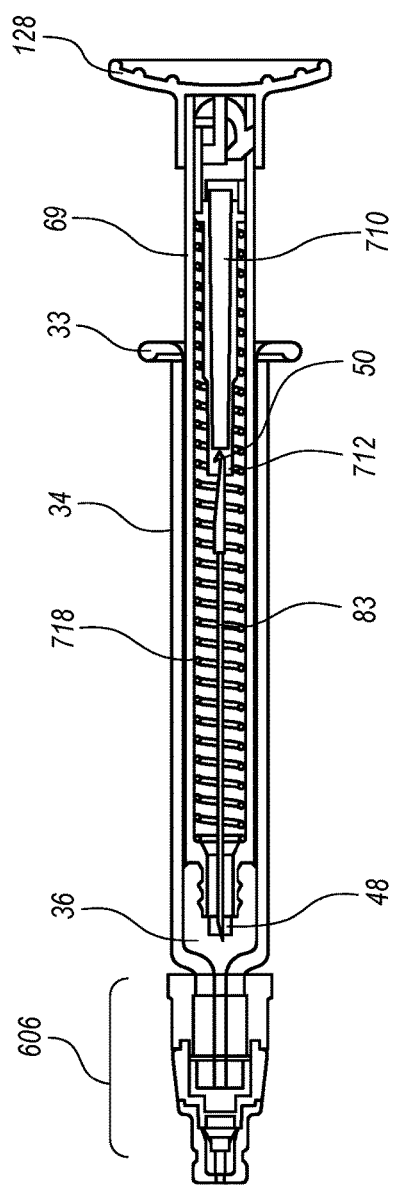
FIG. 59K
FIG. 59L

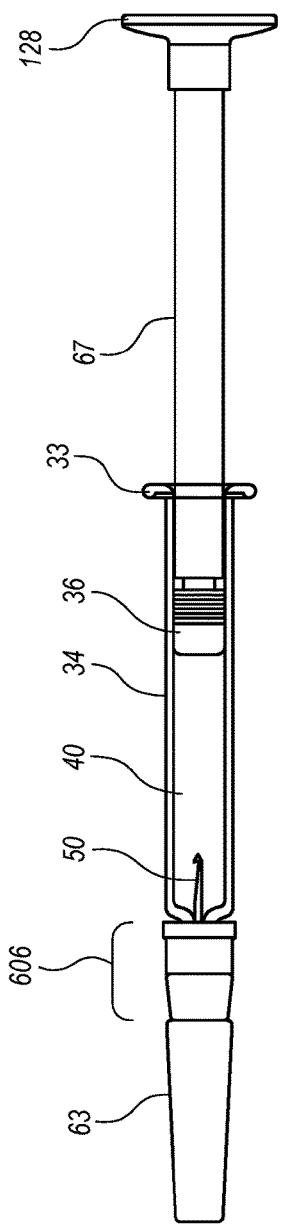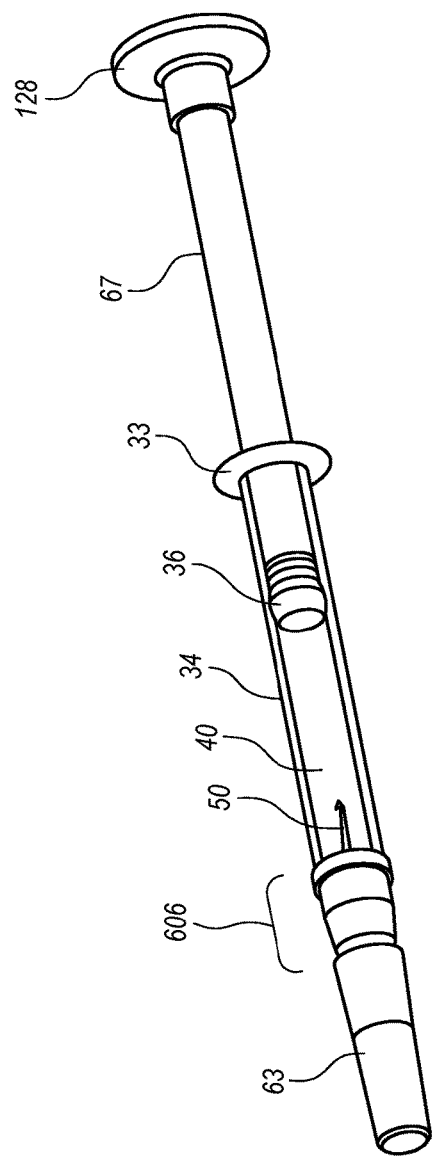

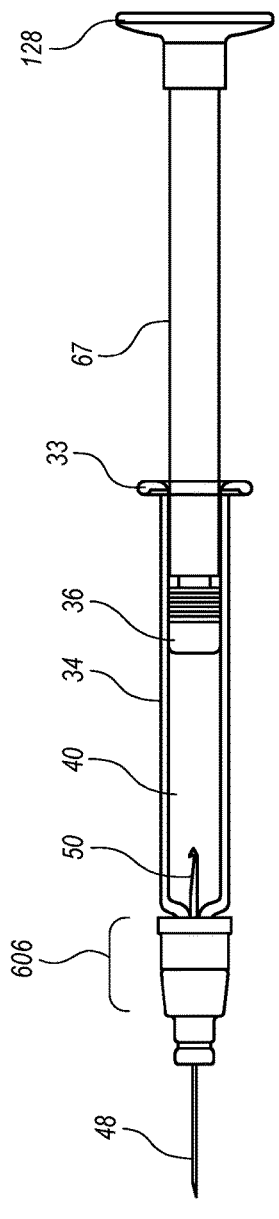
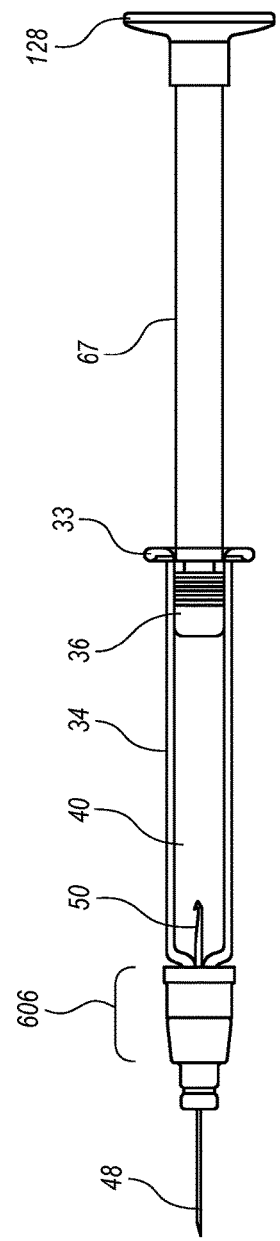
FIG. 60C
FIG. 60D

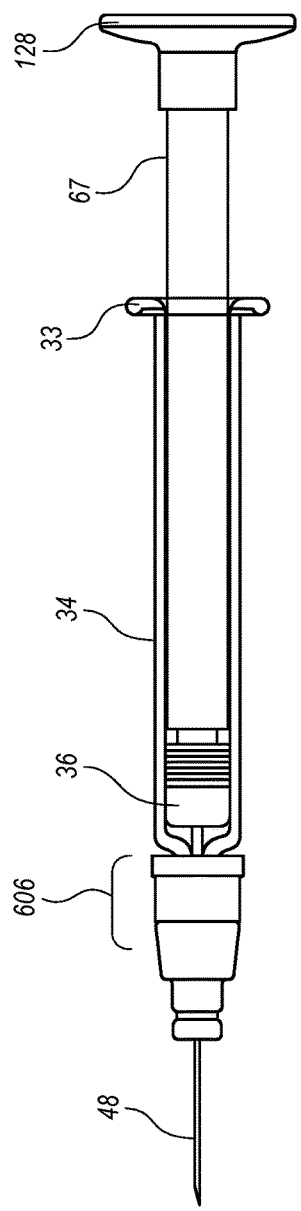
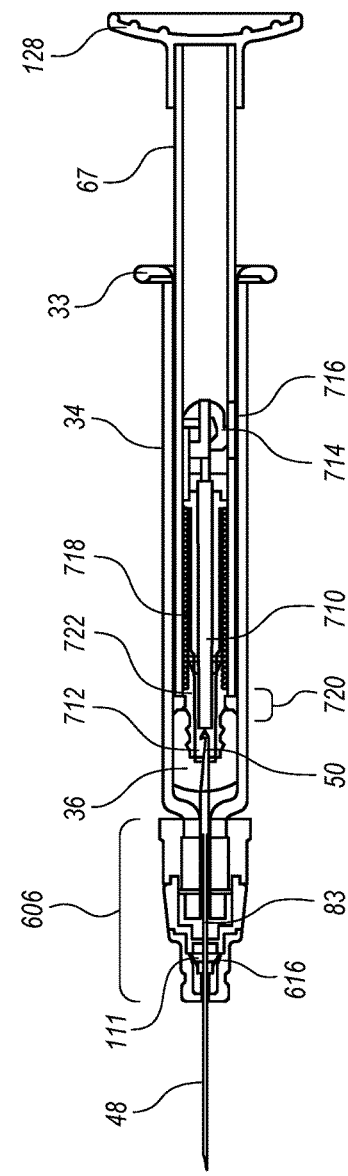

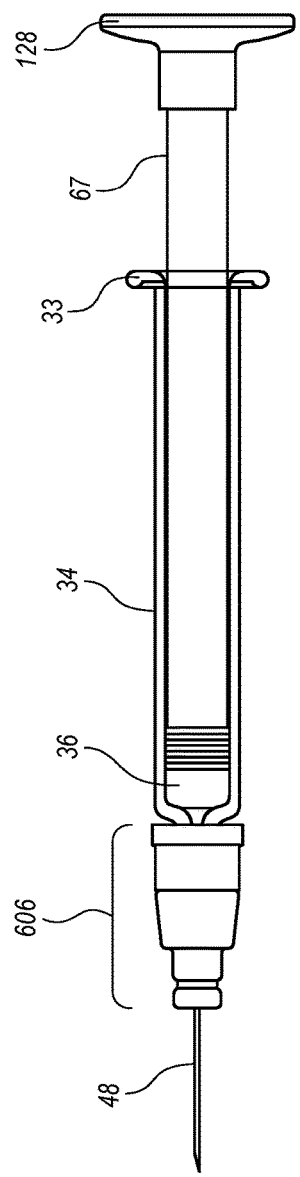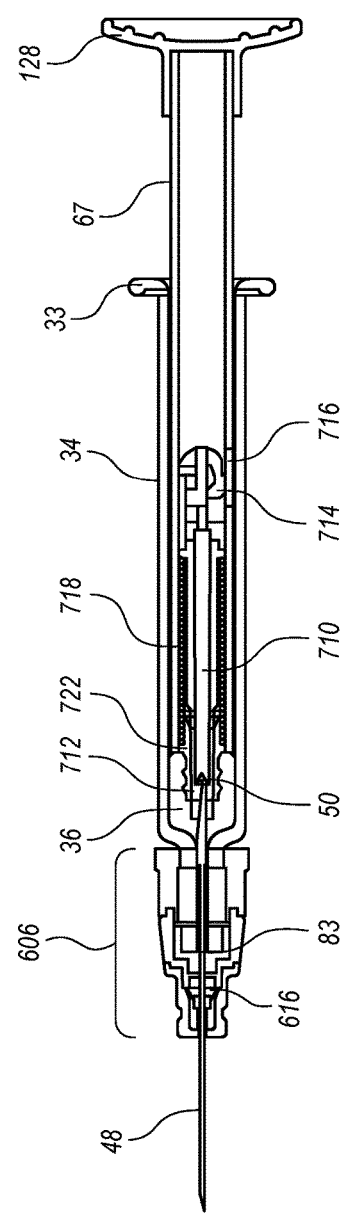

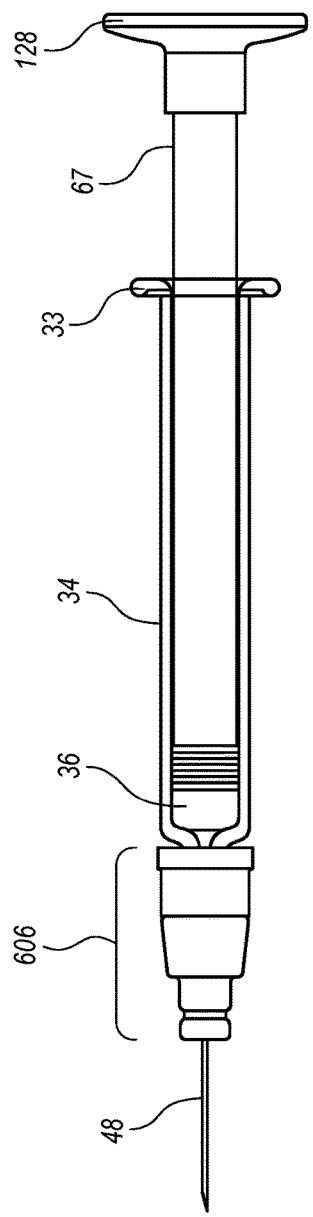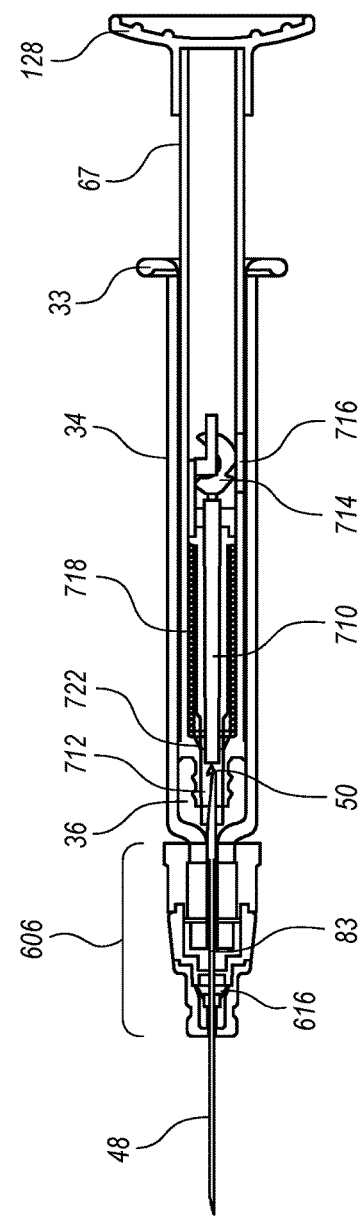

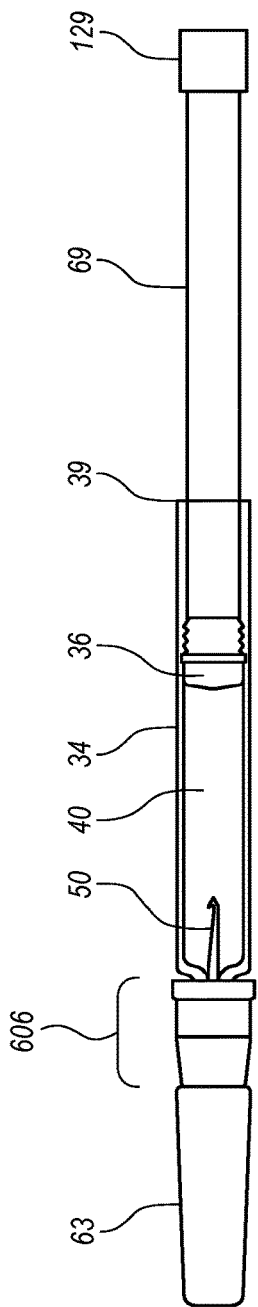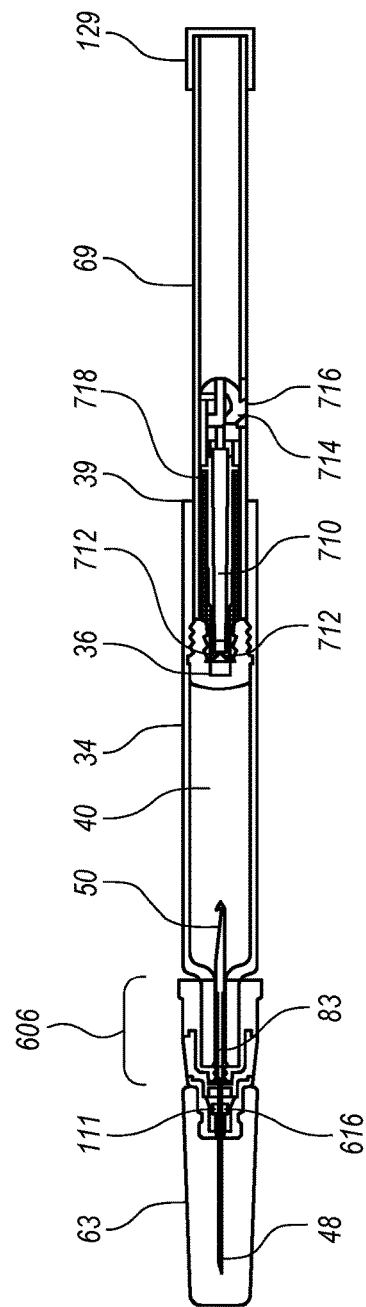

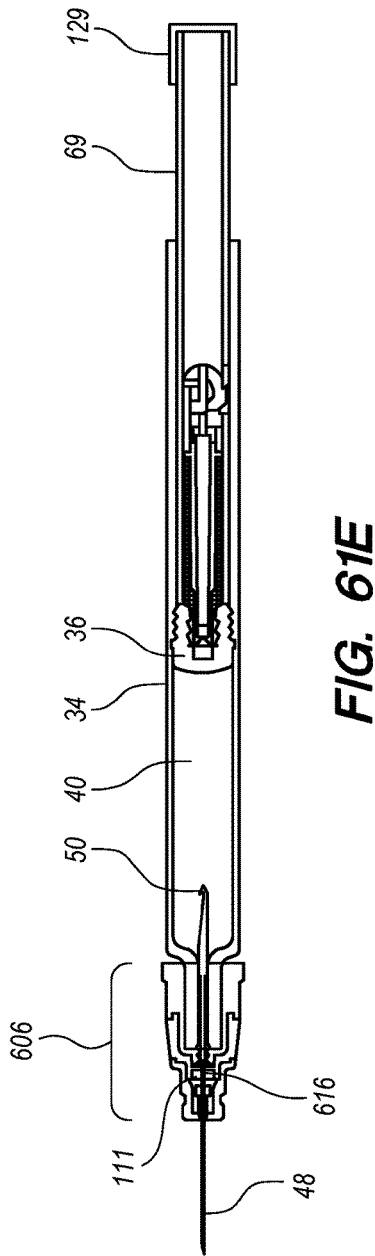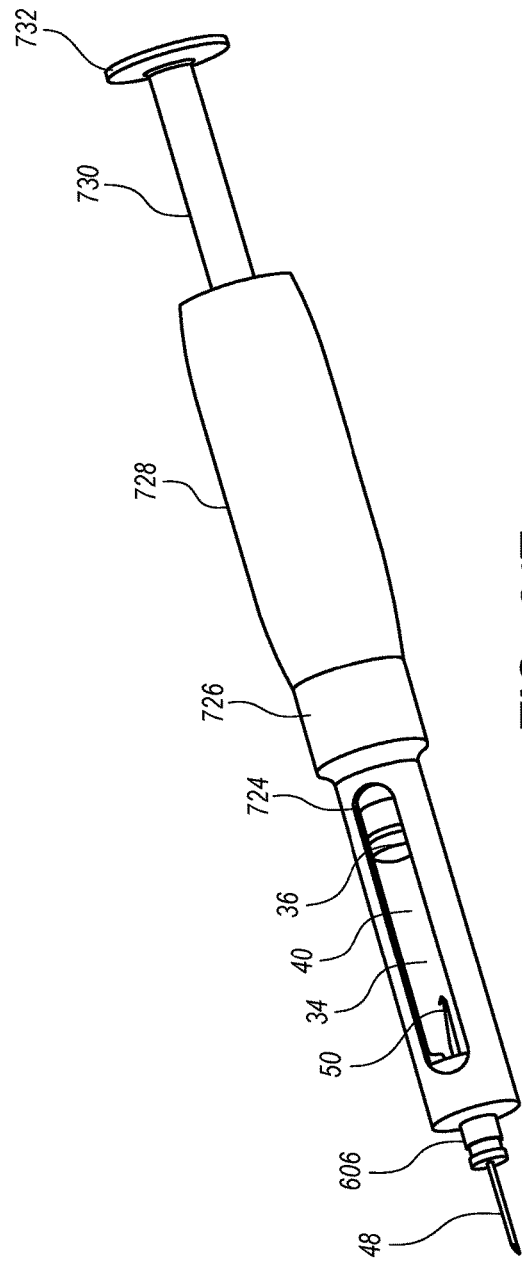

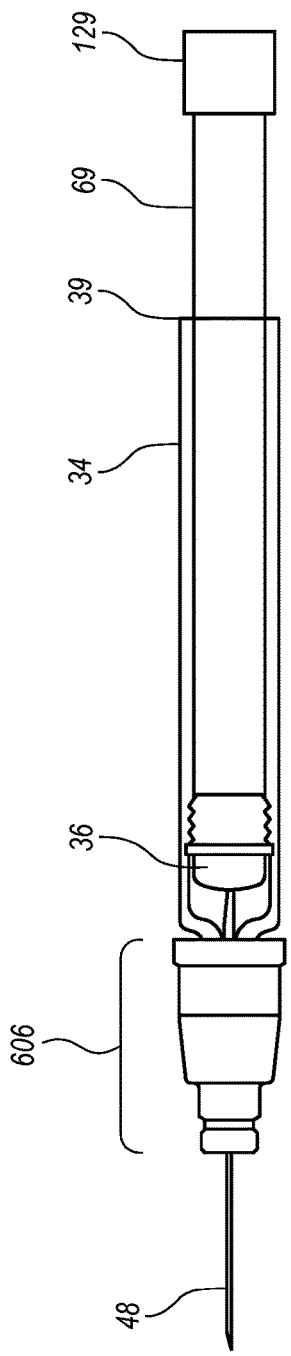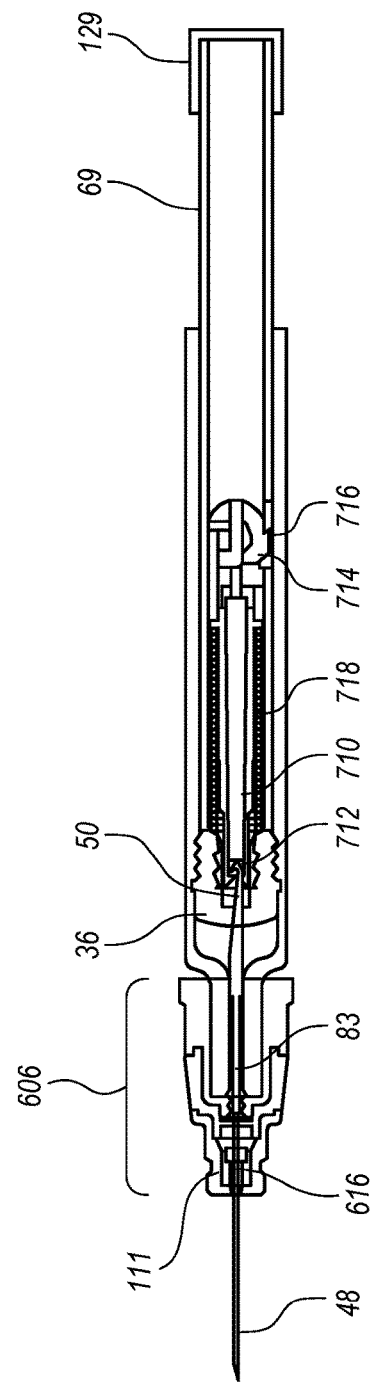
FIG. 61G
FIG. 61H

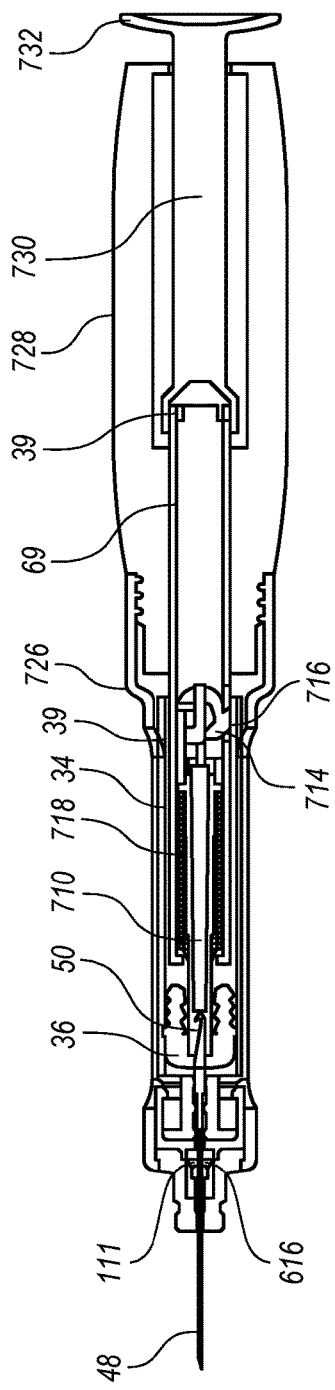
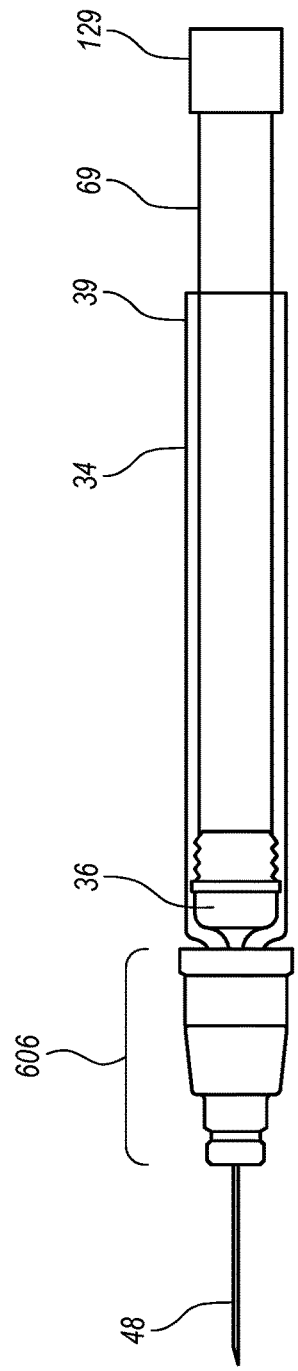
FIG. 61I
FIG. 61J

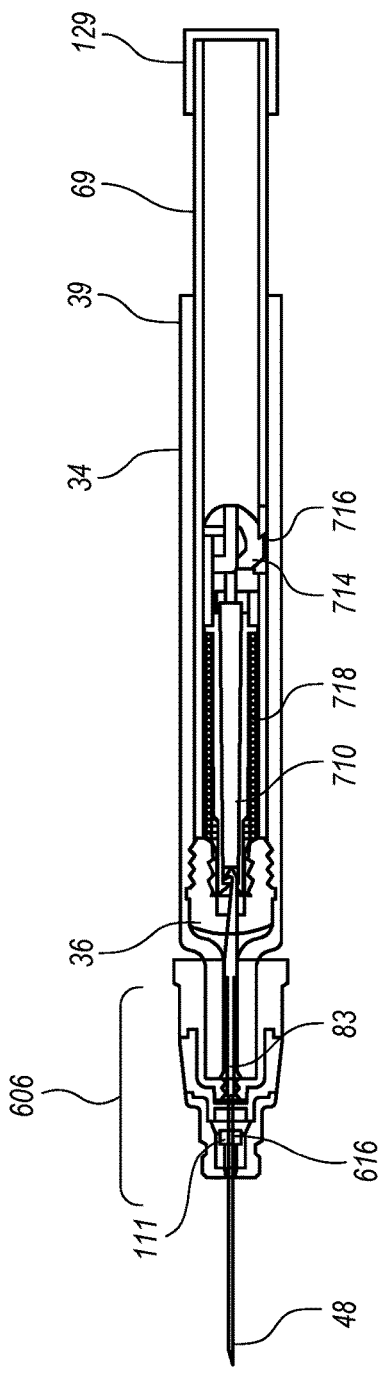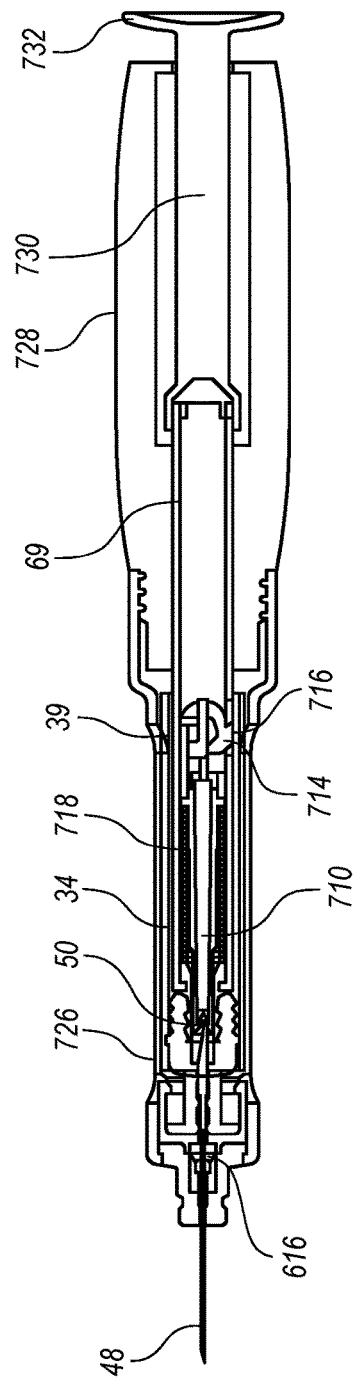
FIG. 61K
FIG. 61L

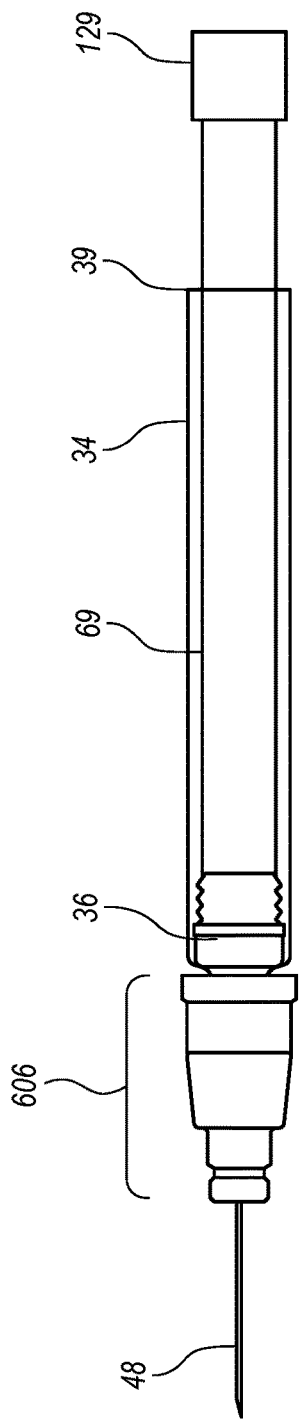
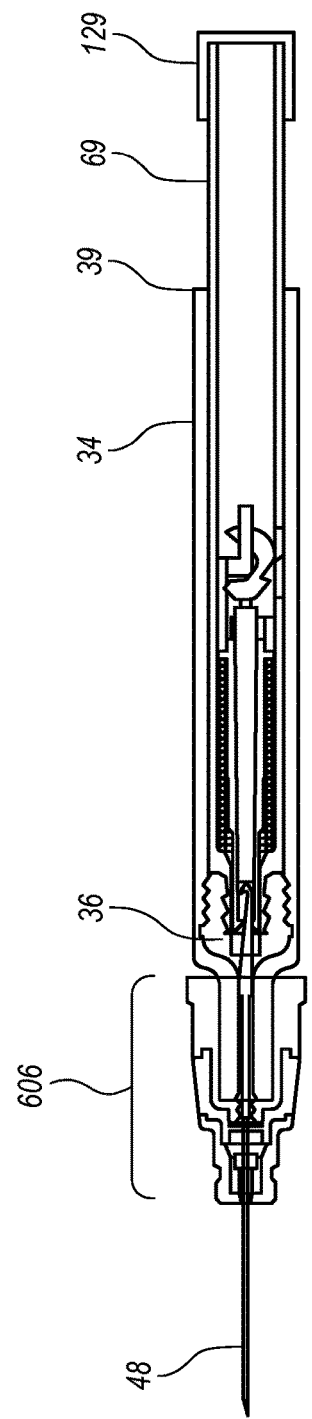
FIG. 61M
FIG. 61N

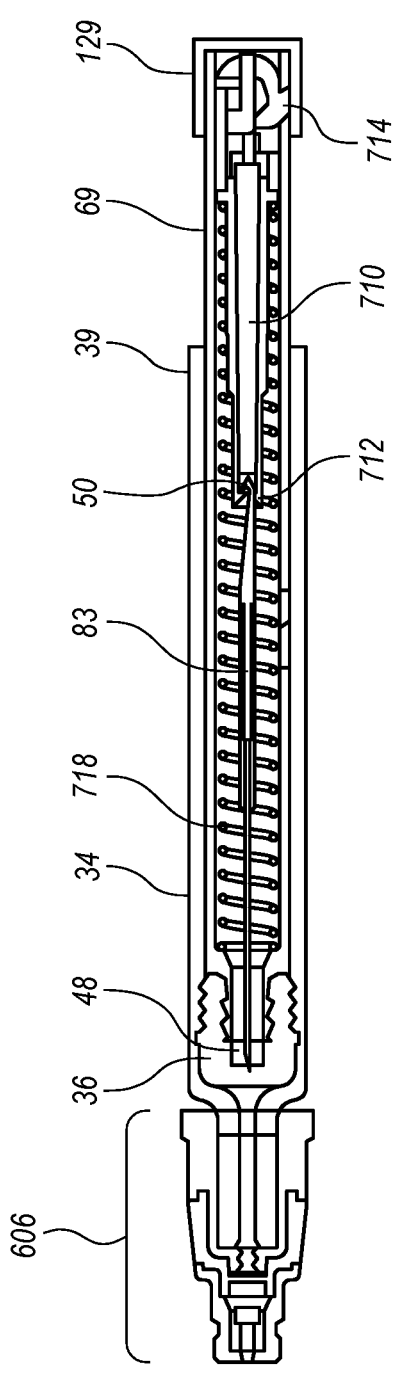
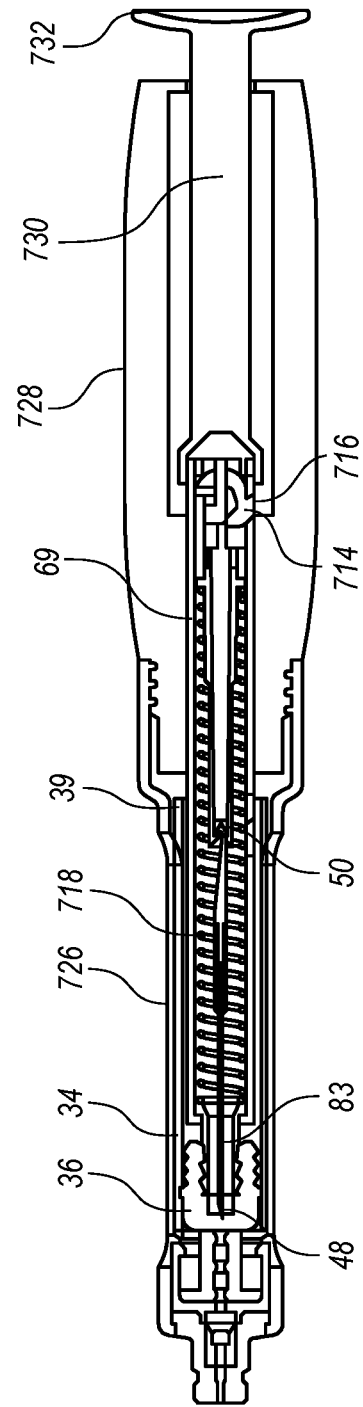
FIG. 61Q
FIG. 61R

SYSTEM AND METHOD FOR SAFETY SYRINGE

RELATED APPLICATION DATA

The present application is a continuation of U.S. patent application Ser. No. 14/696,342 filed on Apr. 24, 2015, which claims the benefit under 35 U.S.C. § 119 to U.S. provisional patent application Ser. No. 61/984,033 filed Apr. 24, 2014, U.S. provisional patent application Ser. No. 62/014,035, filed Jun. 18, 2014. U.S. provisional patent application Ser. No. 62/059,110, filed Oct. 2, 2014, U.S. provisional patent application Ser. No. 62/105,717, filed Jan. 20, 2015, U.S. provisional patent application Ser. No. 62/117,672, filed Feb. 18, 2015 and U.S. provisional patent application Ser. No. 62/150,761, filed Apr. 21, 2015. The foregoing applications are hereby incorporated by reference into the present application in in their entirety.

FIELD OF THE INVENTION

The present invention relates generally to injection systems, devices, and processes for facilitating various levels of control over fluid infusion, and more particularly to systems and methods related to safety syringes in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting which are configured to engage a flange on the female fitting and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during the loading to provide a Luer coupling. The use of needle injection configurations, on the other hand, carries with it the risk of a sharp needle contacting or poking a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for pre-filled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating, to facilitate preferred sealing and relative motion characteristics against the associated syringe body structure and material. The proximal end of the syringe body (34) in FIG. 5B comprises a conventional syringe flange (38), such as that known as a "Gerresheimer" flange configuration. The syringe body (34) preferably comprises a translucent material such as a glass or polymer. To form a contained volume within the medicine chamber or reservoir (40), and to assist with expulsion of the associated fluid through the needle, a plunger tip (36) may be positioned within the syringe body (34). The syringe body may define a substantially cylindrical shape (i.e., so that a plunger tip 36 having a circular cross sectional shape may establish a seal against the syringe body), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

There is a need for improved injection systems which address the shortcomings of currently-available configurations. In particular, there is a need for safety injection solutions which may utilize the existing and relatively well-controlled supply chain of conventionally delivered pre-filled syringe assemblies such as those described in reference to FIGS. 5A and 5B.

SUMMARY

One embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends, the proximal end comprising an anchoring geometry configured to be at least partially inserted into the stopper member such that upon retraction of the stopper member, the needle is pulled proximally along with the stopper to be at least partially contained within the interior medicine chamber.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends; and a coupling member operatively coupled to the syringe body and needle, the coupling member having a first state wherein the needle is removably coupled to the syringe body, and a second state wherein the needle is free to retract relative to the syringe body.

Another embodiment is directed to a system for injecting, comprising a syringe body defining an interior medicine chamber and a distal needle interface; a stopper member configured to be inserted into the interior medicine chamber to contain medicine within the medicine chamber, the stopper member having proximal and distal ends; a plunger member configured to be manually manipulated to insert the stopper member relative to the syringe body; a needle having proximal and distal ends, the proximal end coupled to the distal needle interface of the syringe body; wherein the distal end of the stopper member is configured to have no pre-formed needle coupling features.

Another embodiment is directed to a system for injecting, comprising: a syringe body defining an interior medicine chamber and a distal needle interface defining a Luer taper; a stopper member configured to be inserted into the interior medicine chamber to contain medicine within the medicine chamber, the stopper member having proximal and distal ends; a plunger member configured to be manually manipulated to insert the stopper member relative to the syringe body; a needle having proximal and distal ends, the proximal end coupled to the distal needle interface of the syringe body; wherein the needle proximal end is configured to be removably coupled to an external surface of the Luer taper.

Another embodiment is directed to a system for injecting, comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having proximal and distal ends, the proximal end configured to be coupled to the stopper member upon insertion of the stopper member to a fully-inserted position, such that upon retraction of the stopper member, the needle is pulled proximally along with the stopper to be contained within the interior medicine chamber; wherein upon retraction of the needle into the interior medicine chamber to a position wherein the distal end of the needle is contained within the interior medicine chamber, the needle becomes misaligned with a longitudinal axis of the syringe body such that it is prevented from being reinserted out of the interior medicine chamber.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having a sharpened distal end; and a needle door member movably coupled the syringe body and configured to have a first state wherein the needle door member facilitates insertion of the needle relative to the syringe body, and a second state wherein the needle door member prevents insertion of the needle relative to the syringe body.

Another embodiment is directed to a system for injecting, comprising a syringe body defining an interior medicine chamber and a distal needle interface defining a Luer taper; a stopper member configured to be inserted into the interior medicine chamber to contain medicine within the medicine chamber, the stopper member having proximal and distal ends; a plunger member configured to be manually manipulated to insert the stopper member relative to the syringe body; a medicine cap removably coupled to the distal needle interface and configured to seal the interior medicine chamber; a needle having proximal and distal ends, the proximal end comprising a coupling portion configured to be removably coupled to an external surface of the Luer taper after the medicine cap has been removed, and a retraction portion configured to become coupled to the stopper member such that upon withdrawal of the stopper member relative to the syringe body, the needle may be withdrawn relative to the syringe body.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having sharpened proximal and distal ends; and a needle cover member defining an inner volume configured to temporarily house and protect at least a sharpened distal end of the needle, while also aligning a sharpened proximal end of the needle for interfacing with the syringe body when installed by a user.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having sharpened proximal and distal ends; and a needle cover member defining an inner volume configured to temporarily house and protect at least a sharpened distal end of the needle, the needle cover member removably couplable to the needle with at least one snap-over detent interface.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends and an air bubble exit lumen defined therebetween, the air bubble exit lumen comprising an entry port defined into the needle and positioned immediately adjacent a distal end of the medicine chamber such that air bubbles within the medicine chamber may be expelled with insertion of the stopper member regardless of the level of protrusion of the proximal end of the needle into the medicine chamber.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having sharpened proximal and distal ends; a distal seal element having proximal and distal ends and being sealably disposed within the medicine chamber, the distal seal element being releasably couplable to the needle proximal end such that a sealed interface may be provided therebetween; wherein in a first coupled mode, the sharpened proximal end of the needle is positioned at least partially through the distal seal element such that the distal seal element grips onto the needle proximal end; and wherein in a second release mode, a dilating element dilates the interface between the distal seal element and the sharpened proximal end of the needle such that the needle becomes releasable from the distal seal element.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having sharpened proximal and distal ends; a distal seal element removably coupled around at least a portion of the proximal end of the needle and configured to grip onto the proximal end of the needle until dilated away therefrom; and a dilating element coupled to the needle proximal end and configured to dilate the distal seal element away from the proximal end of the needle to release the needle from the distal seal element by advancement of the distal seal element toward the dilating element while the dilating element and intercoupled needle remain substantially stationary relative to the syringe body.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end coupled to a distal end of the syringe body; and a needle sheath operatively coupled to the syringe body and defining a lumen through which at least the distal end of the needle may be passed, the needle sheath configured to have a first state, wherein the needle sheath is compressed toward the proximal end of the needle to expose the distal end of the needle for injecting, and a second state, wherein the needle sheath is advanced forward over the needle distal end to substantially cover the needle and prevent contact with the distal end of the needle; wherein in the first state, an energy storage member is compressed to bias the needle sheath to spring forward into the second state but for a sheath retention element which retains the needle sheath in the first position until the stopper member has been advanced to a predetermined position relative to the syringe body.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end coupled to a distal end of the syringe body; and a telescoping needle sheath operatively coupled to the syringe body and defining a lumen through which at least the distal end of the needle may be passed, the needle sheath configured to have a first state, wherein the telescoping needle sheath is telescopically compressed toward the proximal end of the needle to expose the distal end of the needle for injecting, and a second state, wherein the needle sheath is telescopically advanced forward over the needle distal end to substantially cover the needle and prevent contact with the distal end of the needle; wherein in the first state, an energy storage member is compressed to bias the needle sheath to spring forward into the second state but for a sheath retention element which retains the needle sheath in the first position until the stopper member has been advanced to a predetermined position relative to the syringe body.

Another embodiment is directed to a system for injecting, comprising a syringe body defining an interior medicine chamber and a distal needle interface comprising a Luer taper defining an inner surface that is fluidly coupled to the interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends, the proximal end removably attached to the inner surface of the Luer taper.

Another embodiment is directed to a system for injecting, comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; a needle having proximal and distal ends, the proximal end removably attached to the syringe body distal needle interface; and a needle seal operatively coupled between the needle and distal needle interface, the needle seal configured to prevent fluid flow between an outer surface of the needle and the distal needle interface; wherein the needle is coupled to at least one radially-projecting latching feature, the latching feature configured to interface with a mechanical latch to prevent axial movement of the needle relative to the syringe in a latched configuration, and to facilitate movement of the needle of the needle relative to the syringe body in an unlatched configuration.

Another embodiment is directed to a system for injecting, comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; a needle having proximal and distal ends, the proximal end removably attached to the syringe body distal needle interface; a needle seal operatively coupled between the needle and distal needle interface, the needle seal configured to prevent fluid flow between an outer surface of the needle and the distal needle interface; and a latching collar coupled to a distal end of the syringe body, the latching collar configured to have a latching recess and a retraction aperture; wherein the needle is coupled to at least one leaf spring latching feature, the latching feature having proximal and distal ends, wherein the distal end is fixedly coupled to the needle, and wherein when unconstrained, the proximal end is free to move in cantilevered bending relative to the distal end but is biased to return to a position substantially flush against the needle; and wherein in a latched configuration, the leaf spring latching feature proximal end is cantilevered into the latching recess to prevent axial retraction of the needle relative to the syringe body; and wherein upon slight insertion of the needle relative to the syringe body, the leaf spring latching feature proximal end is removed from the latching recess and bends back to a position substantially flush against the needle such that the needle and leaf spring latching feature assume an unlatched configuration and are free to be retracted through the retraction aperture relative to the syringe body.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends, the proximal end comprising an anchoring geometry configured to be at least partially inserted into the plunger member such that upon retraction of the plunger member, the needle is pulled proximally to be at least partially contained within the interior medicine chamber.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends, the proximal end comprising an anchoring geometry configured to stab across at least a portion of the stopper member to form a fluidly sealed coupling between the needle proximal end and the stopper member, the fluidly sealed coupling substantially preventing the passage of fluid out across the stopper member at the interface between the needle proximal end and the stopper member.

Another embodiment is directed to a system for injecting, comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having proximal and distal ends, the proximal end being removably coupled to the distal needle interface of the syringe body and at least partially retractable into the interior medicine chamber upon manipulation of the plunger member relative to the syringe body to transform a plunger latching member from a latched state to an unlatched state, the plunger latching member intercoupled between the syringe body and the plunger member; wherein the plunger latching member is substantially disposed within a lumen defined by the plunger member. The syringe body may comprise an off-the-shelf syringe body. The syringe body may comprise a generally cylindrical geometry. The medicine chamber may be configured to contain between about 0.5 cc and about 5 cc of medicine. The medicine chamber may be configured to contain a volume of medicine selected from the group consisting of: 0.5 cc, 1 cc, 2.25 cc, 3 cc, and 5 cc. The syringe body may comprise a glass material. The syringe body may comprise a polymeric material. The polymeric material may be selected from the group consisting of: COP, COC, polyester, and polypropylene. The syringe body may comprise a metal. The syringe body may comprise a distal outer geometry configured to be mechanically coupled to one or more other device elements. The syringe body distal outer geometry may comprise a luer lock interface. The syringe body distal outer geometry may comprise a luer taper interface. The syringe body may define a distal medicine port. The needle may have a maximum outside diameter selected to be insertable through the distal medicine port of the syringe body. The distal medicine port may comprise an inner diameter of about 1 mm. The needle may have a size between about 34 gauge and about 20 gauge. The stopper member may be configured to be at least partially pierced by a sharpened proximal end of the needle. The needle may have at least one anchoring element configured to resist pullout subsequent to being at least partially pierced into the stopper member. The at least one anchoring element may be selected from the group consisting of: a barb, a skive cut, hook geometry, an arrowhead geometry, an undulating radius geometry, an expandable faceted barb configuration, and a deformable member configured to be insertable in a relatively small cross-sectional state and to be deformed to a larger cross-sectional state. The stopper may have an outer geometry selected to substantially match an inner geometry of the syringe body to substantially seal with the syringe body. The stopper may comprise an elastomeric material selected from the group consisting of: chlorobutyl rubber, bromobutyl rubber, and silicon rubber. The system further may comprise a sealant coating applied to at least a portion of the stopper to isolate medicine materials from the stopper. The sealant coating may comprise a PTFE film. The system further may comprise a lubricant layer introduced between the stopper and the syringe body. The lubricant layer may comprise silicon oil. A distal portion of the stopper member may comprise a conventional off-the-shelf compliant stopper. The stopper member may comprise an unmodified solid compliant member with no recesses or projections for coupling to a needle. The needle may comprise at least one radially-projecting latching surface feature. The proximal end of the needle may comprise at least one piercing element located proximally relative to at least one anchoring element. The piercing element may comprise a sharpened tip. The piercing element may comprise a solid construction without a lumen or aperture defined therethrough. The needle may define an injection passage therethrough, the injection passage selected to lead from the distal tip of the needle to a location proximal to that of the anchoring element. The needle may comprise a cannula member, a hub member, and a proximal member. The cannula member and hub member may be formed from the same piece of material. The cannula member and hub member may comprise separately formed elements that are fixedly coupled together to form portions of the needle. The proximal member also may comprise a separately formed element that is fixedly coupled to the cannula member and hub member to form a portion of the needle. The hub member may be formed from a piece of tubing. The proximal member may comprise a piece of flat sheet metal having a proximal coupling interface. The cannula member may comprise a metal. The hub may comprise a metal or plastic material. The proximal member may comprise a metal or plastic material. The system further may comprise an energy-storing member operatively coupled between the stopper member and the syringe body, the energy-storing member configured to facilitate retraction of the stopper member relative to the syringe body. The plunger member may comprise a plunger member body that defines an interior volume, and wherein the energy-storing member is housed substantially inside of the plunger member body interior volume. The system further may comprise a latch member operatively coupled to the plunger member and housed substantially within the plunger member body interior volume, the latch member being configured to have a first mechanical state wherein the latch member maintains the energy storing member in an energy-storing state, and a second mechanical state wherein the latch member allows the energy-storing member to release energy stored by the energy-storing member to assist in retraction of the stopper member relative to the syringe body. The latch member may comprise a triggering portion configured to extend outside of the plunger member body interior volume and operatively couple to the syringe body such that the energy-storing member may be automatically released when the plunger member and intercoupled stopper member reach a predetermined insertional position relative to the syringe body. The predetermined insertional position may be one wherein the stopper is positioned in a full insertion state relative to the syringe body. The energy-storing member may be a spring. The spring may comprise a material selected from the group consisting of: stainless steel, carbon steel, beryllium copper alloy, nickel-titanium alloy, chrome-silicon alloy, and cobalt-nickel alloy. The spring may comprise an elastomeric polymer. The elastomeric polymer may be selected from the group consisting of: a styrenic polymer, a co-polyester polymer, polyurethane, polyamide, a polyolefin blend, a polyolefin alloy, a polyolefin plastomer, a polyolefin plastomer, and rubber. The energy-storing member may comprise a solid pellet member. The solid pellet member may be an elastomeric polymer selected from the group consisting of: a styrenic polymer, a co-polyester polymer, polyurethane, polyamide, a polyolefin blend, a polyolefin alloy, a polyolefin plastomer, a polyolefin plastomer, and rubber. The spring may comprise a single generally helically-shaped coil. The spring may comprise a plurality of generally helically-shaped coils. At least two of the coils comprising the plurality of generally helically-shaped coils may be co-axially aligned. At least two of the coils comprising the plurality of generally helically-shaped coils may be longitudinally parallel aligned. The co-axially aligned helically-shaped coils also may be longitudinally parallel aligned. The co-axially and longitudinally parallel aligned helically-shaped coils may be helically wound with opposite winding directions relative to each other to prevent coil interference upon compression of the coils. The system may be configured such that retraction of the plunger retracts the intercoupled stopper member and needle, such that at least a portion of the needle is withdrawn into the interior medicine chamber of the syringe body. The plunger may comprise a proximal thumb pad configured to facilitate manual insertion and retraction control of the plunger relative to the syringe body. The plunger may comprise a plunger distal end screw interface configured to be helically inserted into the stopper member and coupled thereto by virtue of such insertion. The plunger member may comprise a plurality of ratchet features positioned on a surface of the plunger member, the ratchet features configured to prevent re-insertion of the plunger member relative to the syringe body after the plunger member has initially been inserted to a predetermined position relative to the syringe body. The predetermined position may be one wherein the stopper member has been advanced to a fully-inserted position by the plunger member relative to the syringe body. The system further may comprise a latch member operatively coupled between the plunger member and the syringe body, wherein the latch comprises at least one ratchet tooth engageable with the ratchet features, as well as a proximal interface engageable with a handle portion of the syringe body. The system further may comprise a trigger engagement member coupled to the syringe body and configured to engage the triggering portion of the latch member through a trigger engagement window defined through at least a portion of the plunger member. The system further may comprise a proximal seal configured to encapsulate the stopper member within the interior medicine chamber of the syringe body such that a vacuum load is developed as the stopper is inserted into the interior medicine chamber. The system further may comprise a braking member operatively coupled to the plunger member and the syringe body, the braking member configured to facilitate insertion of the plunger member relative to the syringe body, but to resist retraction of the plunger member relative to the syringe body in a first mode until the braking member has been placed in a released braking configuration second mode. The braking member may comprise a plate-aperture brake. The plate-aperture brake may comprise a piece of sheet metal with an aperture formed therethrough. The system further may comprise a spring member configured to facilitate retraction of the plunger relative to the syringe body after the plunger has been fully inserted relative to the syringe body. The plate-aperture brake may be configured to switch from the first mode to the second mode by inducing plastic deformation of at least a portion of the spring member. Retraction of the plunger member may be facilitated in the second mode through application of a retraction starter load. The retraction starter load may be applied by a spring member operatively coupled to the braking member. The retraction starter load may be applied by a spring member coupled between the plunger member and the syringe body. The spring member may be selected from the group consisting of: a coil spring, a leaf spring, and an elastomeric spring element. The spring member may be selected from the group consisting of: a coil spring, a leaf spring, and an elastomeric spring element. The vacuum load may be sufficient to at least partially retract the plunger relative to the syringe body. Retraction of the plunger may retract the intercoupled stopper member and needle, such that at least a portion of the needle is withdrawn into the interior medicine chamber of the syringe body. The system further may comprise a needle cover member defining an inner volume configured to temporarily house and protect at least a sharpened distal end of the needle, while also aligning a sharpened proximal end of the needle for interfacing with the syringe body when installed by a user. The needle cover member may be removably coupled to the needle with at least one snap-over detent interface. The needle cover member may be removably coupled to the needle with at least two snap-over detent interfaces. A snap-over detent interface may be oriented to prevent rotation of the needle cover member about an axis substantially aligned with that of the needle until the detent has been mechanically overcome with a torsional load. A snap-over detent interface may be oriented to prevent axial motion of the needle cover member relative to the needle until the detent has been mechanically overcome by an axial load. The inner volume of the needle cover member may comprise a plurality internally-facing radial projection surfaces configured to guide the sharpened proximal end of the needle relative to the syringe body as the needle and syringe body are being manually intercoupled. The medicine chamber may be defined by a chamber length, and the needle is defined by a needle length that is equal to or longer than the chamber length. The system further may comprise an extension member coupled to a proximal end of the syringe body, the extension member operatively coupled to the plunger member and configured to house at least a portion of the needle when the needle is withdrawn entirely into a volume defined by the interior medicine chamber and the extension member. The system further may comprise an extension member coupled to a proximal end of the syringe body, the extension member operatively coupled to the plunger member and configured to contain the stopper member if the stopper is withdrawn to such an extent that it at least partially exits the interior medicine chamber, the extension member comprising a fluid containment surface positioned immediately adjacent the distal surface upon withdrawal of the stopper member into the extension chamber, the fluid containment surface configured to contain residual droplets of medicine which may remain coupled to the distal surface of the stopper member until they become contained by the fluid containment surface. The plunger member may be configured to be manually retracted by an operator when the plunger latching member is in the unlatched state. The distal end of the needle may become structurally encapsulated within the interior medicine chamber. The distal end of the needle may become structurally encapsulated by a needle door member movably coupled the syringe body and be configured to have a first state wherein the needle door member facilitates insertion of the needle relative to the syringe body, and a second state wherein the needle door member prevents insertion of the needle relative to the syringe body.

Another embodiment is directed to a system for injecting, comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having proximal and distal ends, the proximal end being removably coupled to the distal needle interface of the syringe body and at least partially retractable into the interior medicine chamber upon manipulation of the plunger member relative to the syringe body to transform a plunger latching member from a latched state to an unlatched state, the plunger latching member slidably and rotatably intercoupled between the syringe body and the plunger member such that upon substantially full insertion of the plunger member relative to the syringe member, the plunger latch member is axially moved and also rotated to convert from the latched state to the unlatched state, and also to allow the plunger member to insert the stopper member to a full insertion position wherein substantially all of the contents of the interior medicine chamber may be expelled out of the needle.

Another embodiment is directed to a system for injecting, comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body using a proximal manipulation interface; a spring member disposed within a lumen defined through the plunger member; a needle having proximal and distal ends, the proximal end being removably coupled to the distal needle interface of the syringe body and at least partially retractable into the interior medicine chamber upon manipulation of the plunger member relative to the syringe body to transform a plunger latching member from a latched state to an unlatched state, the plunger latching member intercoupled between the syringe body and the plunger member; wherein the plunger latching member is substantially disposed within the plunger member lumen and coupled to the spring member such that the spring member is compressed more in the latched state than it is in the unlatched state; and wherein the proximal manipulation interface is configured to facilitate manual engagement to control a rate of plunger member retraction in the unlatched state.

Another embodiment is directed to a system for injecting, comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having a proximal end and a sharpened distal end, the proximal end being removably coupled to the distal needle interface of the syringe body and at least partially retractable into the interior medicine chamber upon manipulation of the plunger member relative to the syringe body to transform a plunger latching member from a latched state to an unlatched state, the plunger latching member intercoupled between the syringe body and the plunger member; wherein the plunger latching member is substantially disposed within a lumen defined by the plunger member; and wherein in the unlatched state, the plunger member is at least partially prevented from being re-inserted relative to the syringe body by one or more toothlike structures comprising the plunger latching member which are configured to prevent movement of the plunger member syringe body.

Another embodiment is directed to a system for injecting, comprising a syringe body defining an interior medicine chamber; a stopper member configured to be inserted into the interior medicine chamber to contain medicine within the medicine chamber; a plunger member configured to be coupled to the stopper member, and to insert the stopper member relative to the syringe body; and a needle having proximal and distal ends, the proximal end comprising an anchoring geometry configured to be at least partially inserted into the stopper member such that upon retraction of the stopper member, the needle is pulled proximally along with the stopper to be at least partially contained within the interior medicine chamber; wherein the stopper member defines a threaded proximal interface, and wherein the plunger member has a distal threaded interface configured to be helically coupled into the threaded proximal interface of the stopper member, the distal threaded interface being purposely undersized relative to the threaded proximal interface of the stopper member, such that upon such helical coupling, an outer geometry of the stopper member is not substantially increased by virtue of the helical intercoupling between the stopper member and plunger member distal threaded interface.

Another embodiment is directed to a system for injecting, comprising a syringe body having proximal and distal ends and defining an interior medicine chamber; a stopper member configured to be inserted into the interior medicine chamber to contain medicine within the medicine chamber; a plunger member comprising a proximal interface configured to be manually manipulated to move the stopper member relative to the syringe body; a needle having a sharpened distal end; and a flange extension member coupled to the proximal end of the syringe body, the extension member operatively coupled to the plunger member and configured to provide a proximal manipulation interface for the syringe body that decreases an axial compression throw distance required to cause insertion of the plunger member relative to the syringe body.

Another embodiment is directed to a system for injecting, comprising a syringe body having proximal and distal ends and defining an interior medicine chamber having a chamber length; a stopper member configured to be inserted into the interior medicine chamber to contain medicine within the medicine chamber; a plunger member comprising a proximal interface configured to be manually manipulated to move the stopper member relative to the syringe body; a needle having a sharpened distal end and being defined by a needle length that is equal to or longer than the chamber length; and an extension member coupled to the proximal end of the syringe body, the extension member operatively coupled to the plunger member and configured to house at least a portion of the needle when the needle is withdrawn entirely into a volume defined by the interior medicine chamber and the extension member.

Another embodiment is directed to a system for injecting, comprising a syringe body defining an interior medicine chamber; a stopper member configured to be inserted into the interior medicine chamber to contain medicine within the medicine chamber; a plunger member comprising a proximal interface and configured to be manually manipulated to insert the stopper member relative to the syringe body; and a needle having proximal and distal ends, the proximal end comprising an anchoring geometry configured to be at least partially inserted into the stopper member such that upon retraction of the stopper member, the needle is pulled proximally along with the stopper to be at least partially contained within the interior medicine chamber; a flange member coupled to the proximal end of the syringe body and configured to provide a proximal manipulation interface for the syringe body relative to the plunger member proximal interface; wherein the flange member comprises an assembly of two or more parts configured to be assembled with coupling features that are intentionally difficult to decouple, thus retaining a movably coupled state between the plunger member and the syringe body.

Another embodiment is directed to a system for injecting, comprising a syringe body defining an interior medicine chamber and fixedly coupled to a distally-positioned threaded Luer-lock connector; a stopper member configured to be inserted into the interior medicine chamber to contain medicine within the medicine chamber; a plunger member configured to be manually manipulated to insert the stopper member relative to the syringe body; and a needle having proximal and distal ends, the needle proximal end coupled to the Luer-lock connector using a needle coupling member, the needle coupling member comprising a ratcheted coupling engagement relative to the Luer-lock connector such that the needle coupling member may be easily threaded onto the Luer-lock connector with rotation in a first direction, but prevented from being uncoupled by rotation in a second direction opposite of the first direction.

Another embodiment is directed to a system for injecting, comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end comprising an anchoring geometry configured to be at least partially inserted into the stopper member such that upon retraction of the stopper member, the needle is pulled proximally along with the stopper to be at least partially contained within the interior medicine chamber; a first imaging marker coupled to a first known location on the needle; a second imaging marker coupled to a second known location on the needle; and an imaging system configured to detect the positions of the first and second imaging markers such that the orientation of the needle may be determined relative to a global coordinate system.

Another embodiment is directed to a system for injecting, comprising a syringe body having proximal and distal ends and defining an interior medicine chamber; a stopper member configured to be inserted into the interior medicine chamber to contain medicine within the medicine chamber, the stopper member comprising a distal surface configured to be directly interfaced with the medicine within the medicine chamber; a plunger member comprising a proximal interface configured to be manually manipulated to move the stopper member relative to the syringe body; a needle having a sharpened distal end; and an extension member coupled to the proximal end of the syringe body, the extension member operatively coupled to the plunger member and configured to contain the stopper member if the stopper is withdrawn to such an extent that it at least partially exits the interior medicine chamber, the extension member comprising a fluid containment surface positioned immediately adjacent the distal surface upon withdrawal of the stopper member into the extension chamber, the fluid containment surface configured to contain residual droplets of medicine which may remain coupled to the distal surface of the stopper member until they become contained by the fluid containment surface.

Another embodiment of the invention is directed to a retractable safety syringe injection system for administering to a patient injectable medication which may be provided in a lyophilized form. The system may comprise features for preventing inadvertent activation of a needle retraction mechanism while reconstituting or combining the lyophilized medicine component with a dilulent component which may be housed within a syringe body of the injection system. The system may comprise a depth stop attached to a vial adaptor component that is configured to prevent inadvertent activation of the needle retraction mechanism by temporarily preventing the latch of the retraction mechanism from moving.

Another embodiment of the invention is directed to a retractable safety syringe injection system for administering to a patient injectable medication which may be provided in a lyophilized form, wherein the lyophilized form of medication may be initially contained in a vial, and wherein an adaptor may be provided to couple the vial to a syringe body comprising the retractable safety syringe injection system such that dilulent contained within a medicine chamber of the syringe body may be securely mixed, such as by manually-induced shaking or agitation, with the lyophilized medication. The lyophilized medicine vial adaptor may comprise a clutch mechanism configured to release at a predetermined load and/or torque to indicate to an operator that the vial adaptor and syringe body are appropriately coupled. The clutch mechanism may be configured to prevent over-torquing of a syringe body luer lock ring, thereby preventing damage or dislodgement of the ring, which may cause the vial adaptor to disengage from the syringe body upon shaking or agitation. The vial adaptor may comprise an elongated shape configured to strengthen the coupling between the syringe body and the lyophilized medicine vial by at least partially encapsulating the syringe body with portions of the elongated vial adaptor shape which may attach to a finger manipulation flange component coupled to or comprising a portion of the syringe body. The system may comprise a needle cover or shield configured to isolate one or more portions of an injection needle member, guide a portion of the needle member into a coupling position relative to the syringe body, and provide a clutch mechanism to cause the needle to be attached to a luer lock adaptor of the syringe body within a predetermined torque loading window. The needle cover or shield may be configured to not release until a maximum predetermined torque load is achieved. A vial adaptor, needle assembly, and dilulent filled safe injection syringe body may be presented to an end user as a kit in one embodiment. The system may comprise a proximal mechanism configured to prevent inadvertent activation of the needle member retraction mechanism by preventing the latch member of the retraction mechanism from moving until retraction may be desired.

Another embodiment of the invention is directed to a retractable safe injection syringe system with a needle attached in a staked needle configuration relative to a distal portion of a syringe body. A staked needle assembly, needle latching mechanism, and plunger structure may be operatively coupled with a syringe body, with the plunger structure having predetermined axial compliance to assist in ensuring that a full dosage of medicine be expelled from the medicine chamber of the syringe body prior to activation of a needle retraction mechanism. Latching mechanisms for controlling activation of the needle retraction mechanism may comprise one or more elements configured to move away from or relative to one or more features defined into one or more portions of a needle assembly component to free the retraction mechanism to retract the needle relative to the syringe body.

Another embodiment of the invention is directed to a retractable safety needle syringe injection system for administering to a patient injectable medication which is provided in a lyophilized form and presented to an operator in the form of a dual-chamber syringe body, wherein both a first medication component, such as a lyophilized medication component, and a second medication component, such as a liquid dilulent, are housed within the same syringe body, and which may be mixed in preparation for injection into the patient, by operating a plunger component of the system before fully inserting the plunger to inject the mixed medicine out through a needle member distal tip into the patient. The system may be configured to mix the two components by delivering one component to the other through a portion of the needle, and/or around a portion of a plunger tip or stopper assembly. In one embodiment a bypass geometry may be created into the syringe body to facilitate passage of one component around a portion of a plunger tip or stopper assembly at a predetermined longitudinal relative positioning of the plunger assembly relative to the syringe body.

Another embodiment of the invention is directed to a retractable safety needle syringe injection system for administering to a patient injectable medication, wherein a retraction mechanism is configured to retract a needle member substantially or completely into the confines of the plunger assembly. The needle member may be configured to retract into the inner diameter of a plunger assembly housing after it is retracted through a compliant plunger tip or stopper at the distal end of the plunger assembly. A cartridge-based configuration may be utilized to conduct an injection, wherein a re-usable housing, pen-style housing configuration, or auto-injector configuration is fitted around a retractable safety needle syringe injection system.

The aforementioned and other embodiments of the invention are described in the Detailed Description which follows.

BRIEF DESCRIPTION OF THE DRAWINGS

FIGS. 9A-9C illustrate various aspects of a safe injection system wherein a keyed needle and latching member interface disposed adjacent the distal end of a syringe body medicine chamber may be utilized to controllably release a needle for retraction to a safe position.

FIGS. 13A-13J and 14A-14H illustrate various aspects of safe injection systems and portions thereof.

FIGS. 15-37 illustrate processes for conducting injection procedures utilizing safe injection configurations such as those described in reference to FIGS. 6A-12O.

DETAILED DESCRIPTION

Figure 1A:
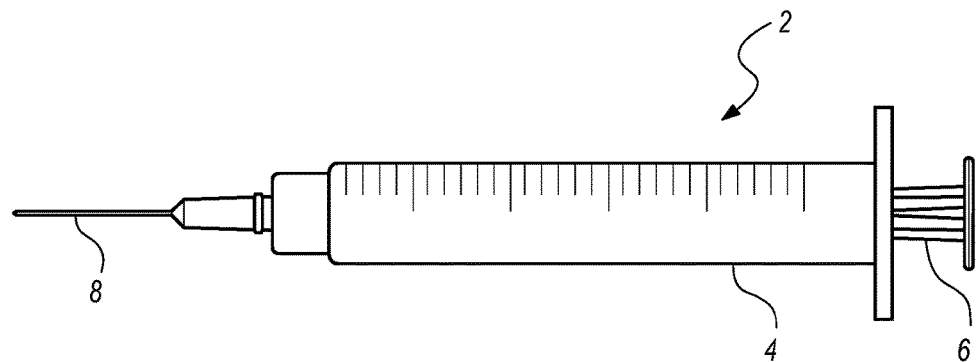
FIGS. 1A-5C illustrate various aspects of conventional injection syringe configurations.
Figure 1B:
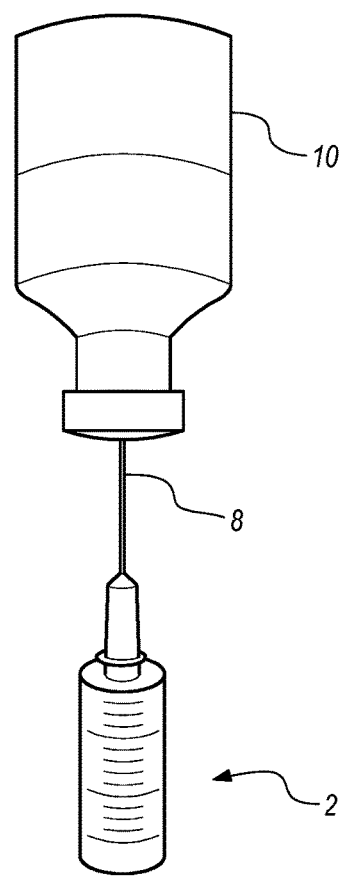
Figure 2A:
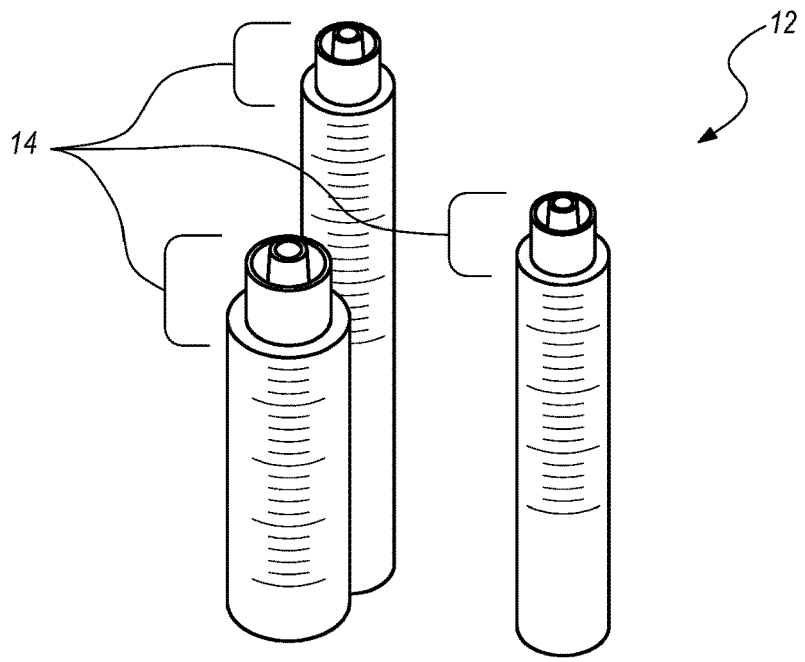
Figure 2B:
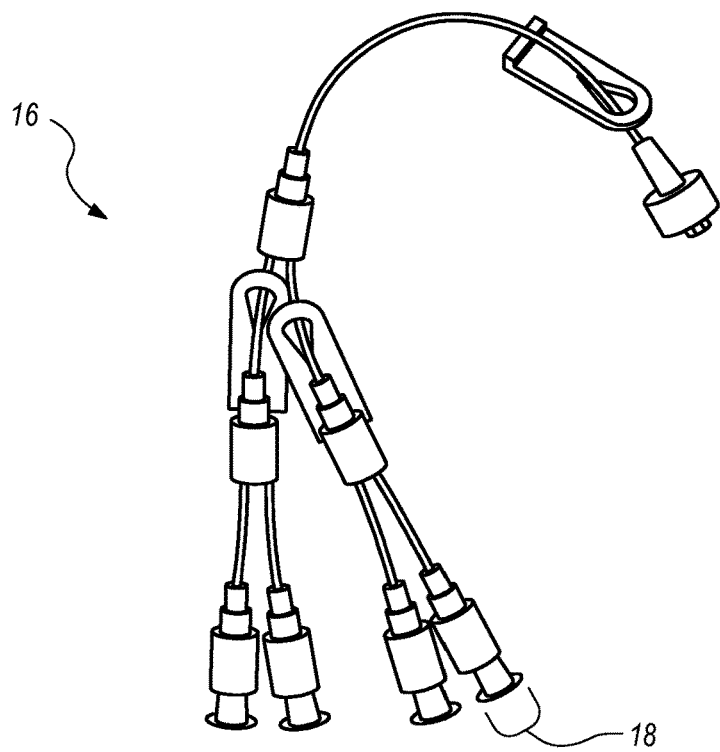
Figure 3:
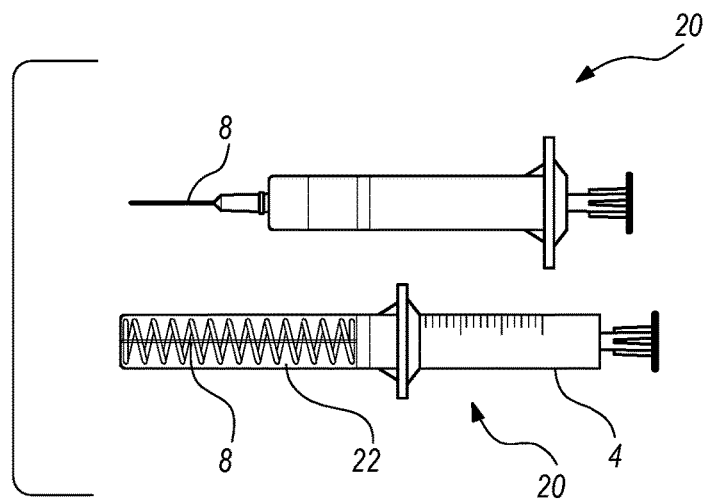
Figure 4A:
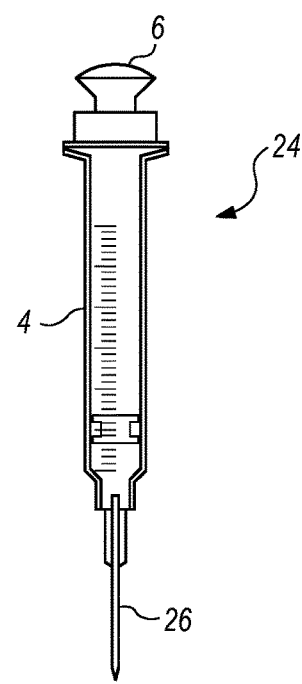
Figure 4B:
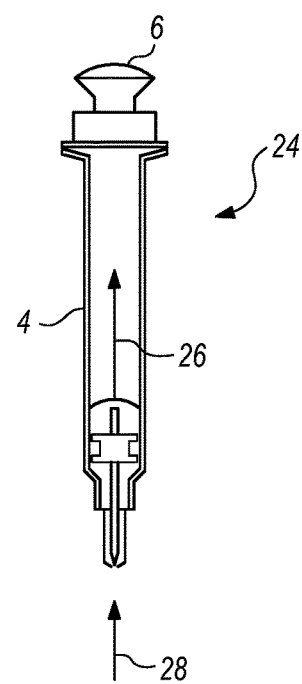
Figure 5A:
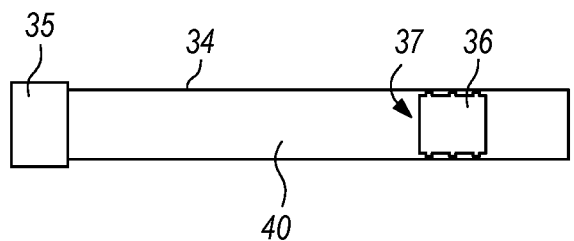
Figure 5B:
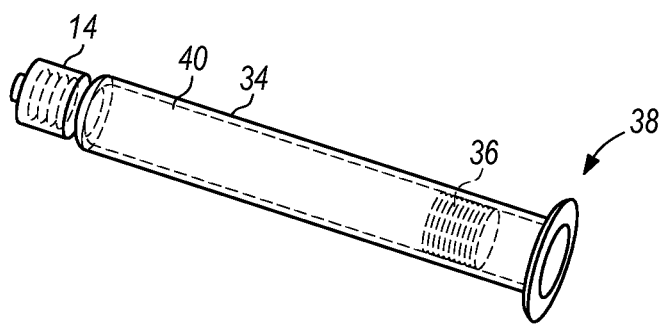
Figure 5C:
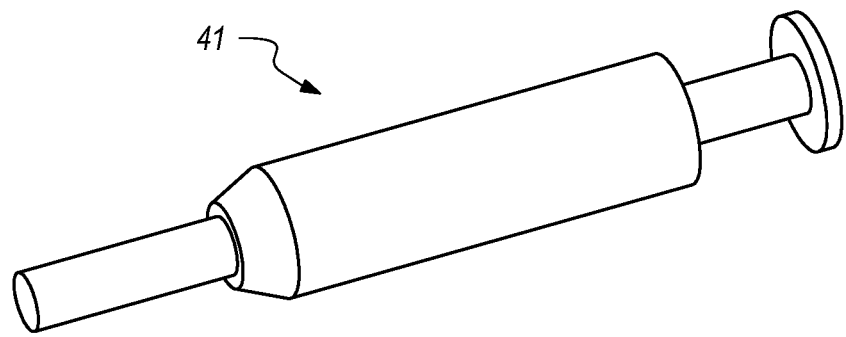
Figure 6A:
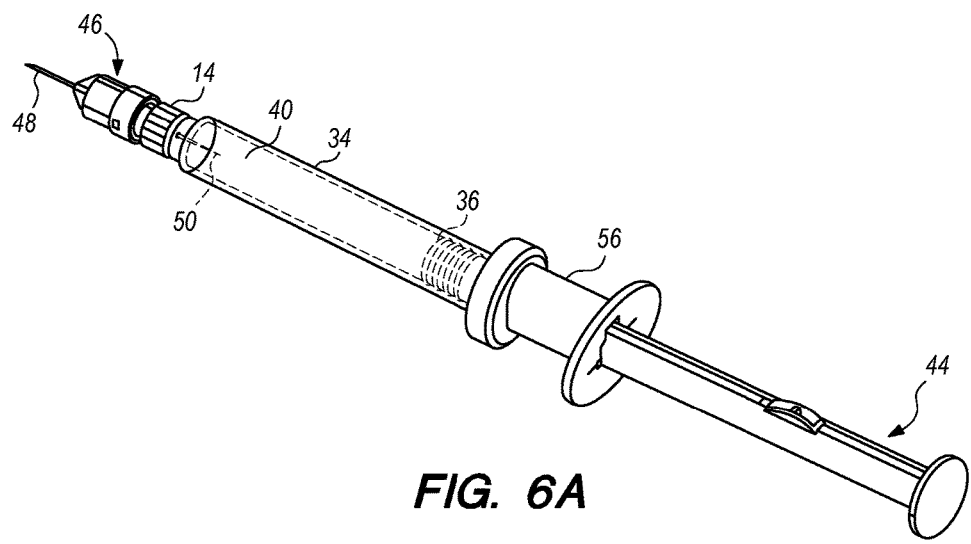
FIGS. 6A-7J illustrate various aspects of a safe injection system configuration wherein a distal needle tip may be withdrawn into a protected configuration after use.
Figure 6B:
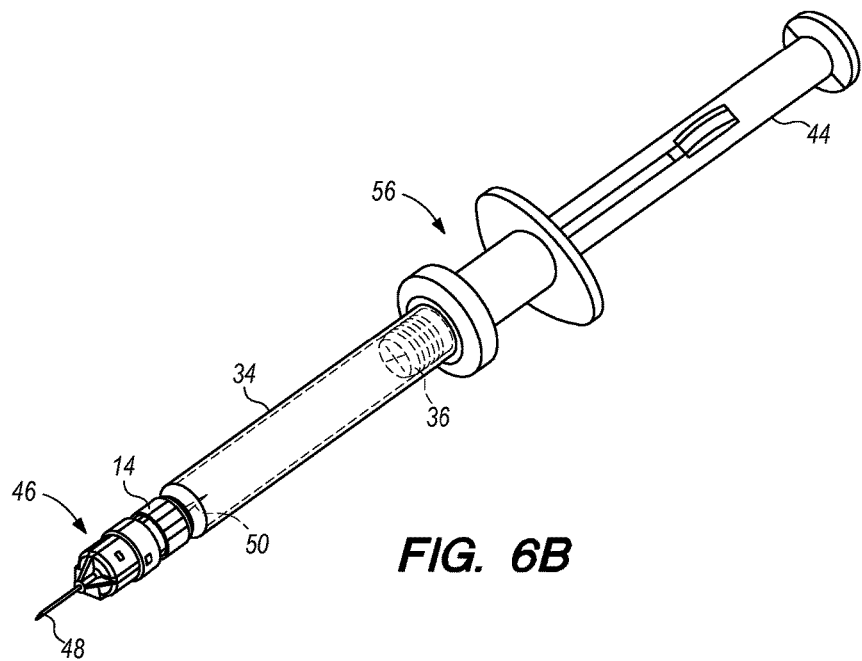

Referring to FIGS. 6A-6B, two orthogonal views of a safe injection system are shown, with a conventional off-the-shelf pre-filled syringe body (34) defining a medicine chamber (40); a stopper member (36) occludes the proximal aspect of the medicine chamber, while a needle assembly (46), shown ready for injection with the distal needle tip (48) exposed, controls exit of medicine from the chamber (40) distally subject to insertion of the plunger assembly (44) relative to the syringe body (34) by an operator. The needle assembly (46) is removably coupled to the syringe body (34) using a Luer interface (14), with the proximal end (50) of the needle member extending through the Luer interface (14) and into the medicine chamber (40). A flange coupling assembly (56) comprising two mating sides configured to be difficult to uncouple once forcibly coupled (i.e., by virtue of closely-toleranced snap fittings) is fitted to the proximal end of the syringe body (34) and provides a slidable interface for the plunger assembly (44) as it is inserted or retracted relative to the syringe body (34).

Figure 6C:
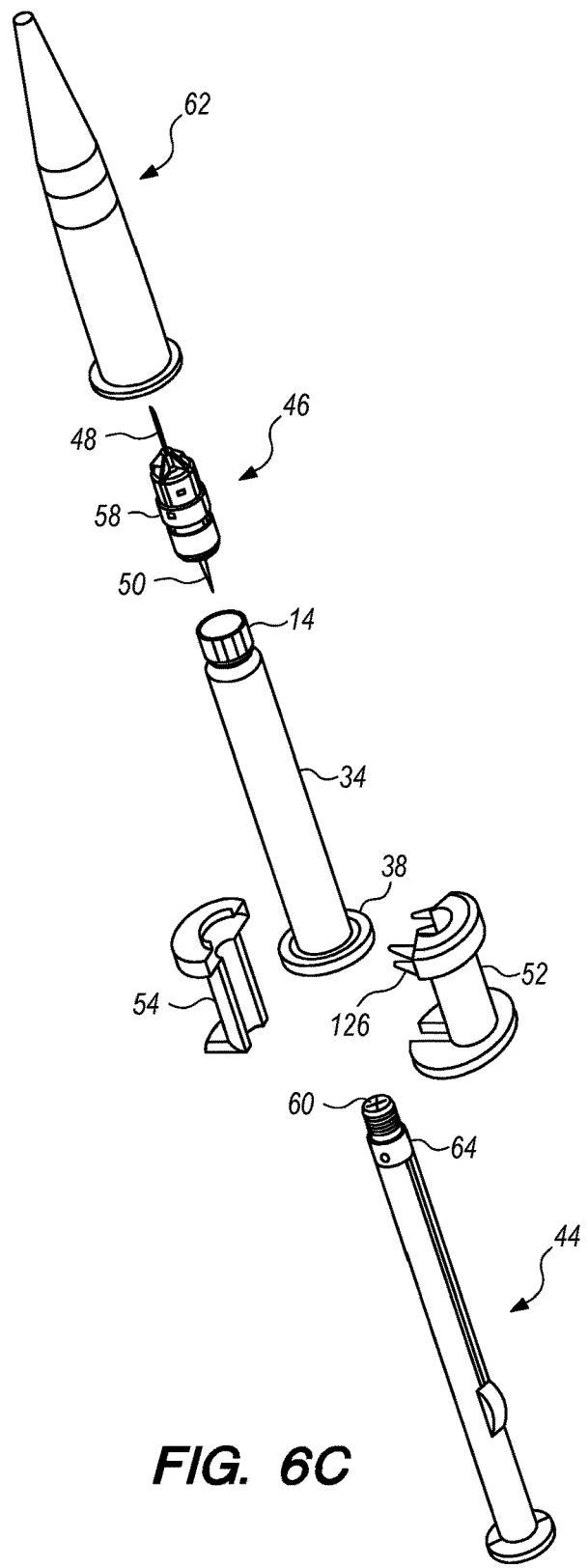

FIG. 6C illustrates an exploded view of a configuration such as that shown in FIG. 6A, and also with the addition of a needle cover member (62) configured to be protectively coupled over the exposed distal needle tip (48). The needle assembly (46) comprises a needle hub member (58) coupled between the proximal (50) and distal (48) needle portions. The two mating portions (52, 54) of the flange coupling assembly (56) are shown disassembled and adjacent the flange geometry (38) of the conventional syringe body (34) to which they may be coupled. The larger of the two mating portions (54) comprises a latch stop feature that projects inward and functions to interface with a latch configuration, as described further below. The plunger assembly (44) comprises a plunger hub member (64) that is coupled to a threaded interface (60) configured to be threaded into the compliant material (i.e., such as butyl rubber material) that comprises the conventional stopper member (36).

Figure 6D:
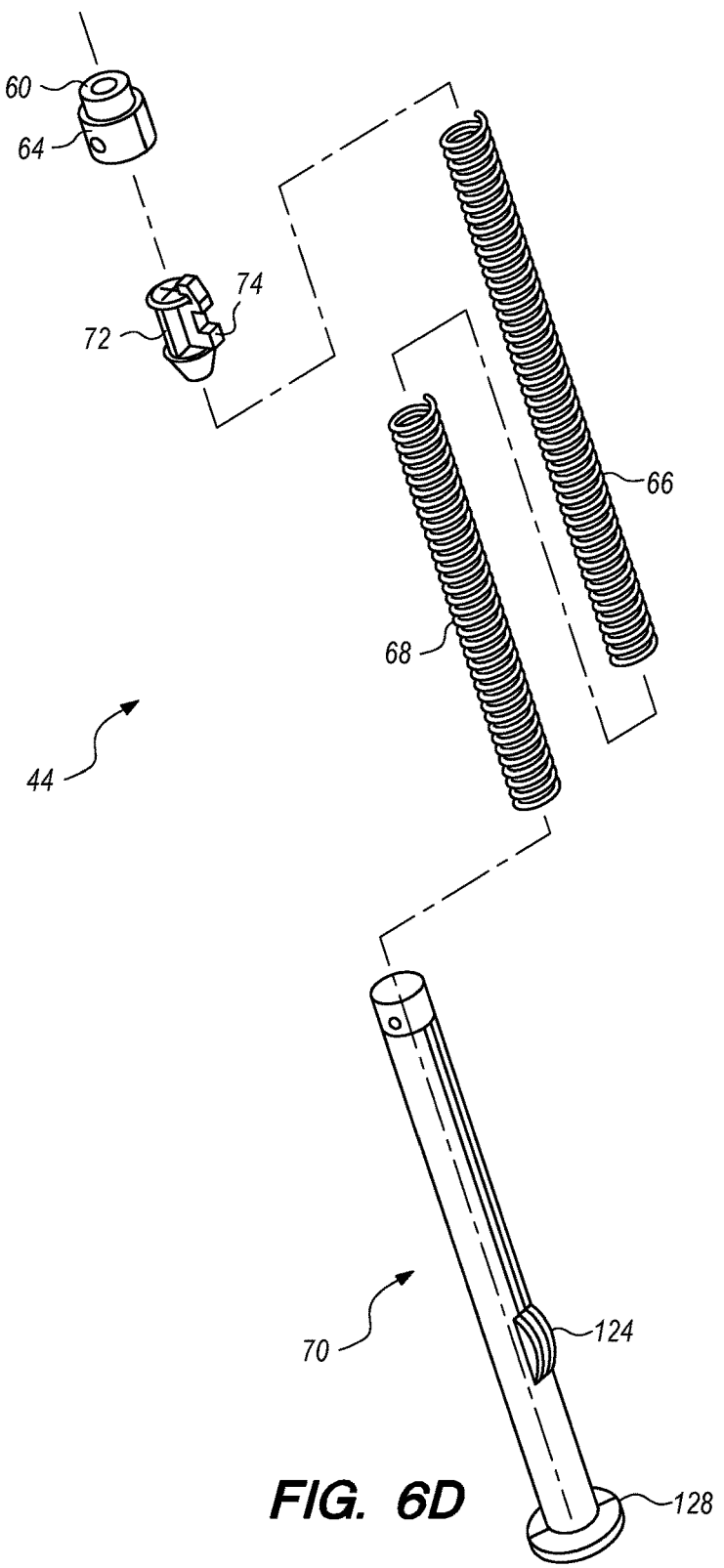

FIG. 6D illustrates an exploded view of the plunger assembly (44) featuring a plunger housing member (70) featuring a plunger manipulation interface (128), such as a thumb pad, a latch rotation housing feature (124), as described below, and an internal chamber defined to house one or more energy-storing members, such as the two spring members (66, 68) depicted, which are configured to be coaxially disposed within the plunger housing member (70) to provide a desired springe constant performance. The spring members (66, 68) are configured to provide a load against a latch hub member (72) that is rotatably coupled to a latching member (74) for controlled release relative to the plunger housing member (70), as described below. When released, the latch hub member (72) pushes against the latch stop feature of the flange coupling member (52) to cause the stopper (36) to be retracted proximally, as described below in further detail.

Figures 6E, 6F:
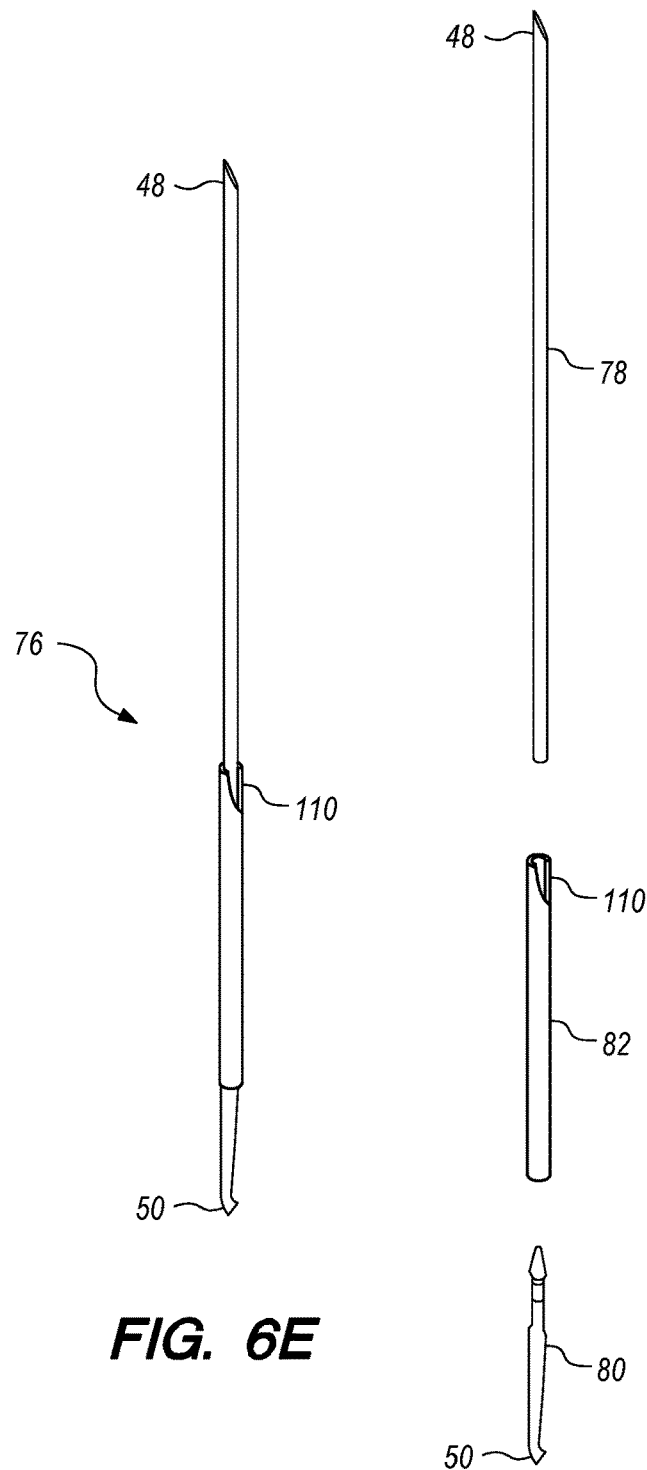
Figure 6G:
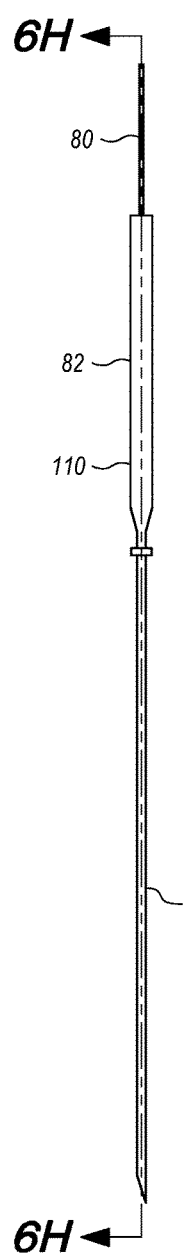
Figure 6H:
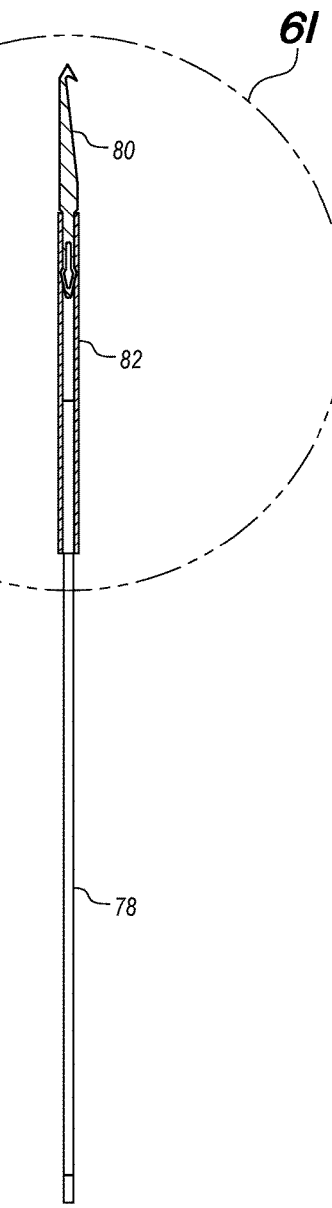
Figure 6I:
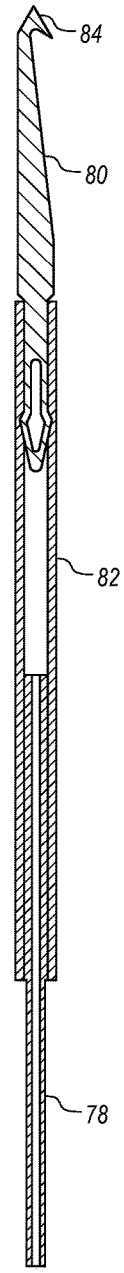
Figure 6J:
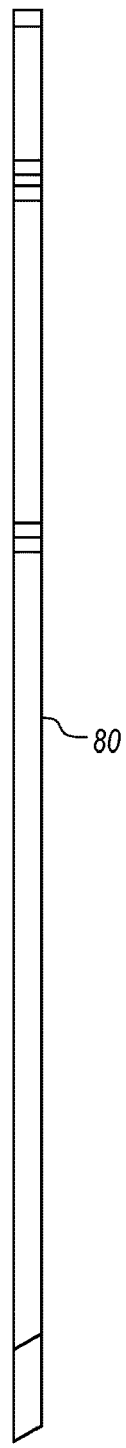
Figure 6K:
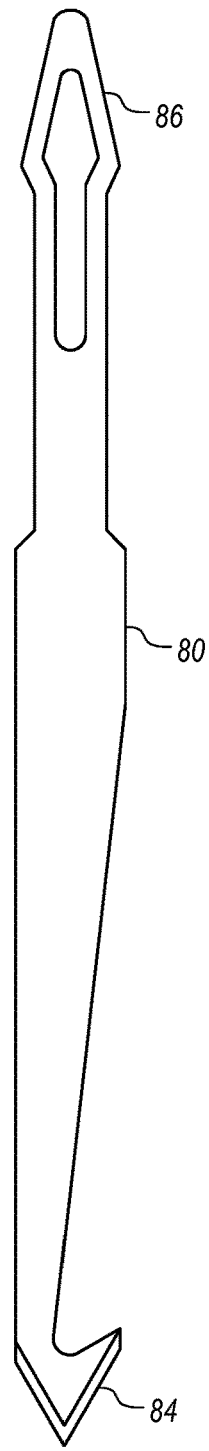
Figure 6L:
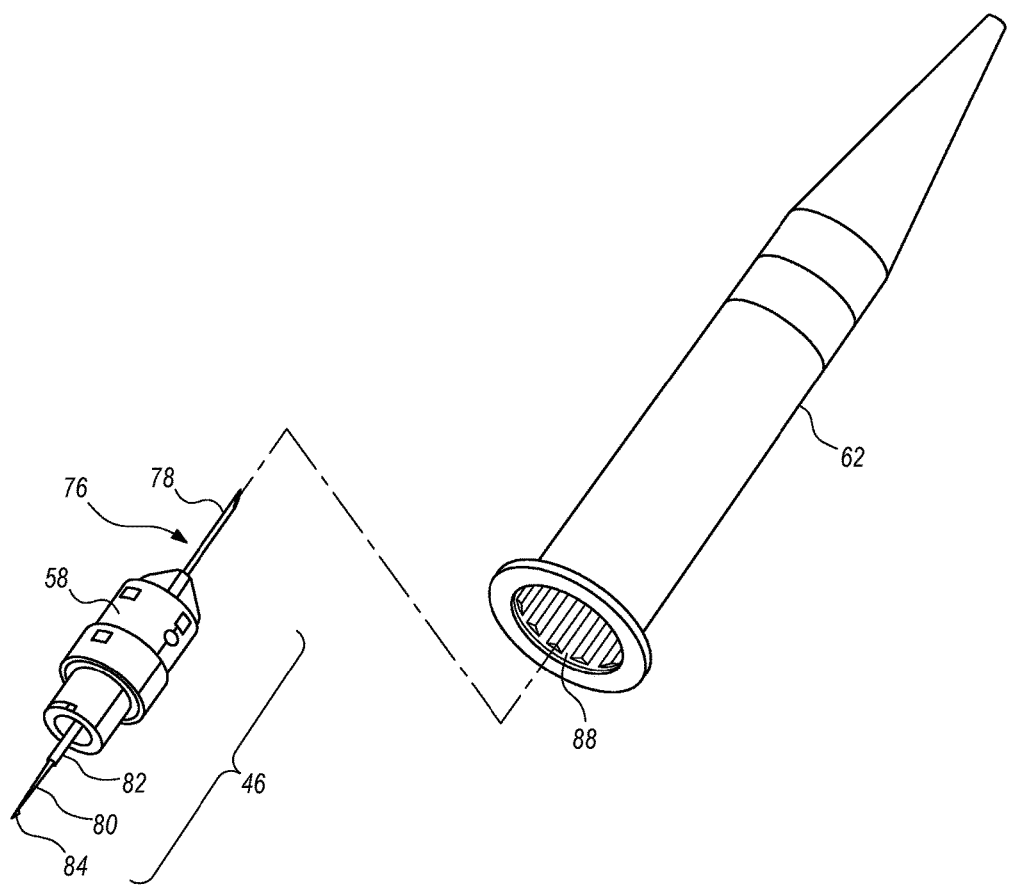

FIGS. 6E-6K illustrate aspects of a needle spine assembly (76), comprising the elements of the previously depicted needle assembly (46) without the needle hub assembly (58). Referring to FIG. 6E, the distal portion (48) of the needle spine assembly (76) comprises a sharpened hypodermic needle tip formed on an injection member (78). The proximal portion (50) also comprises a sharpened tip that is formed into the coupling member (80) that forms the distal portion. A hollow joining member (82) with a distal relief geometry (110) formed therein couples the coupling member to the tubular injection member (78). These elements are shown in greater magnification and cross section in FIGS. 6G-6I. In particular, referring to the close-up cross sectional view of FIG. 6I, the intercoupling of the injection member (78), coupling member (80), and hollow joining member (82) is shown. These elements may be held together with interference fits, welds, and/or adhesives. The most proximal end of the coupling member (84) in the depicted embodiment comprises a "harpoon" style geometry configured to stab into and hold onto a compliant member to which it may be interfaced, such as a portion of a stopper member, as described in further detail below. FIGS. 6J and 6K illustrate close up views of various aspects of the coupling member, which may be formed from a thin sheet metal component using laser cutting, etching, and/or machining techniques, for example. The end of the coupling member (80) opposite the harpoon geometry may comprise a joining interface (86) configured to be interference fit with a slight spring load into the joining member (82).

Figure 6M:
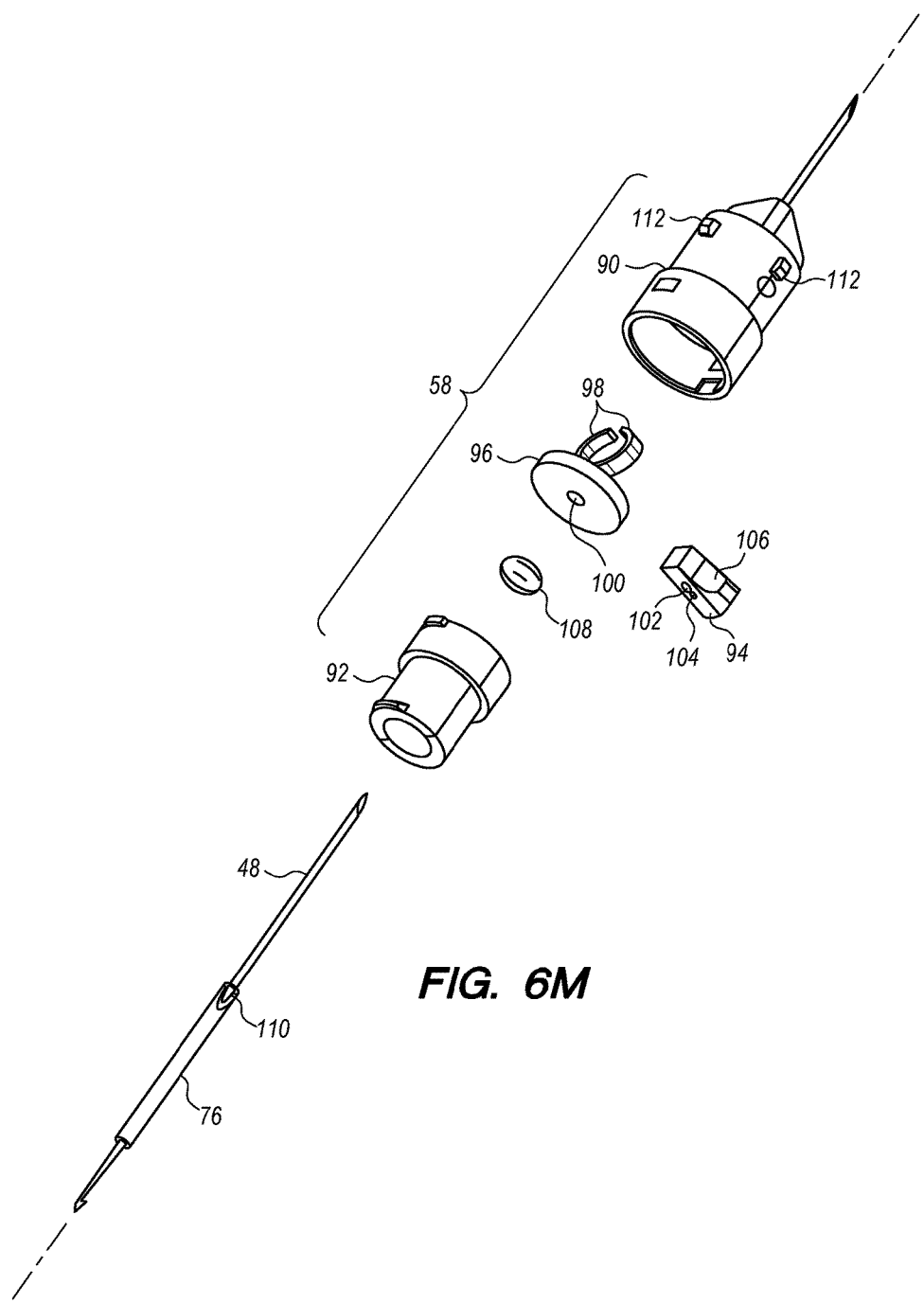
Figure 6N:
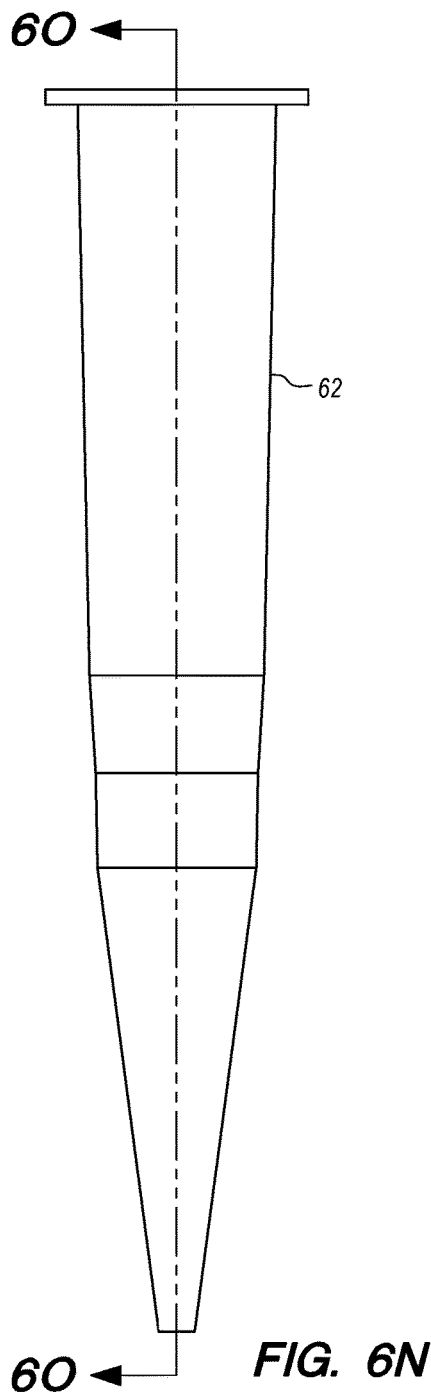
Figure 6O:
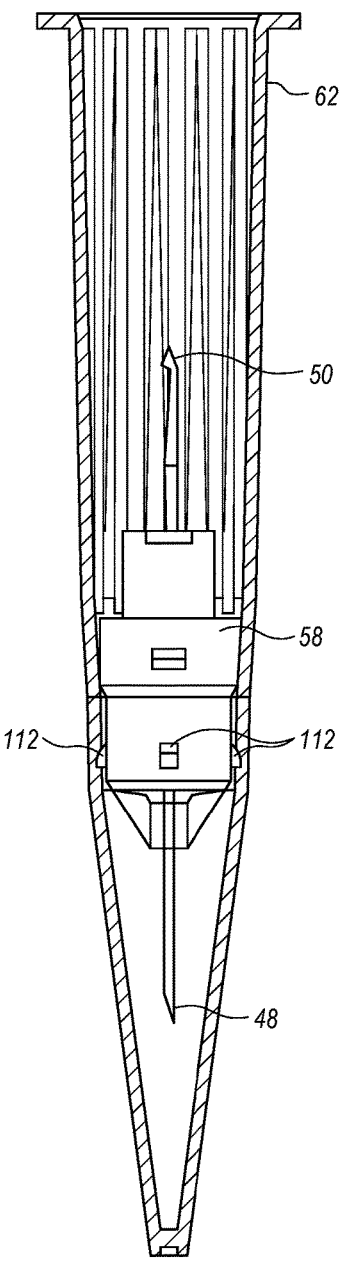

Referring to FIGS. 6L-6S, a needle assembly (46) comprising a needle spine assembly (76; comprising an injection member (78), joining member (82), and coupling member (80)) and needle hub assembly (58) may be inserted into an interior chamber formed within a needle cover (62) which may feature a plurality of internally facing radial projection surfaces (88) configured to maintain alignment of the needle assembly (46) relative to the needle cover (62) so that the needle assembly can remain housed predictably within the needle cover, and also so that the needle assembly may be coupled to a syringe body predictably. FIG. 6M illustrates an exploded view of one embodiment of a needle hub assembly (58) to configured to at least temporarily and at least partially house the needle spine assembly (76) while also being controllably convertible to a configuration wherein it will prevent reinsertion of the distal needle end (48) past the needle hub assembly (58) wherein it may be exposed and potentially reused or become dangerous. Similar to as described in U.S. Patent Application Ser. No. 61/841,702, which is incorporated by reference herein in its entirety, the needle hub assembly may comprise a coupling member (96) having two bendable arms (98) configured to be interfaced with a slidable door member (94) so that when assembled as in FIG. 6L, the needle spine assembly (76) is passed through the proximal housing (92), through a sealing o-ring (108), through an aperture (100) formed in the coupling member (96), between the two arms (98), through an aperture (102) formed in the slidable door member (94), and through the distal housing (90). When the needle spine assembly (76) is moved proximally relative to the needle housing assembly (58), as soon as the distal portion (48) of the injection member (78) has passed out of the slidable door member (94) aperture (102), the loads of the arms (98) that have been in bending against sloped interface geometries (106) of the sides of the door member (94) cause the slidable door member (106) to slide or displace orthogonally relative to the longitudinal axis of the needle spine (76), placing a portion (104) of the door member (94) featuring a dimple or depression, but not a clear aperture or passageway through the door, in the pathway of the needle tip (48) should a subsequent attempt be made to insert such needle tip (48) out past the needle hub assembly (58); in other words, the door (94) now blocks further reinsertion of the needle out past the needle hub assembly (58).

FIGS. 6N-6S illustrate interfacing of a needle assembly (46) with a needle cover member (62). In the depicted embodiment, a plurality of lug interface features (112) are formed into the outer surface of the needle hub assembly (58) and configured to be interfaced with a plurality of "L-shaped" slots (113) with detent interface features for both insertion (114) and roll (116) such that the needle assembly (46) is inserted into the needle cover member, is guided by the plurality of internally facing radial projection surfaces (88) engaging the needle hub assembly (58) to maintain axial alignment of the needle cover and needle assembly (46), and then the needle hub assembly lug interface features (112) may be snapped over the detent interface features (114, 116) as they are inserted and twisted through the "L-shaped" slots (113). Such a relatively robust coupling of needle cover (62) and needle assembly (46) is configured to assist in manual coupling of the needle assembly (46) to the syringe body (34), in that the proximal portion (50) is vectored straight into the Luer adaptor (14) of the subject syringe body (34) with the assistance of the internally facing radial projection surfaces (88) after the needle cover (62) detent interfacing features (i.e., one for twist, one for insertion/retraction) have been manually overcome. In one embodiment, the detent interface geometry is specifically configured (i.e., geometrically sized and tolerance) such that the rotational load required to pass the rotationally-resisting detent and remove the needle cover (62) to expose the needle is greater than or equal to the rotational load required to confirm that the needle assembly has been adequately rotationally coupled to the syringe body. Such a configuration provides extra confirmation that the needle assembly is, indeed, adequately coupled to the syringe body before the needle is removed from the needle cover (62). This series of rotational and axial detents may be used with retractable needle and hub assemblies, such as those illustrated and described herein, or with conventional injection systems (i.e., on non-retractable needle and hub assemblies).

Figure 7A:
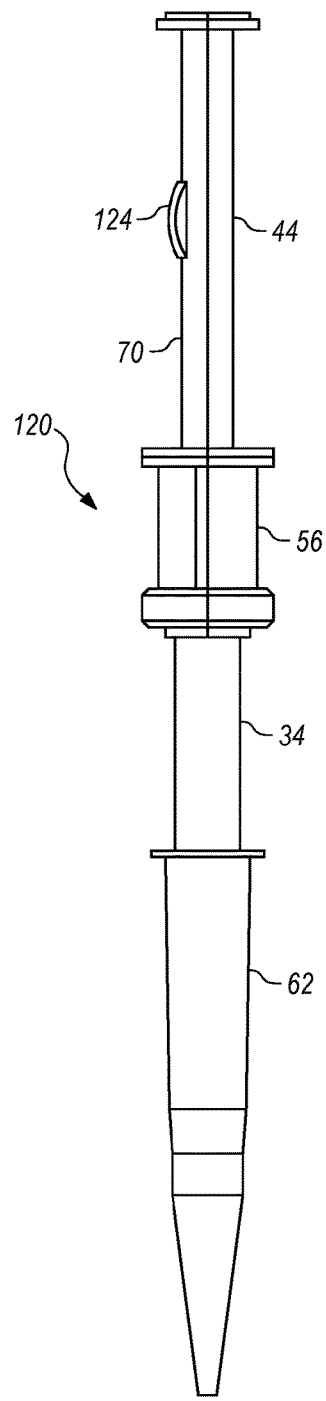
Figure 7B:
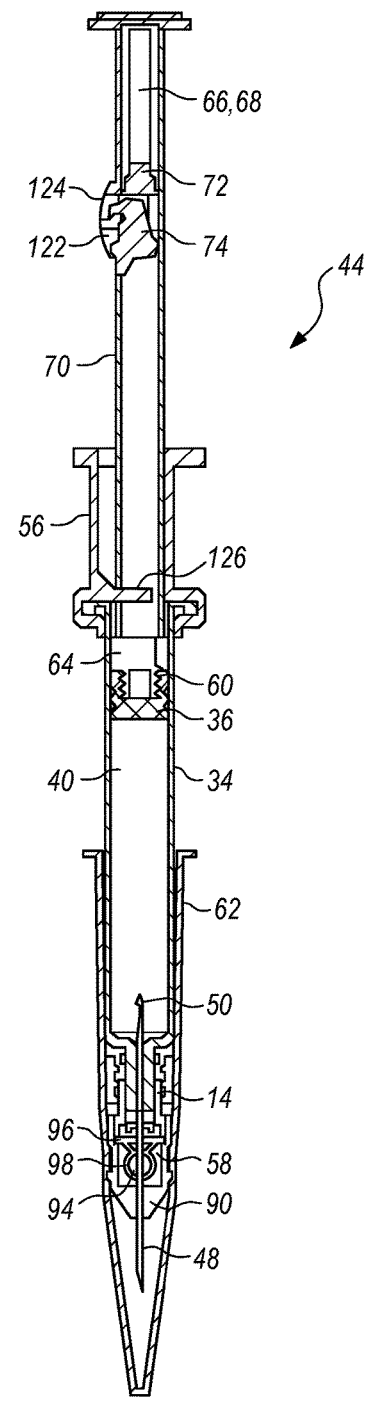
Figure 7C:
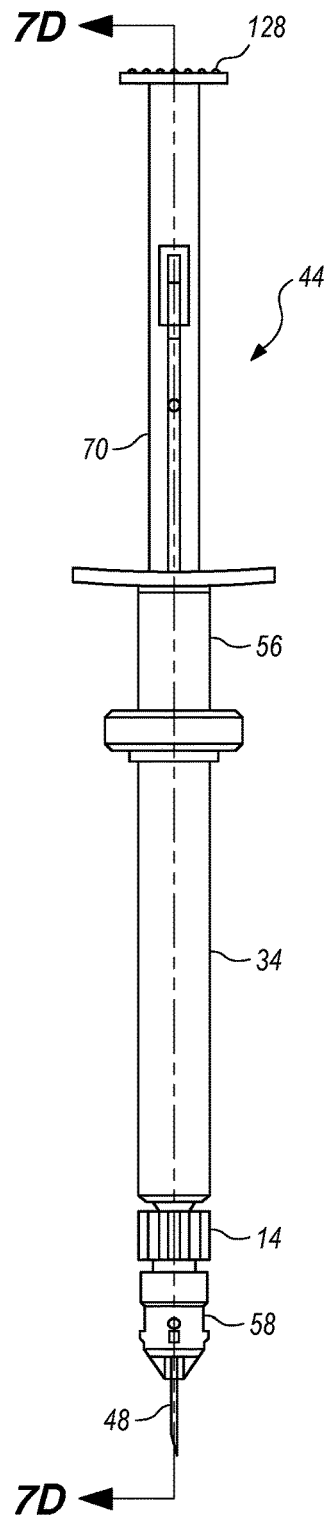
Figure 7D:
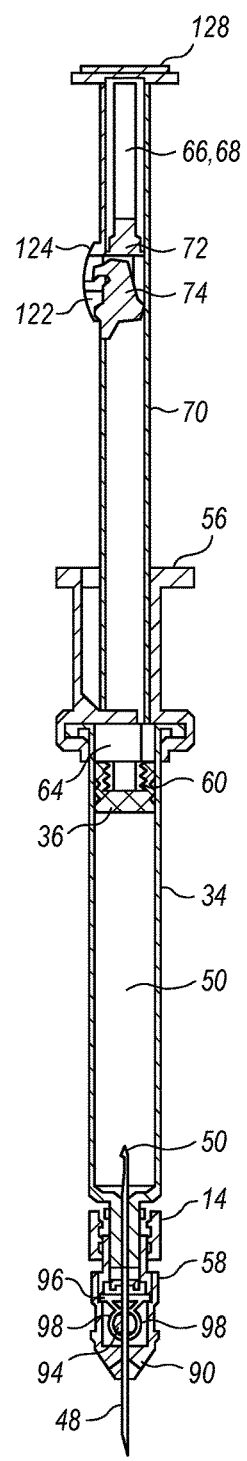
Figure 7E:
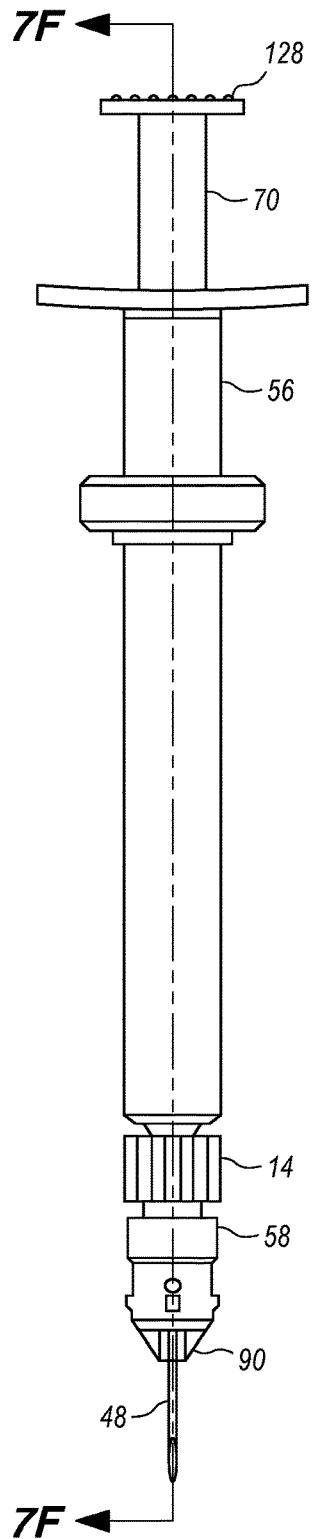
Figure 7F:
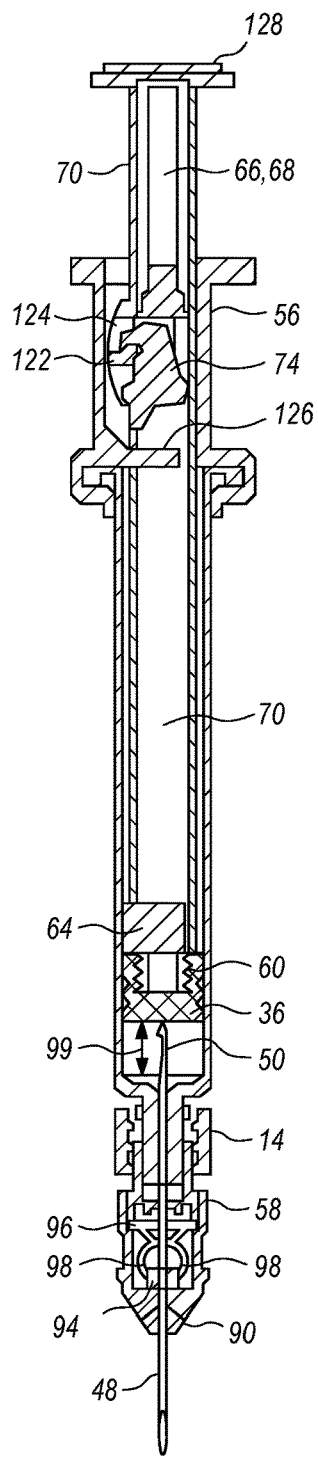
Figure 7G:
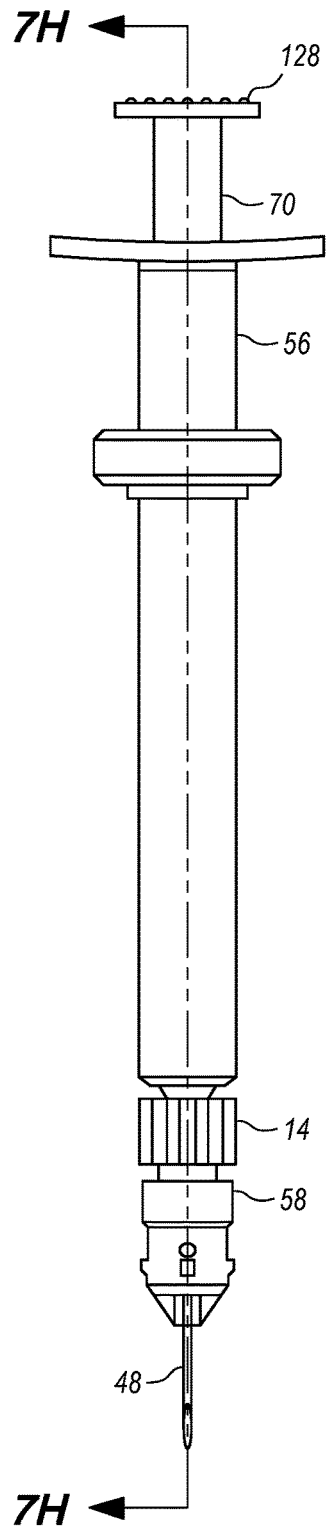
Figure 7H:
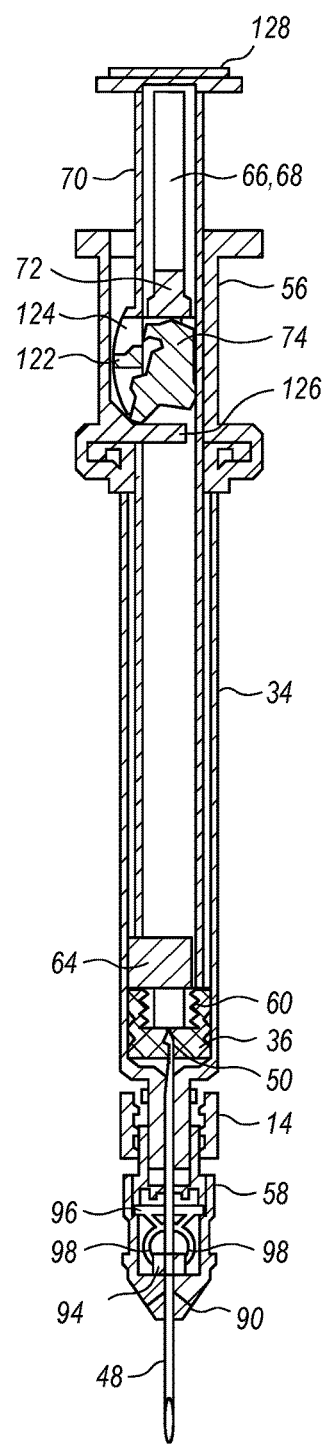

Referring to FIGS. 7A-7J, various illustrative process steps for a safe injection system are shown. Referring to FIGS. 7A and 7B, a complete safe injection system is shown with a needle cover over the distal portion (48) of the needle assembly. The cross sectional view of FIG. 7B shows that the spring members (66, 68) are compressed in a stored-potential-energy configuration that is retained by the latch hub member (72) as held in place by the latching member (74). Referring to FIGS. 7C and 7D, the needle cover (62) has been removed (i.e., such as by twisting, then pulling relative to the needle hub assembly to overcome the two retaining detent features described above) to expose the needle distal portion (48) in a ready-to-inject configuration relative to a patient. Referring to FIGS. 7E and 7F, by manipulation of the plunger (70) and stopper (36) relative to the syringe body (34), such as by thumb depression on the proximal plunger interface (128) combined with finger capture of the flange coupling assembly (56) that is coupled to the syringe body (34), the contents of the medicine chamber (40) have been almost completely expelled out of the needle (48) distal tip (48). As shown in the cross sectional view of FIG. 7F, a slight bit (99) of stopper (36) insertion throw distance remains until full insertion of the stopper (36) and plunger (70). The spring members (66, 68) remain in the stored-potential-energy configuration, as retained by the latching member (74). Referring to FIGS. 7G and 7H, the stopper member (36) has just been completely inserted relative to the syringe body (34) and has been stabbed by the harpoon geometry of the proximal end of the needle (50) so that the stopper (36) and needle (50) are now coupled. The latching member (74) has interfaced with the latch stop feature (126) of the flange coupling assembly (56), causing the latching member (74) to rotate as shown (facilitated by the relief provided by the latch rotation housing feature 124 of the plunger housing member 70), such that it becomes uncoupled from the latch interface feature (122) and releases the latch hub member (72) to use the stored potential energy of the spring members (66, 68) to apply a compressive load between the plunger housing (70) and the latch stop feature (126) of the flange coupling assembly (56), causing the plunger housing (70), stopper member (36), and now intercoupled needle assembly (48, 50) to be withdrawn proximally along with the plunger housing (70) such that the distal portion of the needle (48) is now safely housed within the medicine chamber (40) of the syringe body (34), as shown in FIGS. 7I-7J. In addition, any further attempts to advance the needle so that the distal portion (48) thereof can be externally exposed are defeated by the closure of the slidable door member (94) within the needle hub assembly (58), as described above.

Referring ahead to FIGS. 13A-14H, a configuration similar to that described in reference to FIGS. 6A-7J is shown, with the exception that the syringe body (34) in the configurations of FIGS. 13A-14H is significantly shorter than that of FIGS. 6A-7J. For example, in one variation the syringe body of embodiments of FIGS. 6A-7J may be an off-the-shelf 3 milliliter syringe body, while that of FIGS. 13A-14H may be an off-the-shelf 1 milliliter syringe body, having a medicine chamber length that is less than the length of the needle assembly, thereby complicating the objective of preventing sharps danger or re-use by positioning at least partially within the protective custody of the medicine chamber of the syringe body. As shown in FIGS. 13G-13J, a safety functionality similar to that of the embodiment of FIGS. 6A-7J may be accomplished using an elongated length dimension (130) of the flange coupling assembly (56; mating components 52 and 54), the length dimension (130) configured to accommodate proximal portions of the needle/plunger intercoupled assembly which may need to be retracted out past the proximal aspect of the syringe body (34) to be able to place the distal tip of the needle (48) within the confines of the syringe body (34). Referring to FIGS. 13G and 13H, to prevent remaining droplets of medicine previously contained within the medicine chamber (40) from exiting the nearby vicinity, wicking surface features and geometry (132) have been formed into a surface that the stopper passes as it is withdrawn out of the syringe body (34) and into the internal volume formed within the flange coupling assembly (56). FIGS. 14A-14H illustrate an injection system process that parallels that of FIGS. 7A-7J, with FIGS. 14A-14B depicting a ready to use assembly with a needle cover (62) in place; FIGS. 14C-14D illustrating the ready to use assembly with the needle cover removed and the needle distal tip (48) exposed; FIGS. 14E-14F showing full stopper member (36) insertion with the proximal portion of the needle member (50) stabbed into and coupled to the stopper member (36)—and also the latching member (74) being rotated by the latch stop feature (126) so that the spring members (66, 68) are free to cause retraction of the plunger/stopper/needle assembly, such retraction being shown in FIGS. 14G and 14H, wherein the stopper member (36) has been retracted past the wicking surface features and geometry (132) to leave any residual medicine droplets contained there as the stopper member (36) and proximal portion of the needle (50) are contained within the internal volume formed within the flange coupling assembly (56); the slidable door member (94) has moved into a blocking position to prevent any reinsertion of the distal portion (48) of the needle member relative to the syringe body (34). As described above, the length of the flange coupling assembly may be lengthened to accommodate various lengths of needle members relative to syringe body lengths. The configuration illustrated in FIGS. 14G-14H has just enough length to withdraw the distal end (48) of the needle past the slidable door member (94) such that reinsertion may be blocked; further flange coupling assembly (56) length (130) may be included in other variations to place the needle distal tip (49) well within the confines of the syringe body (34) at retraction of the stopper (36) and plunger (70).

While the embodiments described above in reference to FIGS. 6A-7J and 13A-14H feature a spring retraction configuration, other embodiments may avoid the spring hardware and feature retraction by manual means (such as by retractive pulling upon the plunger manipulation interface 128), or by vacuum assisted retraction configurations, such as those described in the aforementioned incorporated by reference application, whereby a vacuum load is developed within the confines of the syringe body (34) during manual stopper insertion that may be used to assist during retraction of the same stopper, as it pulls along portions of the needle assembly into a safe configuration.

Referring to FIGS. 8A-12O, various safe injection system configurations are illustrated for needle/syringe body interface configurations which may be termed "staked needle" configurations due to the fact that in each such configuration, a portion of the needle is supported by, or "staked" within, the conventional distal taper construct (144) (i.e., such as a Luer taper) of the syringe body (34). These configurations illustrate that needles may be "staked" for injection usage, and then controllably released from these staked intercouplings for retraction, safe storage, and re-use prevention in manners somewhat akin to those of the aforementioned configurations.

Figure 8A:
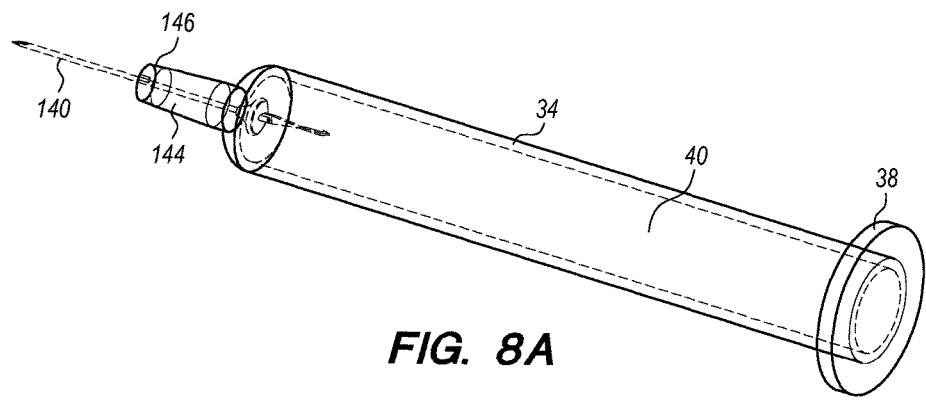
FIGS. 8A-8P illustrate various aspects of a safe injection system wherein a distally-disposed keyed needle and latching member interface may be utilized to controllably release a needle for retraction to a safe position.
Figure 8B:
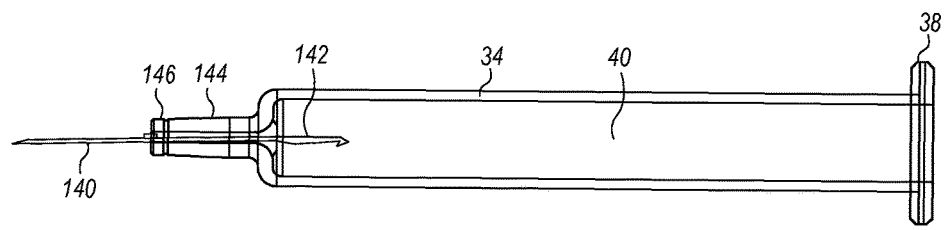
Figure 8C:
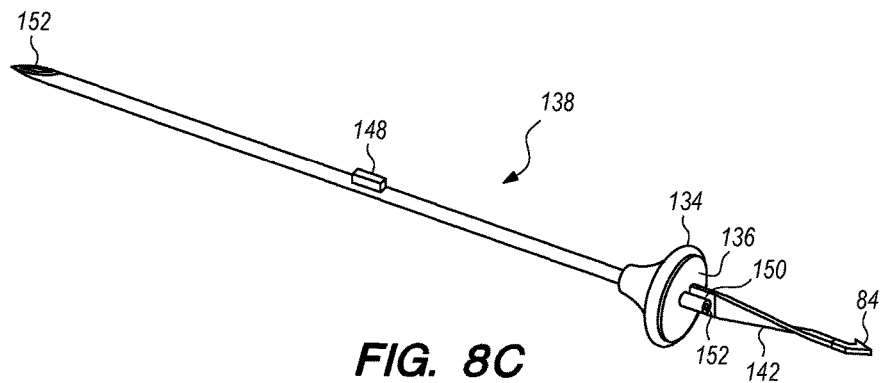
Figure 8H:
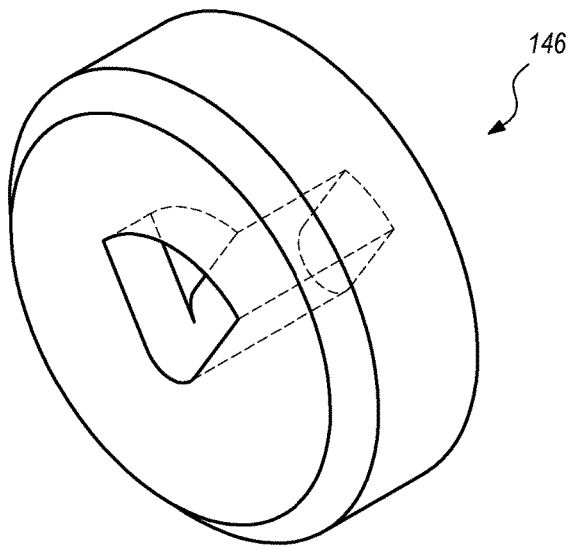
Figure 8I:
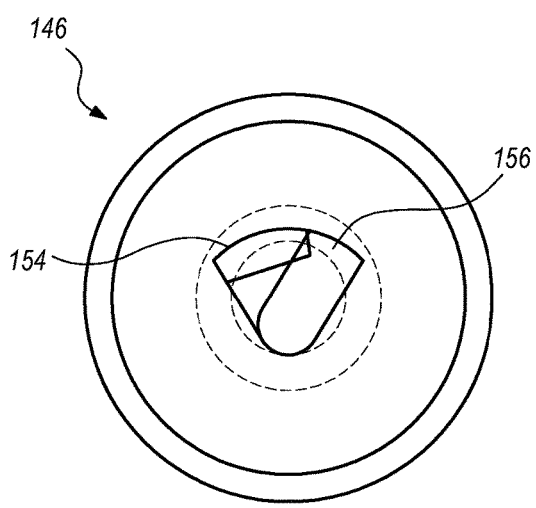
Figure 8J:
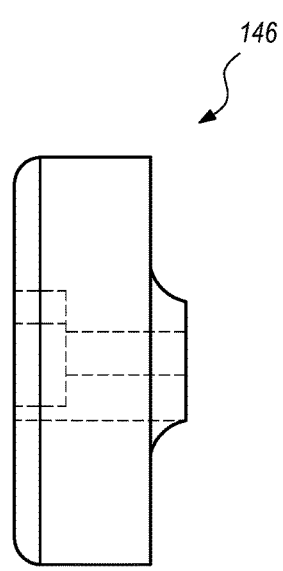
Figure 8M:
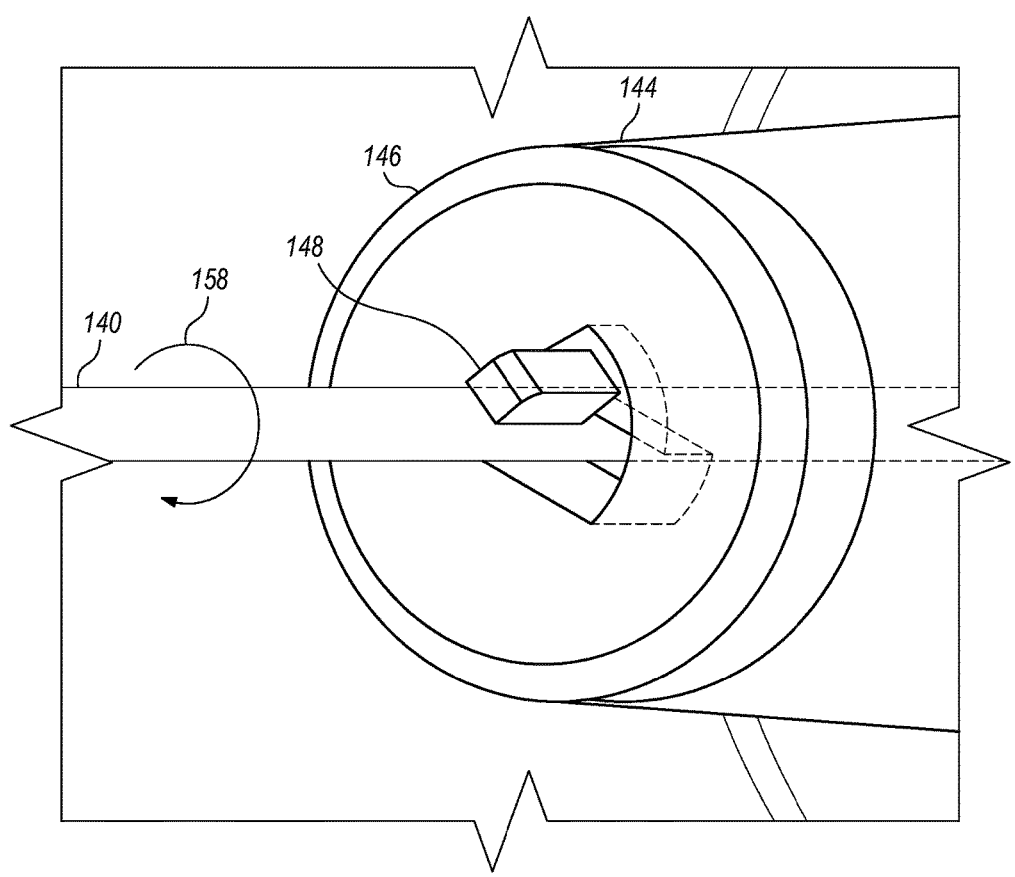
Figure 8N:
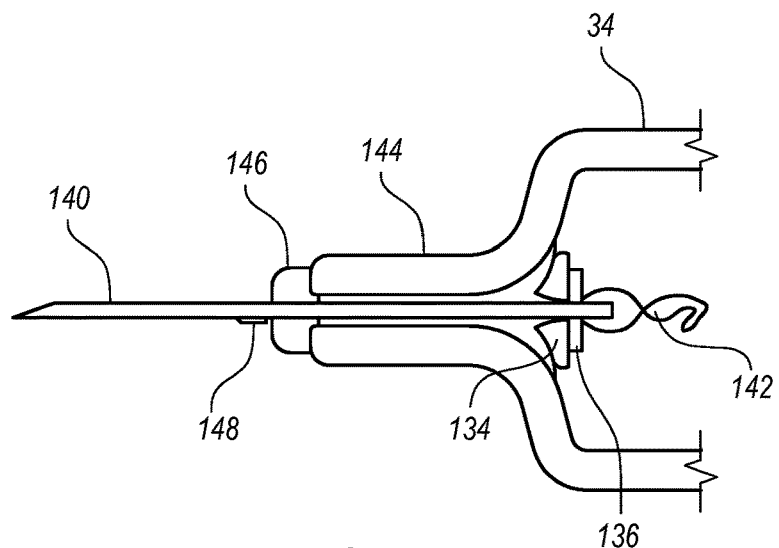
Figure 8O:
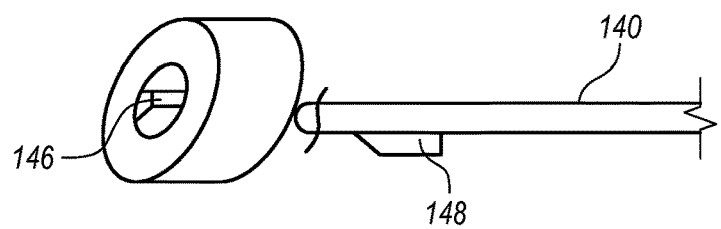
Figure 8P:
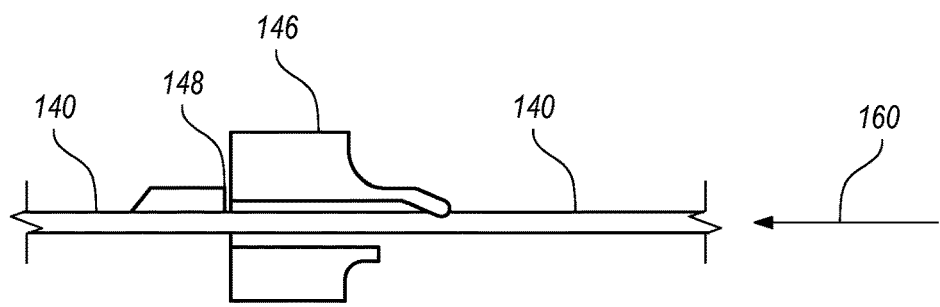

Referring to FIGS. 8A-8P, various aspects of a configuration for controllably coupling a needle into a staked configuration, and releasing the needle from the staked configuration are shown. As shown in FIG. 8A, a needle assembly (138) may comprise a distal end (140) having a cannula-like geometry and a sharpened distal tip (152). A radially projecting latching surface feature (148) may be formed into or fixedly coupled to the distal needle portion (140) and configured to perform a keying function in the coupling and release of the needle from a staked configuration relative to a syringe body having a distally disposed latching member (146) as shown, wherein a keyed interface allows for "locking in" or "unlocking" the needle relative to the syringe body using the radially projecting latching surface feature (148), as described in further detail below. The needle assembly (138) further may comprise a seal member (134) and loading plate (136) coupled to the proximal end of the distal needle portion (140), to which the distal end of a proximal needle member (142) is fixedly coupled at a coupling point (152). These members are shown in uncoupled form in FIGS. 8D-8G. The proximal end (142) of the needle assembly comprises a twisted sheet metal piece with harpoon proximal end features (84), the twisting intentionally configured such that a twisting moment load is stored up when the proximal end is inserted, or stabbed, into a compliant member with relative turning prevented or constrained; upon release of such rotational constraint, the moment load creates relative rolling motion, which can be utilized to unlock the keyed interface. In other words, referring to FIGS. 8H-8J, the latching member (146) is configured so that the distal needle member (140) may be positioned therethrough, with the radially projecting latching surface feature (148) either in a first position (154), wherein retraction motion between the latching member and radially projecting latching surface feature (148) is prevented, or rolled to a second position (156), wherein the latching member is configured to accommodate axial removal/withdrawal of the radially projecting latching surface feature (148) through the latching member. Thus to assemble a needle assembly (138) into a staked position relative to an off-the-shelf syringe body (34), the needle assembly (138) may be inserted through the medicine chamber (40) as shown in FIG. 8K until the seal member (134) is seated against the distal wall of the interior of the medicine chamber (40) of the syringe body (34); then the latching member may be inserted over the distal portion of the needle (140) and the needle assembly, including the radially projecting latching surface feature (148), may be inserted and rotated relative to the latching member so that the radially projecting latching surface feature (148) is first passed through the fitted aperture or hole (i.e., in the second position described above, with the 156 position in FIG. 8I) through the latching member (146), and then rotated to reposition the radially projecting latching surface feature (148) into the locked position (i.e., in the first position described above, with the 154 position in FIG. 8I such that the needle member cannot be withdrawn relative to the latching member 146). Such action is further illustrated, for example, in FIGS. 8N-8P. As shown in FIG. 8M, to unlock the needle assembly relative to the syringe body and intercoupled latching member (146), a combined loading paradigm of insertion of the needle assembly toward the syringe body (34) along with a rotational moment to rotationally roll the radially projecting latching surface feature (148) into the second position described above may be utilized, wherein the radially projecting latching surface feature (148) may be withdrawn out past the latching member (146). Thus in one embodiment, having a plunger member (70) push a stopper member (36) onto the proximal twisted end (142) of the needle member accomplishes three things: it builds up a moment load for twisting the radially projecting latching surface feature (148) relative to the latching member (146), it pushes the radially projecting latching surface feature (148) relative to the latching member (146), and it stabs the harpoon feature of the proximal needle (142) into a coupling relationship with the stopper member (36) such that it may be retracted into a safe position, using spring-loaded, vacuum, or manual retraction means, as described above.

Figure 9C:
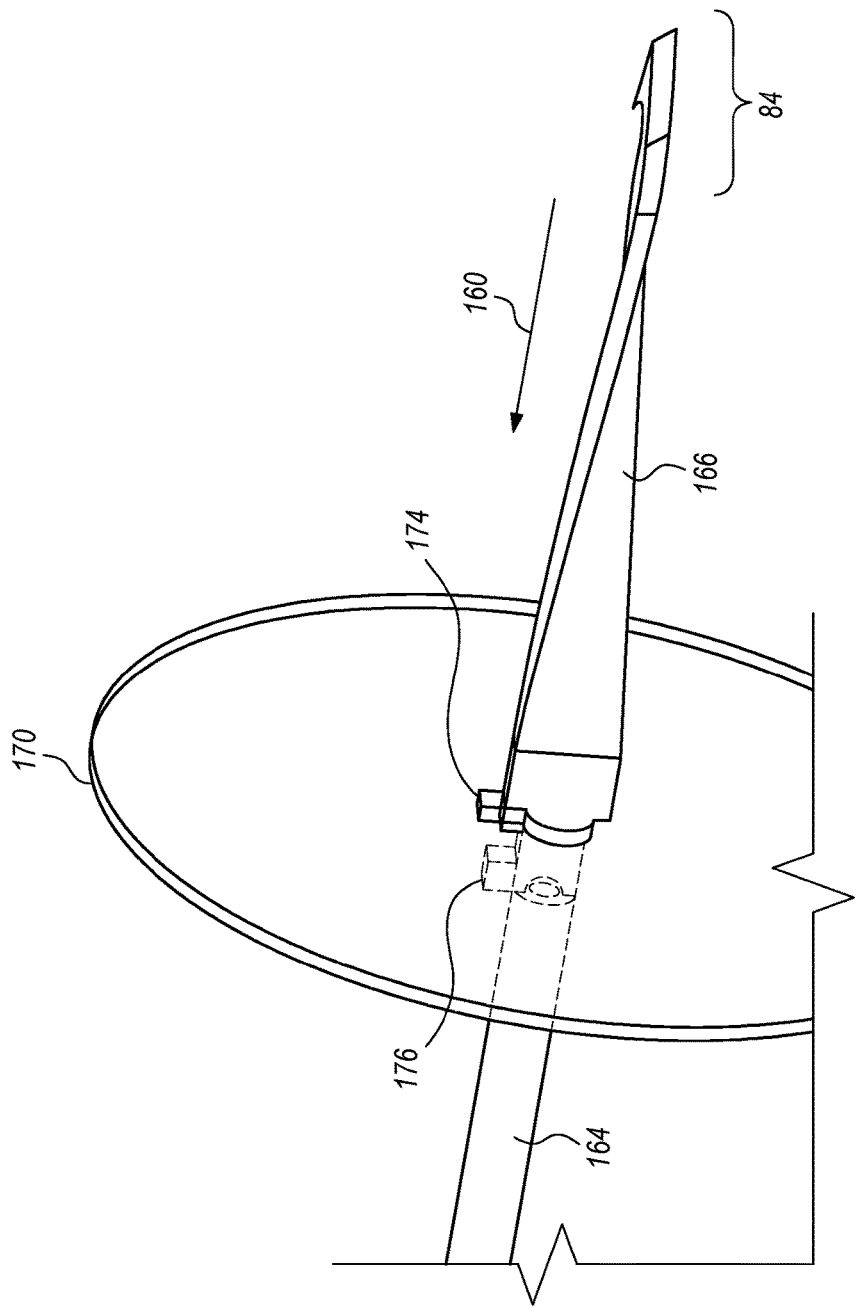

Referring to FIGS. 9A-9C, another keyed needle staking/unstaking configuration is illustrated, wherein the proximal needle portion (166) has a distal portion that comprises a keying feature (176) which may be lockably/unlockably interfaced through a slot (174) formed through a loading plate (170) that is positioned between a seal member (168) configured to seal to the inner diameter of the syringe body (34), and an expansion ring (172). The locking and unlocking action as interfaced with a stopper and plunger may be similar to that described above, with the keyed interface being positioned internally to the syringe body (34) rather than externally, as in the embodiment of FIGS. 8A-8P.

Figure 10A:
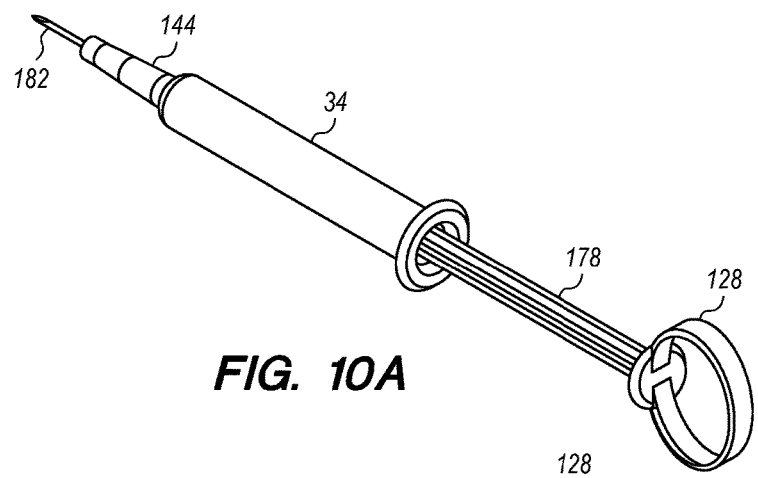
FIGS. 10A-10L illustrate various aspects of a safe injection system wherein a cantilevered latching feature may be utilized to controllably release a needle for retraction to a safe position.
Figure 10B:
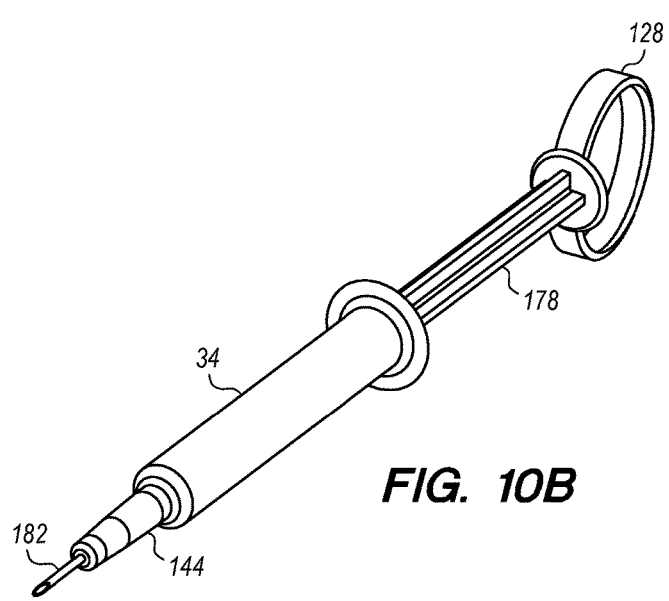
Figure 10C:
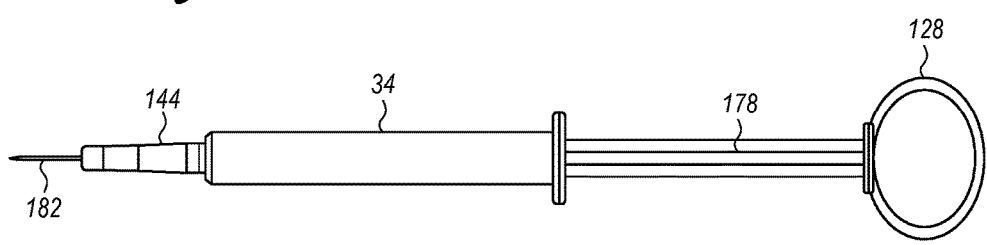
Figure 10D:
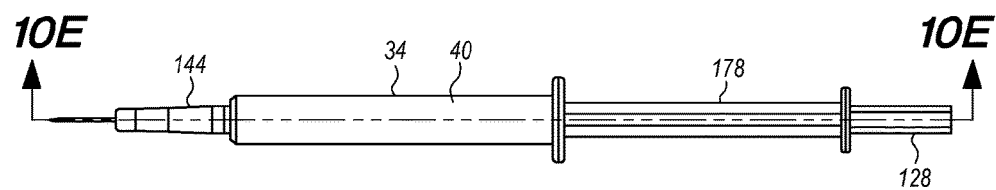
Figure 10E:
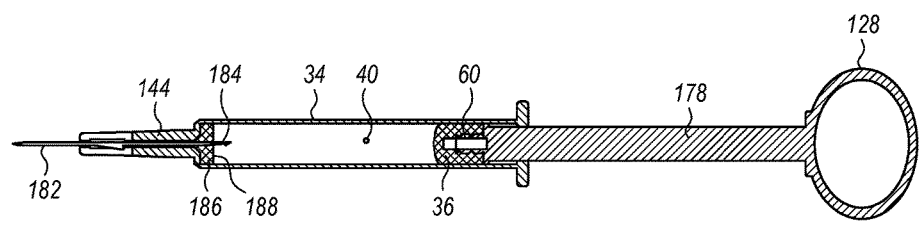
Figure 10F:
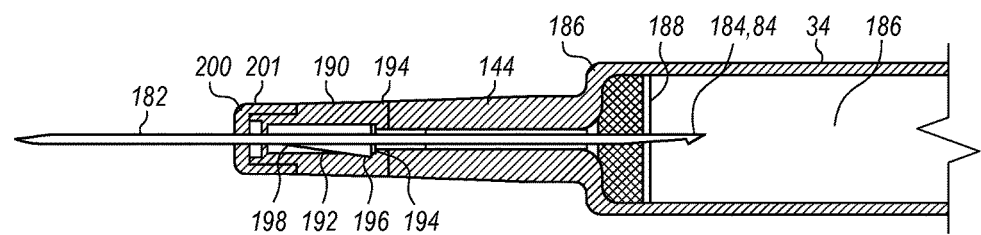
Figure 10G:
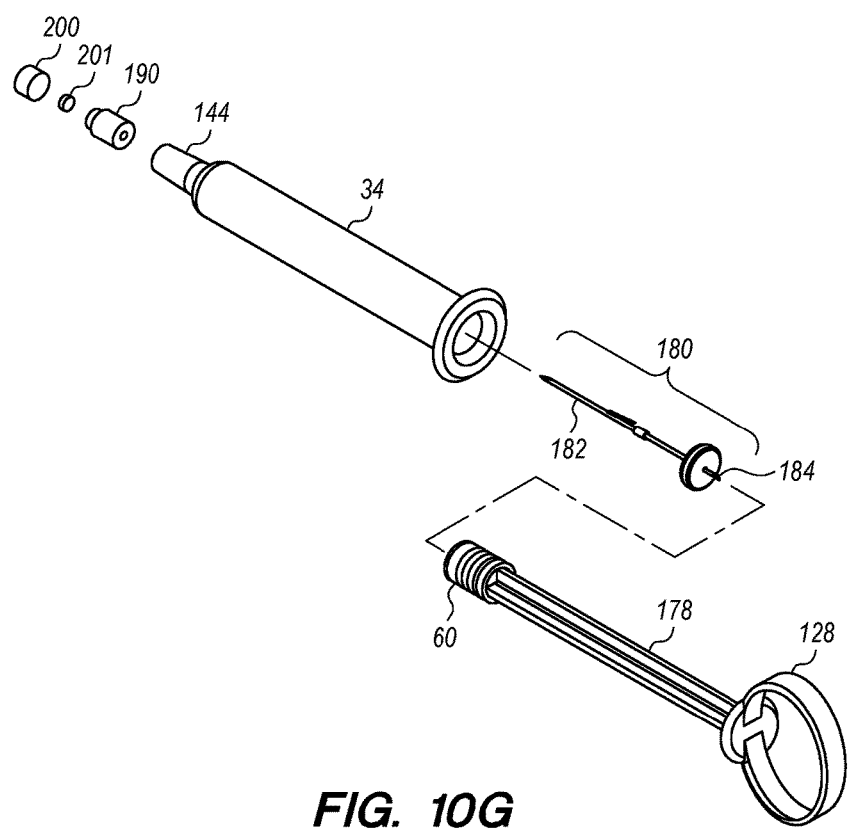
Figure 10H:
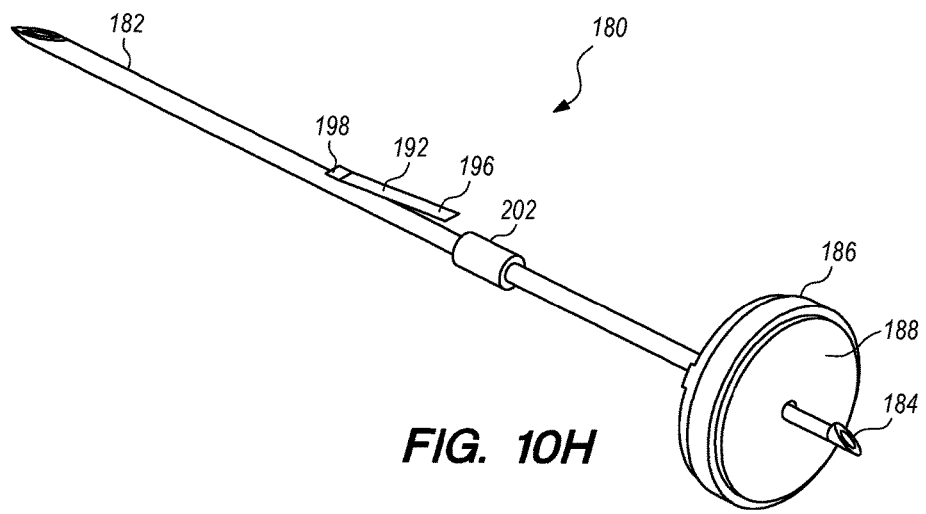
Figure 10I:
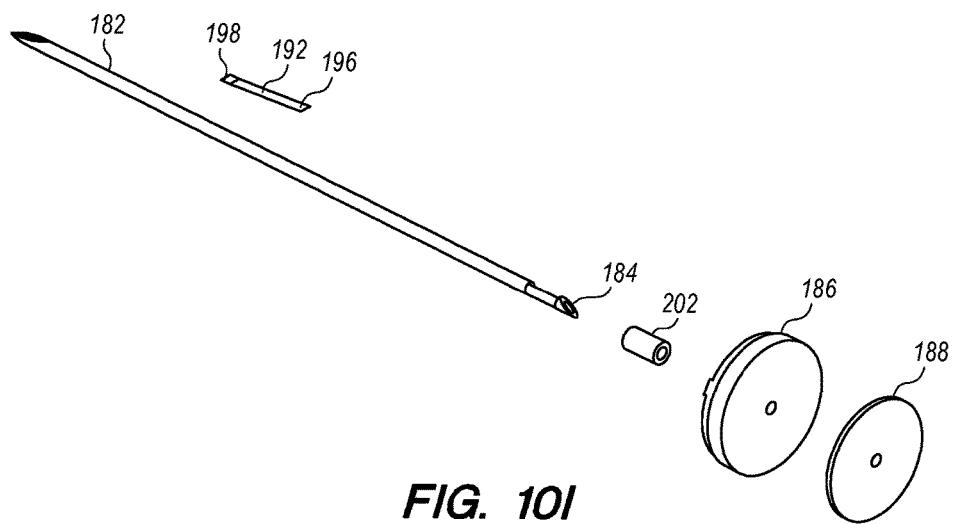
Figure 10J:
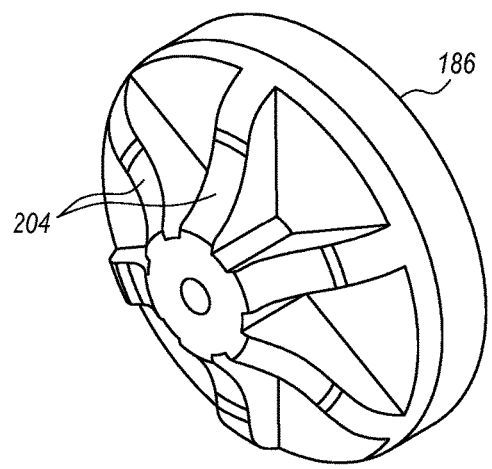
Figure 10K:
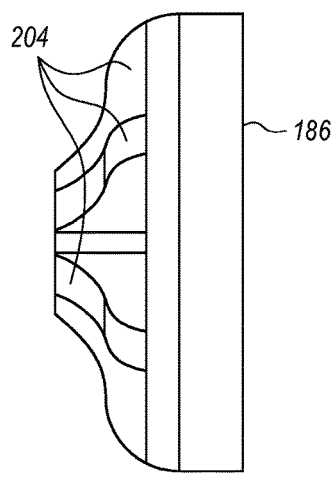
Figure 10L:
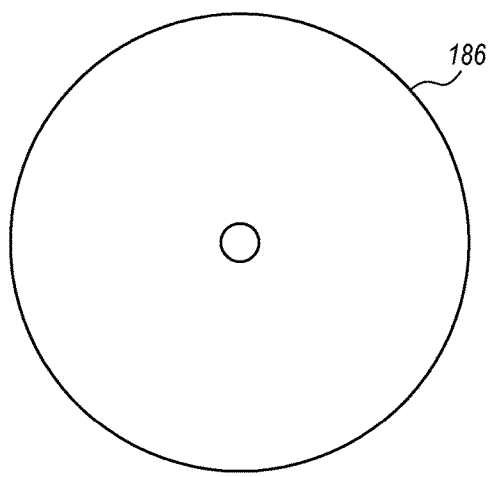

FIGS. 10A-10L illustrate another staking/unstaking configuration for a needle assembly relative to an off-the-shelf syringe body (34), wherein a cantilevered latching feature (192) fixedly attached distally to a distal portion (182) of a needle assembly (180), with a proximal aspect free to rotate or bend relative to the needle assembly (180), may be used for controlled unlatching with only an insertion load (i.e., without a twisting or moment load as well, as in the aforementioned configurations). FIGS. 10A-10E illustrate a ready-to-use injection system with a needle assembly latched in a position wherein it is configured to not retract when axially loaded during entry into a patient's tissue; as shown in FIG. 10F, this is due to the fact that in such configuration, the cantilevered latching feature (192) proximal end (196) is captured in a recess (194) formed in the latching member nose piece (190). As shown in the exploded view of FIG. 10G and detail views of FIGS. 10H and 10I, the needle assembly (180) may comprise a distal needle portion (182), a proximal needle portion (184), a needle-centering bushing (202), a seal member (186; to increase compliance, may be configured to have ribs and/or other relief geometries (204), as shown in FIGS. 10J and 10K), and a loading plate (186) configured to be interfaced with a stopper (36) coupled to a plunger member (70), as shown in FIG. 10G. Also shown in FIG. 10G is the latching member nose piece (190), an occlusion element (201), and a cap member (200). In system assembly, the needle assembly (180) may be inserted through the off-the-shelf syringe body (34) as shown in FIG. 10G, with the needle distal end (182) threaded through the distal end (144) of the syringe body (34) and the proximal end (196) of the latching feature (192) exposed (it preferably is biased to bend toward the needle distal end 182 into a "flush" configuration for retraction); then the latching feature (192) distal end (196) may be bent outward and fitted into the recess (194) of the latching member nose piece (190), followed by threading of the occlusion element (201) and cap member (200) over the needle distal portion (182), to result in a construct as shown in FIG. 10F. Upon full insertion of a plunger to push the stopper member against the loading plate (188), the needle assembly (180) is inserted just enough to allow the distal end (196) of the latching feature (192) to come out of the recess (194) and snap into the flush position against the needle member (182), which allows the needle assembly (180) to be withdrawn into a safe position relative to the syringe body (34), such as by a spring-loaded mechanism, vacuum load assisting, or manual retraction, as described above. With retraction of the distal tip of the needle distal portion (182) past the occlusion member (201), the occlusion member (201) is configured to become free to move/reorient around inside of the small compartment containing the occlusion member (201), such that it would be quite difficult to realign such occlusion member (201) to allow re-insertion of the needle distal portion (182) past this occlusion member (201); thus the occlusion member (201) functionally occludes the distal needle passageway and functions somewhat akin to the aforementioned slidable door member (94) in preventing reexposure of the needle.

Figure 11A:
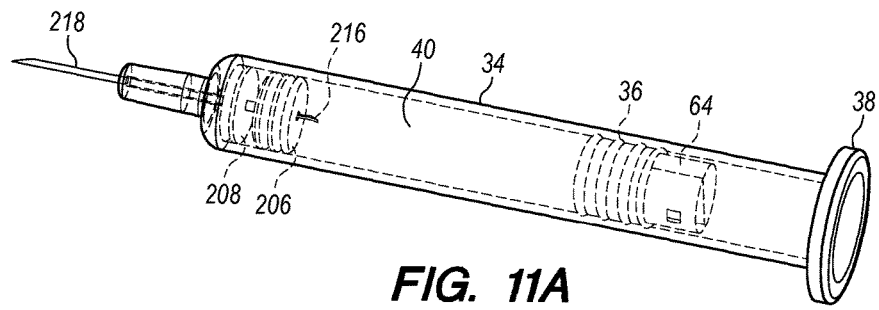
FIGS. 11A-11D illustrate various aspects of a safe injection system wherein a portion of a coupling member may be controllably disrupted to release a needle for retraction to a safe position.
Figure 11B:
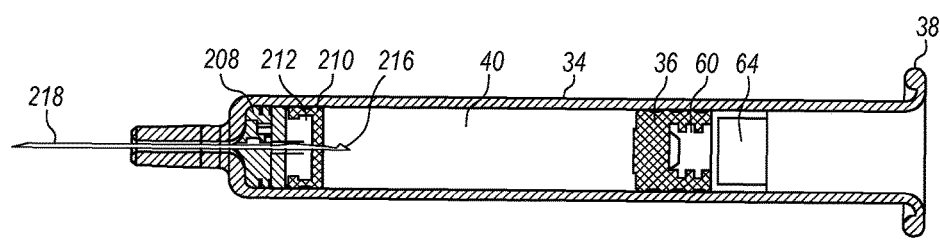
Figure 11C:
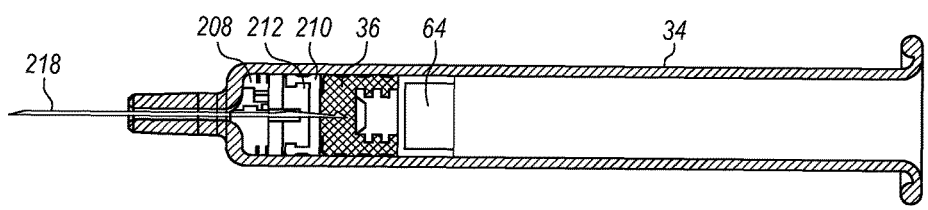
Figure 11D:
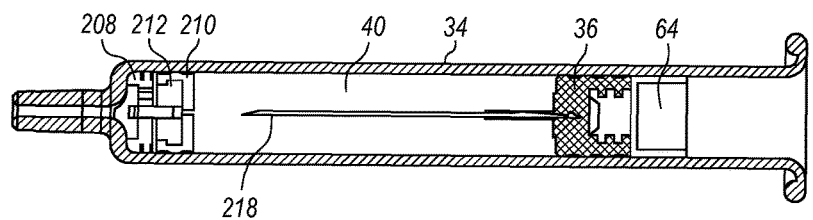

Referring to FIGS. 11A-11D, in another embodiment, one or more structural and/or sealing members may be altered to release a needle from a staked configured to an unstaked configuration wherein it may be withdrawn to a safe position. As shown in FIG. 11A, a needle assembly may comprise a distal portion (218), and a proximal portion (216) coupled to one or more sealing and/or structure members (208, 206) configured to fixedly hold the needle assembly in a staked configuration during injection of medicine into a patient, and then at a full insertion position of the stopper member (36) and plunger (70) relative to the syringe body (34), to release the grasp of the one or more sealing and/or structural members (208, 206) such that the needle member may be withdrawn proximally, leaving the one or more sealing and/or structural members (208, 206) behind. As shown in the cross sectional depiction in FIG. 11B, the needle is in a staked configuration, ready for injection. As shown in FIG. 11C, with the stopper member (36) fully inserted relative to the syringe body (34), the sealing member (208) remains intact, but a portion of the needle assembly fractures or cuts a portion of the composite stabilizing member (206; here comprising a compliant sealing/grasping portion 212 and a more rigid structural portion 210), such as the sealing/grasping portion 212, causing the needle to be axially released relative to the stabilizing member (206), so that it may be retracted (such as is shown in FIG. 11D) into a safe position relative to the syringe body (34), such as by a spring-loaded mechanism, vacuum load assisting, or manual retraction, as described above.

Figure 12A:
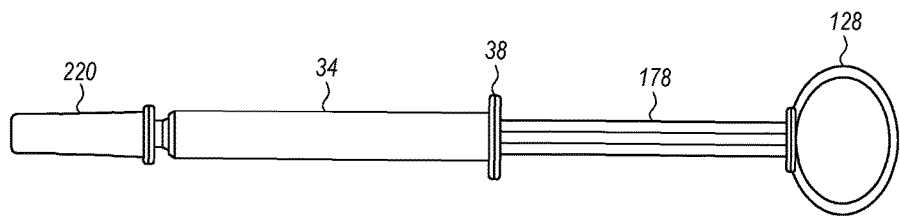
FIGS. 12A-12O illustrate various aspects of a safe injection system wherein a portion of a coupling member may be controllably dilated to release a needle for retraction to a safe position.
Figure 12B:
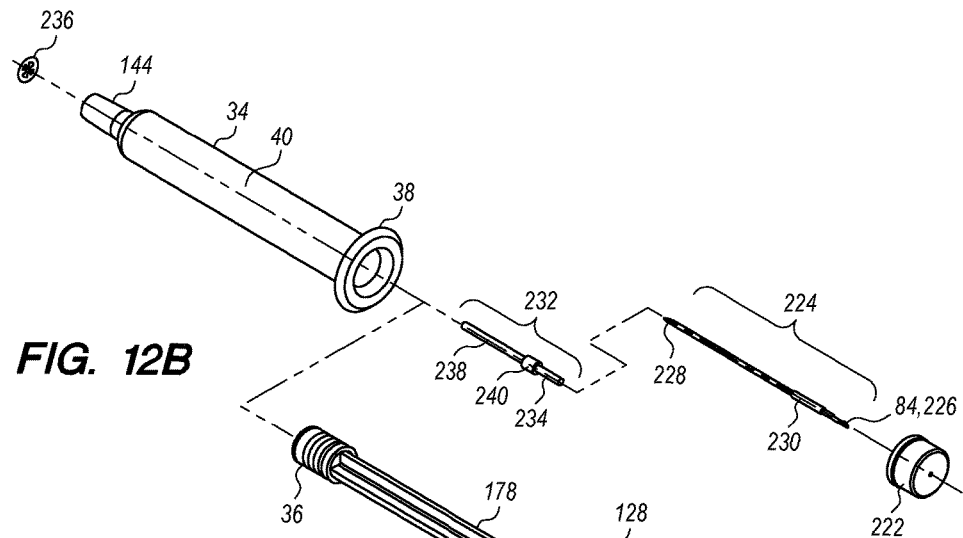
Figure 12C:
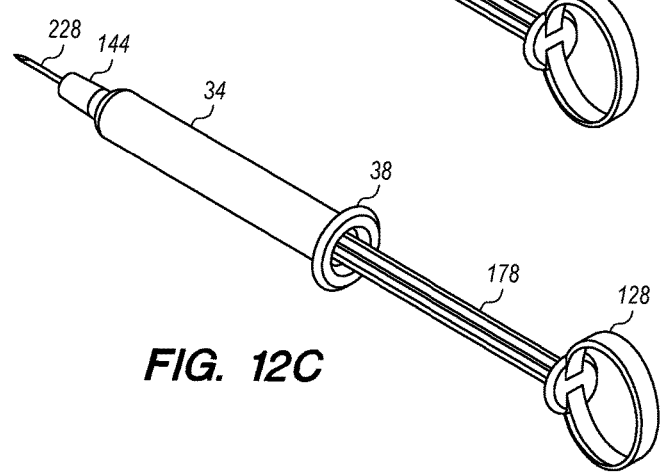
Figure 12D:
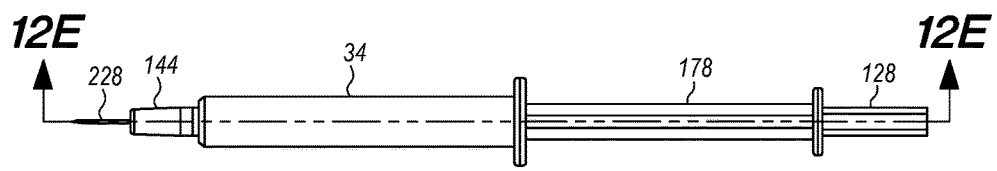
Figure 12E:
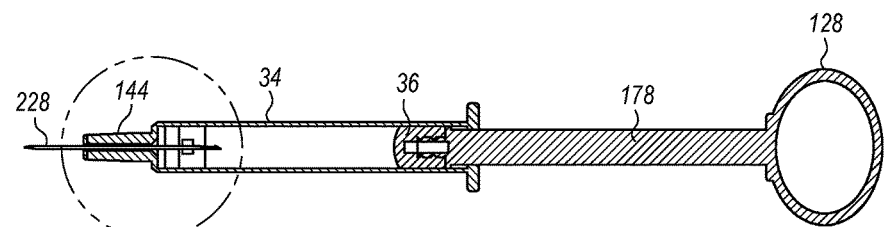
Figure 12F:
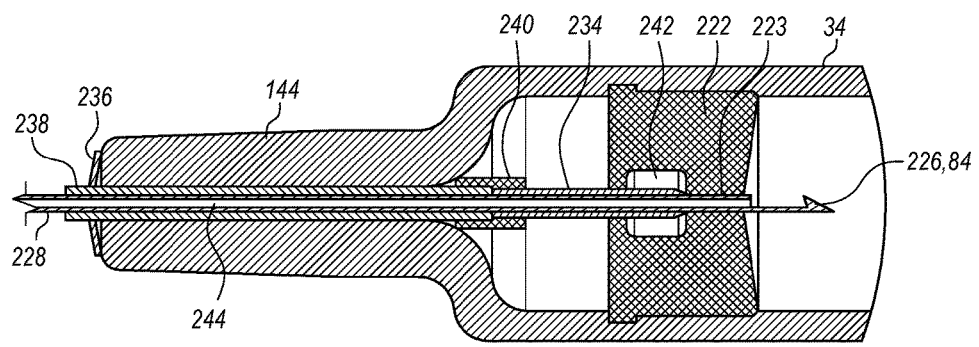
Figure 12G:
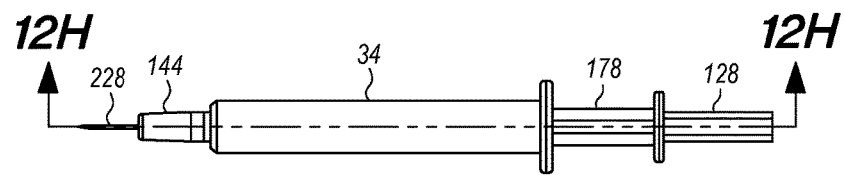
Figure 12H:
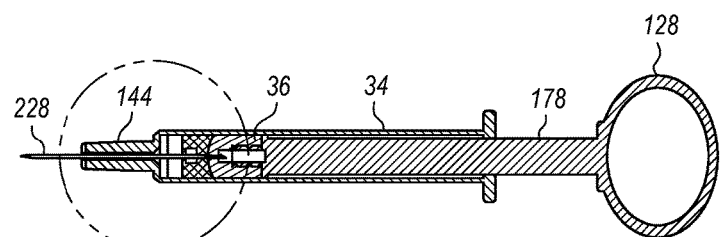
Figure 12I:
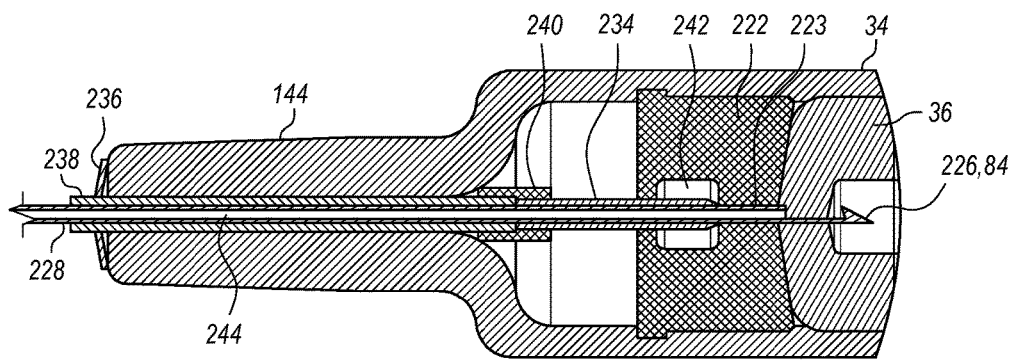
Figure 12J:
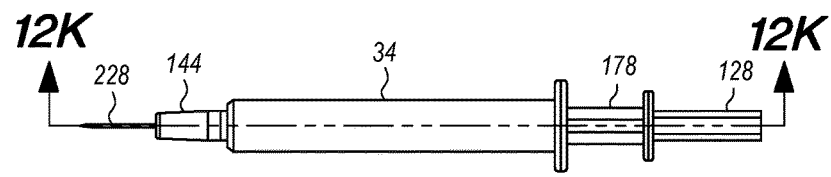
Figure 12K:
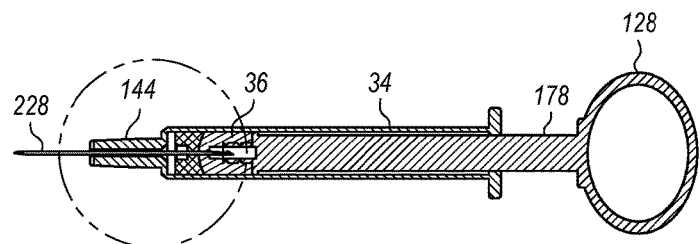
Figure 12L:
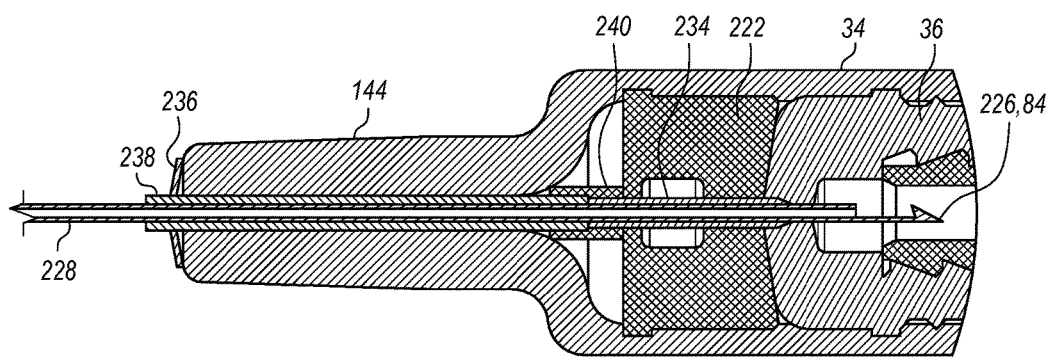
Figure 12M:
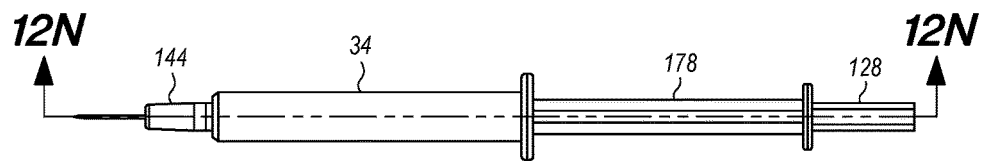
Figure 12N:
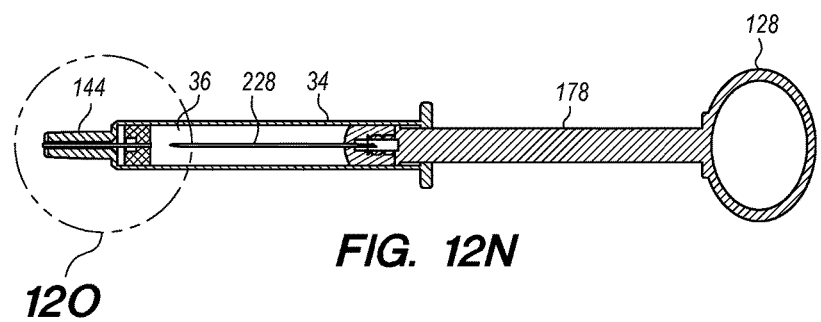
Figure 12O:
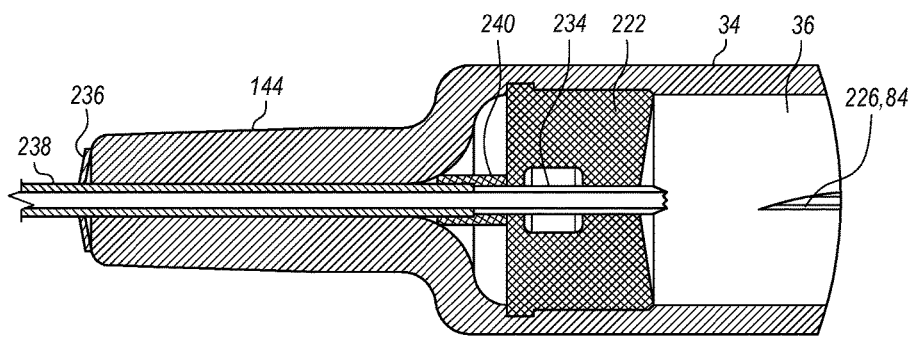
Figure 13A:
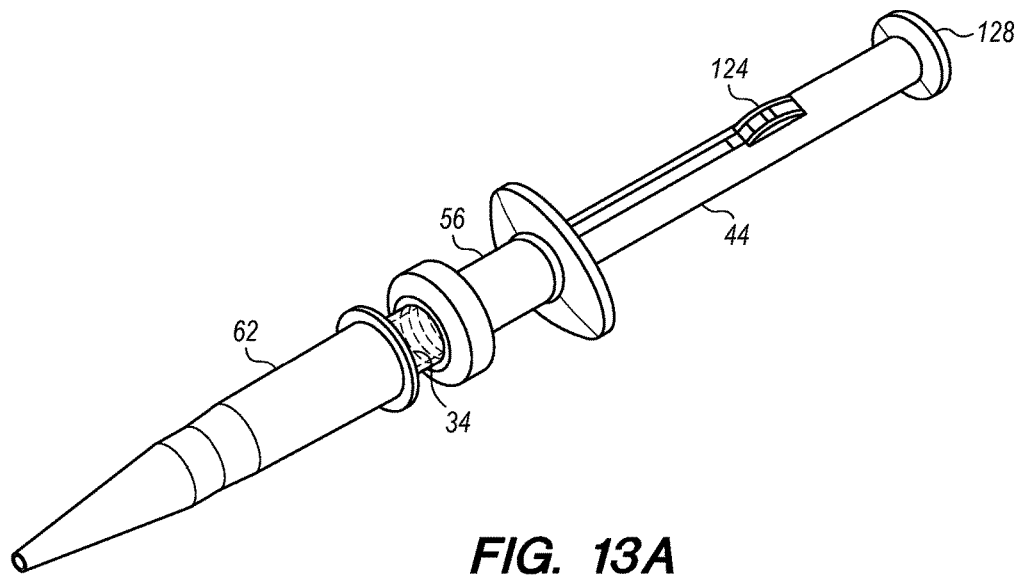
Figure 13B:
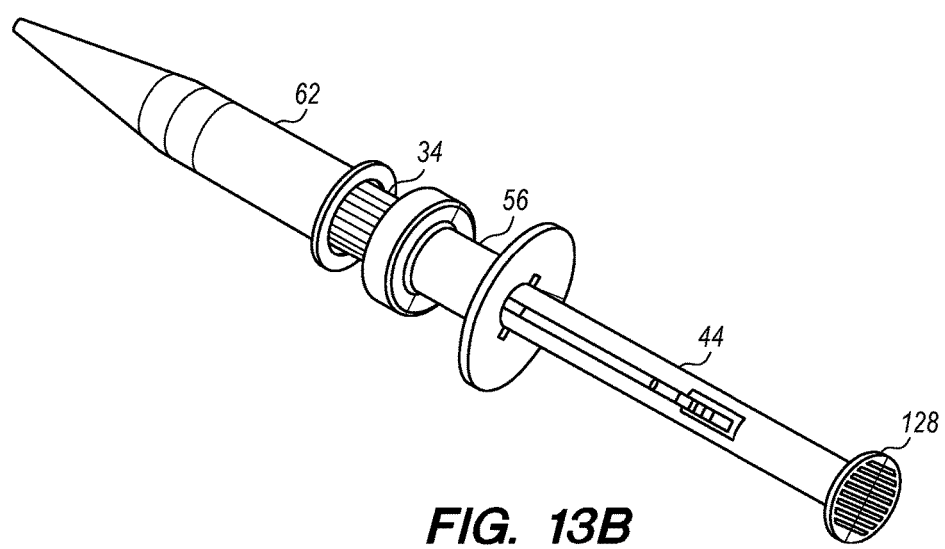
Figure 13C:
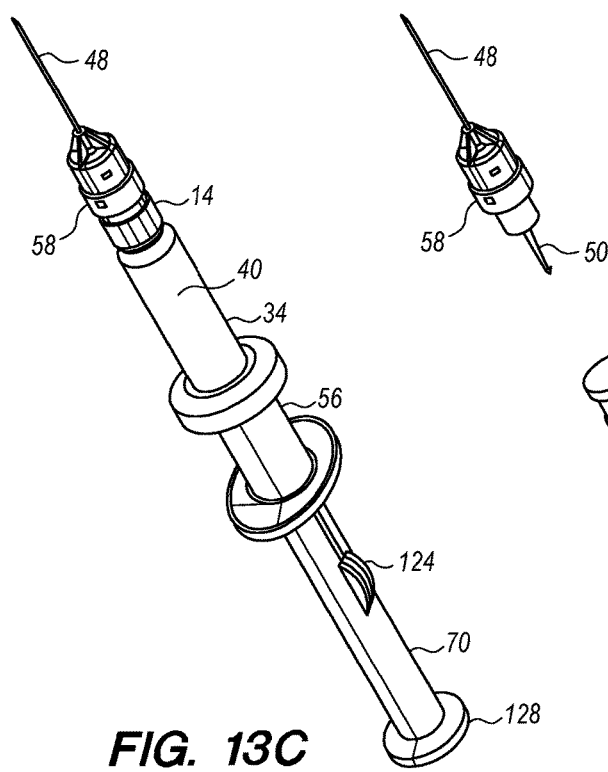
Figure 13D:
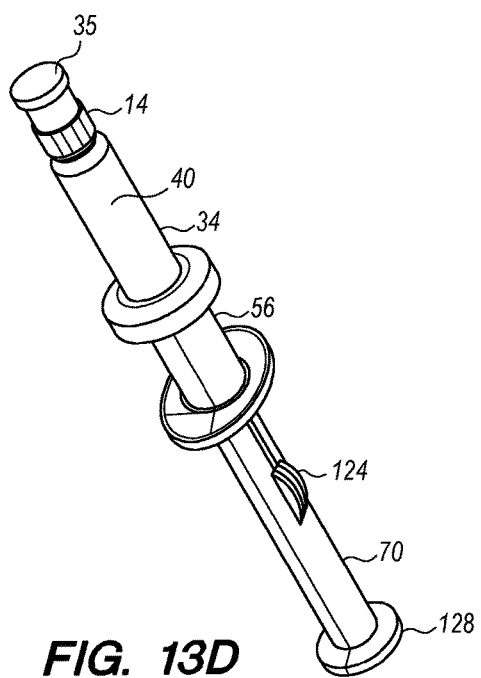
Figure 13E:
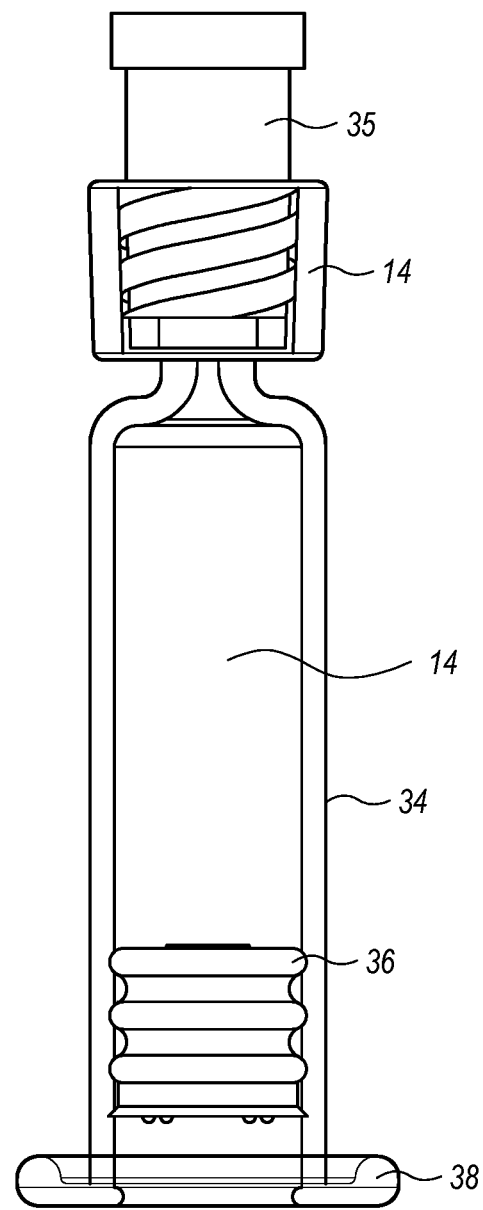
Figure 13F:
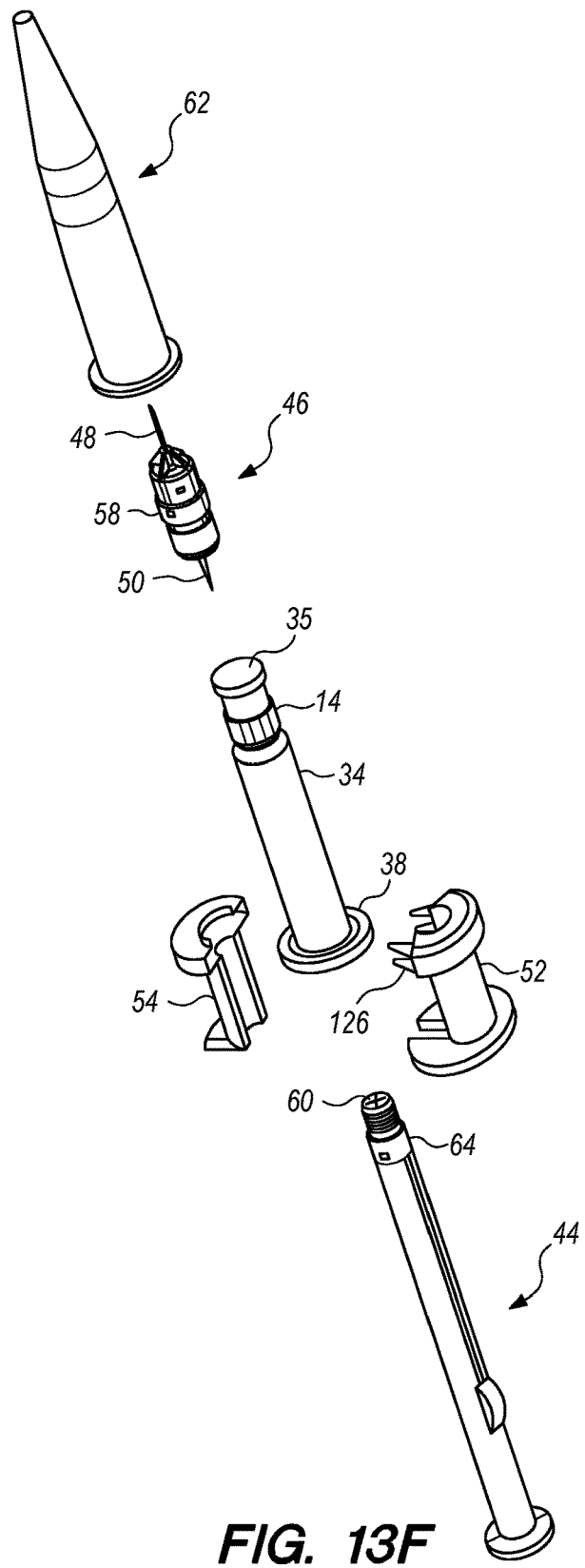
Figure 13G:
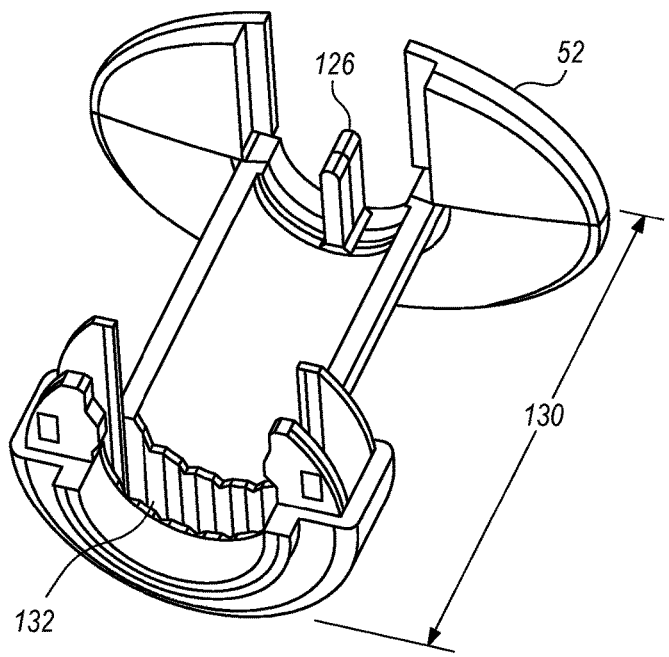
Figure 13H:
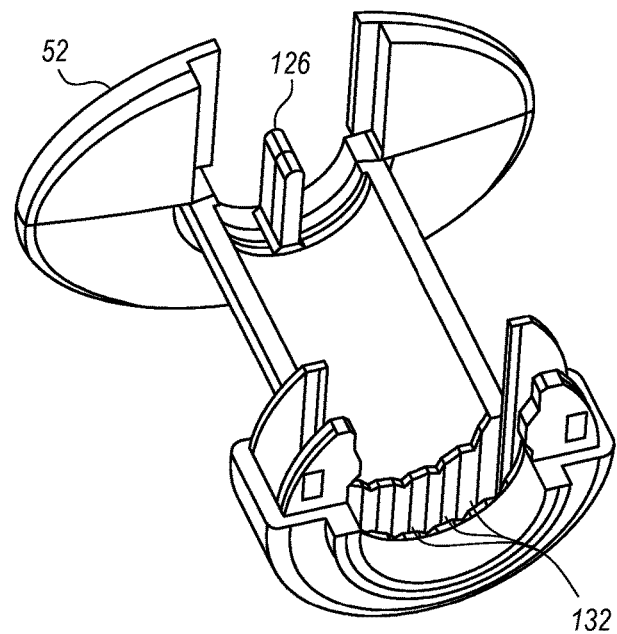
Figure 13I:
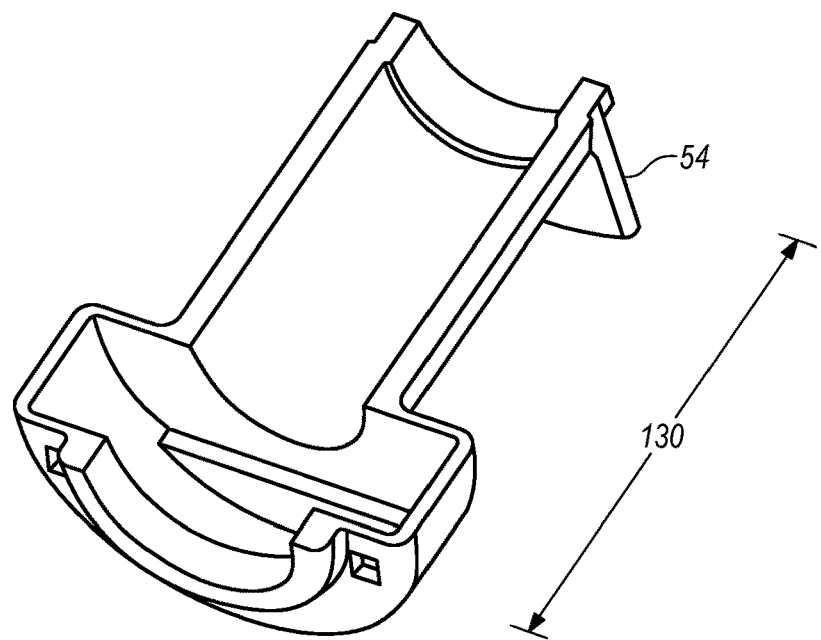
Figure 13J:
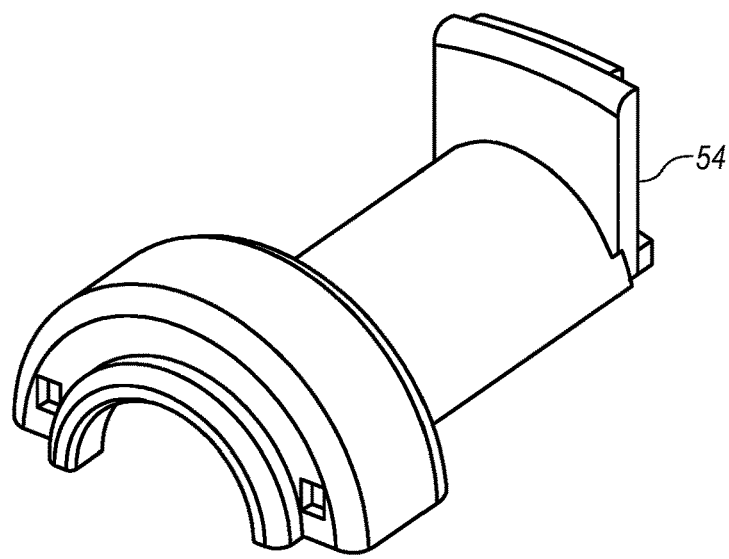
Figure 14A:
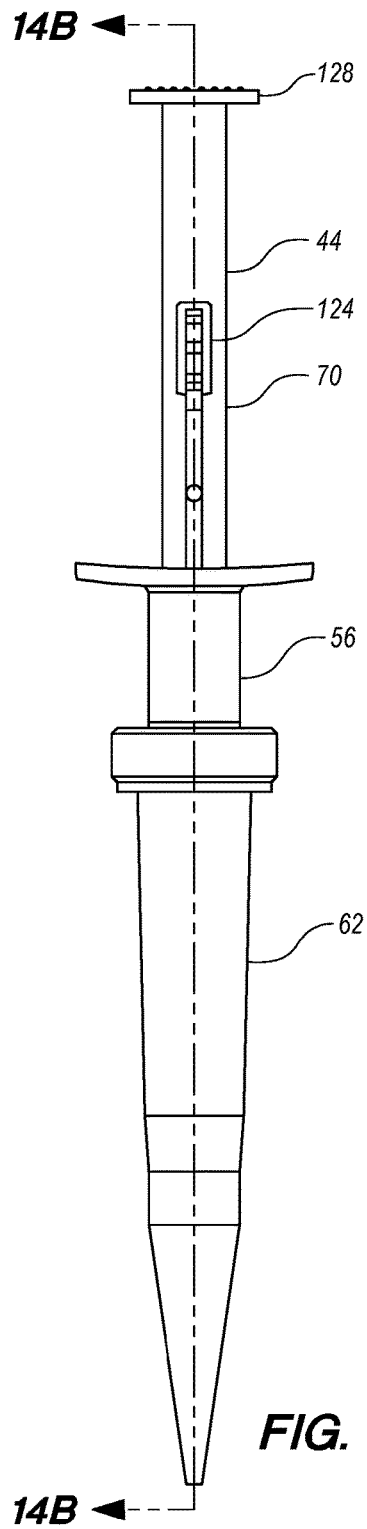
Figure 14B:
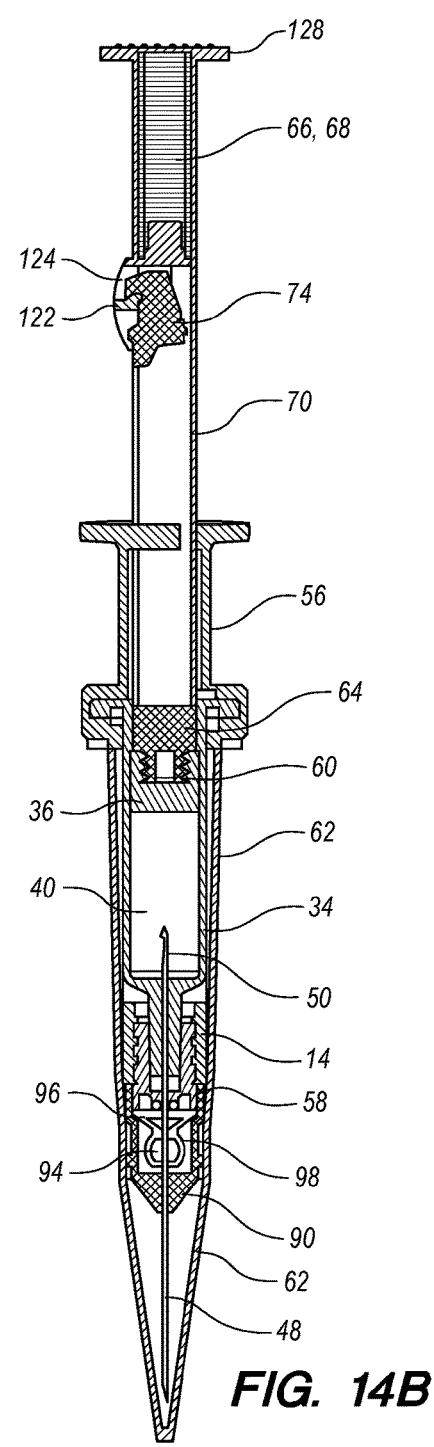

Referring to FIGS. 12A-12O, an embodiment somewhat similar to that of FIGS. 11A-11D is illustrated, wherein a sealing/grasping grommet member (222) is dilated by a dilator portion (234) of a spacer/dilator assembly (232) that is coupled to a needle assembly (224), the dilation converting the grommet from a gripping stabilizing configuration that holds the needle assembly (224) in a "staked" type of configuration for patient injection usage, to an "unstaked" configuration wherein the needle assembly (224) may be withdrawn, such as in FIGS. 12M-12O, into a safe position relative to the syringe body (34), such as by a spring-loaded mechanism, vacuum load assisting, or manual retraction, as described above. FIGS. 12A, 12C, and 12D-12F illustrate a safe injection system ready to use, FIG. 12A also showing a protective needle cap (220) over the needle before use. As shown in FIGS. 12B, 12E, and 12F, the needle assembly (224), comprising a proximal end (226) featuring a harpoon configuration (84), a sharpened distal end (228) for injection into a patient, and a coupling collar (230) to couple the proximal and distal ends, may be inserted through a spacer/dilator assembly (232) featuring a spacer member (238) coupled to a dilator tube (234) by a coupling collar (240); the spacer may be fixedly held against the distal end (144) of the syringe body (34) using a snap ring (236), the needle assembly being slidable through the interior of the spacer/dilator assembly (232) but for the grasping of the grommet member (222) upon the proximal portion (226) of the needle member around the location labelled "223" in FIG. 12F. This grasping is configured to be substantial enough to withstand conventional injection-into-tissue loads, thus placing the needle into a "staked" configuration relative to the syringe body (34). FIGS. 12G-12I illustrate that a plunger and stopper may be inserted to inject medicine into the patient through the injection lumen (244). Referring to FIGS. 12J-12L, with further insertional loading of the plunger and stopper (36) to a fully-seated configuration as shown in detail in FIG. 12L, the dilator tube (234) is advanced across what previously was the grasping region (i.e., as in FIG. 12F), so that the needle is now free to be retracted relative to the spacer/dilator assembly and syringe body, into a safe position relative to the syringe body (34), such as by a spring-loaded mechanism, vacuum load assisting, or manual retraction, as described above, as shown in FIGS. 12M-12O.

Suitable polymeric materials for the various components of these embodiments include but are not limited to acetal, polycarbonate, poly vinyl chloride, polypropylene, polystyrene, ABS, nylon, glass-filled nylon, glass-filled acetal, peek, glass-filled peek, carbon-fiber-filled peek, COC (cyclic olefin copolymer), COP (cyclic olefin polymer), PEI (Ultem), glass-filled PEI, and pekk, as well as copolymers thereof.

Suitable structural metals for structures such as the plunger insertion member include but are not limited to stainless steel, steel with chrome coating, brass, nickel, and titanium, as well as alloys thereof.

Suitable needle member sizes range from about 34 gauge/6 millimeters long—to about 20 gauge/2.5 inches long.

Referring to FIGS. 15-37, processes for conducting injection procedures utilizing safe injection configurations such as those described in reference to FIGS. 6A-12O are illustrated.

Figure 15:
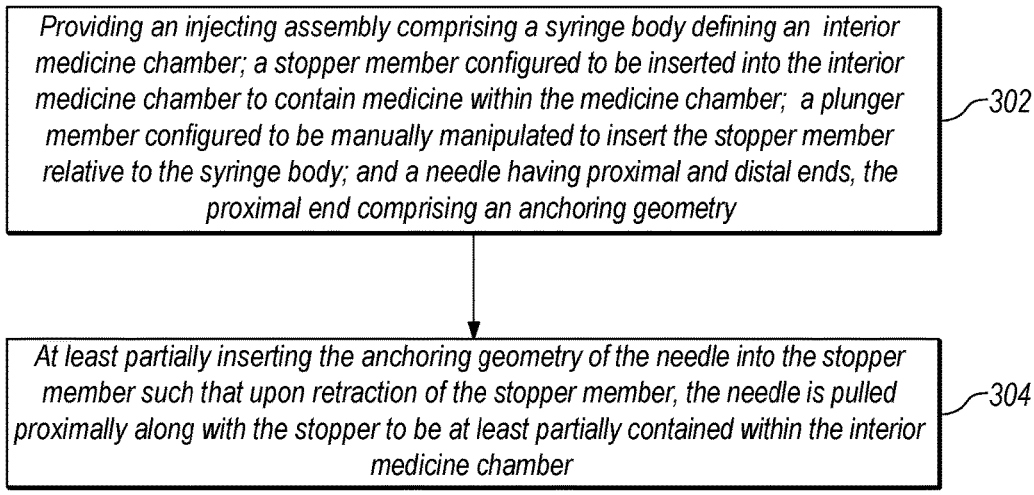

Referring to FIG. 15, one method may comprise providing (302) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends, the proximal end comprising an anchoring geometry; and (304) at least partially inserting the anchoring geometry of the needle into the stopper member such that upon retraction of the stopper member, the needle is pulled proximally along with the stopper to be at least partially contained within the interior medicine chamber.

Figure 16:
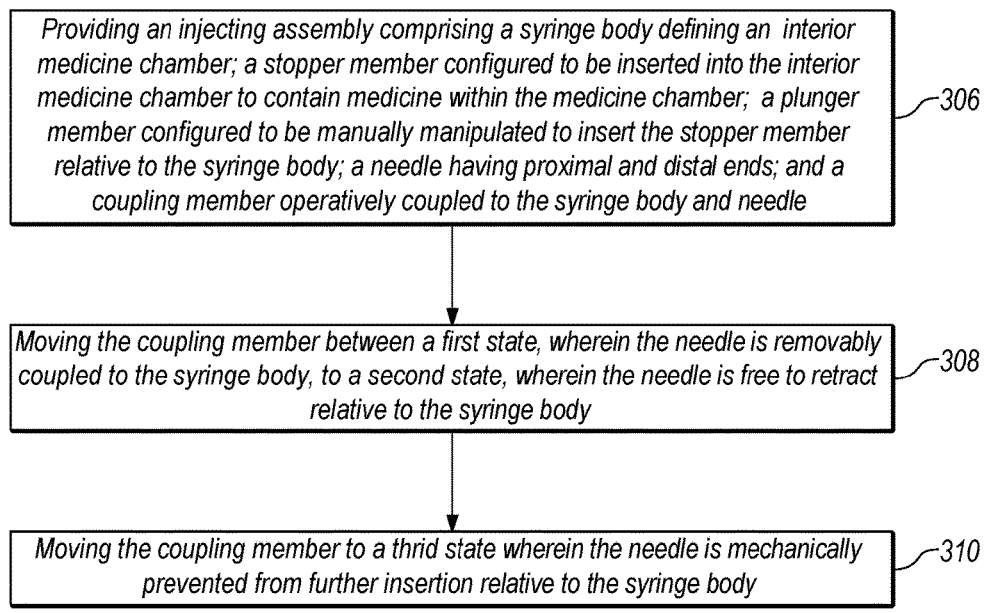

Referring to FIG. 16, one method may comprise providing (306) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends; and a coupling member operatively coupled to the syringe body and needle; and (308) moving the coupling member between a first state, wherein the needle is removably coupled to the syringe body, to a second state, wherein the needle is free to retract relative to the syringe body; and (310) moving the coupling member to a third state wherein the needle is mechanically prevented from further insertion relative to the syringe body.

Referring to FIG. 17, one method may comprise providing (312) an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having proximal and distal ends, the proximal end configured to be coupled to the stopper member upon insertion of the stopper member to a fully-inserted position, such that upon retraction of the stopper member, the needle is pulled proximally along with the stopper to be contained within the interior medicine chamber; and (314) upon retraction of the needle into the interior medicine chamber to a position wherein the distal end of the needle is contained within the interior medicine chamber, misaligning the needle with a longitudinal axis of the syringe body such that it is prevented from being reinserted out of the interior medicine chamber; and (316) configuring the needle to plastically deform (such as by bending of at least one portion of the needle) upon attempt to re-insert the needle relative to the syringe body after the needle becomes misaligned with a longitudinal axis of the syringe body.

Referring to FIG. 18A, one method may comprise providing (318) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having a sharpened distal end; and a needle door member movably coupled the syringe body; and (320) moving the needle door member from a first state wherein the needle door member facilitates insertion of the needle relative to the syringe body, to a second state wherein the needle door member prevents insertion of the needle relative to the syringe body; and (322) slidably moving the needle door member in a plane relative to the longitudinal axis of the needle (such as a plane that is substantially perpendicular relative to the longitudinal axis of the needle).

Figure 18B:
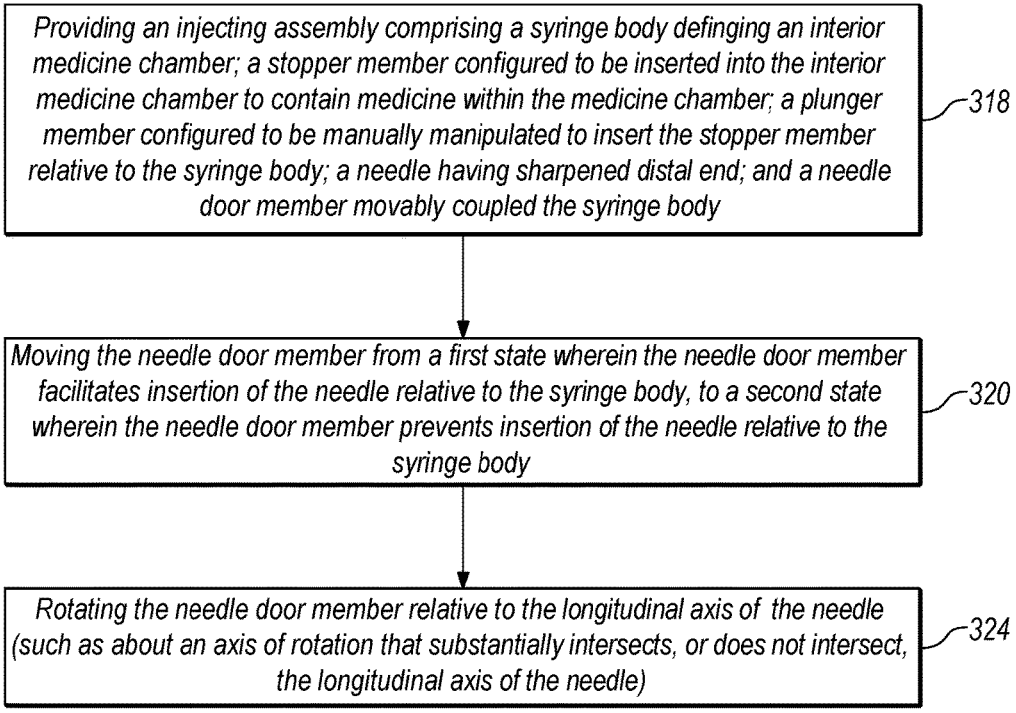

Referring to FIG. 18B, one method may comprise providing (318) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having a sharpened distal end; and a needle door member movably coupled the syringe body; and (320) moving the needle door member from a first state wherein the needle door member facilitates insertion of the needle relative to the syringe body, to a second state wherein the needle door member prevents insertion of the needle relative to the syringe body; and (324) rotating the needle door member relative to the longitudinal axis of the needle (such as about an axis of rotation that substantially intersects, or does not intersect, the longitudinal axis of the needle).

Figure 19:
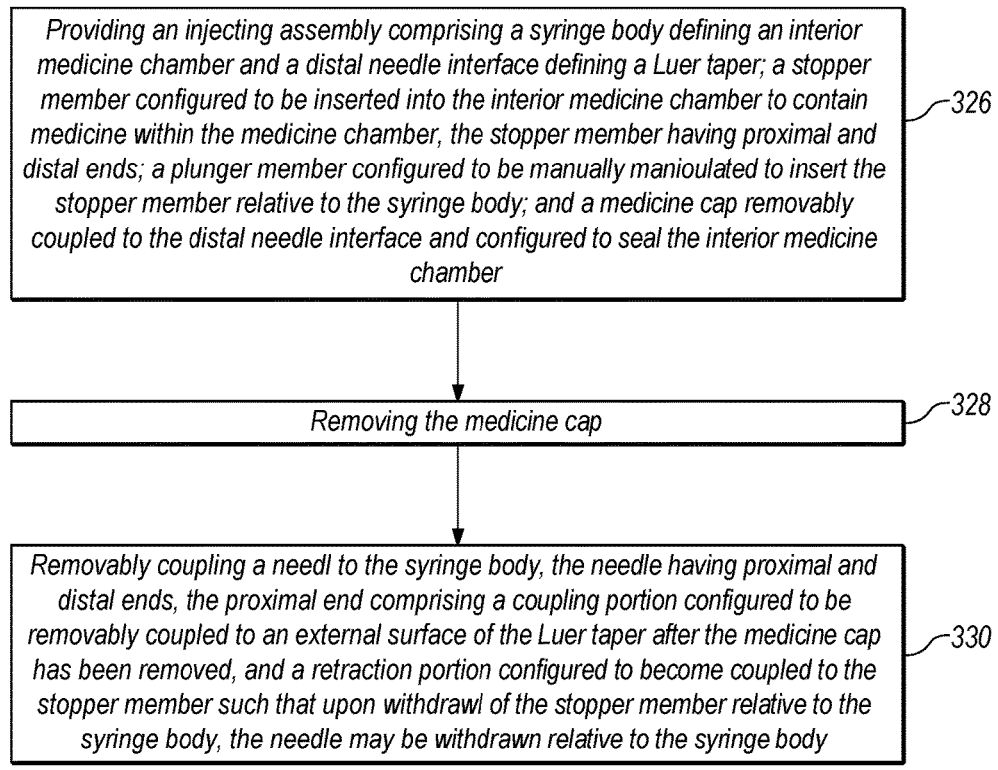

Referring to FIG. 19, one method may comprise providing (326) an injecting assembly comprising a syringe body defining an interior medicine chamber and a distal needle interface defining a Luer taper; a stopper member configured to be inserted into the interior medicine chamber to contain medicine within the medicine chamber, the stopper member having proximal and distal ends; a plunger member configured to be manually manipulated to insert the stopper member relative to the syringe body; and a medicine cap removably coupled to the distal needle interface and configured to seal the interior medicine chamber; and (328) removing the medicine cap; and (330) removably coupling a needle to the syringe body, the needle having proximal and distal ends, the proximal end comprising a coupling portion configured to be removably coupled to an external surface of the Luer taper after the medicine cap has been removed, and a retraction portion configured to become coupled to the stopper member such that upon withdrawal of the stopper member relative to the syringe body, the needle may be withdrawn relative to the syringe body.

Figure 20:
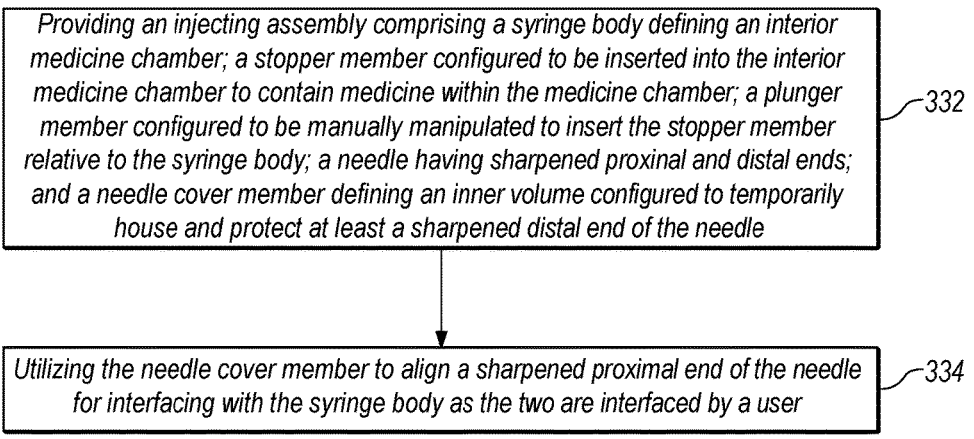

Referring to FIG. 20, one method may comprise providing (332) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having sharpened proximal and distal ends; and a needle cover member defining an inner volume configured to temporarily house and protect at least a sharpened distal end of the needle; and (334) utilizing the needle cover member to align a sharpened proximal end of the needle for interfacing with the syringe body as the two are interfaced by a user.

Figure 21:
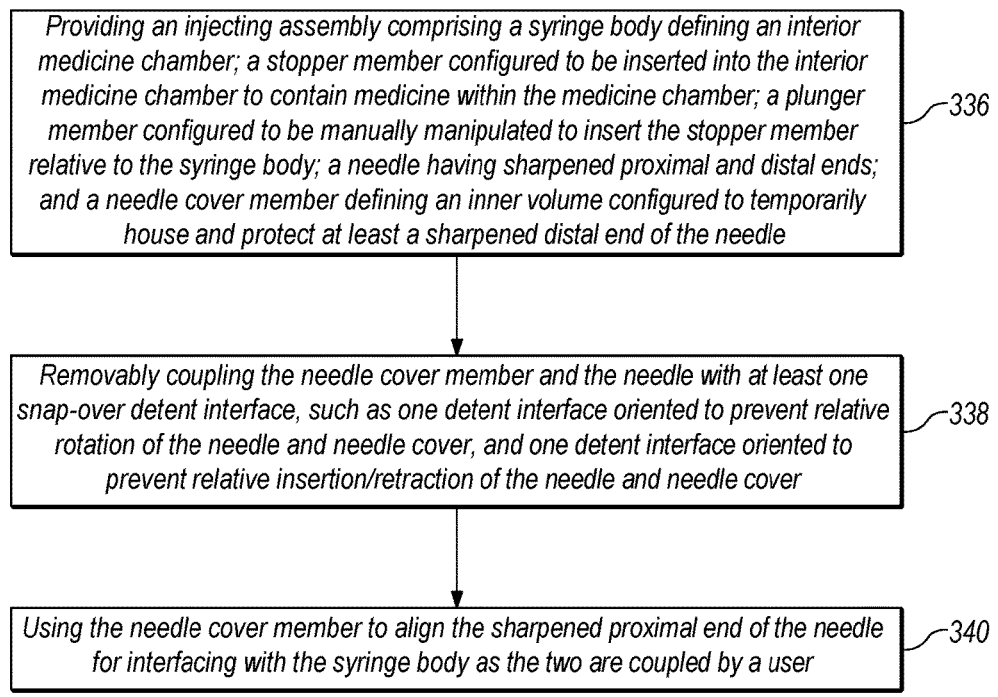

Referring to FIG. 21, one method may comprise providing (336) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having sharpened proximal and distal ends; and a needle cover member defining an inner volume configured to temporarily house and protect at least a sharpened distal end of the needle; and (338) removably coupling the needle cover member and the needle with at least one snap-over detent interface, such as one detent interface oriented to prevent relative rotation of the needle and needle cover, and one detent interface oriented to prevent relative insertion/retraction of the needle and needle cover; and (340) using the needle cover member to align the sharpened proximal end of the needle for interfacing with the syringe body as the two are coupled by a user.

Figure 22:
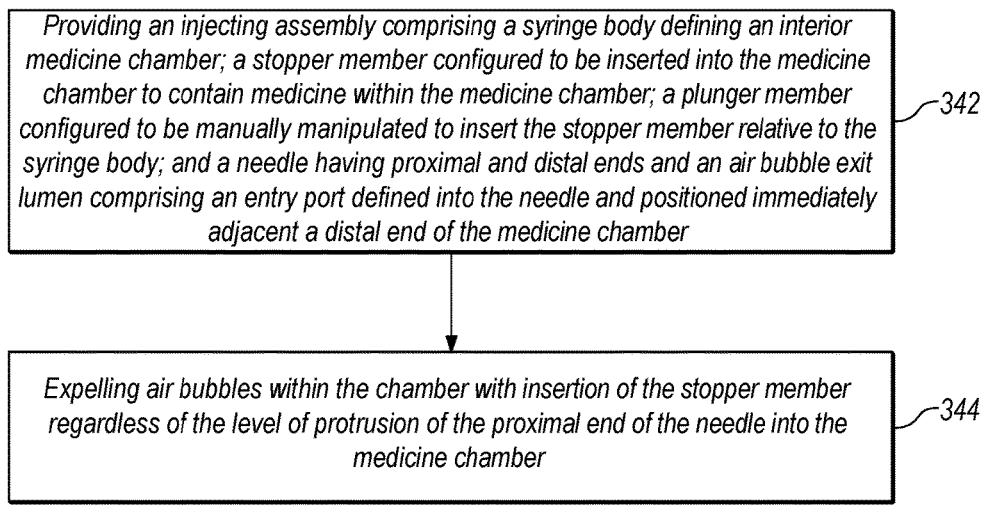

Referring to FIG. 22, one method may comprise providing (342) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends and an air bubble exit lumen defined therebetween, the air bubble exit lumen comprising an entry port defined into the needle and positioned immediately adjacent a distal end of the medicine chamber; and (344) expelling air bubbles within the chamber with insertion of the stopper member regardless of the level of protrusion of the proximal end of the needle into the medicine chamber.

Figure 23:
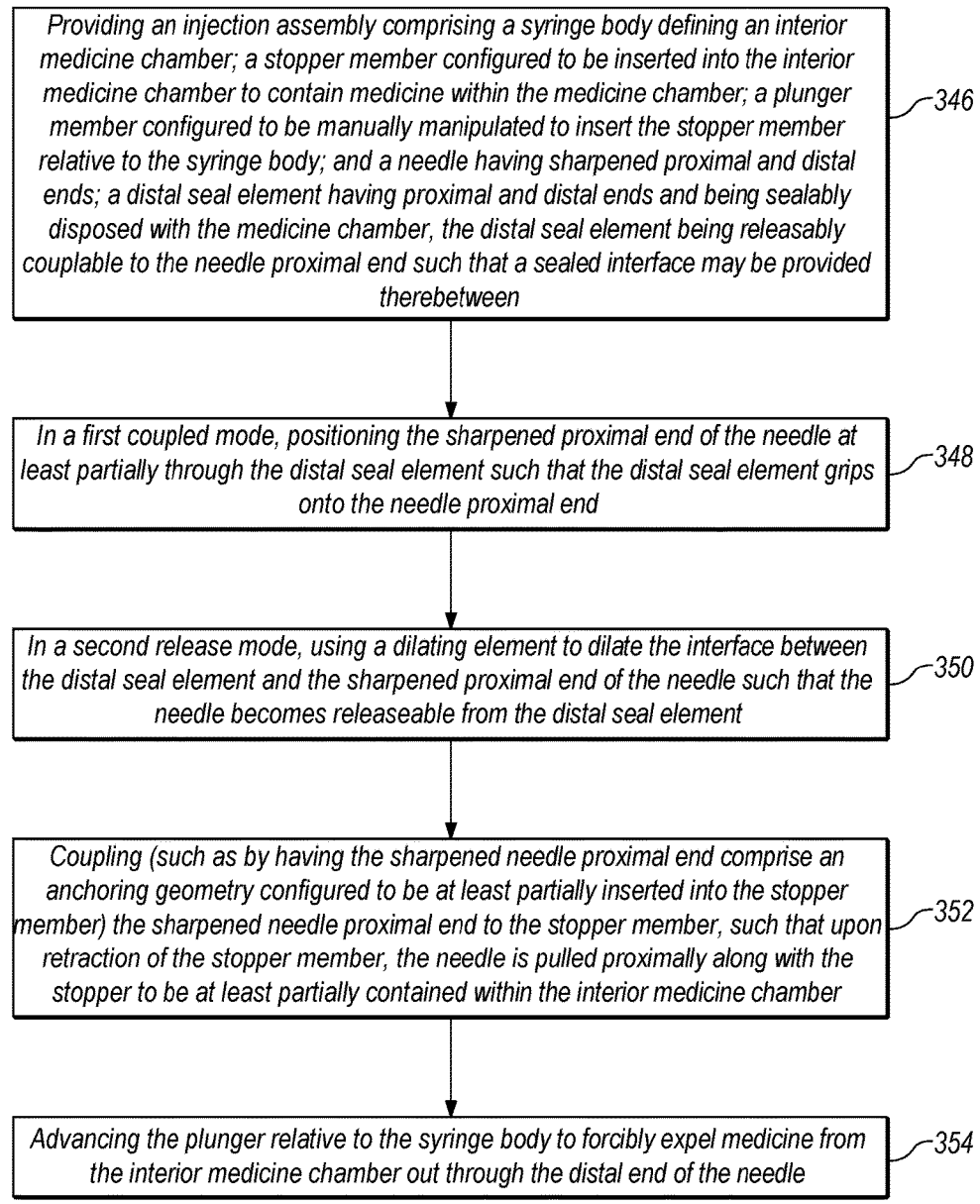

Referring to FIG. 23, one method may comprise providing (346) an injection assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having sharpened proximal and distal ends; a distal seal element having proximal and distal ends and being sealably disposed within the medicine chamber, the distal seal element being releasably couplable to the needle proximal end such that a sealed interface may be provided therebetween; and (348) in a first coupled mode, positioning the sharpened proximal end of the needle at least partially through the distal seal element such that the distal seal element grips onto the needle proximal end; and (350) in a second release mode, using a dilating element to dilate the interface between the distal seal element and the sharpened proximal end of the needle such that the needle becomes releasable from the distal seal element; and (352) coupling (such as by having the sharpened needle proximal end comprise an anchoring geometry configured to be at least partially inserted into the stopper member) the sharpened needle proximal end to the stopper member, such that upon retraction of the stopper member, the needle is pulled proximally along with the stopper to be at least partially contained within the interior medicine chamber; and (354) advancing the plunger relative to the syringe body to forcibly expel medicine from the interior medicine chamber out through the distal end of the needle.

Figure 24:
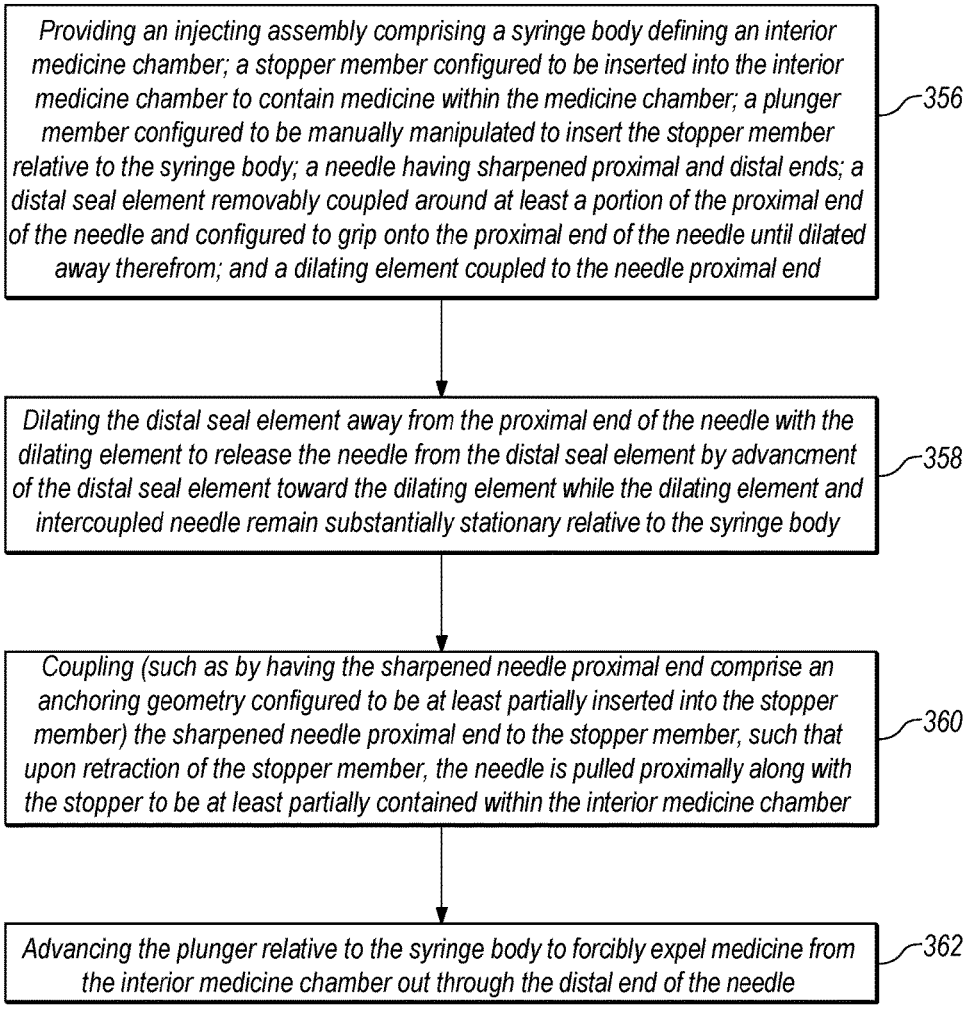

Referring to FIG. 24, one method may comprise providing (356) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having sharpened proximal and distal ends; a distal seal element removably coupled around at least a portion of the proximal end of the needle and configured to grip onto the proximal end of the needle until dilated away therefrom; and a dilating element coupled to the needle proximal end; and (358) dilating the distal seal element away from the proximal end of the needle with the dilating element to release the needle from the distal seal element by advancement of the distal seal element toward the dilating element while the dilating element and intercoupled needle remain substantially stationary relative to the syringe body; and (360) coupling (such as by having the sharpened needle proximal end comprise an anchoring geometry configured to be at least partially inserted into the stopper member) the sharpened needle proximal end to the stopper member, such that upon retraction of the stopper member, the needle is pulled proximally along with the stopper to be at least partially contained within the interior medicine chamber; and (362) advancing the plunger relative to the syringe body to forcibly expel medicine from the interior medicine chamber out through the distal end of the needle.

Referring to FIG. 25, one method may comprise providing (364) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end coupled to a distal end of the syringe body; and a needle sheath operatively coupled to the syringe body and defining a lumen through which at least the distal end of the needle may be passed, the needle sheath configured to have a first state, wherein the needle sheath is compressed toward the proximal end of the needle to expose the distal end of the needle for injecting, and a second state, wherein the needle sheath is advanced forward over the needle distal end to substantially cover the needle and prevent contact with the distal end of the needle; wherein in the first state, an energy storage member (such as a spring) is compressed to bias the needle sheath to spring forward into the second state but for a sheath retention element which retains the needle sheath in the first position until the stopper member has been advanced to a predetermined position relative to the syringe body (such as one wherein the stopper member has been advanced to a maximum advancement position relative to the syringe body; at the predetermined position, the plunger may apply a load against the needle, which may release the sheath retention element); and (366) advancing the stopper member into the predetermined position relative to the syringe body to cause the needle sheath to be advanced forward over the needle distal end; and (368) using a sheath-limiting member to restrain the needle sheath from advancing in the second state past a predetermined axial extension position relative to the syringe body.

Referring to FIG. 26, one method may comprise providing (370) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end coupled to a distal end of the syringe body; and a telescoping needle sheath operatively coupled to the syringe body and defining a lumen through which at least the distal end of the needle may be passed, the needle sheath configured to have a first state, wherein the telescoping needle sheath is telescopically compressed toward the proximal end of the needle to expose the distal end of the needle for injecting, and a second state, wherein the needle sheath is telescopically advanced forward over the needle distal end to substantially cover the needle and prevent contact with the distal end of the needle; wherein in the first state, an energy storage member (such as a spring) is compressed to bias the needle sheath to spring forward into the second state but for a sheath retention element which retains the needle sheath in the first position until the stopper member has been advanced to a predetermined position relative to the syringe body (such as one wherein the stopper member has been advanced to a maximum advancement position relative to the syringe body; at the predetermined position, the plunger may apply a load against the needle, which may release the sheath retention element); and (372) advancing the stopper member into the predetermined position relative to the syringe body to cause the needle sheath to be telescopically advanced forward over the needle distal end; and (374) using a sheath-limiting member to restrain the needle sheath from advancing in the second state past a predetermined axial extension position relative to the syringe body.

Figure 27:
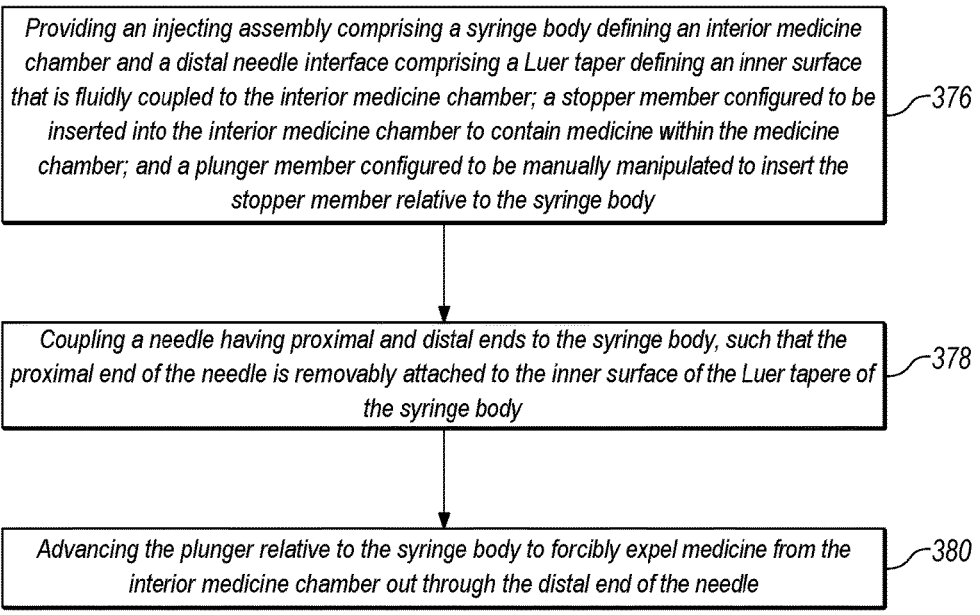

Referring to FIG. 27, one method may comprise providing (376) an injecting assembly comprising a syringe body defining an interior medicine chamber and a distal needle interface comprising a Luer taper defining an inner surface that is fluidly coupled to the interior medicine chamber; a stopper member configured to be inserted into the interior medicine chamber to contain medicine within the medicine chamber; and a plunger member configured to be manually manipulated to insert the stopper member relative to the syringe body; and (378) coupling a needle having proximal and distal ends to the syringe body, such that the proximal end of the needle is removably attached to the inner surface of the Luer tapere of the syringe body; and (380) advancing the plunger relative to the syringe body to forcibly expel medicine from the interior medicine chamber out through the distal end of the needle.

Figure 28:
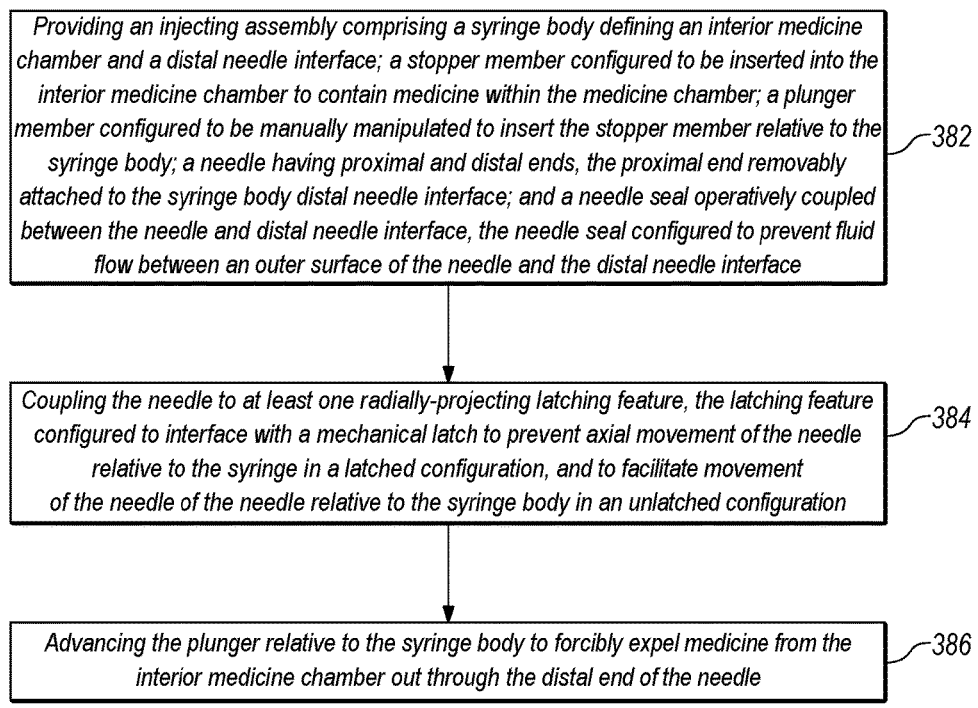

Referring to FIG. 28, one method may comprise providing (382) an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; a needle having proximal and distal ends, the proximal end removably attached to the syringe body distal needle interface; and a needle seal operatively coupled between the needle and distal needle interface, the needle seal configured to prevent fluid flow between an outer surface of the needle and the distal needle interface; and (384) coupling the needle to at least one radially-projecting latching feature, the latching feature configured to interface with a mechanical latch to prevent axial movement of the needle relative to the syringe in a latched configuration, and to facilitate movement of the needle of the needle relative to the syringe body in an unlatched configuration; and (386) advancing the plunger relative to the syringe body to forcibly expel medicine from the interior medicine chamber out through the distal end of the needle.

Figure 29:
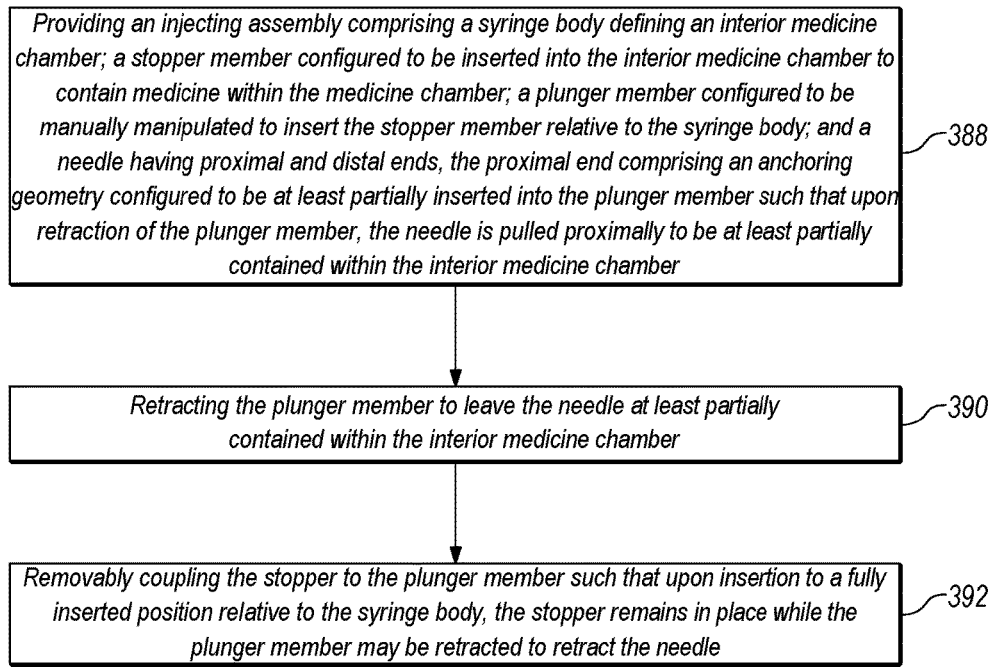

Referring to FIG. 29, one method may comprise providing (388) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; and a needle having proximal and distal ends, the proximal end comprising an anchoring geometry configured to be at least partially inserted into the plunger member such that upon retraction of the plunger member, the needle is pulled proximally to be at least partially contained within the interior medicine chamber; and (390) retracting the plunger member to leave the needle at least partially contained within the interior medicine chamber; and (392) removably coupling the stopper to the plunger member such that upon insertion to a fully inserted position relative to the syringe body, the stopper remains in place while the plunger member may be retracted to retract the needle.

Referring to FIG. 30, one method may comprise providing (394) an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having proximal and distal ends, the proximal end being removably coupled to the distal needle interface of the syringe body and at least partially retractable into the interior medicine chamber; and (396) manipulating the plunger member relative to the syringe body to transform a plunger latching member from a latched state to an unlatched state, the plunger latching member intercoupled between the syringe body and the plunger member, wherein the plunger latching member is substantially disposed within a lumen defined by the plunger member.

Referring to FIG. 31, one method may comprise providing (398) an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having proximal and distal ends, the proximal end being removably coupled to the distal needle interface of the syringe body and at least partially retractable into the interior medicine chamber; and (400) manipulating the plunger member relative to the syringe body to transform a plunger latching member from a latched state to an unlatched state, the plunger latching member slidably and rotatably intercoupled between the syringe body and the plunger member such that upon substantially full insertion of the plunger member relative to the syringe member, the plunger latch member is axially moved and also rotated to convert from the latched state to the unlatched state, and also to allow the plunger member to insert the stopper member to a full insertion position wherein substantially all of the contents of the interior medicine chamber may be expelled out of the needle.

Referring to FIG. 32, one method may comprise providing (402) providing an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body using a proximal manipulation interface; a spring member disposed within a lumen defined through the plunger member; a needle having proximal and distal ends, the proximal end being removably coupled to the distal needle interface of the syringe body and at least partially retractable into the interior medicine chamber; and (404) manipulating the plunger member relative to the syringe body to transform a plunger latching member from a latched state to an unlatched state, the plunger latching member intercoupled between the syringe body and the plunger member; wherein the plunger latching member is substantially disposed within the plunger member lumen and coupled to the spring member such that the spring member is compressed more in the latched state than it is in the unlatched state; and wherein the proximal manipulation interface is configured to facilitate manual engagement to control a rate of plunger member retraction in the unlatched state.

Referring to FIG. 33, one method may comprise providing (406) an injecting assembly comprising a syringe body defining an interior medicine chamber and a distal needle interface; a stopper member configured to be inserted into the interior medicine chamber to contain medicine within the medicine chamber; a plunger member configured to be manually manipulated to insert the stopper member relative to the syringe body; and a needle having a proximal end and a sharpened distal end, the proximal end being removably coupled to the distal needle interface of the syringe body and at least partially retractable into the interior medicine chamber; and (408) manipulating the plunger member relative to the syringe body to transform a plunger latching member from a latched state to an unlatched state, the plunger latching member intercoupled between the syringe body and the plunger member; wherein the plunger latching member is substantially disposed within a lumen defined by the plunger member; and wherein in the unlatched state, the plunger member is at least partially prevented from being re-inserted relative to the syringe body by one or more toothlike structures comprising the plunger latching member which are configured to prevent movement of the plunger member syringe body.

Referring to FIG. 34, one method may comprise providing (410) providing an injecting assembly comprising a syringe body defining an interior medicine chamber; a stopper member configured to be inserted into the interior medicine chamber to contain medicine within the medicine chamber; a plunger member configured to be coupled to the stopper member, and to insert the stopper member relative to the syringe body; and a needle having proximal and distal ends, the proximal end comprising an anchoring geometry configured to be at least partially inserted into the stopper member; and (412) retracting the stopper member to pull the needle proximally along with the stopper to be at least partially contained within the interior medicine chamber; wherein the stopper member defines a threaded proximal interface, and wherein the plunger member has a distal threaded interface configured to be helically coupled into the threaded proximal interface of the stopper member, the distal threaded interface being purposely undersized relative to the threaded proximal interface of the stopper member, such that upon such helical coupling, an outer geometry of the stopper member is not substantially increased by virtue of the helical intercoupling between the stopper member and plunger member distal threaded interface.

Figure 35:
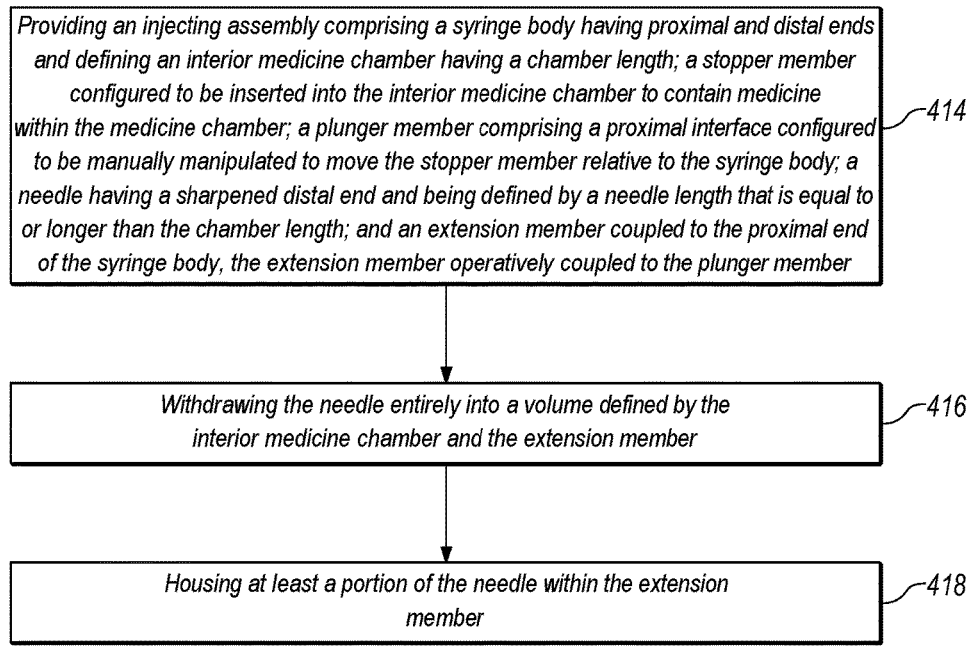

Referring to FIG. 35, one method may comprise providing (414) an injecting assembly comprising a syringe body having proximal and distal ends and defining an interior medicine chamber having a chamber length; a stopper member configured to be inserted into the interior medicine chamber to contain medicine within the medicine chamber; a plunger member comprising a proximal interface configured to be manually manipulated to move the stopper member relative to the syringe body; a needle having a sharpened distal end and being defined by a needle length that is equal to or longer than the chamber length; and an extension member coupled to the proximal end of the syringe body, the extension member operatively coupled to the plunger member; and (416) withdrawing the needle entirely into a volume defined by the interior medicine chamber and the extension member; and (418) housing at least a portion of the needle within the extension member.

Referring to FIG. 36, one method may comprise providing (420) an injecting assembly comprising a syringe body defining an interior medicine chamber; a stopper member configured to be inserted into the interior medicine chamber to contain medicine within the medicine chamber; a plunger member configured to be manually manipulated to insert the stopper member relative to the syringe body; a needle having proximal and distal ends, the proximal end comprising an anchoring geometry configured to be at least partially inserted into the stopper member such that upon retraction of the stopper member, the needle is pulled proximally along with the stopper to be at least partially contained within the interior medicine chamber; a first imaging marker (such as a metallic bead, metallic ring, or a radiation-emitting beacon) coupled to a first known location on the needle; and a second imaging marker (such as a metallic bead, metallic ring, or a radiation-emitting beacon) coupled to a second known location on the needle; and (422) utilizing an imaging system to detect the positions of the first and second imaging markers such that the orientation of the needle may be determined relative to a global coordinate system.

Referring to FIG. 37, one method may comprise providing (424) an injecting assembly comprising a syringe body having proximal and distal ends and defining an interior medicine chamber; a stopper member configured to be inserted into the interior medicine chamber to contain medicine within the medicine chamber, the stopper member comprising a distal surface configured to be directly interfaced with the medicine within the medicine chamber; a plunger member comprising a proximal interface configured to be manually manipulated to move the stopper member relative to the syringe body; a needle having a sharpened distal end; and an extension member coupled to the proximal end of the syringe body, the extension member operatively coupled to the plunger member and configured to contain the stopper member if the stopper is withdrawn to such an extent that it at least partially exits the interior medicine chamber; and (426) withdrawing at least a portion of the stopper member into the extension member; and (428) containing residual droplets of medicine which may remain coupled to the distal surface of the stopper member until they become contained by a fluid containment surface (such as one that defines one or more fluted geometries configured to retain the residual droplets and/or defines one or more perforations configured to retain the residual droplets) positioned immediately adjacent the distal surface upon withdrawal of the stopper member into the extension chamber; an absorbant member may be fluidly coupled to the fluid containment surface, the absorbant member configured to absorb and retain the residual droplets.

Figure 38A:
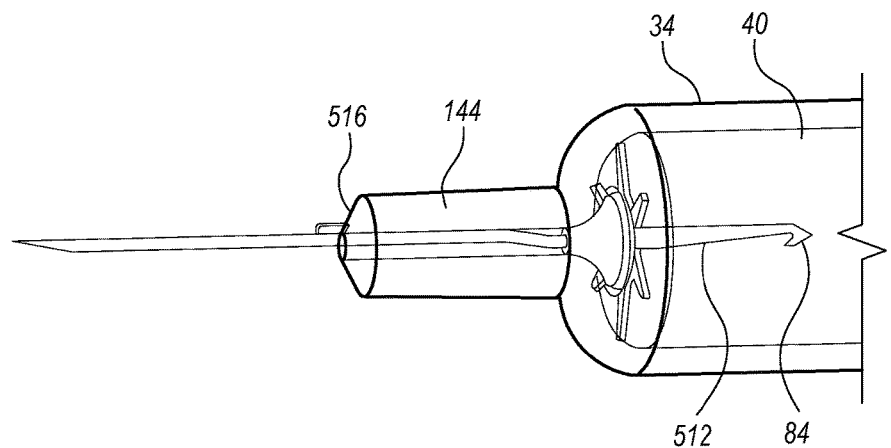
FIGS. 38A-38C illustrate various aspects of a safe injection system configuration wherein a distal needle tip may be withdrawn into a protected configuration after use.
Figure 38B:
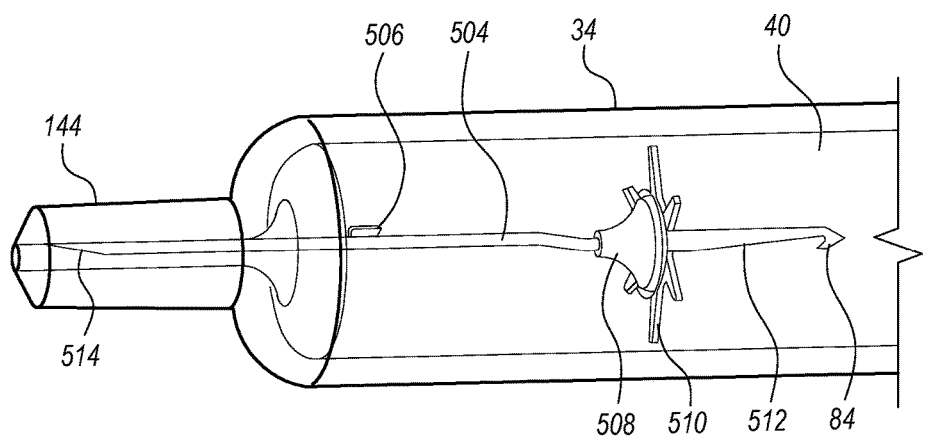
Figure 38C:
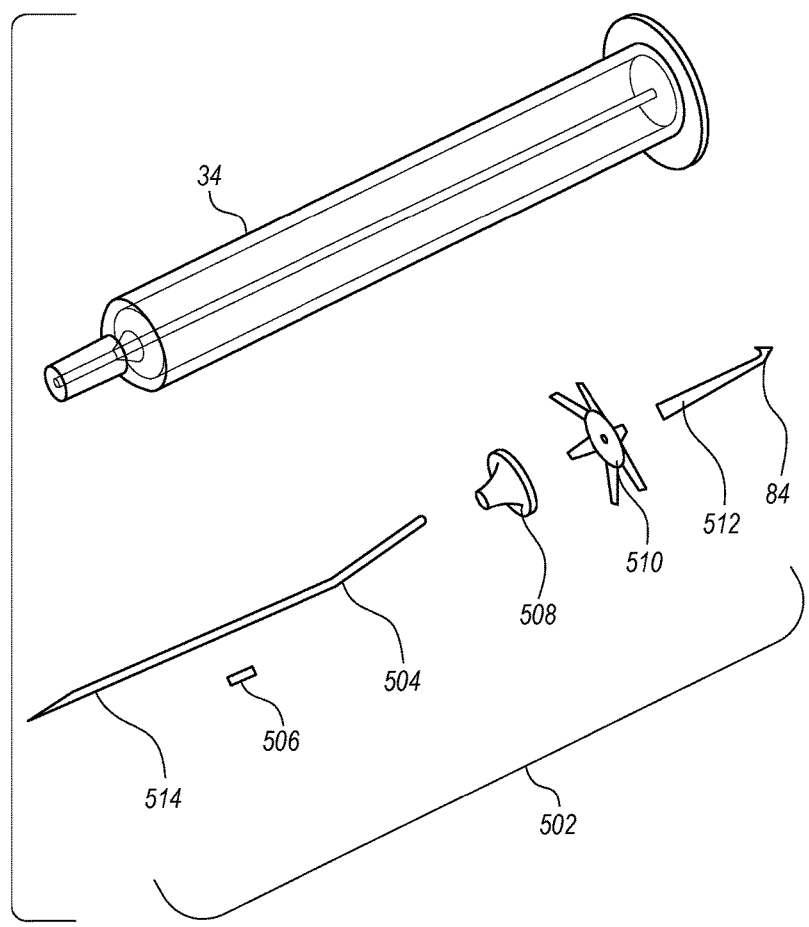

Referring to FIGS. 38A-38C, an embodiment is shown wherein a needle assembly (502) is removably coupleable to a syringe body (34) in a staked needle configuration somewhat akin to that described in reference to FIGS. 8A-8P, with the exception that the embodiment of FIGS. 38A-38C is releasably coupled to the distal end (144) of the syringe body (34) through the use of a mechanical block member (506) that is fixedly coupled to bent-shaped needle member (504). Referring to FIG. 38A, in a ready-to-use (i.e., inject medicine into a patient) configuration, the needle assembly is held in place by the mechanical interfacing of the block member (506) and a distal surface (516) of the syringe body (34) end (144). When the plunger (not shown) is fully inserted, it presents a compressive load against a spring member (510), here a star-shaped configuration to provide a desired spring constant, which ultimately inserts the bent needle member (504) distally relative to the syringe body (34) end (144) by a distance large enough to decouple the block member (506) from the distal surface (516) of the syringe body (34) end (144), thereby allowing the bent needle member (504) to freely deflect to its unloaded position whereby the block member is free to slip through the aperture of the syringe body (34) end (144) so that the needle may be retracted along with retraction of the plunger, such as by a harpoon interface as described above, wherein the harpoon-shaped (84) proximal end (512) of the needle member is stabbed into and coupled to the plunger member so that the distal tip of the needle member (514) may be withdrawn into a safe configuration by the plunger member whereby it is shielded by the syringe body (34). FIG. 38C illustrates an exploded view of the aforementioned components.

Referring to FIGS. 39A-41F, configurations are presented that allow for the plunger to be fully or almost fully inserted relative to a syringe body without triggering the needle-withdrawing latching mechanism described above. This may be useful in scenarios wherein it is useful to first expel the contents of the medicine chamber (40) by inserting the plunger member, then retract the plunger member to re-fill the medicine chamber, only to finally insert the plunger member to conduct an injection into a patient, after which needle retraction is desired. One such scenario involves the use of lyophilized, or freeze-dried, medications. In certain lyophilized medication scenarios, one portion of the medication is supplied in a powder form in a vial, while another portion of the medication is supplied in liquid form, such as in a pre-filled syringe body. The configurations described herein in reference to FIGS. 39A-41F may be utilized to a) couple the syringe body to an external lyophilized medicine vial; b) facilitate injection of the liquid contents of the syringe body medicine chamber into the external lyophilized medicine vial by insertion of the plunger member relative to the syringe body, such that the liquid and powdered contents may be combined and/or mixed in the external vial; c) facilitate introduction of the mixed medicine contents from the external via into the medicine chamber of the syringe body by retraction of the plunger; d) facilitate decoupling of the external vial from the syringe body and coupling of an injection needle assembly in its place; e) facilitate injection of the mixed medicine contents of the medicine chamber into the patient through the needle, followed by retraction of the needle into a safe configuration relative to the syringe body, as described above. In simplified, terms, such configurations allow the plunger to be inserted and retracted without triggering the automatic needle retraction mechanisms, until such retraction is desired (generally after the actual injection stroke to expel the medicine from the medicine chamber, through the needle member, and into the patient).

Figure 39A:
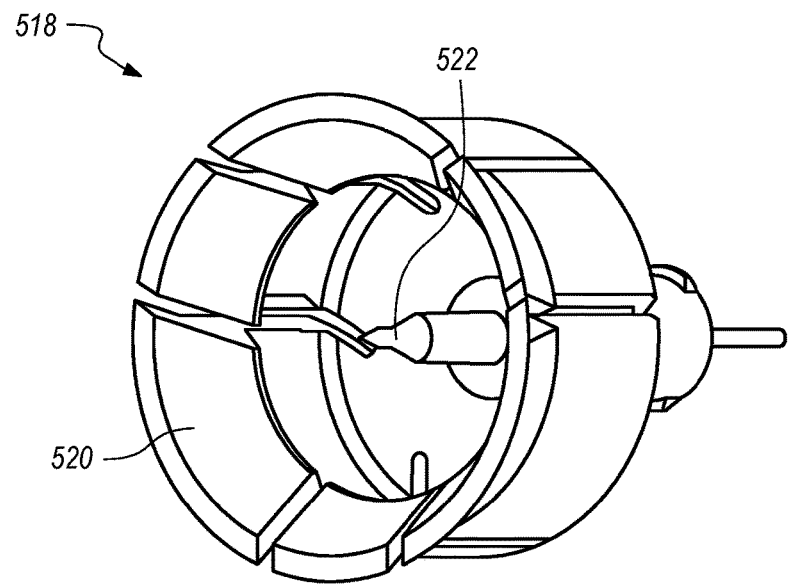
FIGS. 39A-41F illustrate various aspects of safe injection system configurations wherein a plunger and/or needle retraction mechanism may be temporarily bypassed or disabled to facilitate movement of the plunger without actuation of the retraction mechanism.
Figure 39B:
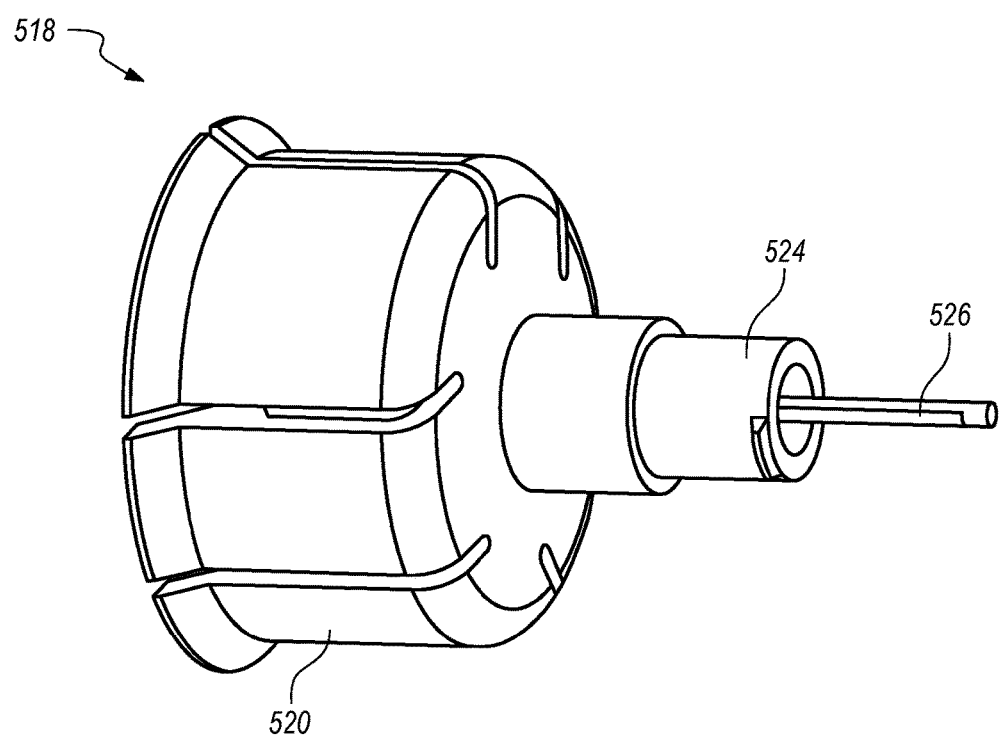
Figure 40A:
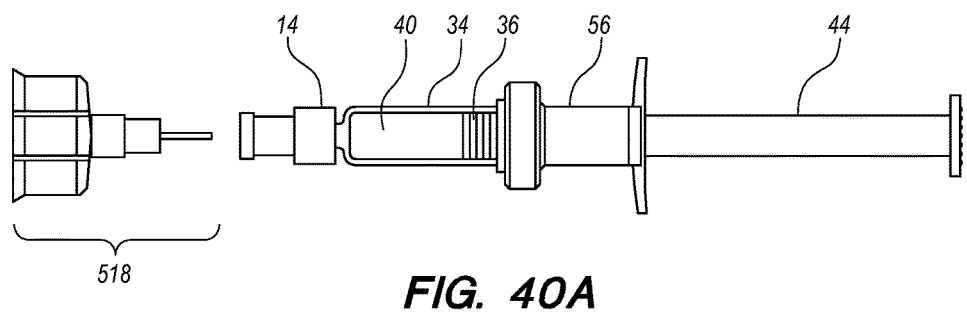
Figure 40B:
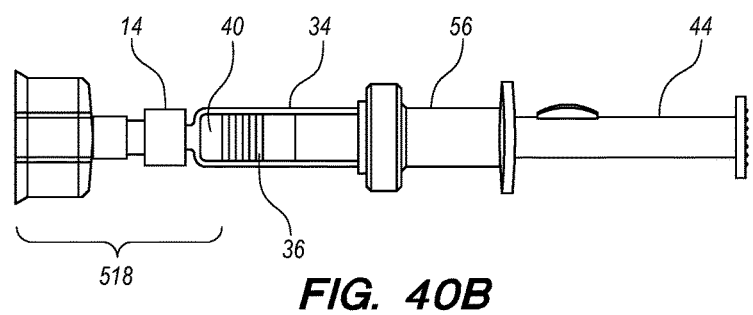
Figure 40C:
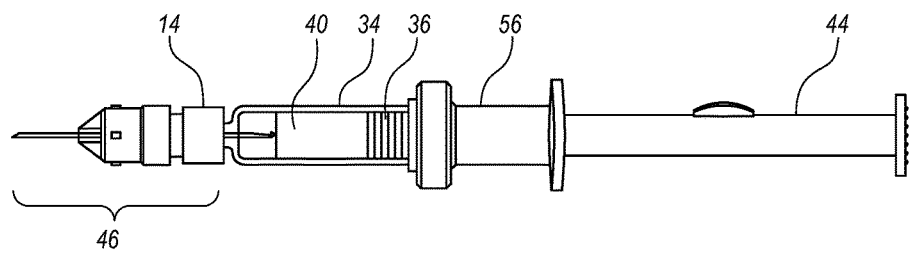

Referring to FIGS. 39A-39B, a vial adaptor assembly (518) is depicted which comprises an external vial adaptor cap (520) coupled to a sharpened medicine retrieval interface (522) configured to stab through a seal of an external medicine vial to gain access to the associated medicine. The proximal end of the assembly (518) comprises a Luer interface (524) configured to be removably coupled to a similar interface of the syringe assembly, and fixedly coupled through the Luer interface (524) is a plunger insertion stop member (526) which is configured to prevent full insertion of the plunger of the associated syringe assembly—which prevents full function of the associated latching mechanism, which, in turn, prevents retraction of the plunger as described above. Referring to FIGS. 40A-40C, a sequence is illustrated wherein a vial adaptor assembly (518) is coupled, using Luer interfacing, to the distal end of the needle assembly to allow for the plunger (36) of the needle assembly to be inserted (as shown in FIG. 40B) without activating the plunger/needle retraction mechanism. The plunger may then be retracted to bring the combined medicine into the syringe body (34) medicine chamber (40), after which the vial adaptor assembly (518) may be removed and replaced with a needle assembly (46), as shown in FIG. 40C, such that the combined medicine may be injected into a patient, followed by retraction of the plunger and needle member as described above using the pertinent retraction mechanism.

Figure 41A:
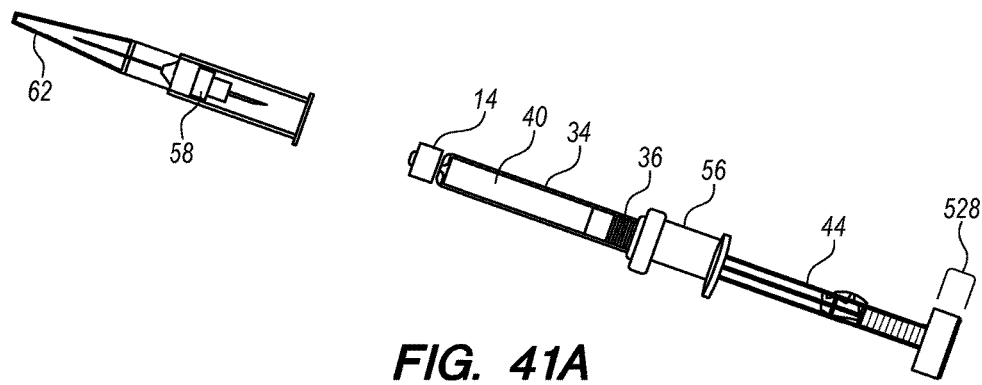
Figure 41B:
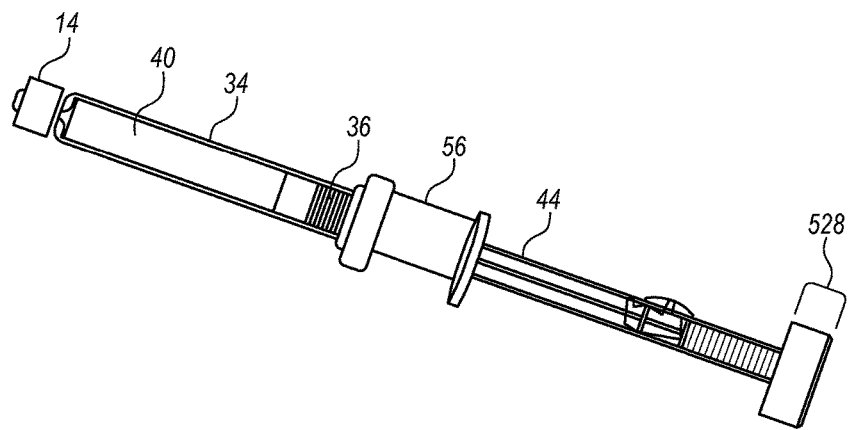
Figure 41C:
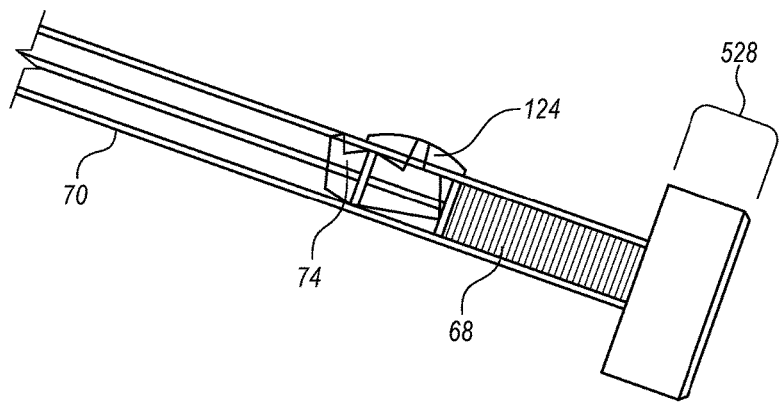
Figure 41D:
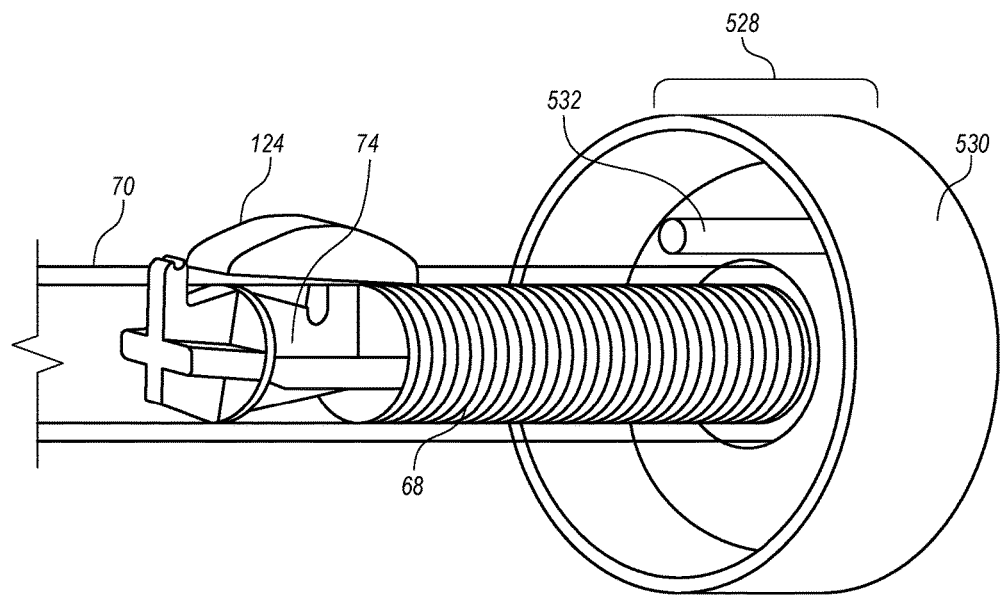

Referring to FIGS. 41A-41F, in another embodiment, rather than blocking full insertion of the plunger relative to the syringe body to prevent retraction actuation, as described above in reference to FIGS. 39A-40C, retraction actuation may be temporarily prevented by preventing movement (i.e., preventing rotation of a latching member 74 relative to the plunger housing 70 or latch rotation housing feature 124) of the latching/retraction componentry. FIGS. 41A-41C illustrate differently zoomed in views of an assembly similar to that of FIG. 7B, but with a different proximal interface assembly (528) that comprises a latch rotation blocking member (532) configured to prevent rotation of the latching member (74) relative to the plunger housing 70 or latch rotation housing feature 124 upon initial insertion. Referring to FIG. 41D, a close in view is shown wherein the latch rotation blocking member (532) extends distally toward the latch member (74); with full insertion, this latch rotation blocking member (532) fits into the latch rotation housing feature 124 and prevents rotation of the latch member (74), thereby preventing the plunger retraction mechanism from being triggered. When the outer housing member (530) of the proximal interface assembly (528) is tensioned relative to the syringe body or plunger housing (70), a spring plate (534), which is fixedly coupled to the latch rotation blocking member (532), moves into a movably-coupled configuration relative to the outer housing member (530) which facilitates motion of the latch rotation blocking member (532) that is sufficient to prevent it from becoming a mechanical block to rotation of the latch member (74) relative to the plunger housing 70 or latch rotation housing feature 124. In other words, after the spring plate (534) has moved to the movably coupled configuration relative to the outer housing member (530), the latching mechanism and full retraction of the plunger member (36) and needle member via the spring (68) shall be in operation as described above in relation to FIGS.

Figure 41E:
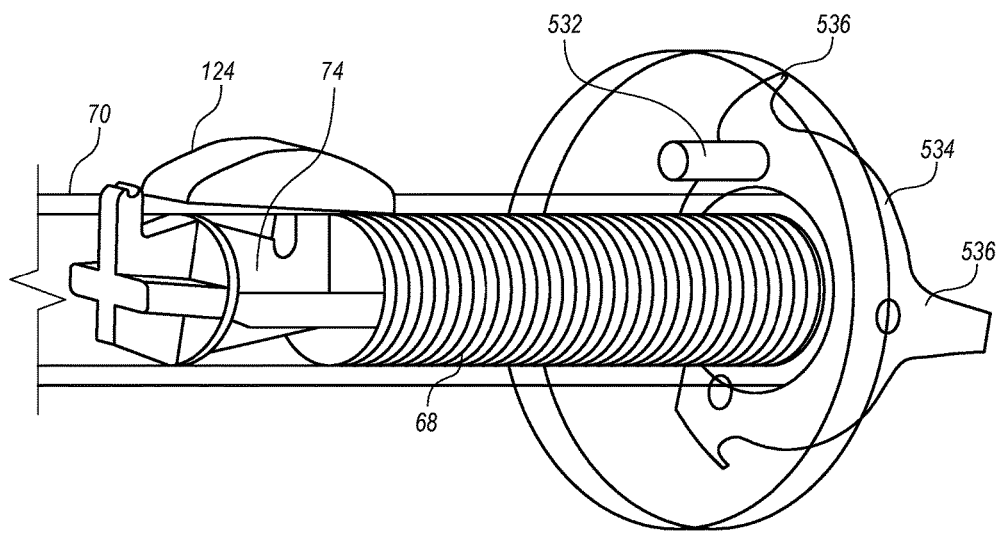
Figure 41F:
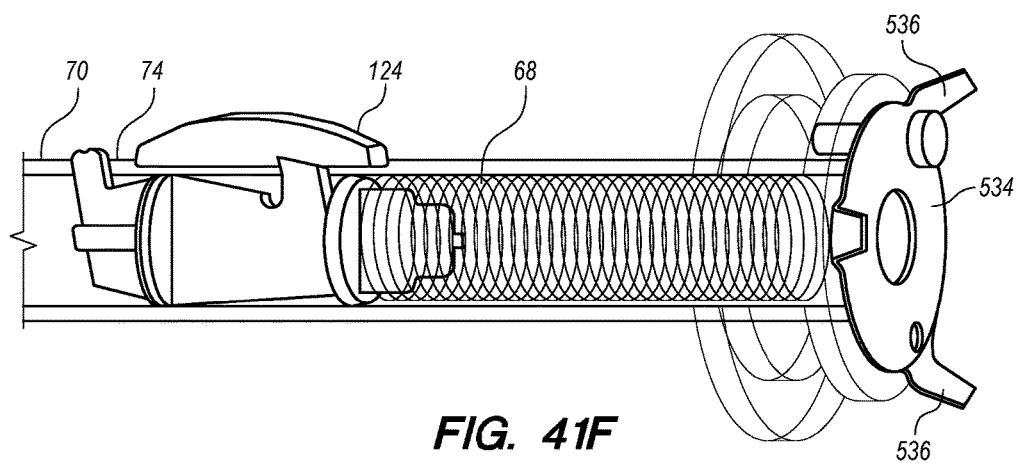
Figure 42:
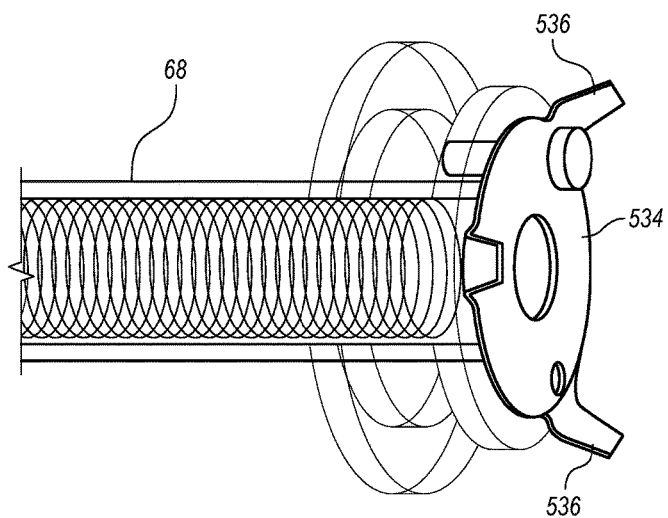
FIG. 42 is a close up view of the structures illustrated in FIG. 41F.

7A-7J, for example. FIGS. 41E and 41F show the outer housing member removed to illustrate the spring plate (534) with plurality of spring members (536) configured to be engaged against the inside of the outer housing member before the spring plate (534) has moved to the movably coupled configuration relative to the outer housing member (530). FIG. 42 illustrates a close-in view of a portion of the structures illustrated in FIG. 41F.

Figure 43A:
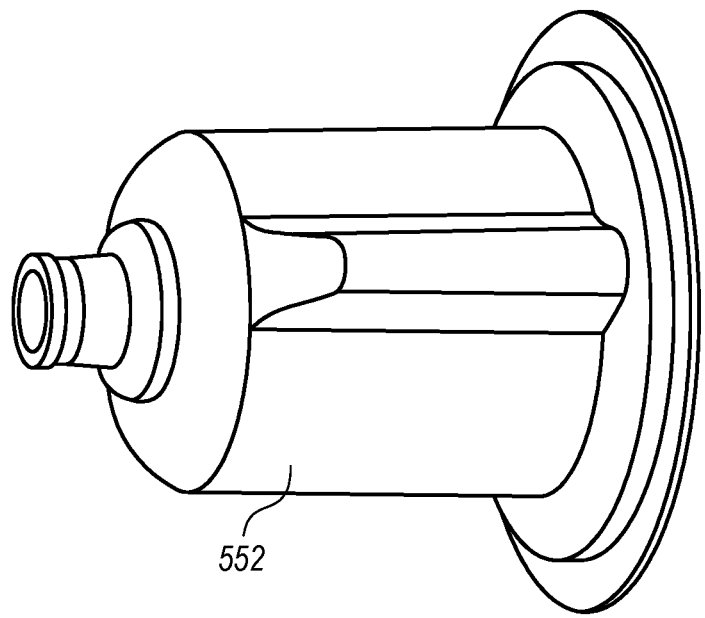
FIGS. 43A-43H illustrate various aspects of a clutched vial adaptor configuration.
Figure 43B:
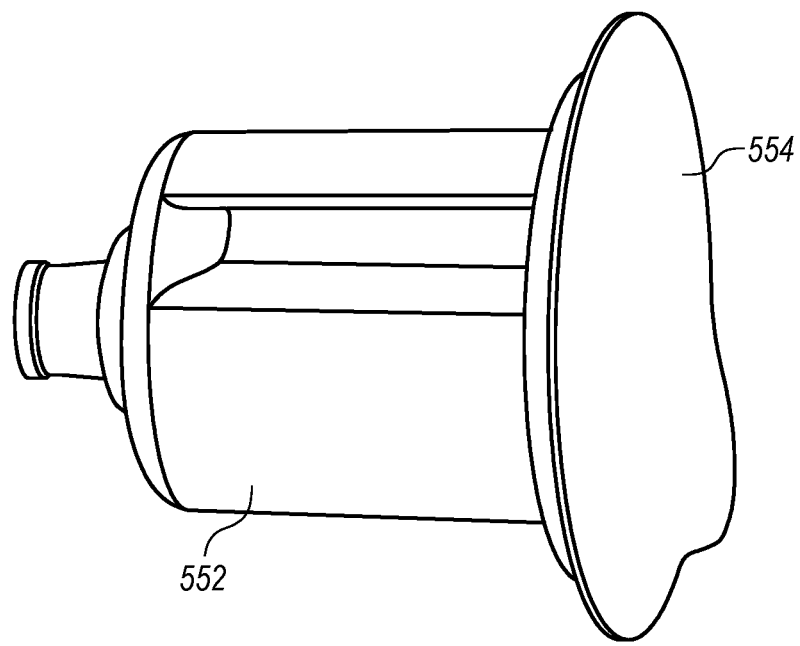
Figure 43C:
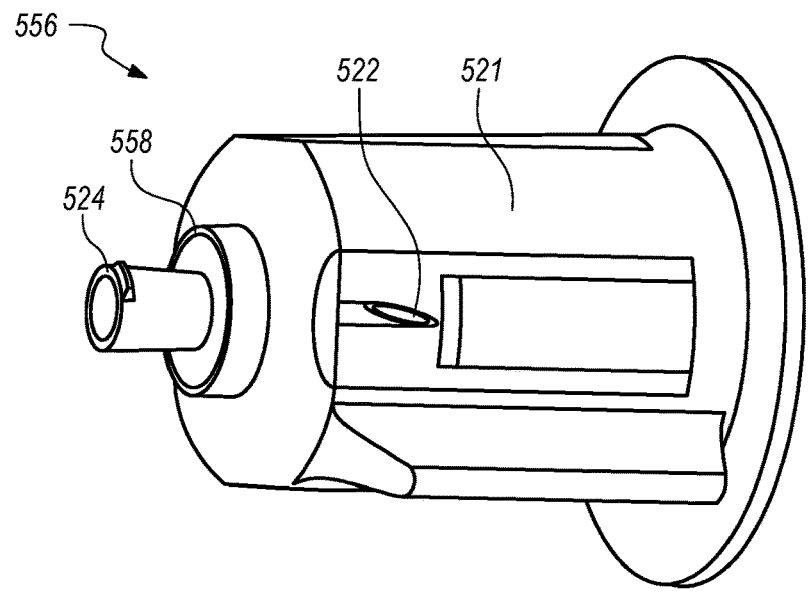
Figure 43D:
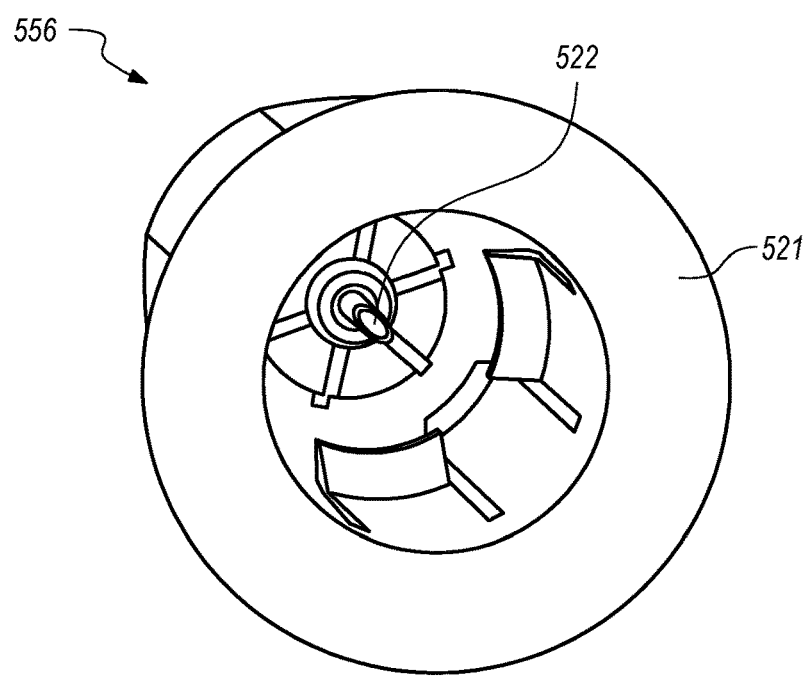
Figure 43E:
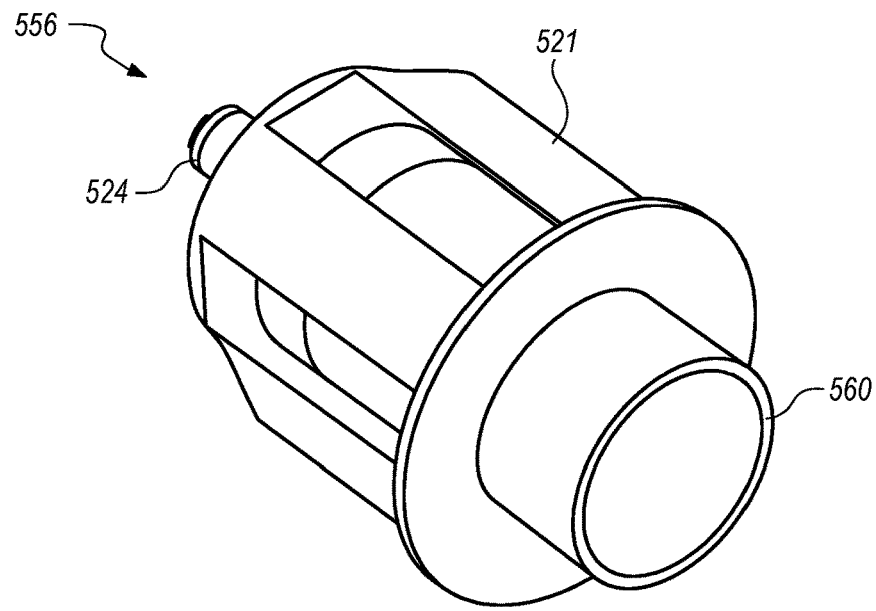
Figure 43F:
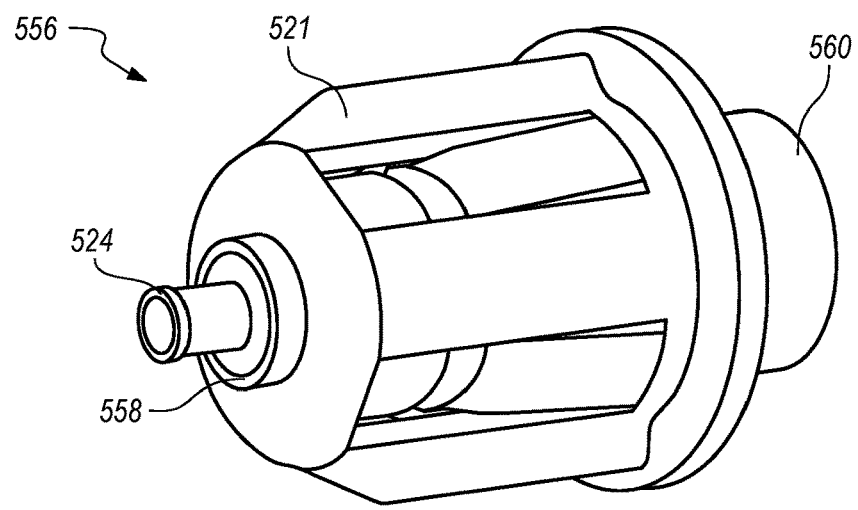
Figure 43G:
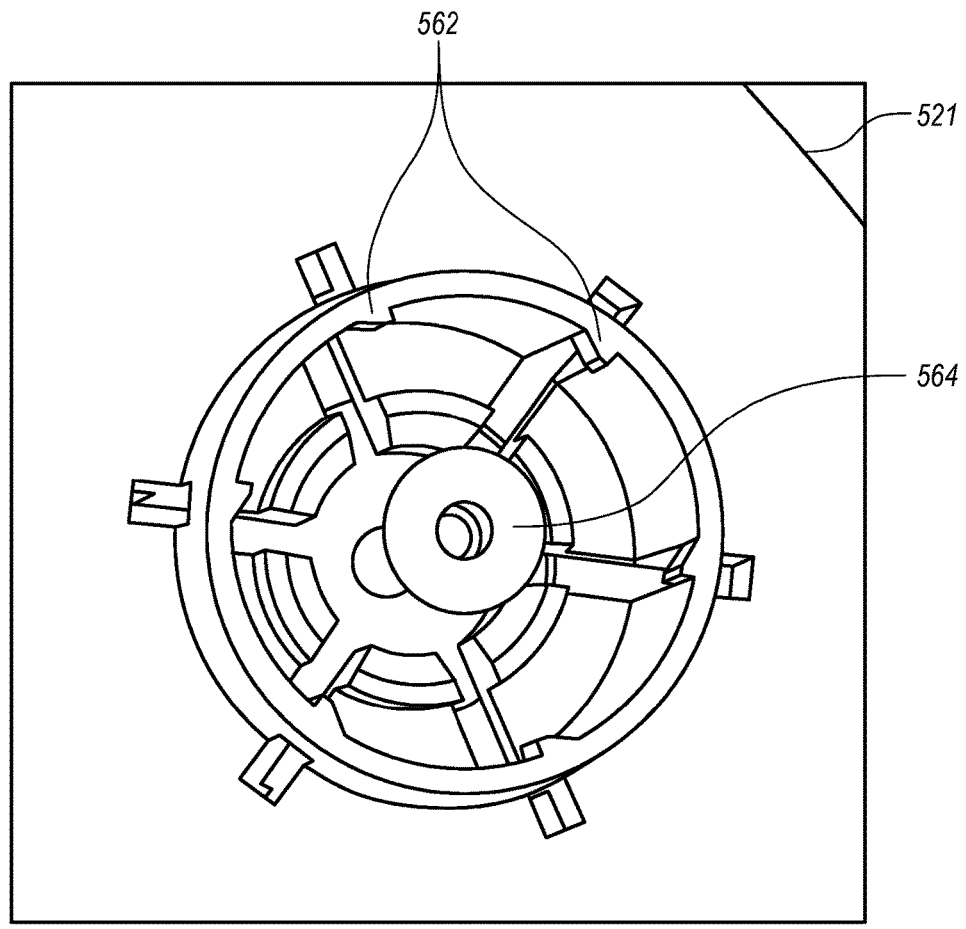
Figure 43H:
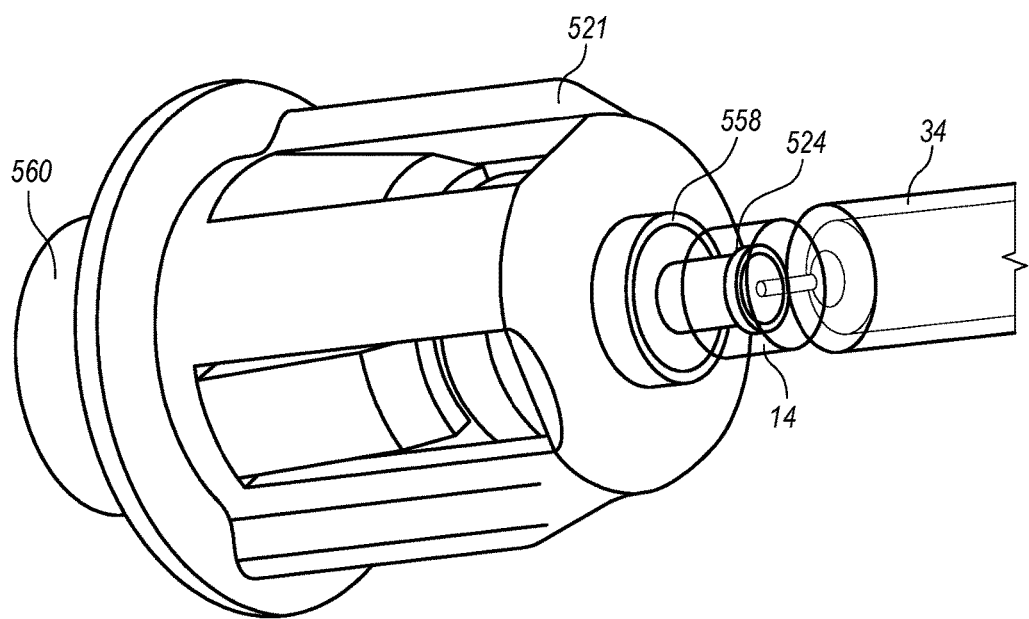

Referring to FIGS. 43A-43H, various aspects of a vial adaptor assembly configuration are illustrated, wherein a clutched Luer configuration prevents over-torquing of the vial adaptor and associated vial relative to a syringe body (34) during preparation for injection. Referring to FIGS. 43A and 43B, a vial adaptor assembly may be delivered in an encapsulating housing or cover (552) which features a removable seal (554). Referring to FIGS. 43C and 43D, with the cover removed, the vial adaptor assembly (556) is visible, comprising a vial coupling cap (521) configured to provide a snap fit with the exterior features of a standard vial (560), as shown in FIGS. 43E and 43F. A sharpened medicine retrieval interface (522) is configured to stab into an integrated seal on a vial (560) to provide an intercoupled syringe body with access to the medicine within the vial (560). Another vial adaptor configuration is described above in reference to FIGS. 39A-39B with a Luer interface (524) that is substantially fixed relative to the vial adaptor coupling cap (520—see, for example, FIG. 39B). The vial adaptor assembly (556) illustrated in FIGS. 43A-43H features a Luer interface (524) with a clutched rotatable coupling interface (558) relative to the vial adaptor coupling cap (521), which is configured to prevent over-torquing of the vial adaptor cap (521) relative to the syringe body (34 —see, for example, FIG. 43H), such as torques which may be passed across a Luer lock ring or fitting (14) which may be coupled to the syringe body (34). In the case of select glass or plastic bodied syringe bodies, the luer lock ring or fitting (14, 18) may be coupled to the male luer feature of the syringe body via a snap-fit connection. Over-torquing of the ring during assembly of devices to the syringe may twist the luer lock ring relative to the syringe body, and such twisting may loosen the snap-fit connection of the luer lock ring, preventing future devices from being attached securely to the syringe body. As shown in FIG. 43G, in one embodiment, a plurality of clutch ramp interface features (562) are formed into the inner surface of the vial adaptor cap (521) and configured to engage with a plurality of protruding features on the perimeter of the Luer interface member, such that after a predetermined amount of torque is applied at the interface, the protruding features will move over the clutch ramp interface features (562), allowing the interface to effectively freewheel forward rotationally until the next ramp/protrusion interface becomes engaged. This engagement provides for a clutching configuration whereby after a maximum torque is reached, the interface will roll and effectively release the torque until further advancement to the next ramp/protrusion interfacing configuration is reached. Preventing torque beyond such a predetermined maximum is believed to prevent accidental removal or fracturing of other portions of the overall assembly, such as the press-fit interface between the Luer assembly of the syringe body and the syringe body itself.

Figure 44A:
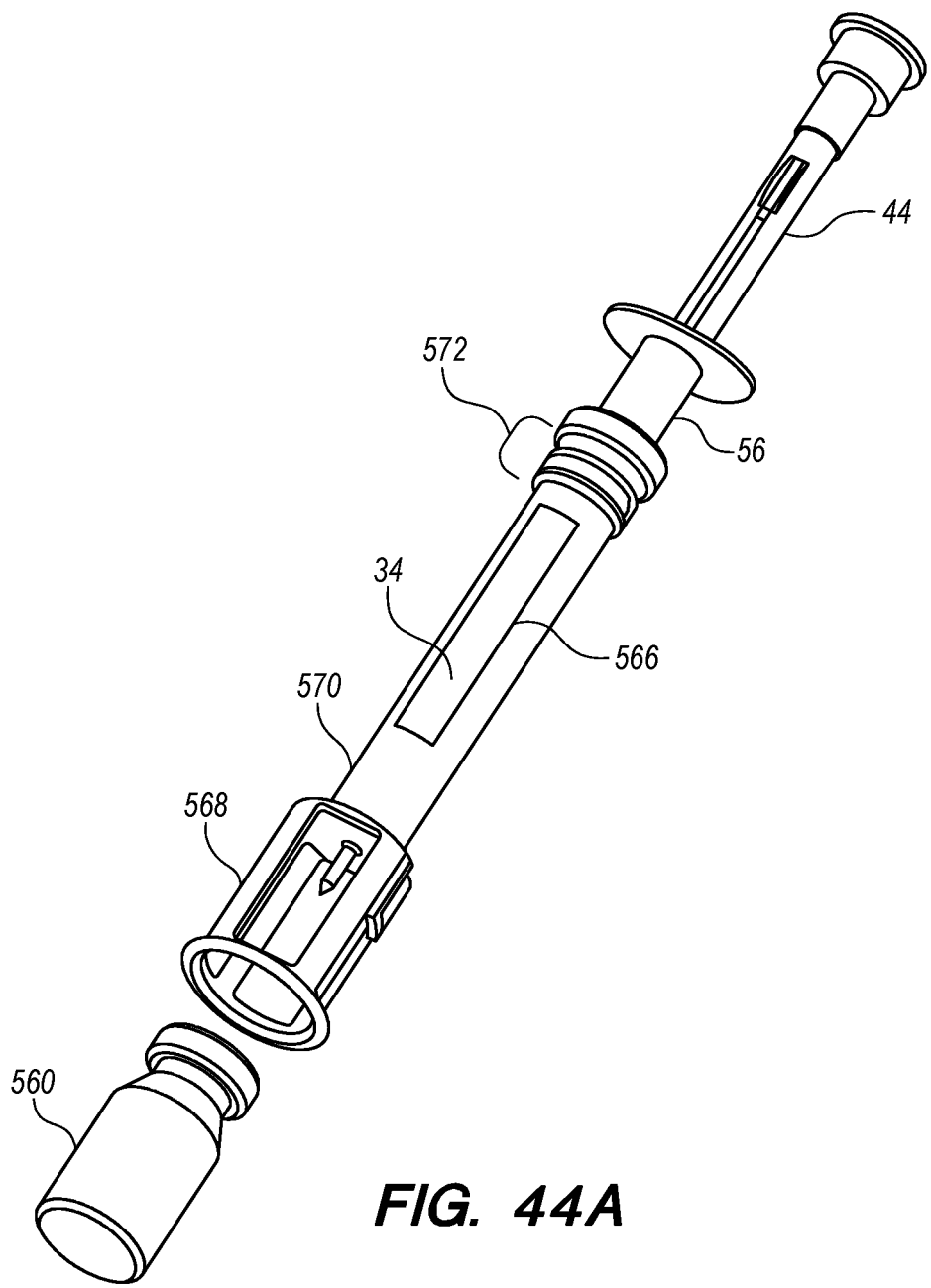
FIGS. 44A-44L illustrate various aspects of a safe mixing and injection system wherein a stabilizer assembly may be utilized to assist in preparation for injection.
Figure 44B:
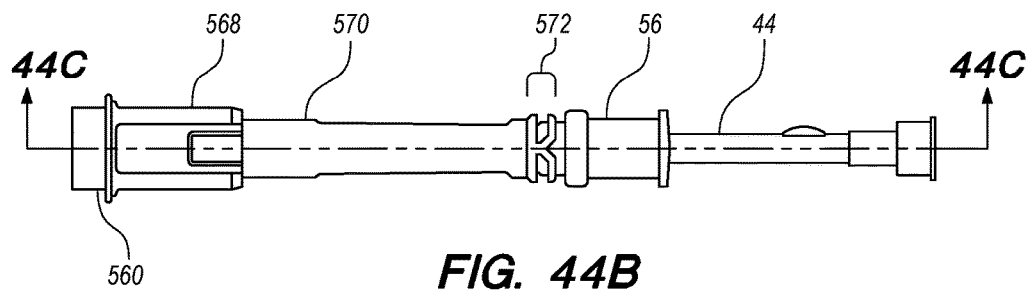
Figure 44C:
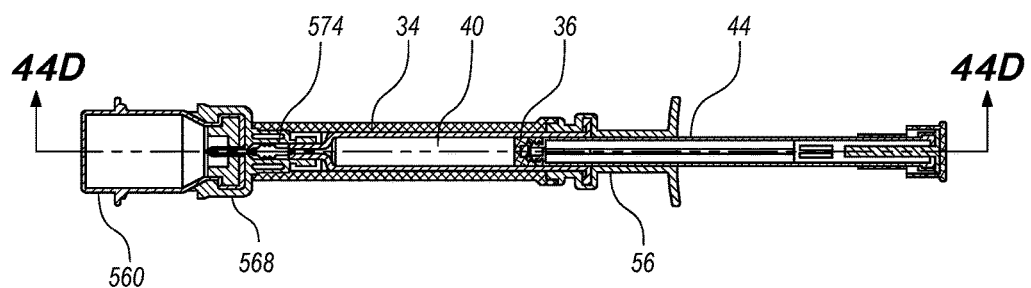
Figure 44D:
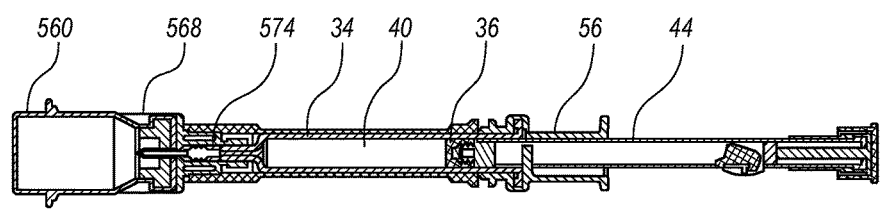
Figure 44E:
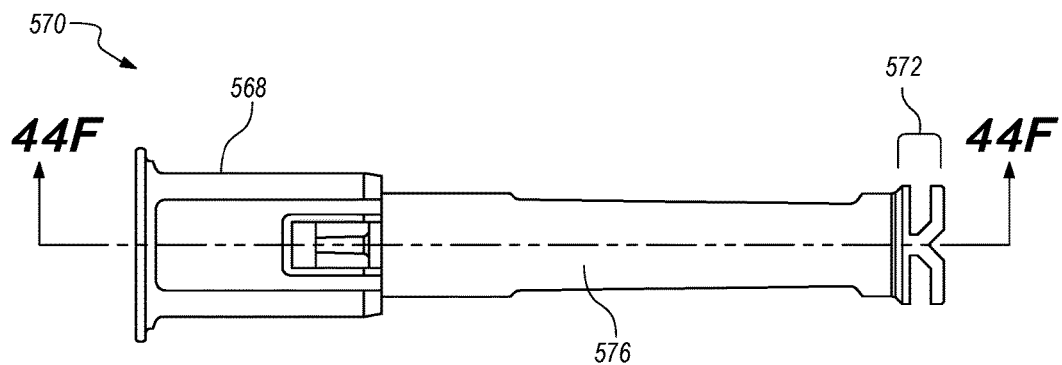
Figure 44F:
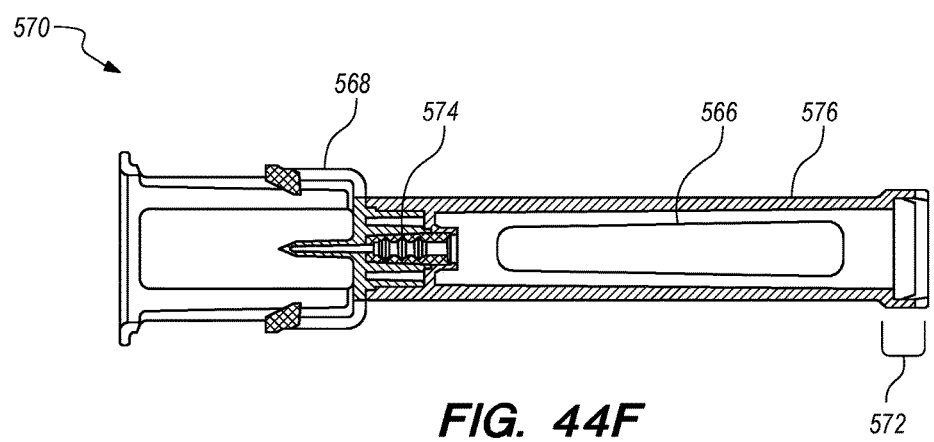
Figure 44G:
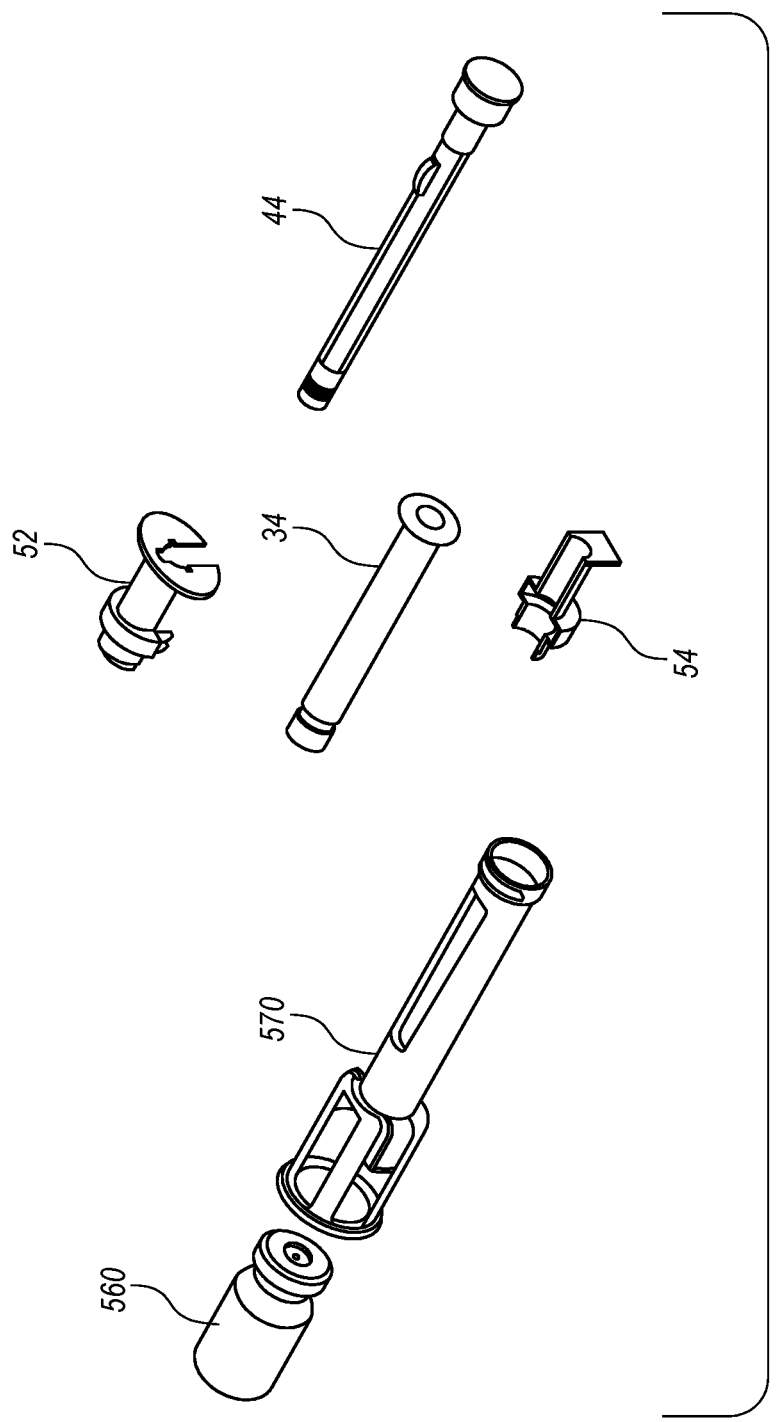
Figure 44H:
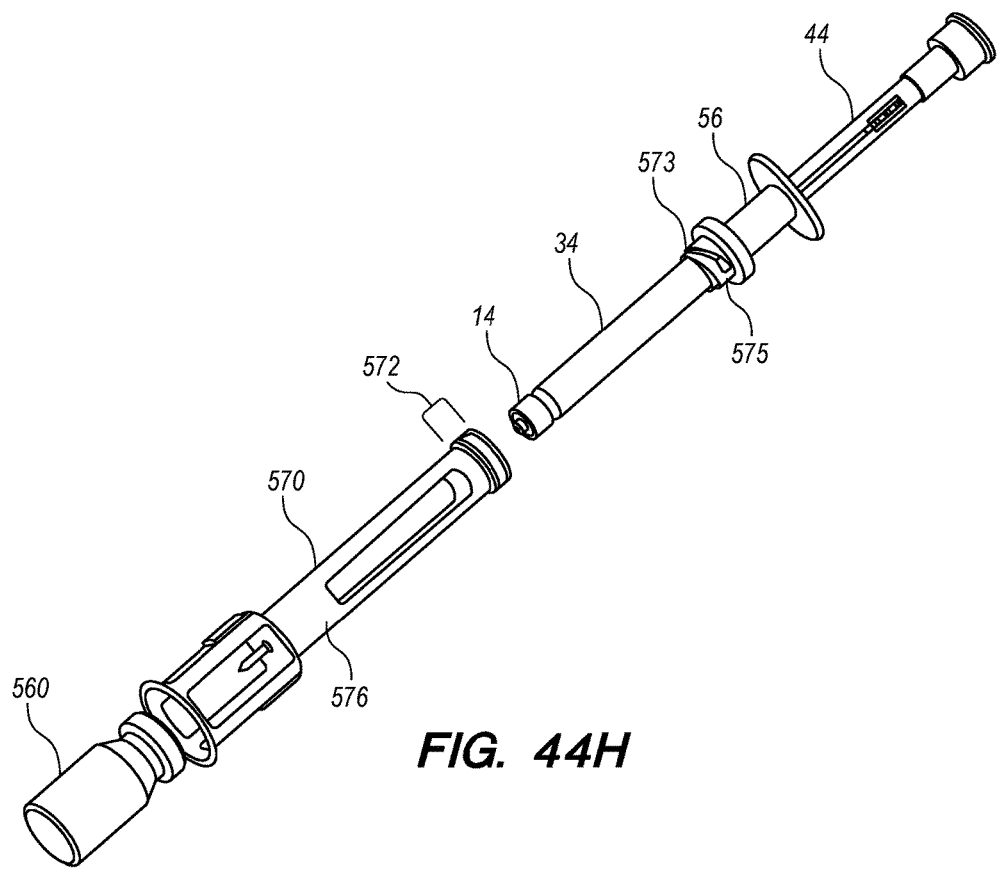
Figure 44I:
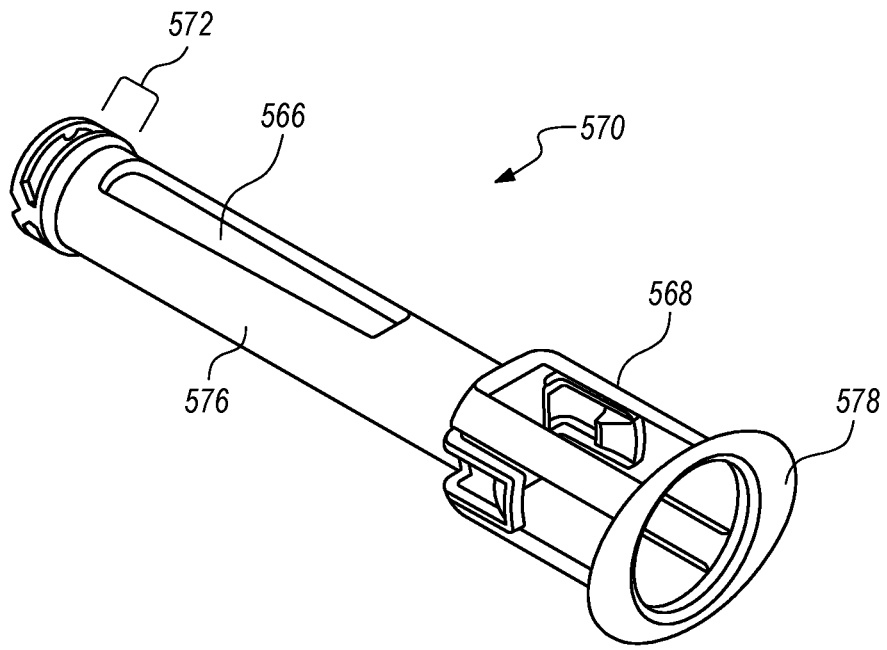
Figure 44J:
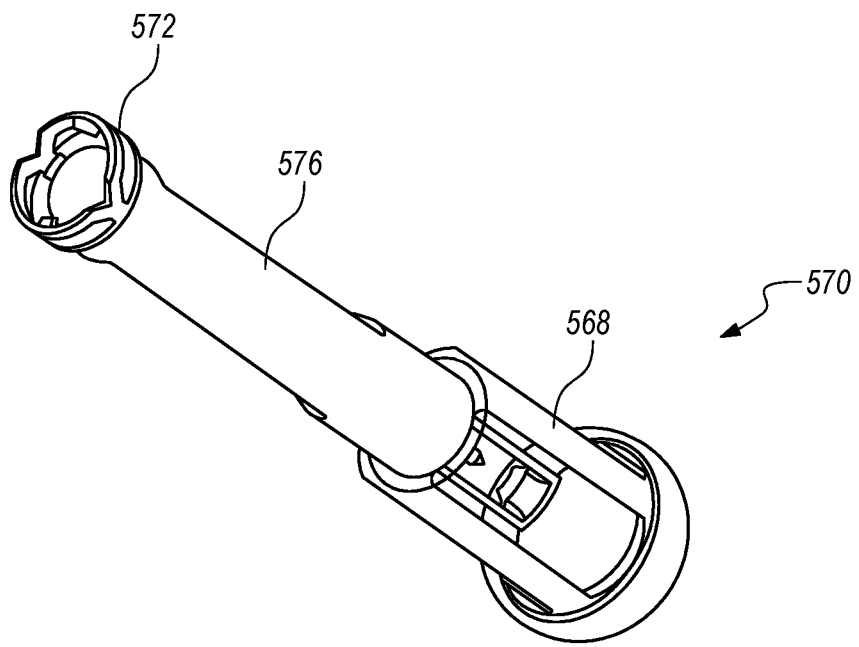
Figure 44K:
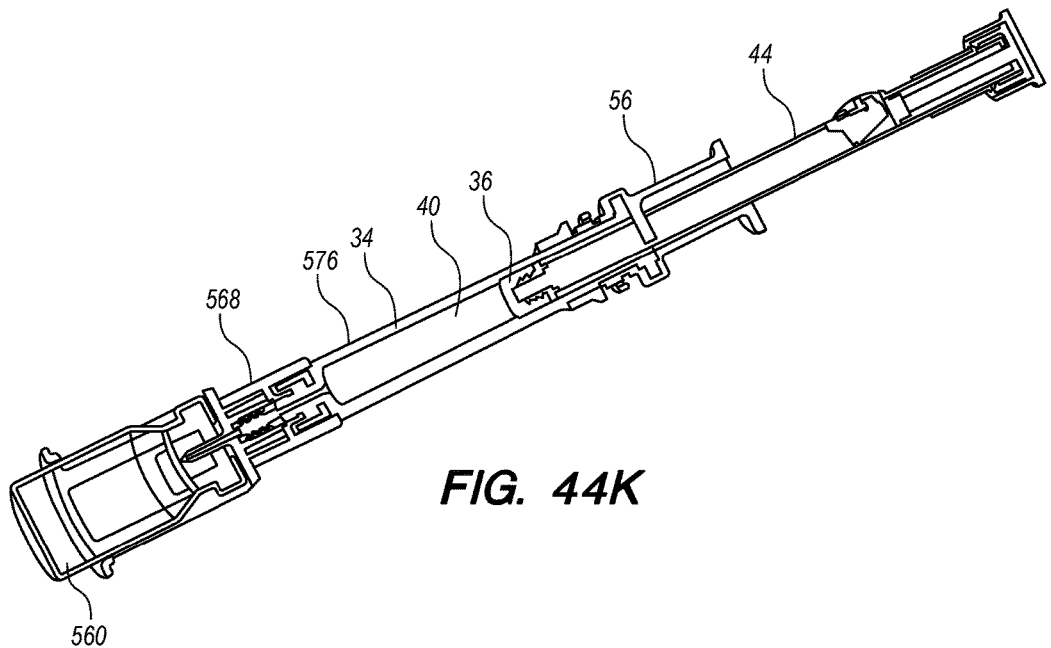
Figure 44L:
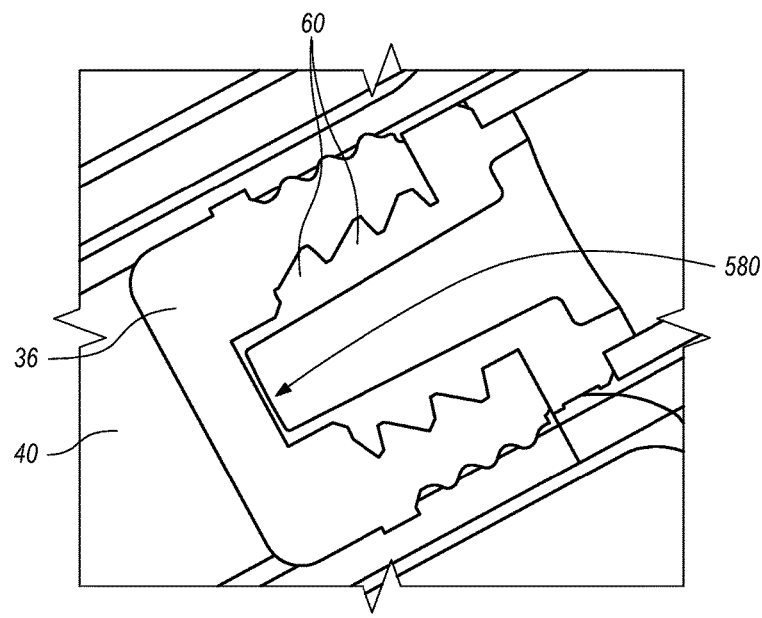

Referring to FIGS. 44A-44L, various aspects of stabilizing configurations are illustrated, which feature a stabilizer assembly designed to mechanically stabilize an assembly of various components when they are being rapidly oscillated in space (such as in the case when it is desirable to use an operator's hand to agitate such components to mix medicine which may be contained therein, as described above in reference to multi-component injection medicine configurations, such as those featuring lyophilized drugs, wherein a powder may need to be mixed with a liquid before injection). Referring to FIG. 44A, a distal end of the depicted stabilizer assembly (570) comprises a vial adaptor coupling cap portion (568) which may closely resemble those featured, for example, in FIGS. 43C and 43D, which is fixedly coupled to a main tubular shaft portion (576) which may have one or more visualization windows (566) defined therethrough so that the syringe body (34) may be viewed. The proximal end of the depicted stabilizer assembly (570) comprises a rotatable coupling interface (572) configured to be threadably coupled to one or more coupling features (573) on the flange coupling assembly (56). The one or more coupling features (573) may comprise a rotational snap over detent (575) to provide a tactile and/or audible indication the operator when a proper connection has been achieved. To create the necessary spring force for the detent (575), the proximal end of the stabilizer assembly (572) may define cut-out portions (see, for example, FIG. 44I) to make the shaft of the stabilizer assembly axially extensible in the region adjacent to the threaded interface (572). Other rotational detent configurations may also be employed in this vial adapter device. Radial projecting detents such as those described herein with reference to the needle assembly and needle cover may be applied to this coupling interface as well. In one embodiment, the threadibly coupled interface between the vial stabilizer (570) and the syringe body (34) also may be configured to indicate to the operator when the connection is not properly connected. If the operator screws the interface together and does not snap over the detent, the thread pitch of the threadable connection may be configured to be large enough to eject the vial stabilizer (570) back away from the syringe. This indicates to the operator to re-connect the interface. As shown in FIG. 44I, the distal end of the vial adaptor coupling cap portion (568) may have an oval or noncircular flange geometry (578) to prevent the assembly from rolling when placed on a flat surface such as a table. FIG. 44B (and cross sectional FIGS. 44C and 44D) illustrate an assembly with a medicine vial (560) engaged, along with a syringe body (34), in a substantially stable configuration designed to be safely shaken by hand without damaging or accidentally decoupling components thereof. A flexible seal component (574) provides a flexible interface which may be compressed or expanded with coupling engagement to pass fluids between the vial (560) and the syringe body (34). Alternatively, the seal between the vial stabilizer coupling cap portion (568) and the syringe (34) may be accomplished by using a luer taper connection, such as a 6 percent luer taper connection. FIG. 44E (and cross section 44F), 44I, and 44J illustrate other views of the stabilizer assembly embodiment. FIG. 44H provides another assembled view, FIG. 44G illustrates an exploded view, and FIG. 44K illustrates a sectional view, to show the various components of a typical assembly. FIG. 44L illustrates a close up view of one portion of the sectional view of FIG. 44K to illustrate that in one embodiment, a thin layer of polymeric material (580), such as Nylon, may be left in place at a location wherein the needle portion is to stab through the plunger tip (36); this extra amount of material (580) may be utilized to enhance the load required for push-through of such needle component, and also to enhance resistance to pulling back the needle out/away from the distal end of the plunger tip (36).

Figure 45A:
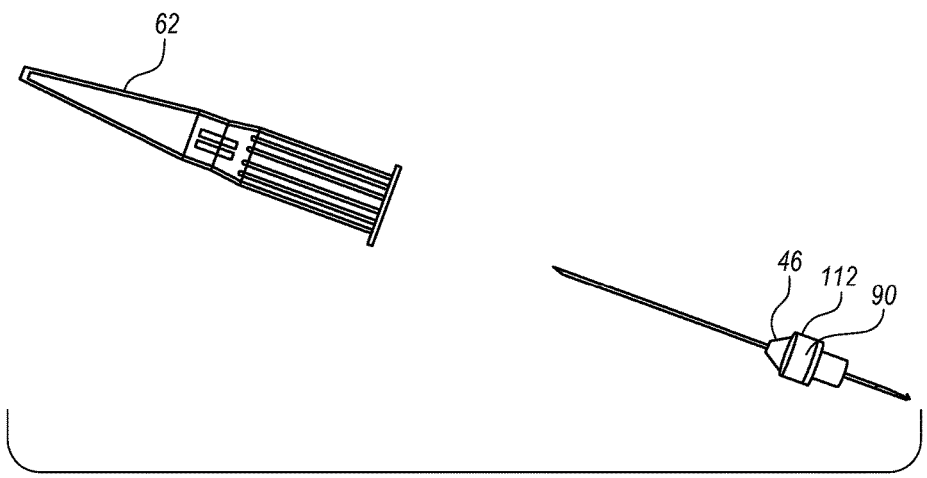
FIGS. 45A-45D illustrate various aspects of needle and needle cover engagement configurations configured to prevent over-torquing.
Figure 45B:
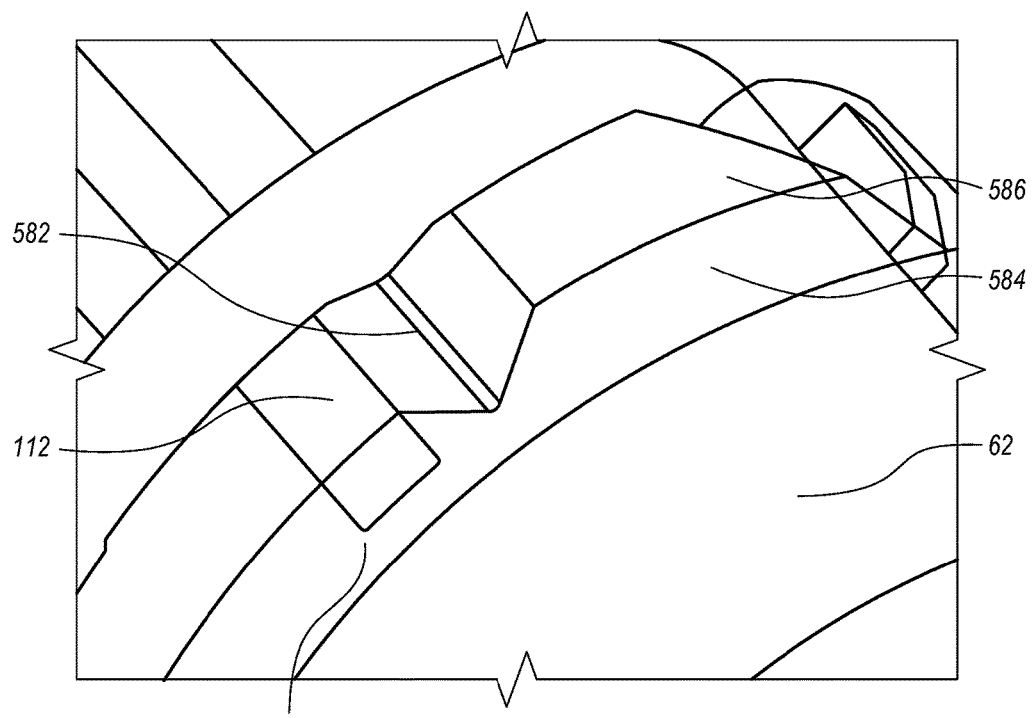
Figure 45C:
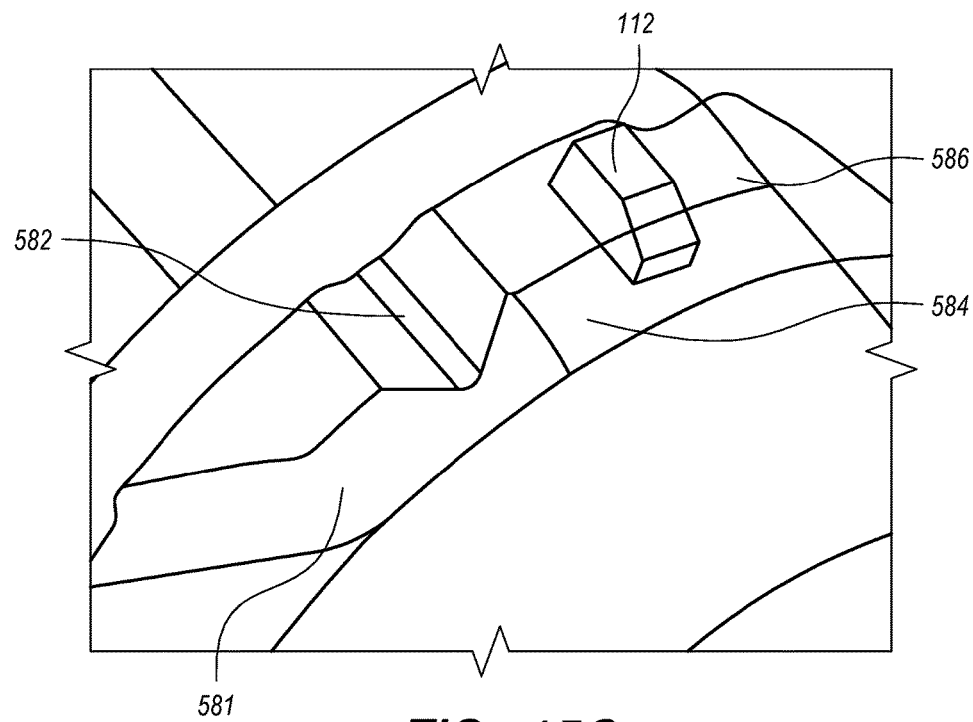
Figure 45D:
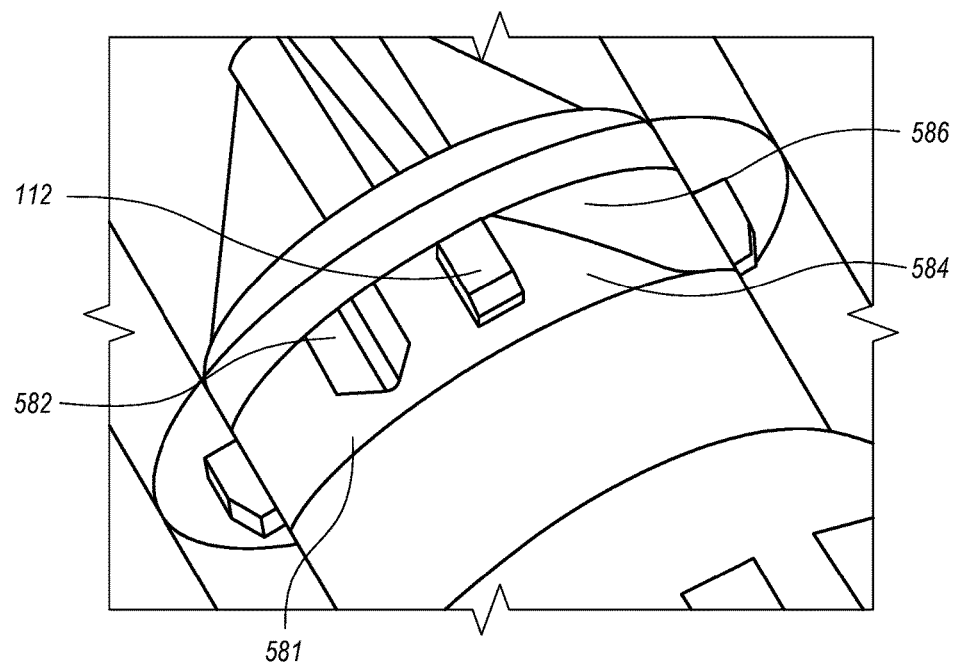

Referring to FIG. 45A a needle cover (62) and needle assembly (46) are illustrated similar as to described above, but with certain added features in the geometry of the mechanical interface. In the depicted embodiment, the needle cover (62) and needle assembly (46) may be joined by insertion and rotation. The needle assembly (46) and needle cover (62) shown in FIG. 45B illustrate a configuration which may be suitable for shipping and or storage, wherein the distal housing lug (112) is trapped between the rotational detent (582) and large axial detent (581) such that the needle is contained within the housing and generally cannot be dislodged until the rotational detent (582) has been snapped over. In use, the depicted needle assembly (46) embodiment may be coupled to the luer lock interface (14) of the syringe assembly by applying a rotational torque to the exterior of the needle cover which is intercoupled to the needle, while holding still or counterloading the syringe to counteract the torque applied to the needle cover (62). A mechanical constraint envelope is effectively created by virtue of the detent interface features (581, 582, 584, 586) to guide the detent into positions of stability, and also to prevent overtorquing, as shown in FIGS. 45B-45D). One side of the mechanical constraint envelope is defined by the rotational detent (582), which is snapped over once a minimum amount of torque has been applied to the luer interface by the needle intercoupled to the needle cover. It is intended that the needle cover cannot be removed from the needle until this rotational detent has been snapped over. This entrapment of the needle within the needle cover prohibits the operator from exposing the needle until a minimum amount of torque has been applied to the luer lock interface from the needle via the intercoupled needle cover, ensuring a leak free and solid mechanical coupling. A second side of the mechanical constraint envelope is defined by the second rotational detent (586) which is configured to dis-engage the needle cover from the needle once a maximum torque has been reached. This second rotational detent has a surface angled with respect to the longitudinal axis of the needle and needle cover, which once contacted by the distal housing lug (112) imparts an axial force to the needle cover, dislodging the needle cover from the needle. A third side of the mechanical constraint envelope is provided by a smaller axial detent (584). This axial detent is encountered by the lugs on the distal housing (112), once the needle has snapped over the first detent (582). The axial detent is intended to provide enough axial force to prevent the needle cover from freely falling off of the needle, while allowing the user to pull the needle cover off of the needle when the operator is ready to give the injection. Referring to the close-up views of FIGS. 45B-45D, in this embodiment, the lug interface features (112) protruding from the exterior of the distal housing (90) of the needle assembly (46), after being inserted into an appropriate insertion position relative to the needle cover (62), may be rolled to first cross over a first rotational detent interface feature (582), after which the particular lug interface feature becomes entrapped (as shown in FIG. 45C) between the first rotational detent interface feature (582), and second (586) and an axial detent interface feature (584), such that it is essentially in a trapped and stable configuration suitable for removal of the cover from the needle to expose the needle for use/injection. In the event that the interface is over-torqued, the lug interface feature (112) will be urged against the third rotational detent interface feature (586), which is configured to have a ramp-like geometry which will cause the needle assembly distal housing (90) to be pushed proximally, in a direction away from the stable coupled configuration relative to the needle cover (62).

Figure 46:
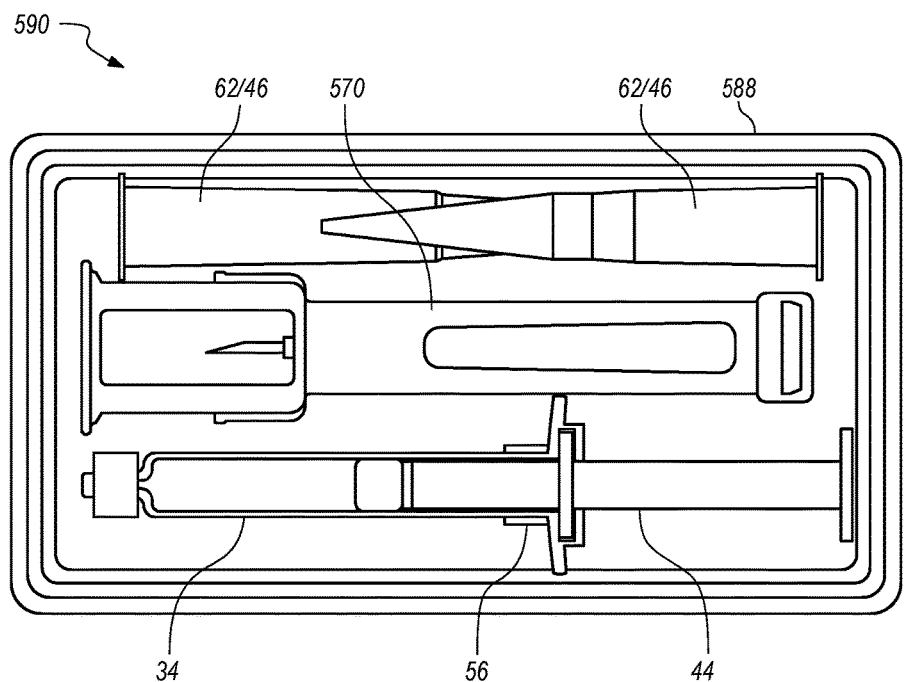
FIG. 46 illustrates a kit configuration.

FIG. 46 illustrates a kit assembly (590) wherein an injection assembly (34, 56, 44) may be packaged with a stabilizer assembly (570) and one or more needle/needle cover assemblies (62/46). The syringe assembly in FIG. 46 is a manual retraction version of the spring retraction syringe shown above. The plunger rod of this manual retraction syringe may have a latch to prevent re-advancement once the needle has been retracted into the syringe. The finger flange (56) of this manual retraction syringe has the threaded interface for connection to the vial access device (570). This finger flange is intended to be single sided, and snapped on from the side instead of a multi-component clamshell as shown in FIG. 44G.

Figure 47A:
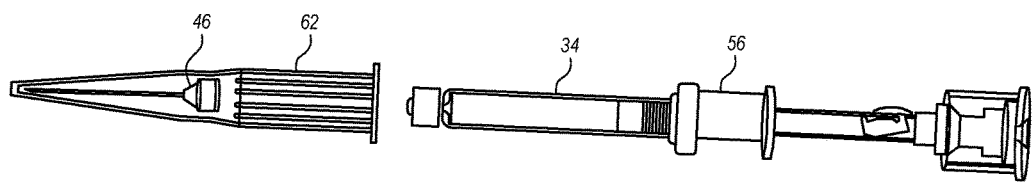
FIGS. 47A-47G illustrate various aspects of a safe injection system wherein a cantilevered latching feature may be utilized to controllably release a needle for retraction to a safe position.
Figure 47B:
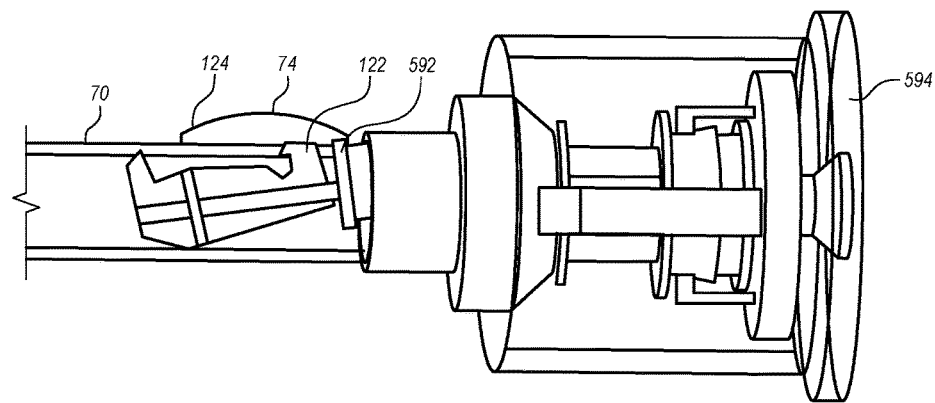
Figure 47C:
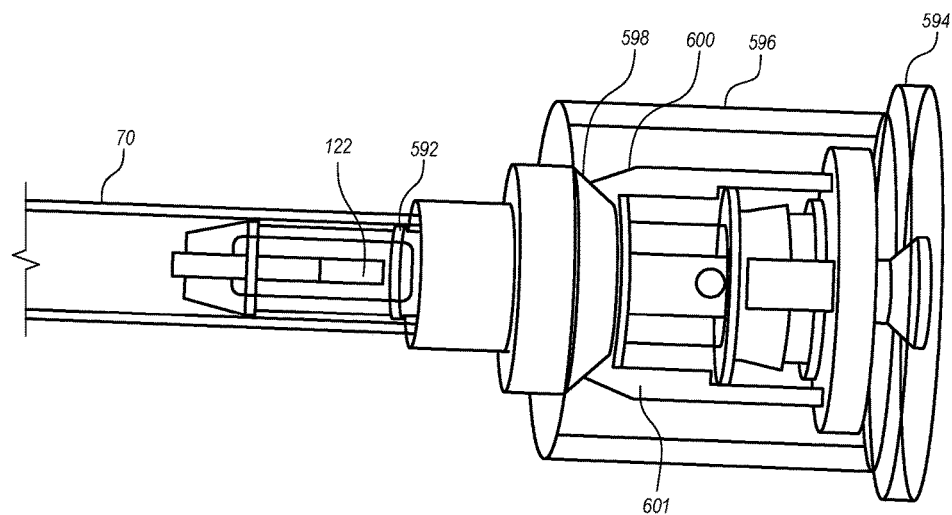
Figure 47D:
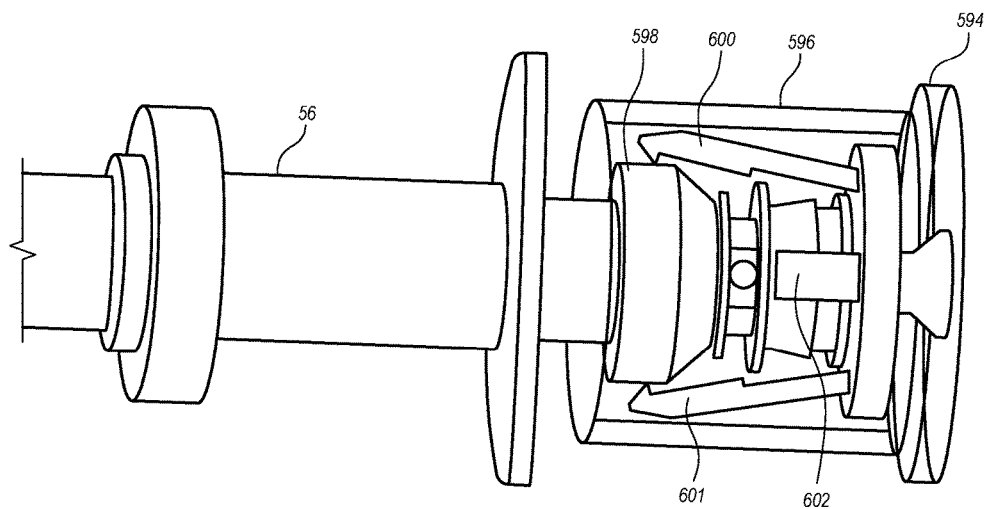
Figure 47E:
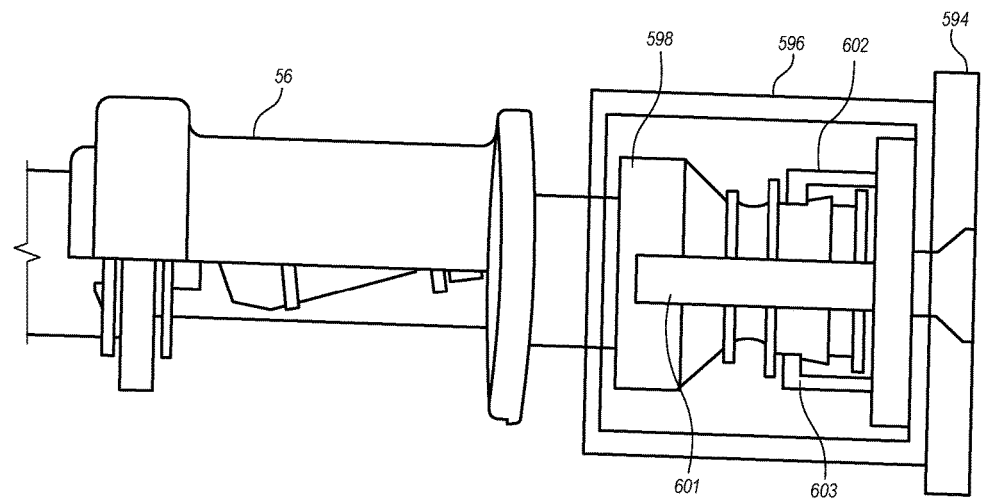
Figure 47F:
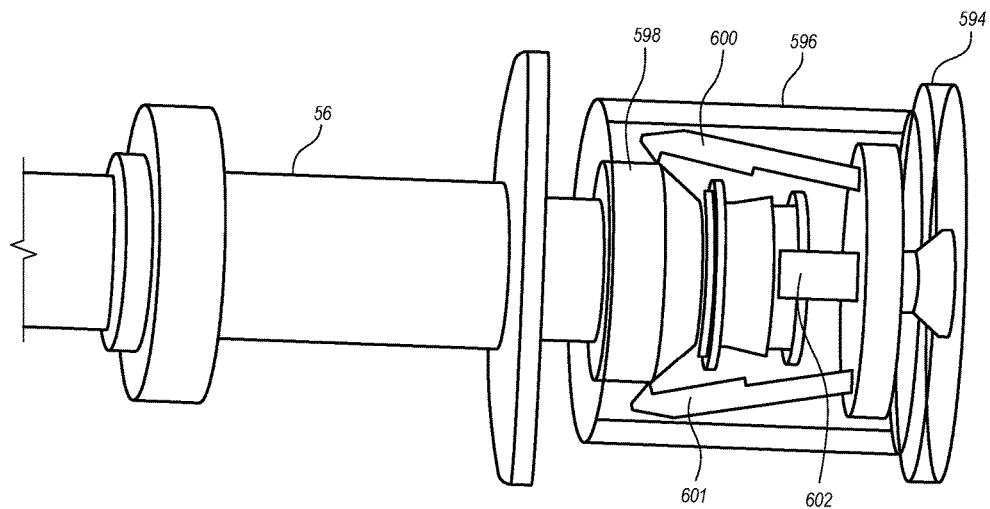
Figure 47G:
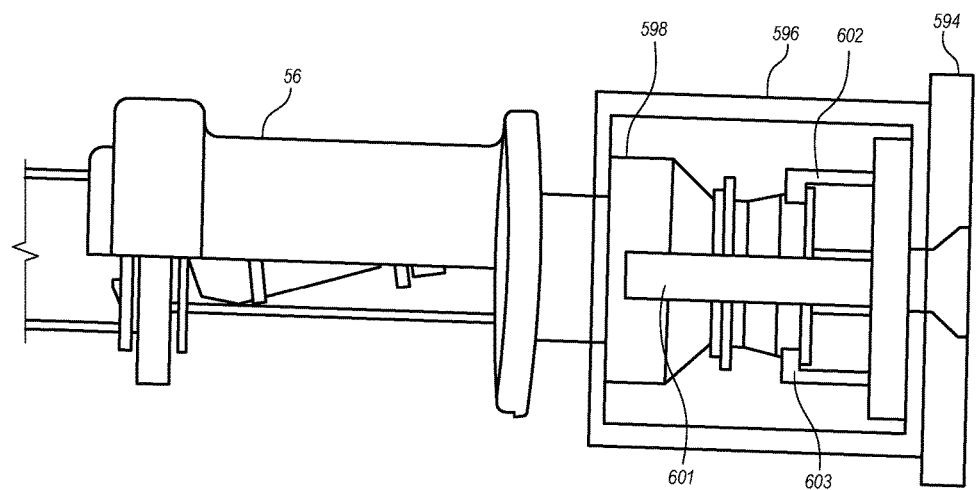

Referring to FIGS. 47A-47G, a proximal insertion assembly may be utilized to prevent withdrawal of a safety needle configuration until desired plunger insertion and withdrawal activities have been completed, such as those described above in reference to medicines which must be mixed before injection. Referring to FIG. 47A and the close up view of FIG. 47B (and FIG. 47C, which is a rotated view of the same assembly of FIG. 47B), a rotation blocking interface (592) may be utilized to temporarily block or prevent rotation of a latching member (74), to prevent the latch interface feature (122) from engaging the needle withdrawal mechanism. Referring to FIG. 47D (and rotated view of FIG. 47E), upon sufficient relative compressive loading between the flange coupling assembly (56) and proximal manipulation interface (594), an interface member (598) with beveled proximal geometry may be utilized to forcibly open a pair of coupling arms (600, 601), such forcing providing a spring-like resistance to the operator. With the movement of the interface member (598), a slight proximal pulling of the proximal manipulation interface (594) relative to the housing (596) pulls a second set of coupling arms (602, 603) over another beveled interface (such forcing providing a spring-like resistance to the operator) and into a stable and locked position, as shown in FIG. 47F (and rotated view FIG. 47G) such that the rotation blocking interface (592) is pulled proximally so that it no longer interferes with rotatable action of the latch member (74), and such that the needle withdrawal mechanism is enabled. Thus without the thoughtful and intentional pulling of the proximal manipulation interface (594) relative to the housing (596) after forcible loading of the flange coupling assembly (56) relative to the proximal manipulation interface (594), the needle withdrawal mechanism does not become enabled.

Referring to FIGS. 48A-53B, various aspects of safe injection configurations which may be referred to as "staked needle" configurations are illustrated; the "staked needle" denomination relates to the fact that upon presentation to the user, the injection end of the needle portion of the syringe or injection assembly of this variety generally already is coupled or "staked" relative to the syringe body (34). In other words, relative to various configurations described above wherein one or more portions of a needle assembly may be removably coupled to the syringe body (34) at the location of usage (i.e., immediately prior to usage), in a staked needle configuration the needle is already coupled to the syringe body (34) and in position for injection, after which it may be safely withdrawn into a protected configuration. Many of the proximal hardware elements from the above non-staked configurations may be utilized in the staked needle configurations, as evidenced by the common illustration elements and labels thereof.

Figure 48A:
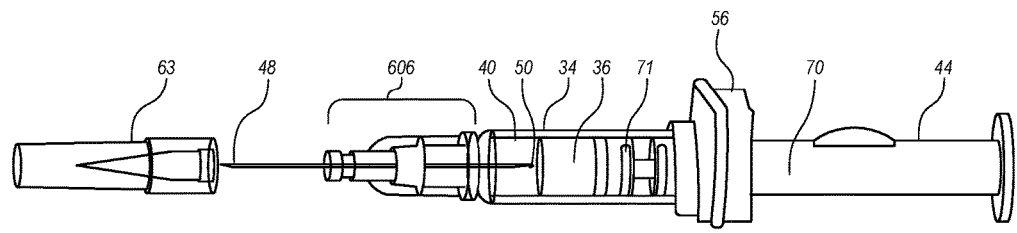
FIGS. 48A-53B illustrate various aspects of safe injection configurations, including but not limited to configurations which may be utilized as "staked needle" injection systems.
Figure 48B:
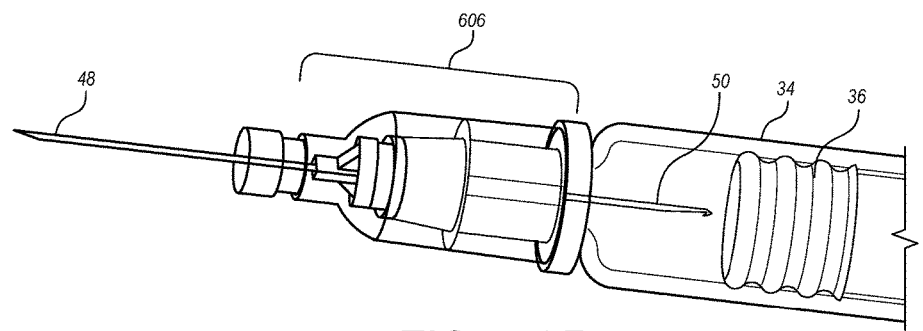
Figure 48C:
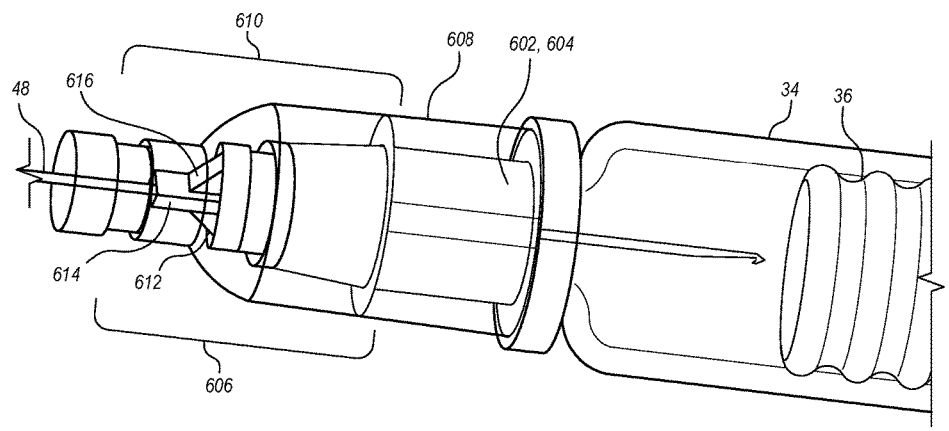
Figure 48D:
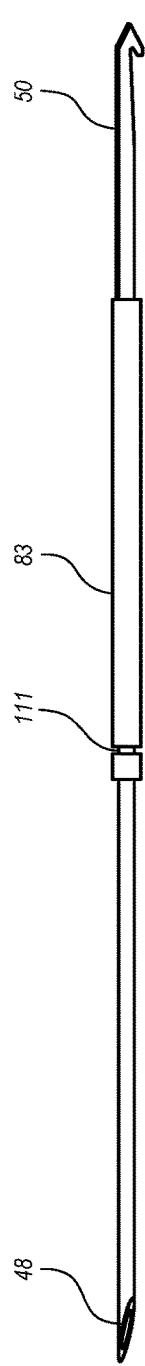
Figure 48E:
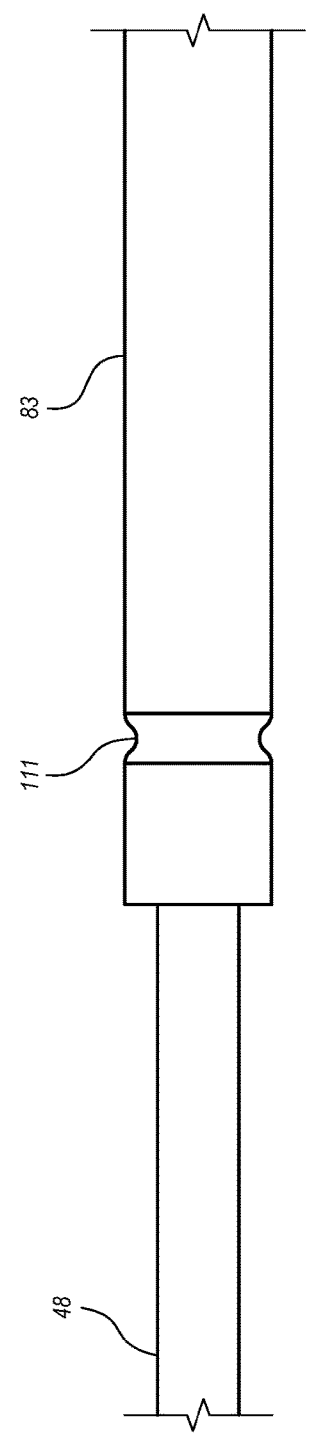
Figure 48F:
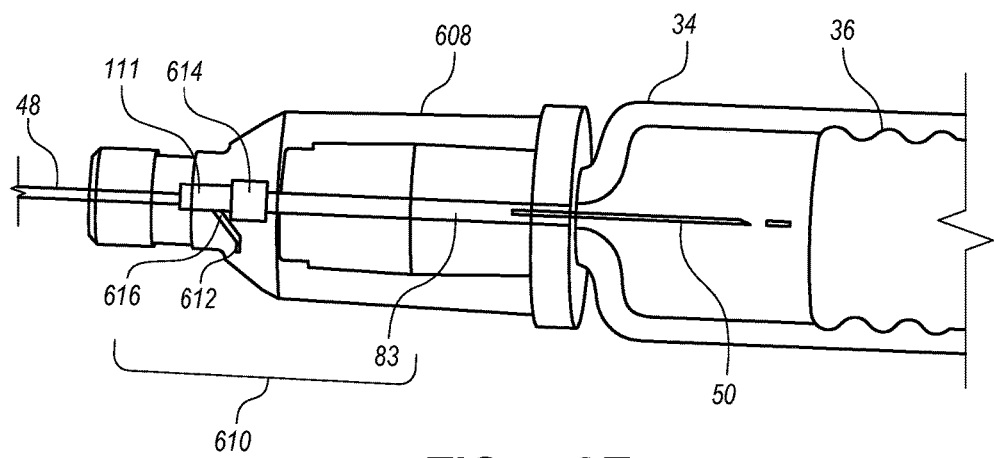
Figure 48G:
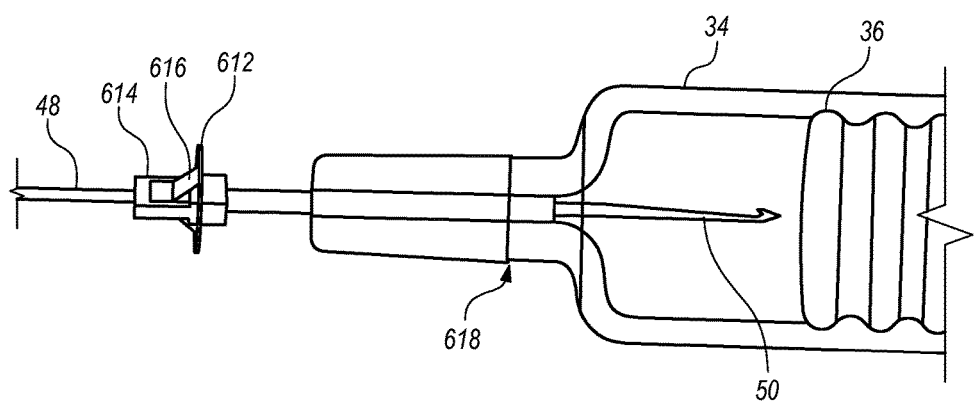
Figure 48H:
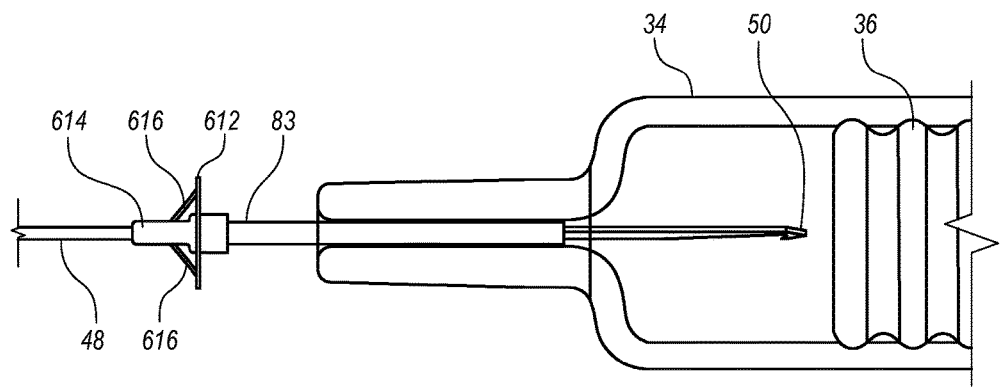
Figure 48I:
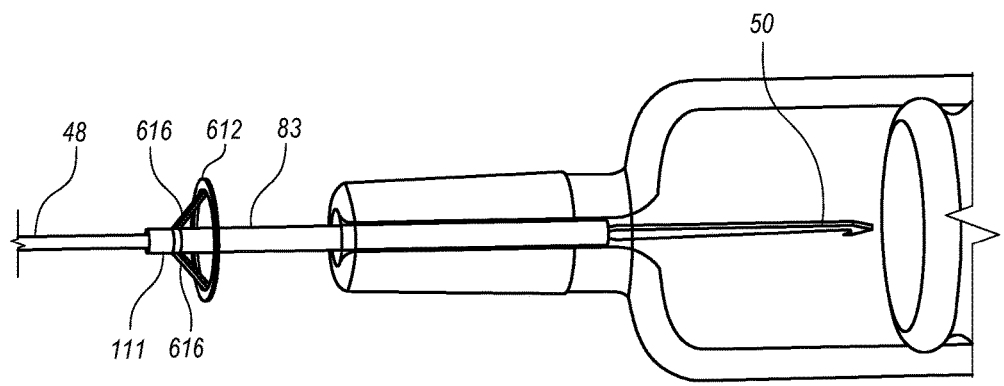
Figure 48J:
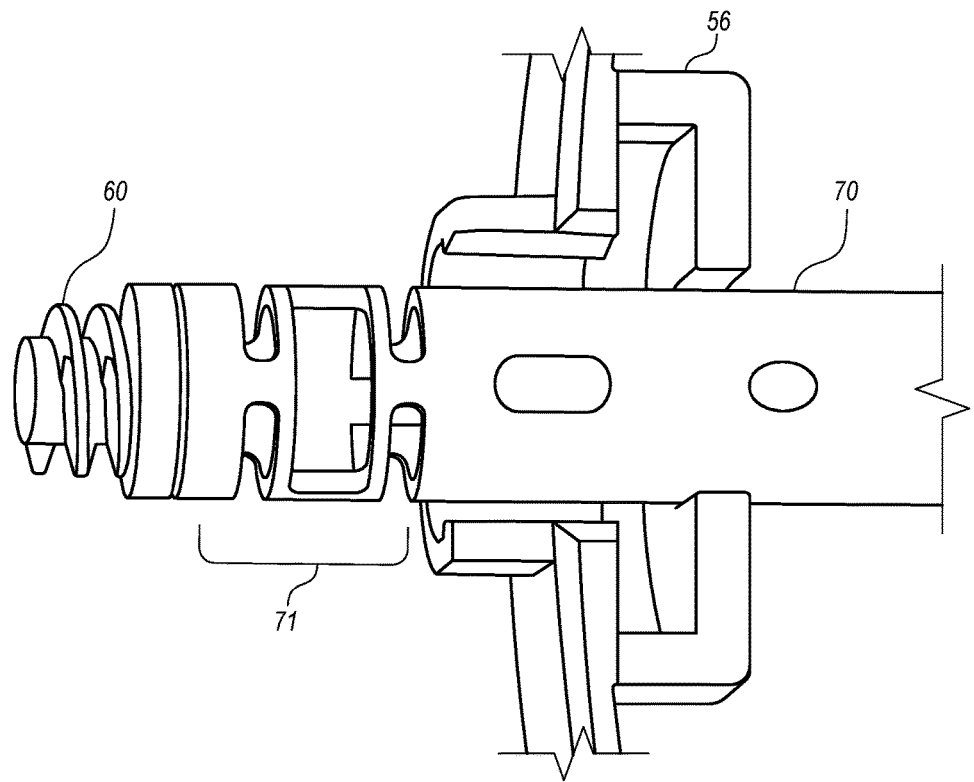
Figure 48K:
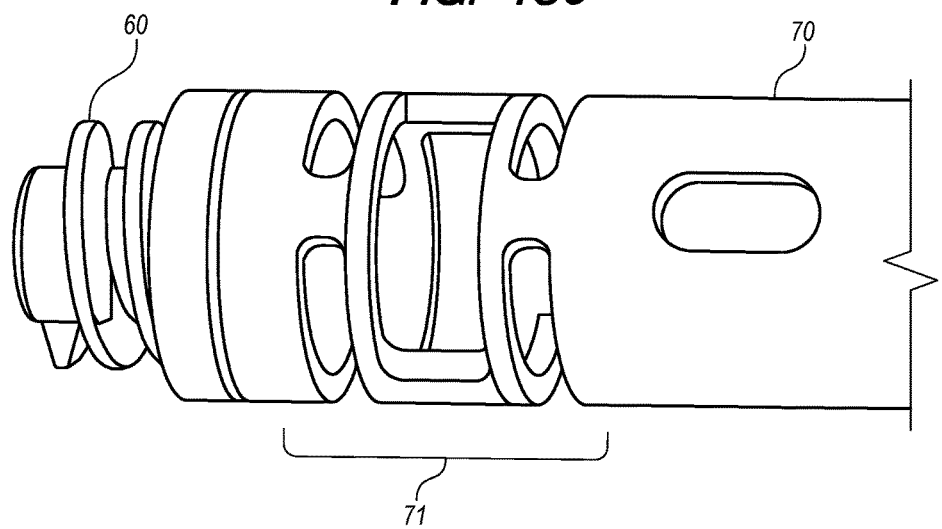

Referring to FIGS. 48A-48k, one staked needle configuration is illustrated wherein upon presentation to the user, the needle assembly, comprising a needle coupling assembly (606; itself comprising a proximal housing portion 608 and a distal housing portion 610), a needle distal tip (48), a needle joining member (83—see, for example, FIG. 48D), and a needle proximal end (50) are mounted in position ready for injection after removal of a needle cover member (63) which may comprise an elastomeric sealing material on its internal surface to interface with the needle distal tip (48) during storage. Referring ahead to FIGS. 48D and 48E, the needle joining member (83) is configured to have a necked-down or radially-reduced portion (111) that is configured to interface with a latching member (612) and movable block member (614) such that during injection, the needle distal tip (48), needle joining member (83), and needle proximal end (50) remain fixed in position relative to the syringe body (34), but after complete insertion of the plunger assembly (44) relative to the flange coupling assembly (56) (i.e., after full expulsion of the medicine which may be contained within the medicine chamber 40 of the syringe body 34), the movable block member (614) is advanced relative to the distal housing portion (610) such that the plurality (two are illustrated) of cantilevered latch members (616) of the latch member (612) are urged out of the way by the movable block member (614) to allow the needle distal end (48), joining member (83), and proximal end (50) to be retracted through their coupling (i.e., via the proximal end being stabbed through the plunger tip 36 which is being pulled proximally by the springs within the plunger assembly 44 after the plunger assembly spring configuration has been activated by the latching mechanism associated therewith, as described above), thereby placing the needle distal end (48) safely within the syringe body (34). In other words, the cantilevered latch members (616) retain the position of the needle distal end (48) during injection, until they are pushed out of the way by the movable block member (614) at full plunger insertion, after which the needle is free to be withdrawn and the spring withdrawal mechanism within the plunger assembly (44) has been triggered to effect a withdrawal. Referring to FIG. 48C, at initial assembly time (i.e., in the factory or processing facility—not in the field in a "staked needle" configuration), the proximal housing assembly (608) is configured to snap-fit (i.e., using a snap ring element 604 comprising or coupled to the proximal housing assembly) over a slightly recessed radial portion (602) of the syringe body which is formed into the syringe body upon manufacture of the syringe body. FIG. 48F illustrates a cross sectional view of such constructs in action, and FIGS. 48G-48I illustrate partial orthogonal wireframe views to more directly visualize the latching member (612) and cantilevered members (616) relative to the needle portions (48, 83, 50, 111). Referring to FIGS. 48J-48K, in one embodiment, at least one elongate portion of the plunger assembly may comprise a recessed geometry (71) configured to provide a limited amount of axial compliance to allow an operator to push the plunger assembly (44) a bit further axially into/relative to the syringe body (34) and flange coupling assembly (56) to ensure that the retraction mechanism becomes fully switched by the latching mechanism therein into the mode of retracting the needle upon full insertion of the plunger tip (36).

Figure 49A:
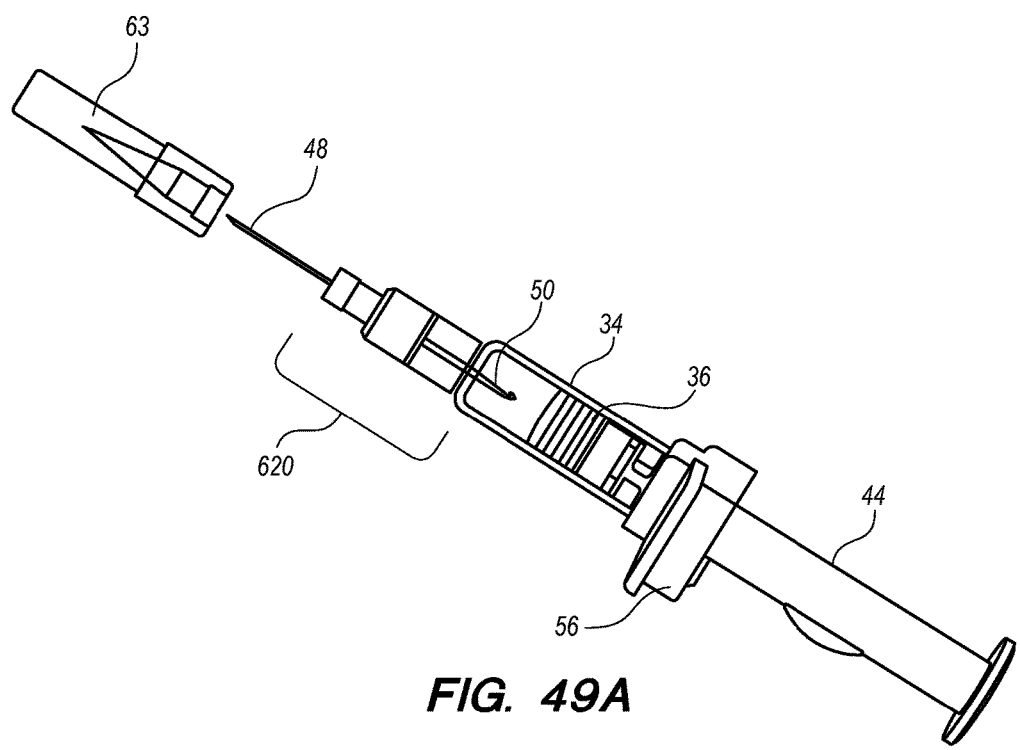
Figure 49B:
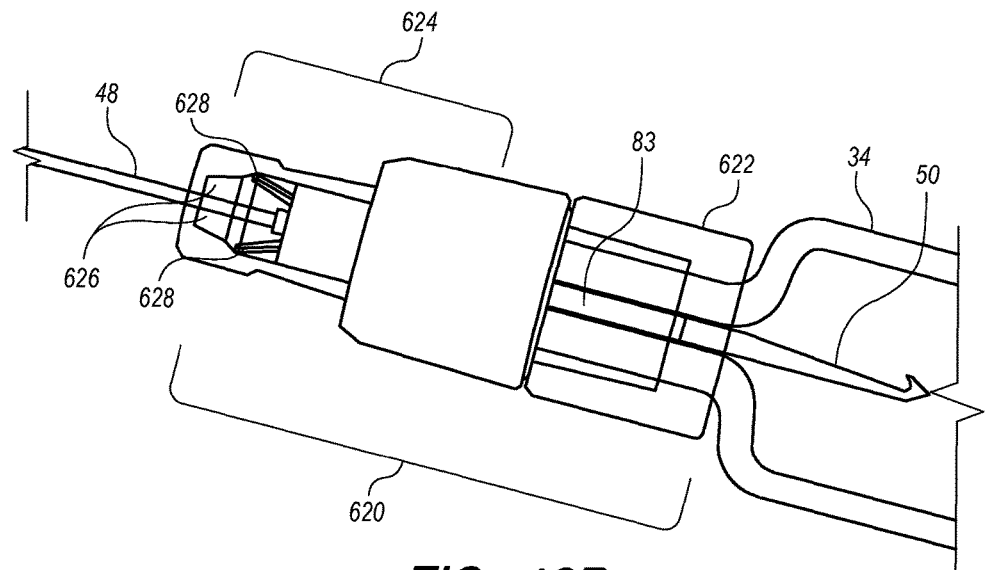
Figure 49C:
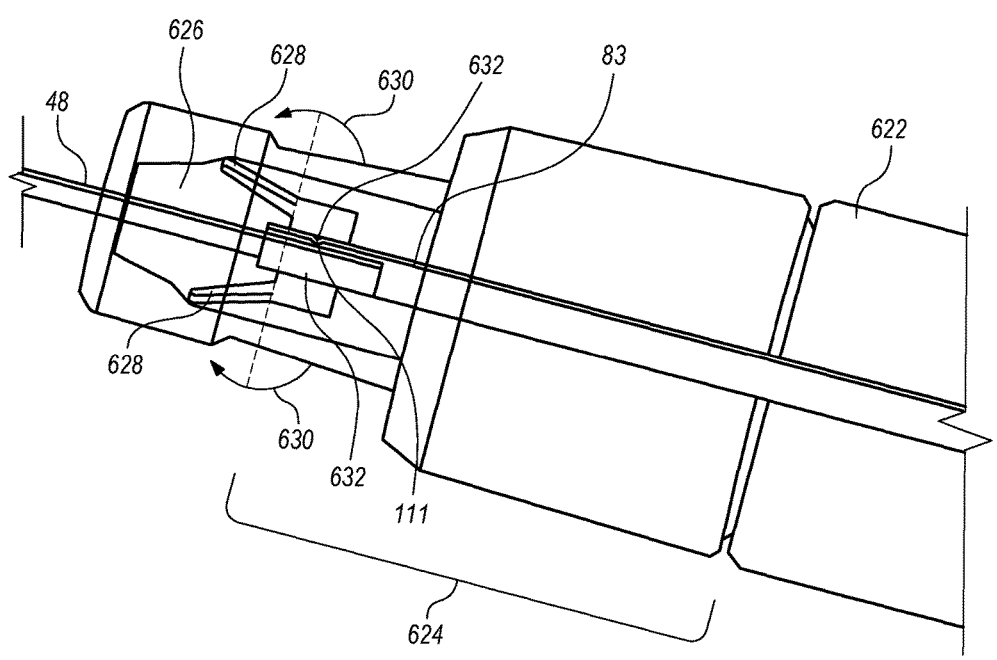

Referring to FIGS. 49A-49C, in another embodiment, a needle coupling assembly (620) comprising a proximal housing portion (622) and distal housing portion (624) is movably coupled about the needle assembly (48, 83, 50) and configured to retain the needle in an axially fixed position for injection, and then after full insertion of the plunger tip (36), each of a plurality of rotatable members (628) are urged into rotation (630) through interfacing with the interior surface of the distal housing to rotate protruding portions (632) of the rotatable members (628) out of engagement with the necked-down portion (111) of the needle joining member (83), thereby allowing for axial motion of the needle joining member (83) and intercoupled needle distal tip (48) and proximal end (50) to effect retraction into a safe position, as described above.

Figure 50E:
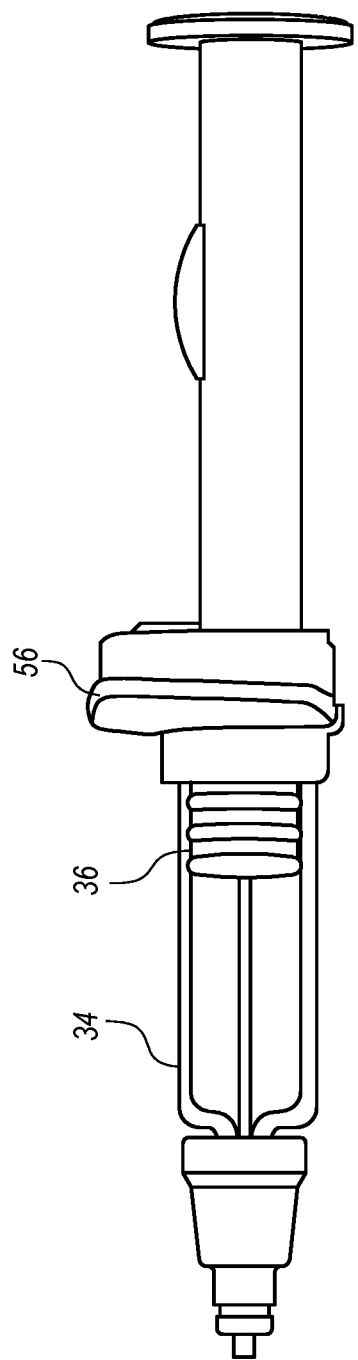
Figure 50F:
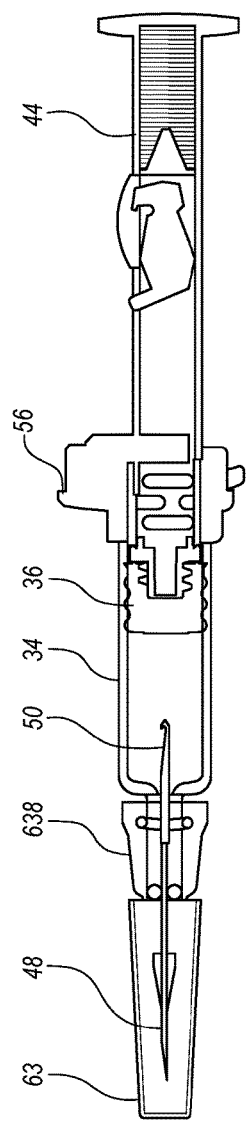
Figure 50G:
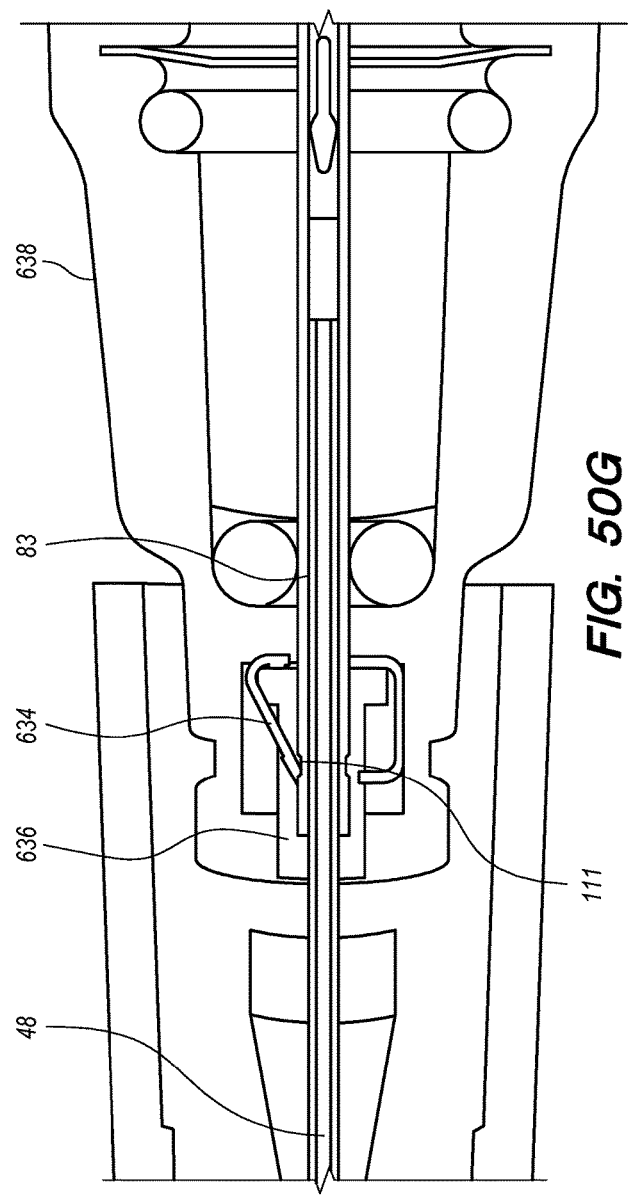
Figure 50J:
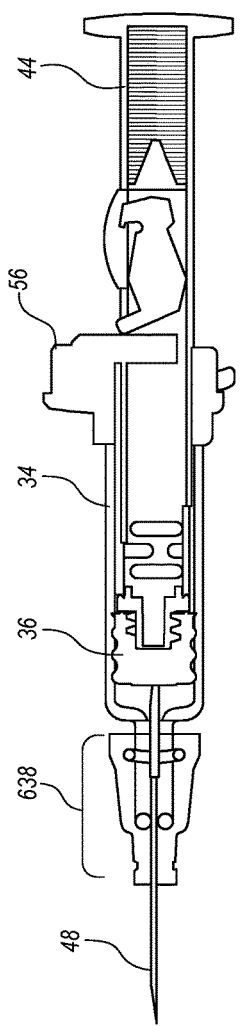
Figure 50K:
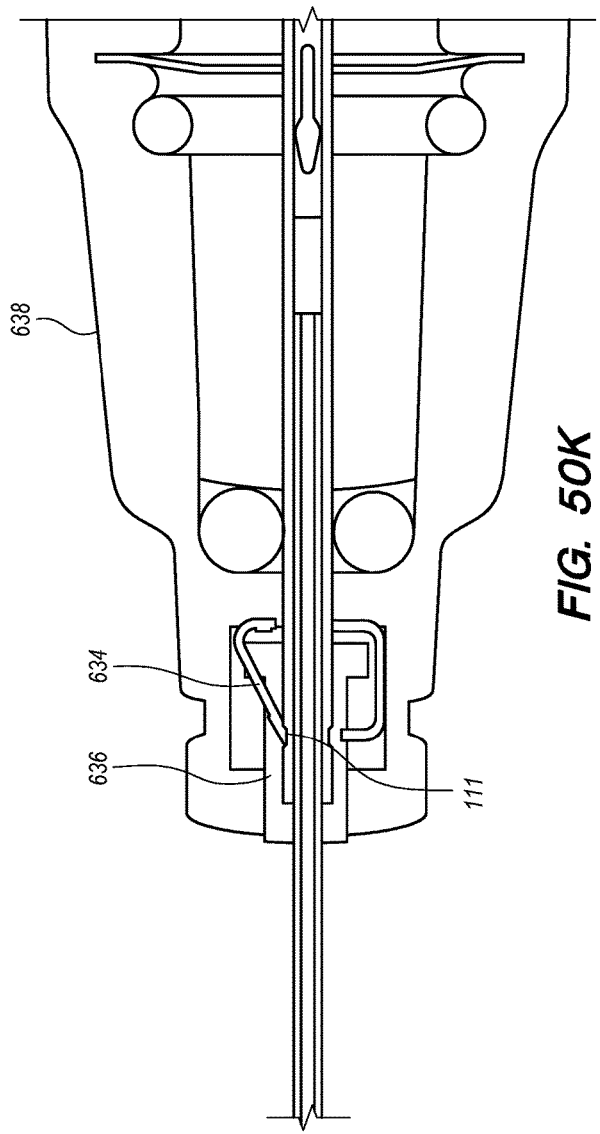
Figure 50P:
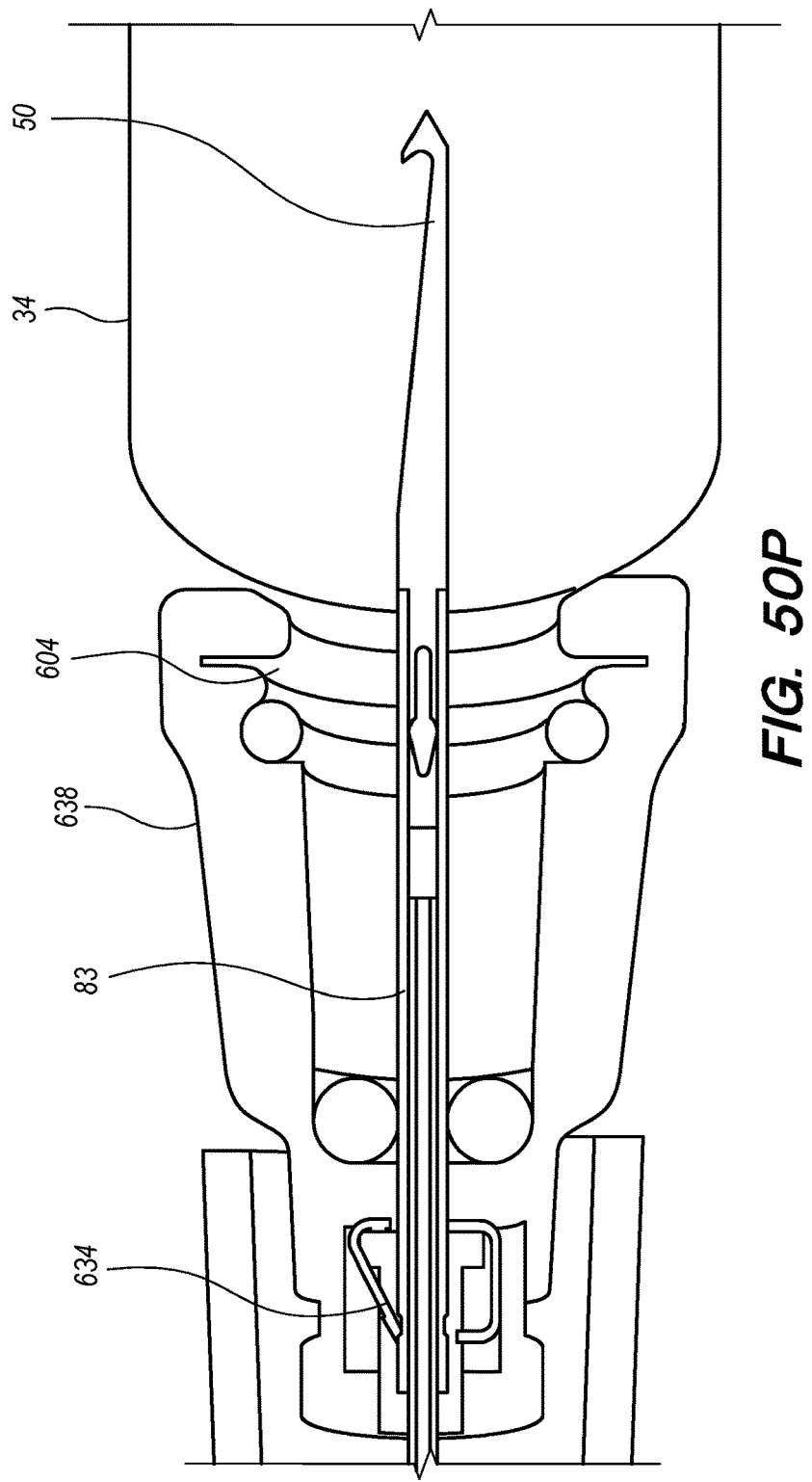

Referring to FIGS. 50A-50P, another embodiment is shown wherein a movable block member (636) is utilized to urge a latch member (634) out of the way to allow for axial retraction of the needle distal portion (48) into a safe position. FIGS. 50A-50E illustrate a succession of configurations during use; FIGS. 50F, 50H, 50J, 50L, and 50N illustrate cross sectional views corresponding to 50A-50E respectively, and FIGS. 50G, 50I, 50K, 50M, 50O, and 50P are close-in cross sectional views of the views of FIGS. 50F, 50H, 50J, 50L, and 50N, respectively.

FIG. 50A illustrates presentation of an assembly ready for use with a needle cap (63) in place, coupled to a needle coupling assembly (638). FIG. 50B illustrates the same assembly with the needle cap (63) removed, ready for injection. As shown in the cross sectional views of FIGS. 50F and 50G, a latch structure (534) is engaged against the recessed or necked-down portion (111) of the needle joining member (83) to provide a temporary axial fixation of the needle distal tip (48) during injection. FIGS. 50B, 50C, and 50D illustrate injection (i.e., into a patient) with the plunger member (36) being advanced relative to the syringe body (34). FIG. 50D and related cross sections (FIGS. 50L and 50M) illustrate full injection with the plunger member (36) seated completely into the syringe body (34) and the movable block member (636) advanced distally, which causes a feature of the movable block member (636) to push the latch member (634) away from the needle joining member (83, 111), thereby allowing the needle joining member (83) to move axially relative to the syringe body (34) and be retracted proximally into a safe position, as shown in FIG. 50E and related cross sections, after which the latch member (634) is configured to spring into an occluding shape to prevent further insertion of the needle distal tip (48). A distal tip portion of the movable block member (636) may be visualized distally from an external perspective, confirming that the syringe has been utilized. FIG. 50P illustrates that the needle coupling assembly (638) may be coupled to the syringe body (34) using a snap ring (604) fitting (i.e., as interfaced with a slight radially step-recessed portion of the syringe body 34).

Figure 51E:
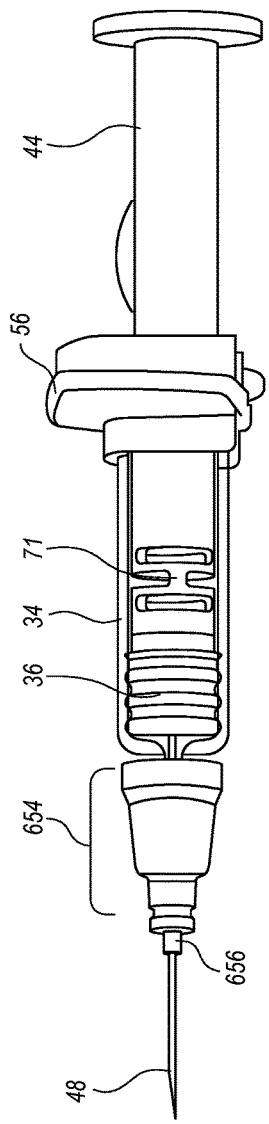
Figure 51F:
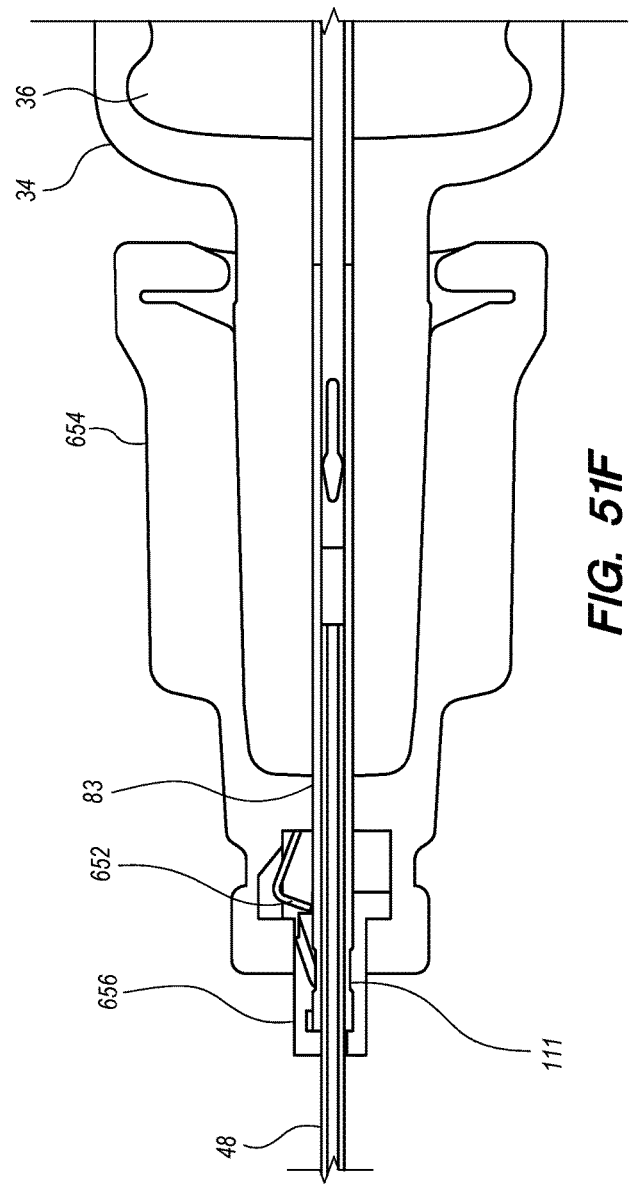
Figure 51G:
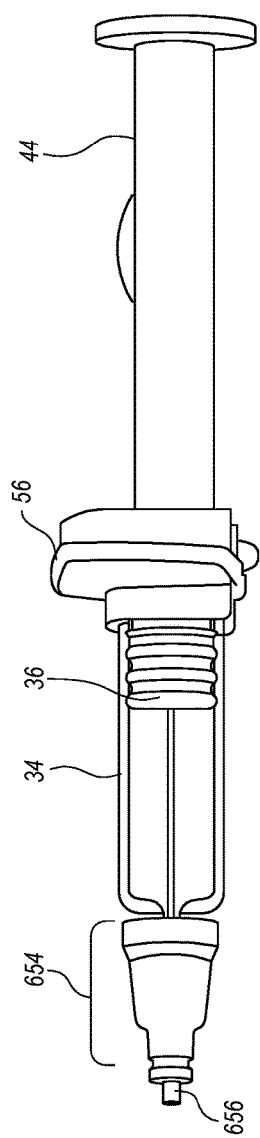
Figure 51H:
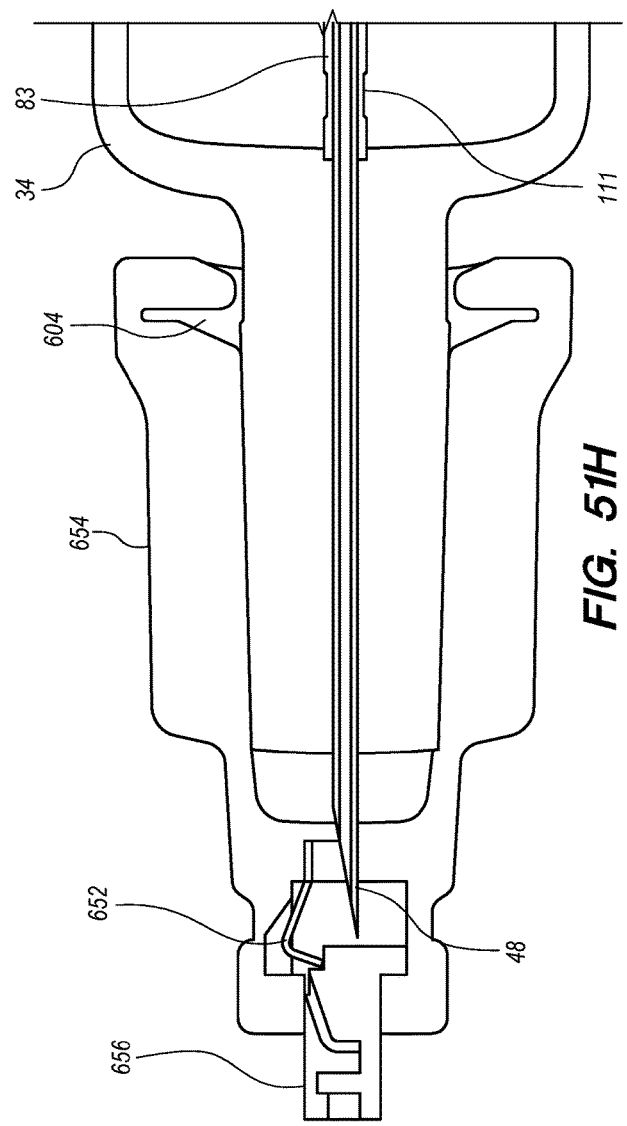

Referring to FIGS. 51A-51H, another safe injection staked needle embodiment is illustrated in sequence, with close-in cross-sectional views in FIGS. 51B, 51D, 51F, and 51H, respectively. Referring to FIG. 51A, a staked needle syringe assembly is ready for use with the cap removed. A latch structure (652) within the needle coupling assembly (654) holds the needle joining member (83) in an axially fixed location by mechanically interfacing with the recessed/necked-down portion (111). FIGS. 51C and 51D illustrate injection with axial advancement of the plunger tip (36). Referring to FIGS. 51E and 51F, with complete insertion of the plunger tip (36) relative to the syringe body (34), the movable block member (656) urges the latch member (652) out of the way, thereby freeing the needle joining member (83) to move axially relative to the syringe body (34) and be retracted into a safe position wherein further insertion of the needle distal portion (48) is blocked. Again the needle coupling assembly (654) may be joined to the syringe body via a snap fit using a snap ring.

Figure 52C:
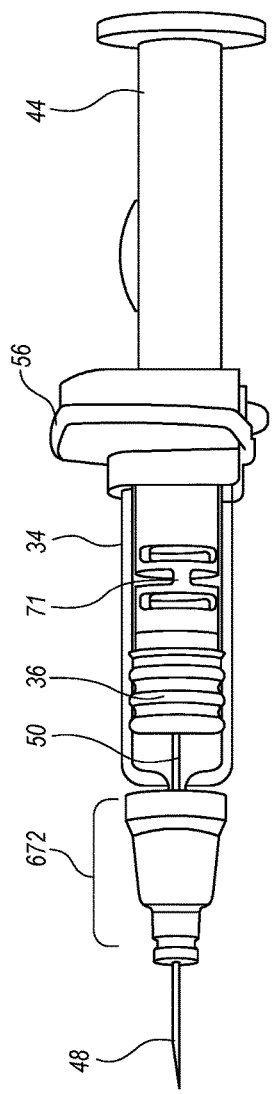
Figure 52D:
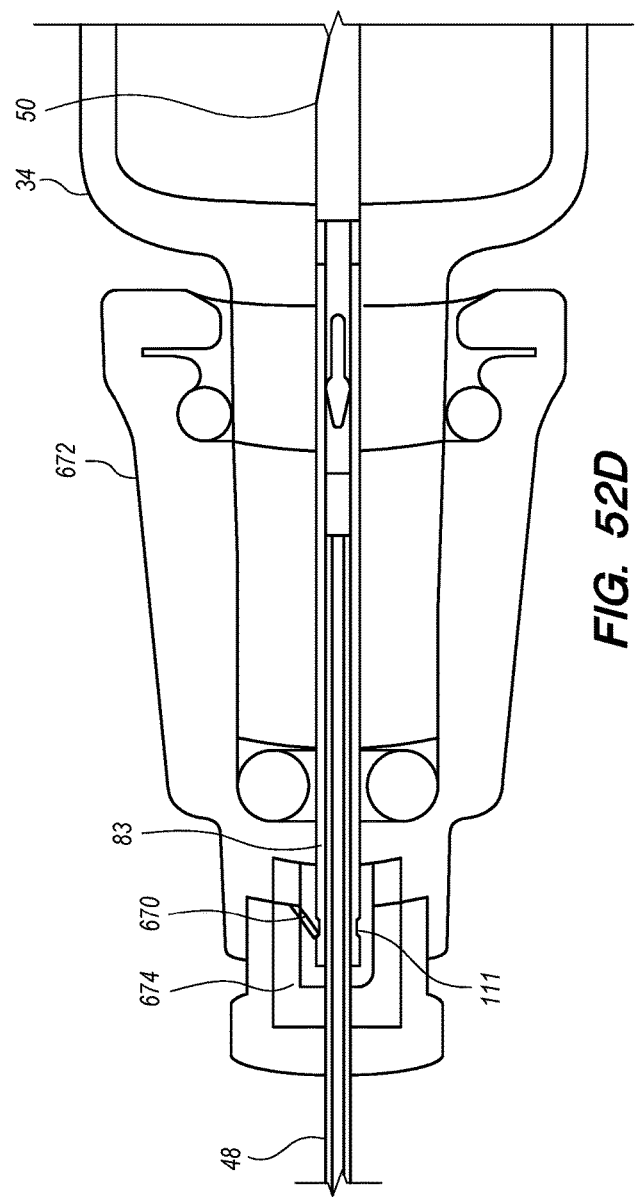
Figure 52E:
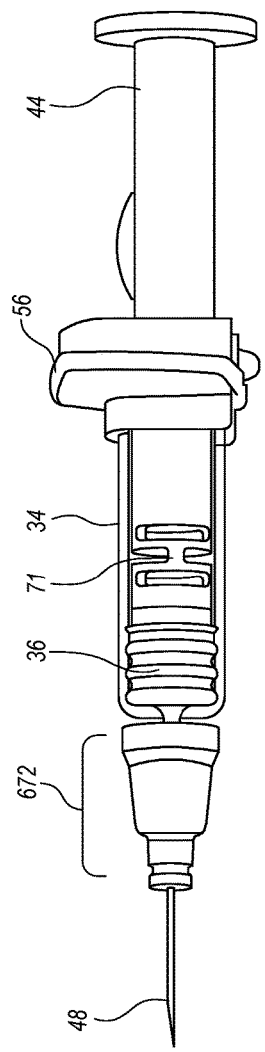
Figure 52F:
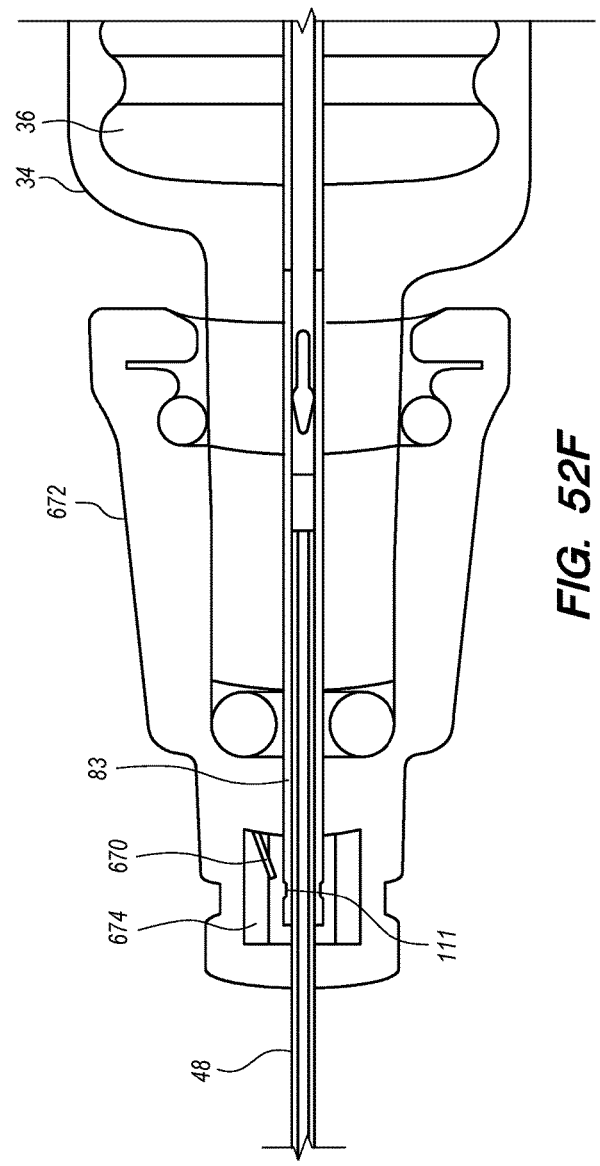

Referring to FIGS. 52A-52H, another safe injection staked needle embodiment is illustrated in sequence, with close-in cross-sectional views in FIGS. 52B, 52D, 52F, and 52H, respectively. Referring to FIG. 52A, a staked needle syringe assembly is ready for use with the cap removed. A latch structure (670) within the needle coupling assembly (672) holds the needle joining member (83) in an axially fixed location by mechanically interfacing with the recessed/necked-down portion (111). FIGS. 52C and 52D illustrate injection with axial advancement of the plunger tip (36). Referring to FIGS. 52E and 52F, with complete insertion of the plunger tip (36) relative to the syringe body (34), the movable block member (674) urges the latch member (670) out of the way, thereby freeing the needle joining member (83) to move axially relative to the syringe body (34) and be retracted into a safe position wherein further insertion of the needle distal portion (48) is blocked. Again the needle coupling assembly (672) may be joined to the syringe body via a snap fit using a snap ring (604).

Figure 53A:
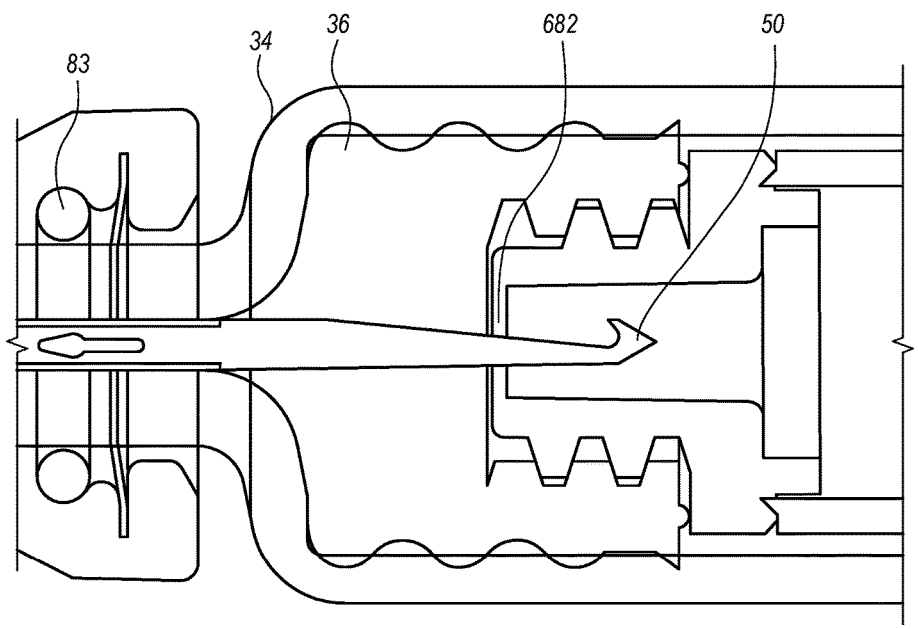
Figure 53B:
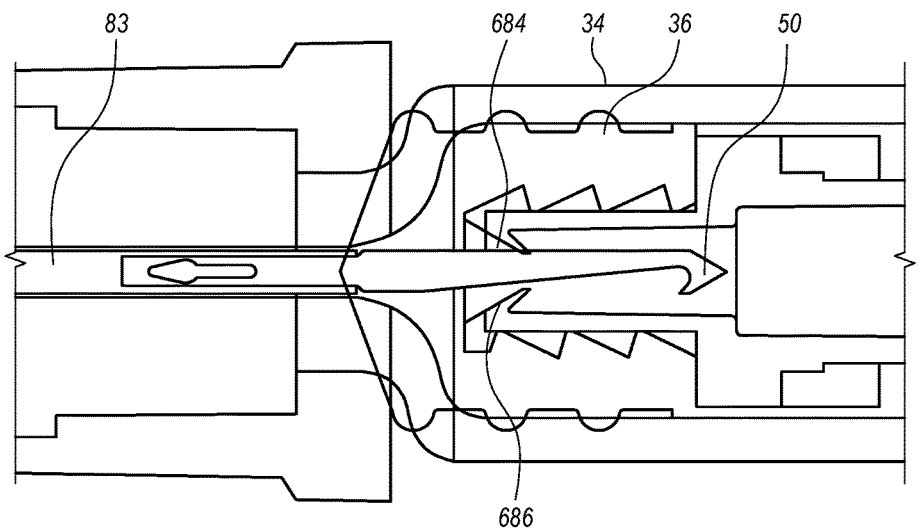

Referring to FIGS. 53A-53B, it has been described above that one configuration for axially coupling a needle proximal end (50) to a plunger tip (36) is by stabbing through both the compliant butyl rubber or other material, as well as a thin layer of harder material, such as a thin layer of polymer (682), as shown in FIG. 53A. FIG. 53B illustrates an alternative configuration wherein the plunger assembly is configured to comprise two or more cantilevered members (684, 686) configured to be relatively easily crossed in the compressive direction (i.e., during the stabbing-in motion with the needle proximal end 50), and relatively difficult to decoupled in the axial tension motion (i.e., with a needle retracting load from the plunger assembly to pull the needle distal tip into a safe configuration).

Referring to FIGS. 54A-58G, various aspects of configurations designed to facilitate injection of multi-part medications are illustrated, wherein two or more medication components are combined to form an injection combination or solution shortly before delivery into the patient. In one variation, a liquid diluent (252) may be combined with a substantially non-liquid form (254), such as a powdered form, of a drug agent, such as a freeze-dried or lyophilized drug component, as discussed above, shortly before injection. The configurations described herein in reference to FIGS. 54A-58G relate to dual-chamber configurations, wherein two or more chambers within the same syringe body (34) are utilized to carry, mix, and inject an injection solution.

Figure 54C:
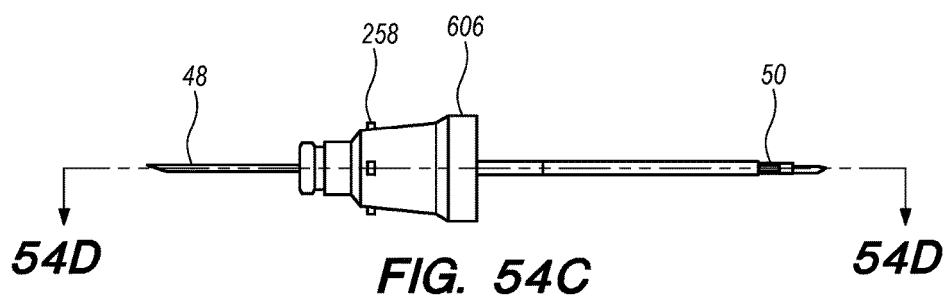
FIGS. 54A-58G illustrate various aspects of safe injection configurations, including but not limited to configurations which may be utilized with medication components designed to be mixed to form an injectable solution shortly before use.
Figure 54D:
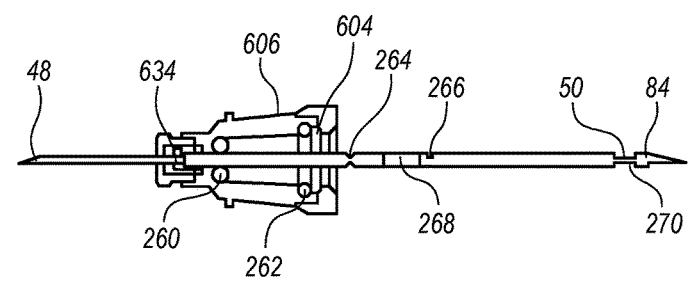
Figure 54E:
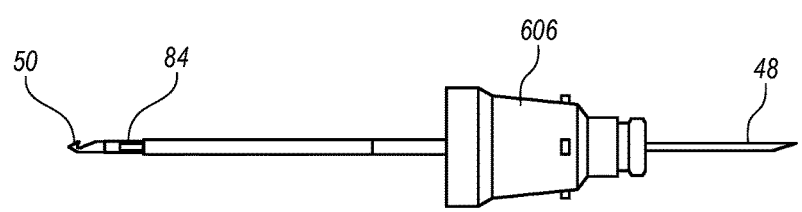
Figure 54F:
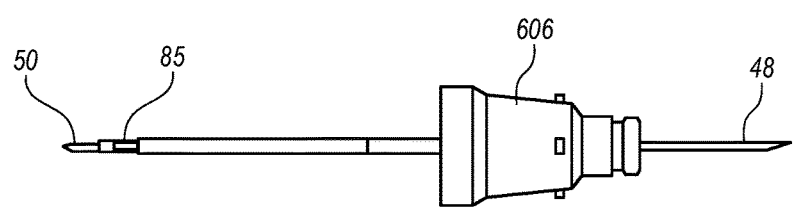
Figure 54G:
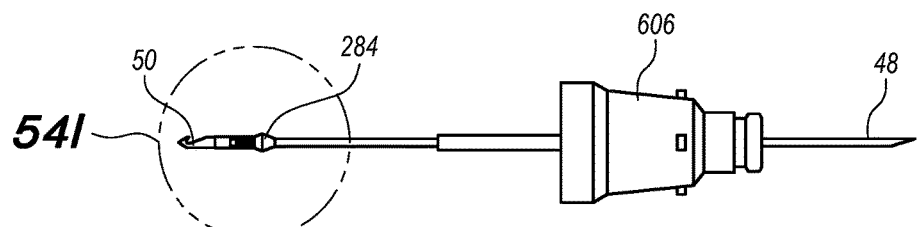
Figure 54H:
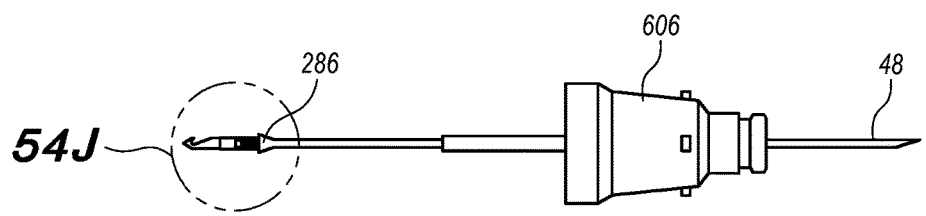
Figure 54I:
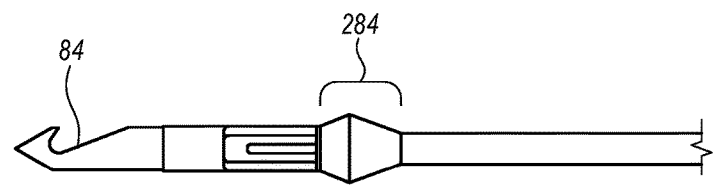
Figure 54J:
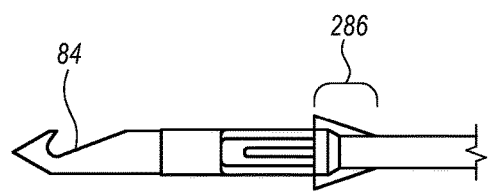
Figure 54K:
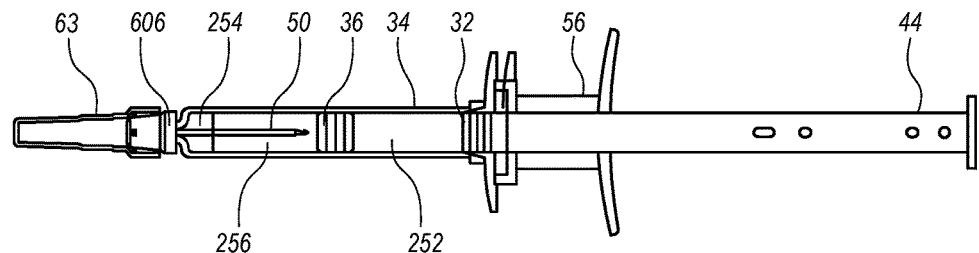
Figure 54L:
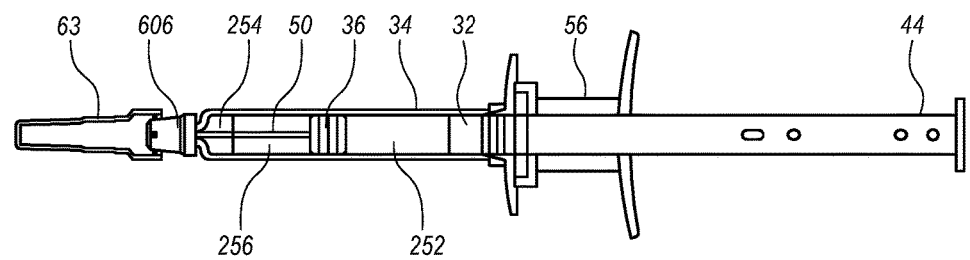
Figure 54M:
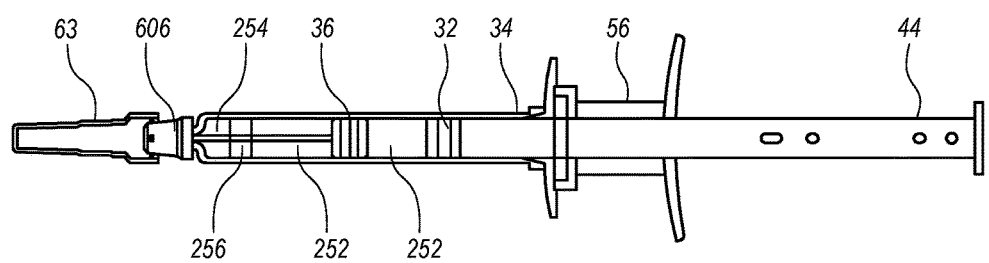
Figure 54N:
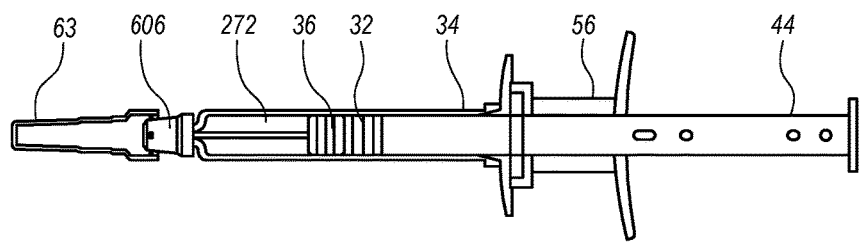
Figure 54O:
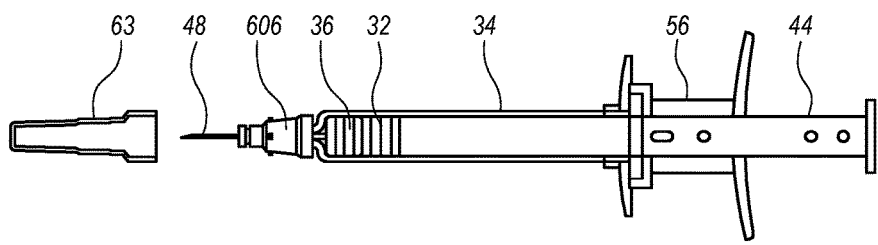
Figure 54P:
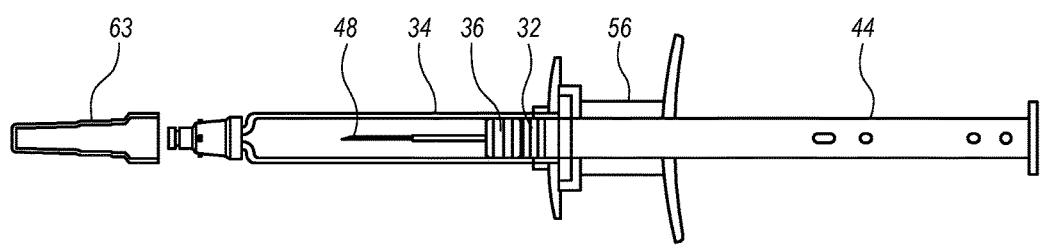

Referring to FIGS. 54A-54P, various aspects of one variation are depicted, wherein two chambers are formed by a stopper member (36) in between two portions of the interior of a syringe body (34), such that a distal portion contains an air or gas gap, as well as a non-liquid medication (254); a proximal portion, on the opposite side of the stopper member (36) contains a liquid diluent (252), which is proximally contained by a second stopper member (32). A cross sectional view is shown in FIG. 54B. Referring to FIG. 54C, and the associated cross sectional view in FIG. 54D, various components of a needle coupling assembly (here a socalled "staked" needle coupling assembly 606 is illustrated, but other needle assemblies as described above, including Luer-coupled as well as staked configurations, may be utilized). Lug features (258) are configured to assist with coupling the needle coupling assembly (606) to a needle cover member (65), as shown in FIG. 54A, for example. A small O-ring may be utilized as a sealing member (260) around the needle shaft, while a larger O-ring may be utilized as a sealing member (262) at the syringe body (34)/needle coupling assembly (606) interface. Alternatively, the small o-ring (260) and the large o-ring (262) may be combined into a single seal that performs both of the o-ring sealing functions. A proximally located mixing port (270) is configured to allow for entry of liquid diluent, to be expelled out of a more distally-located mixing aperture (266); a lumen plug (268) intentionally occludes the needle lumen to create the flow path from the proximal mixing port (270) to the distal mixing aperture (266) under conditions such as those described in reference to FIG. 54M. Referring to FIGS. 54E-54J, various aspects of suitable needle assemblies are illustrated, with several proximal geometric configurations. Referring to FIG. 54E, a proximal harpoon interface (84) is configured to stab into and couple to a stopper member (32, 36)or with a coupling feature (such as a plunger retraction latching feature; suitable plunger retraction latching features are illustrated, for example, in reference to the embodiment of FIG. 55G, element 704) in the plunger rod; FIG. 54F illustrates a spike style harpoon coupling interface (85) that is configured to pierce both stopper members (32, 36) and couple with a latching mechanism in the plunger rod to enforce an intercoupling of the two stoppers against each other during retraction of the needle member after the injection has been given to the patient. FIG. 54G and close-in detail FIG. 54I illustrate a friction bump feature (284) configured to enhance and retain coupling with a stabbed stopper member during transfer of liquid from the proximal to the distal portion of the syringe (34). The section distal to the friction bump feature (284, 286) may be of a reduced outer diameter to decrease the friction as the stopper members (32,36) travel distally during the injection of the drug solution. FIG. 54H and close-in detail FIG. 54J illustrate a triangular friction feature (286) configured to enhance and retain coupling with a stabbed stopper member. FIGS. 54K-54P illustrate a sequence of actions for an injection procedure utilizing a dual chamber configuration such as that described above. Referring to FIG. 54K, an injection assembly is in a stable configuration wherein it may be shipped or brought to an injection patient care scenario; a non-liquid drug component (254) is isolated from a liquid diluent component (252), both within a syringe body on opposite sides of a stopper member (36). FIG. 54L illustrates initial insertion movement of the plunger assembly (44), advancing the distal (36) and proximal (32) stopper members relative to the syringe body (34). Referring to FIG. 54M, with further advancement, sufficient to stab the proximal end of the needle assembly across the distal stopper member (36), a fluid pathway is formed between the two previously isolated chambers of the syringe body (34), such that the diluent fluid (252) may flow into the proximal mixing port and exit the more distal mixing aperture, to reach the non-liquid medication component (254). FIG. 54N illustrates that with further insertion until the stopper members (36, 32) are immediately adjacent each other, the diluent (252) and previously non-liquid component (254) become mixed to form a medication solution (272). Referring to FIG. 54N, with the assembly now ready for injection of the mixed solution (272), the needle cover member (63) may be removed as shown in FIG. 54O and the patient may be injected with the exposed needle distal end (48). With full depression/insertion of the plunger assembly (44) and associated stopper assembly (36, 32) as shown in FIG. 54O, the needle may be retracted to a safe position within the syringe body (34), as described above and shown here in FIG. 54P.

Existing lyophilization manufacturing processes perform the lyopilization (freeze-drying) of the drug inside of the syringe chamber which is sealed proximal to the drug with a stopper and the distal tip of the syringe open, exposing the drug to the lyophilization process through the inside diameter ("ID") of the tip of the syringe. This existing process generally does not allow for the use of traditional glued-in staked needles, as the needle would have to be in place prior to lyophilization due to the glue curing process. The ID of the traditional 25 gauge to 34 gauge staked needles are around 0.010" to 0.003" and generally are too small in cross section to allow lyophilization of the drug in a reasonable time. The staked needle assembly shown in FIGS. 54A-G uses a luer taper tip syringe with a tip ID of about 0.040" that allows for lyophilization. The staked needle of FIGS. 54A-58G is attached to the syringe via a snap-fit after lyophilization has taken place, sealing the drug container, and allowing for the use of the existing lyophilization manufacturing processes.

Figure 55C:
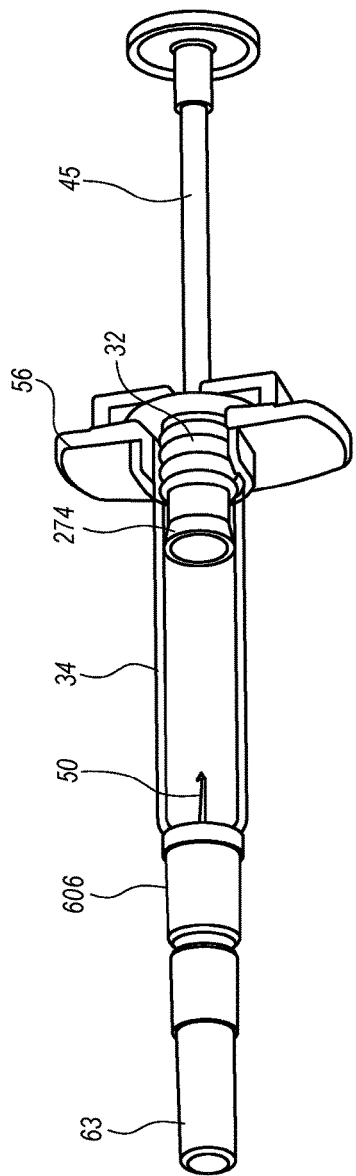
Figure 55D:
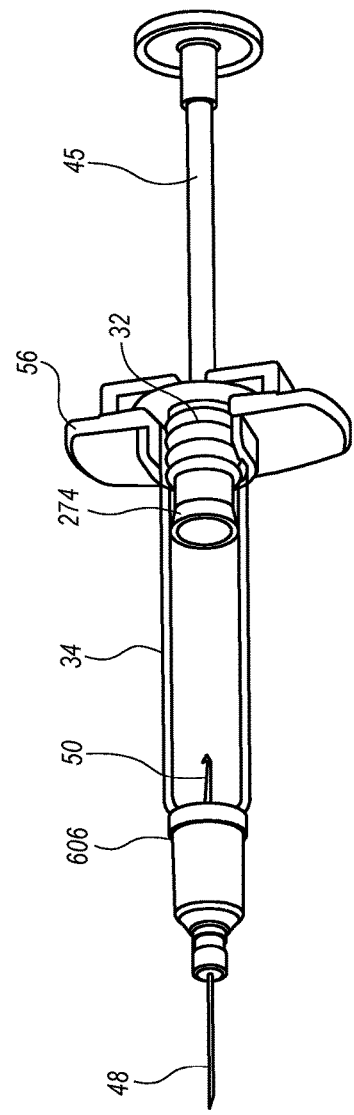
Figure 55G:
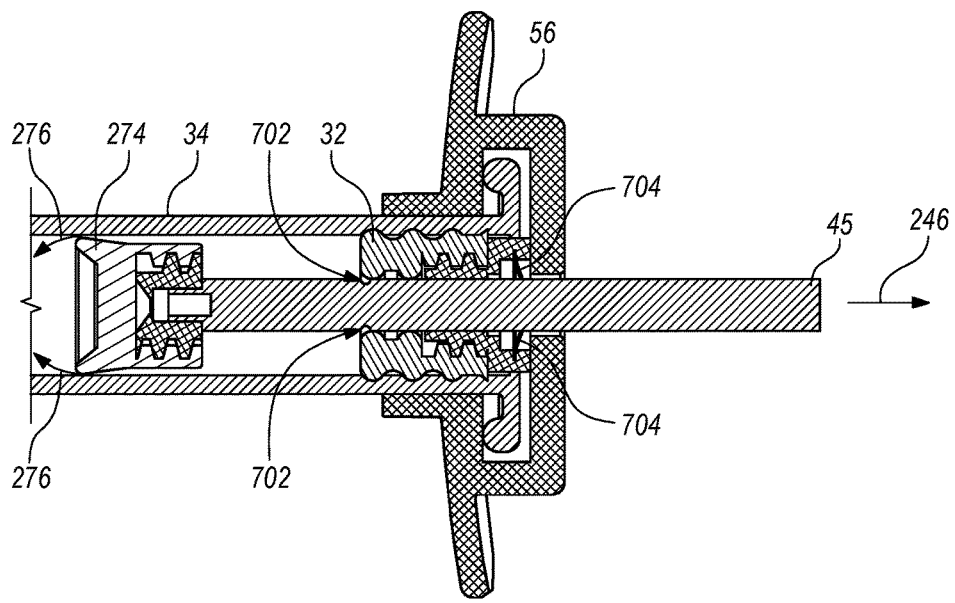
Figure 55H:
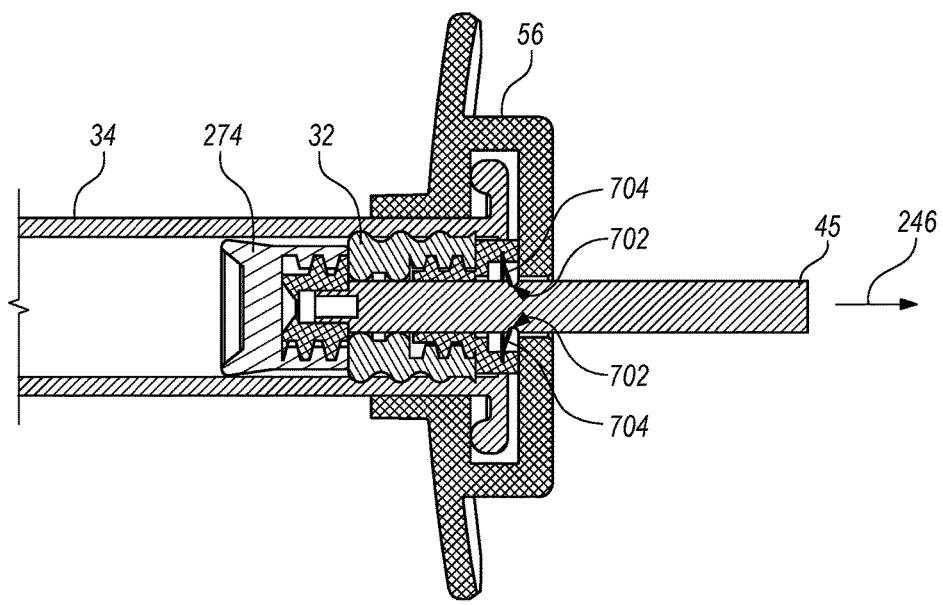

Referring to FIGS. 55A-55H, various aspects of an embodiment are illustrated wherein a generally cylindrical stopper with an enlarged distal circumferential surface (274) is configured to separate two sub-chambers of a syringe body (34) when static, but to allow for passage around of a proximal fluid component (276) when the generally cylindrical stopper (274) is pulled proximally (FIG. 55G depicts a close-in cross sectional view depicting pass-by flow 276), thereby reducing the effective diameter of its flexible distal portion with enlarged distal circumferential surface (274). Thus, referring to FIG. 55C, with the generally cylindrical stopper (274) pulled all the way proximally (a simplified plunger assembly 45 is shown in FIGS. 55A-55H for illustrative purposes, but in other embodiments, retraction assemblies, such as those described above in reference to drawing element 44 may be utilized) so that the generally cylindrical stopper (274) is interfaced directly with a proximal stopper member (32), fluid previously contained between the two stopper members (274, 32) becomes advanced to the other side of the generally cylindrical stopper (274) so that it becomes combined with medication elements which may be contained on such other side of the generally cylindrical stopper (274), such as non-liquid lyophilized drug components. Referring to close-in cross-sectional FIGS. 55G and 55H, to facilitate withdrawal of the needle into the syringe body (34) after patient injection using a plunger assembly configured to automatically withdraw relative to the syringe body (34) as described above in various embodiments, it may be desirable to enforce a coupling between the plunger assembly (45) and one or both of the stoppers (32 proximal; 36, 274, or 280 distal) to which the needle assembly may be coupled (such as by a harpoon-like proximal needle interface 50, 84) after such injection has been completed (i.e., after the plunger assembly has been fully inserted relative to the syringe body). Referring to the embodiment of FIGS. 55G and 55H, one or more necked-down or indented features (702) may be positioned along the plunger assembly (45) such that upon withdrawal (246) of the generally cylindrical stopper (274) for drug mixing before injection, as shown in FIG. 55H, one or more latching members (704) spring down into the indented features to lock the plunger assembly in position relative to the syringe body (34), such that the two stopper members (274, 32) are coupled together by virtue of such latching/indent (704/702) interfacing. With such plunger retraction induced drug component mixing complete, the mixed medication solution may then be injected by removing the needle cover member (63) and advancing the plunger assembly (45) as shown in FIG. 55E; the generally cylindrical stopper (274) is configured such that the distal circumferential surface will seal against the inside of the syringe body (34) when pushed distally (i.e., this unique stopper is somewhat of a one-way valve contained within the syringe body and moved by the plunger assembly 45). With full depression/insertion of the plunger assembly (45) and associated stopper assembly (274, 32), the needle may be retracted to a safe position within the syringe body (34), as described above.

Figure 55I:
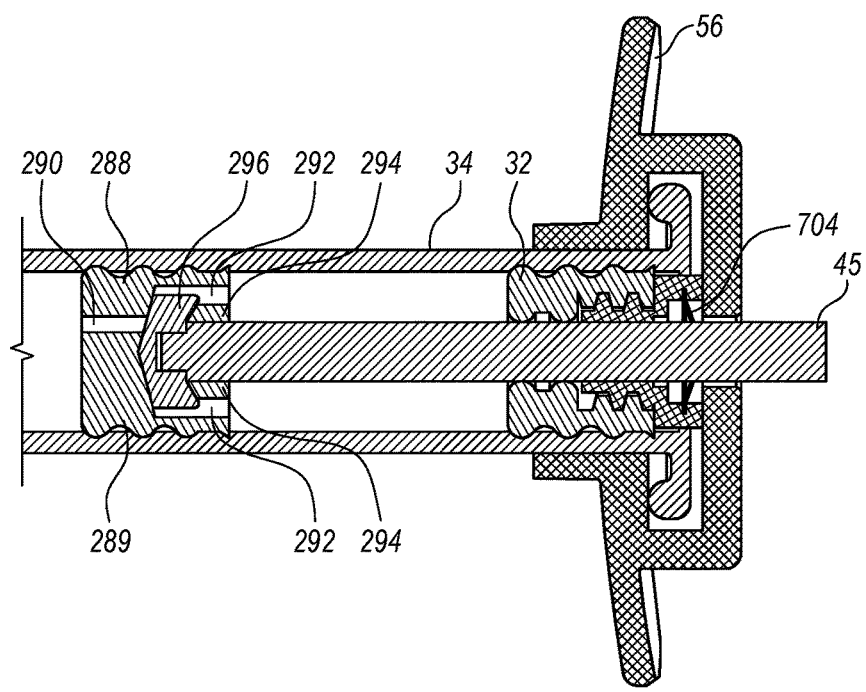
Figure 55J:
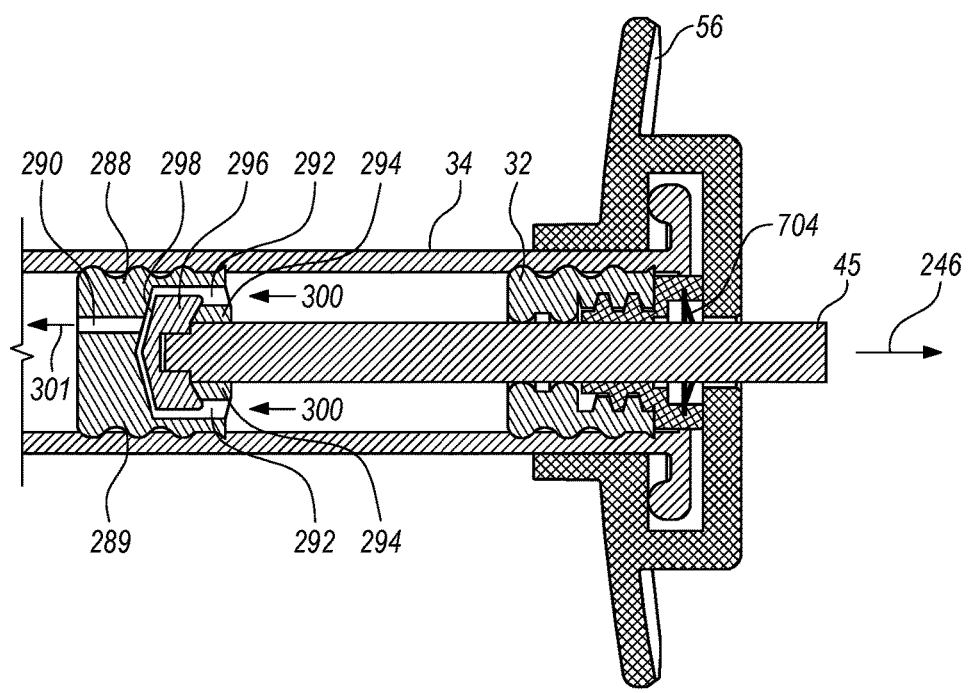

Referring to FIGS. 55I and 55J, an alternative variation is depicted wherein a stopper (288) comprises a valve formed therethrough which may be opened by pulling or withdrawing (246) the plunger assembly attached to the stopper (288) relative to the syringe body (34). Referring to FIG. 55I, with substantially no load, or with a pushing load, applied to the stopper (288) with the plunger assembly (45), fluid is not allowed to pass across the stopper (288). Referring to FIG. 55J, with a retracting or withdrawing (246) load applied to the plunger assembly (45) relative to the syringe body (34), a passageway (298) opens between the main distal stopper body (289) and the distal stopper portion (296) due to transient deformation of the proximal stopper portion (294) such that medicinal fluid may flow (300, 301) across the stopper (288) through one or more proximal channels or lumens (292), across the opened passageway (298), and out the distal channel (290); the structural moduli of the materials, as well as the geometries of the features, such as the proximal stopper portion (294) may be selected specifically to cause this fluid pathway to open during retraction/withdrawal (246) of the plunger assembly (45) relative to the syringe body (34), and to close when not under such loading.

Figure 56A:
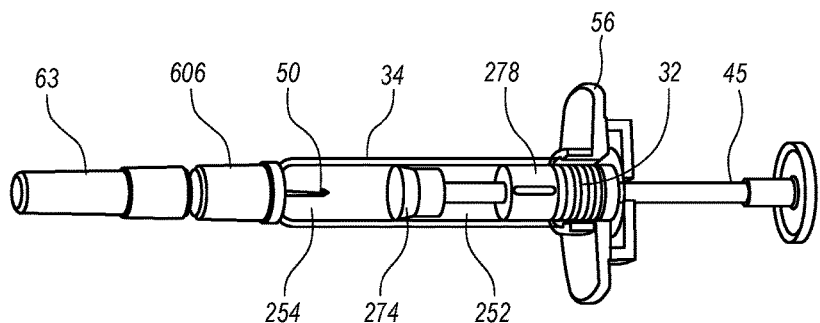
Figure 56B:
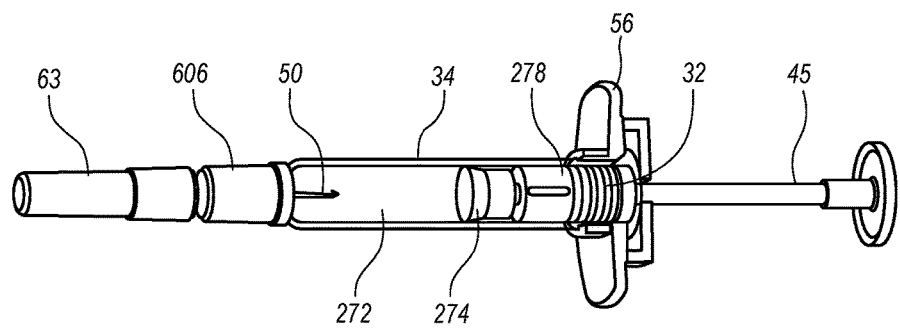
Figure 56C:
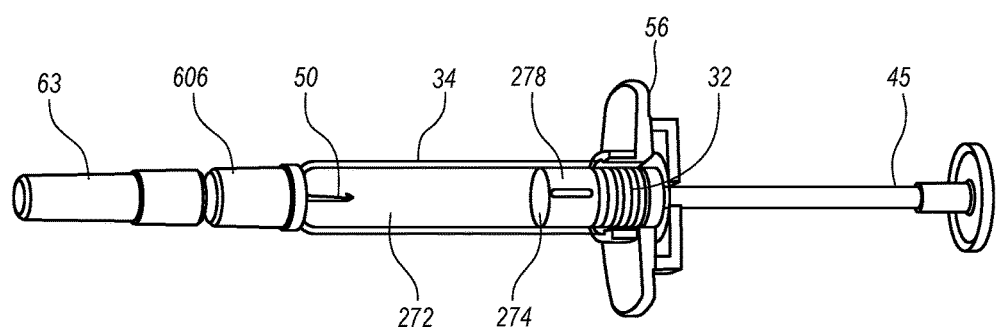
Figure 56D:
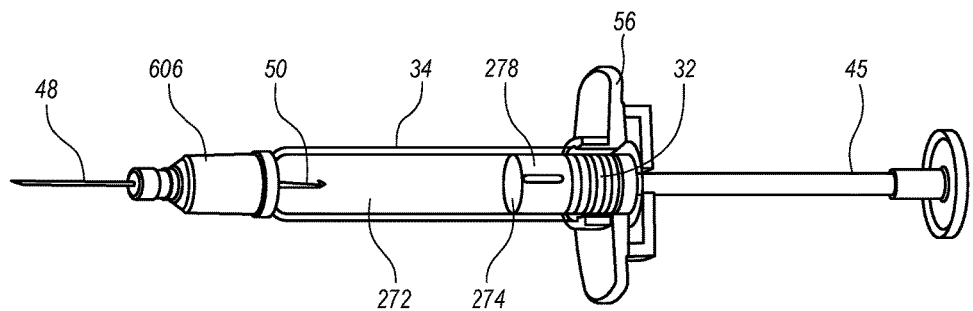
Figure 56E:
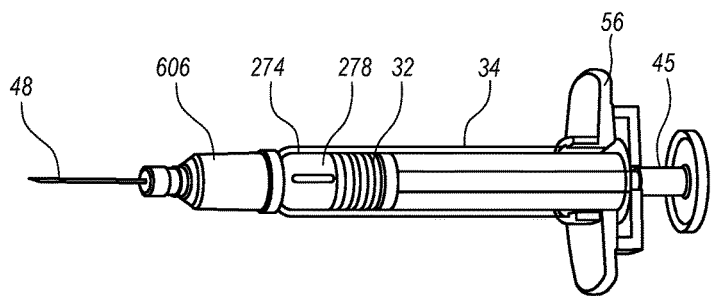
Figure 56F:
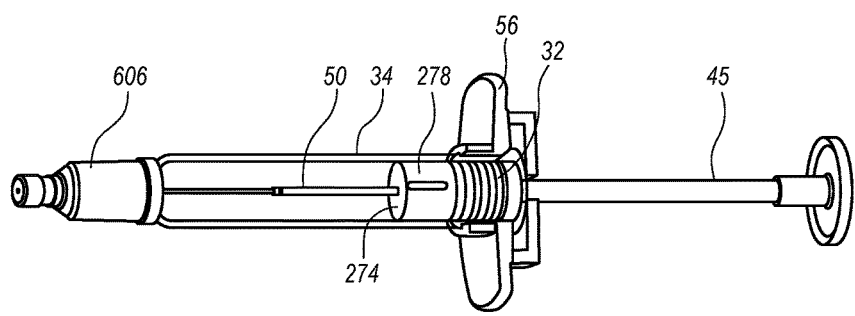

Referring to FIGS. 56A-56F, it may be desirable to physically contain the generally cylindrical stopper (274) after it has been withdrawn to complete mixing of the medication components, to minimize insertion friction during injection of the mixed solution. As shown in FIGS. 56A-56C, upon full retraction, the generally cylindrical stopper (274) becomes physically contained within the stopper containment cup (278) so that upon insertion of the plunger assembly (45), only the proximal stopper member (32) provides a sealing function during injection while the generally cylindrical stopper (274) remains contained within the stopper containment cup (278). As shown in FIG. 56F, with full depression/insertion of the plunger assembly (45) and associated stopper assembly (274, 32), the needle may be retracted to a safe position within the syringe body (34), as described above.

Figure 57A:
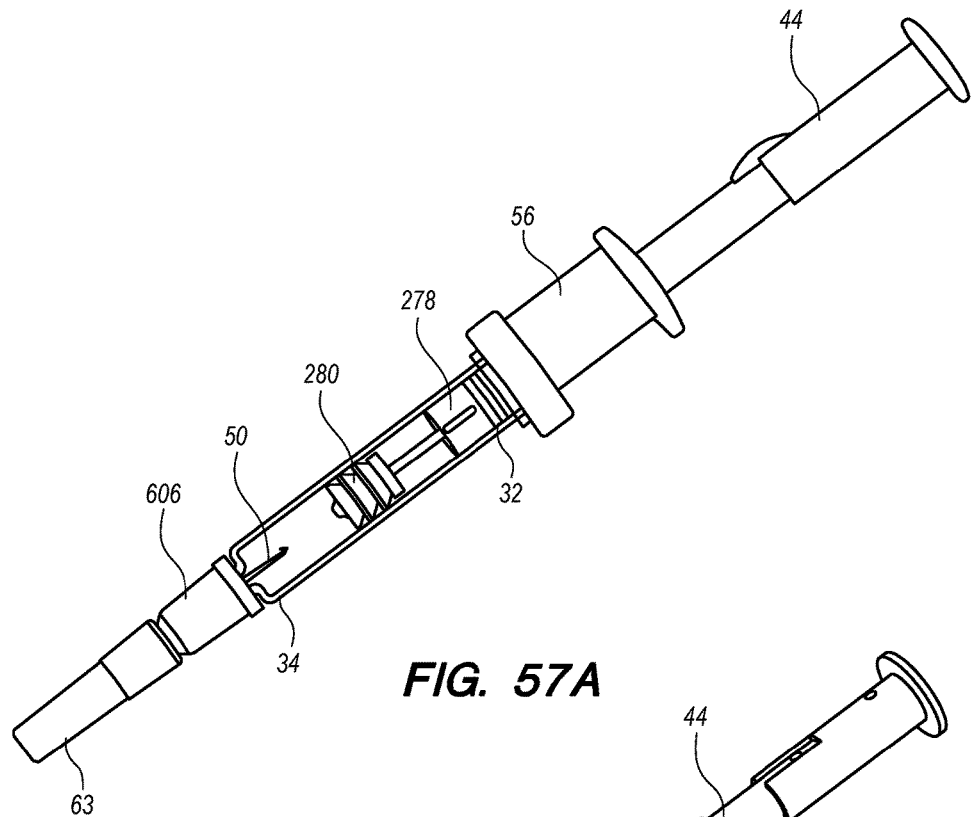
Figure 57B:
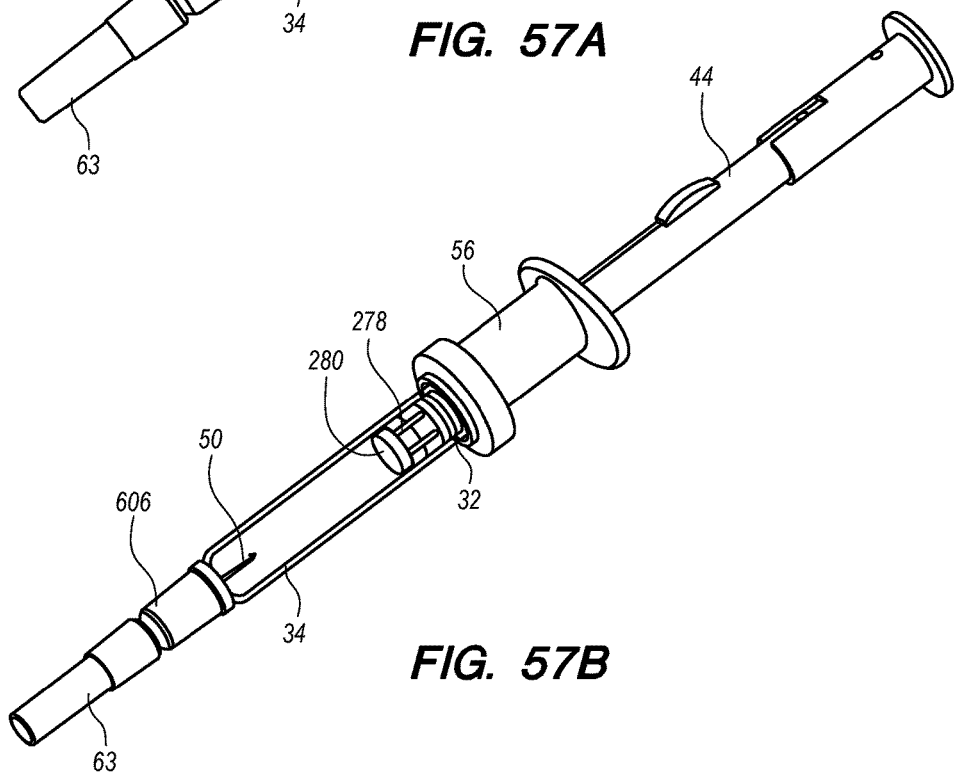
Figure 57C:
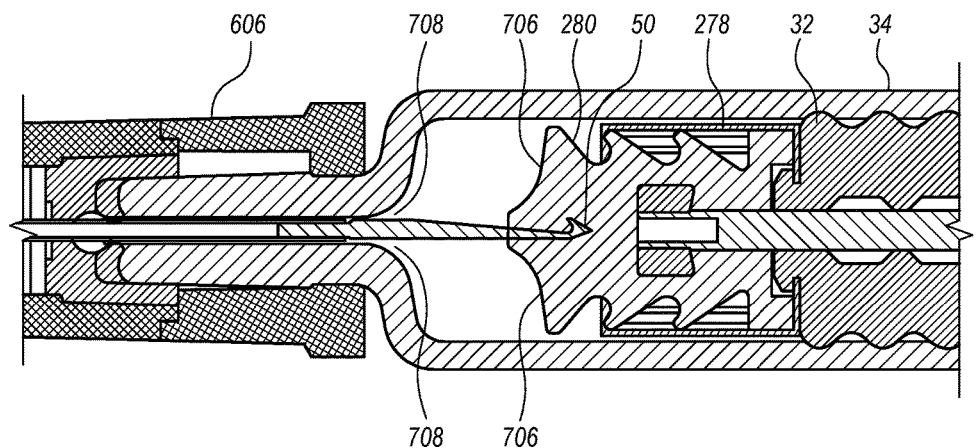

FIGS. 57A-57C illustrate aspects of a configuration similar to that of FIGS. 56A-56F, with the exception that the distal stopper member comprises a generally cylindrical stopper assembly with multiple circumferentially flared "wiping" edges (280) to facilitate a sealing effect when pushed distally (i.e., toward the distal needle tip), and also facilitate fluid passage around such stopper assembly (280) when withdrawn proximally. Referring to FIG. 57C, of the distal surface (706) of the stopper assembly (280) is contoured to closely match the the interfacing surface (708) of the distal end of the interior of the syringe body (34) to minimize any residual drug in the chamber after the injection has been performed, ensuring an accurate medicine dosage.

Figure 58A:
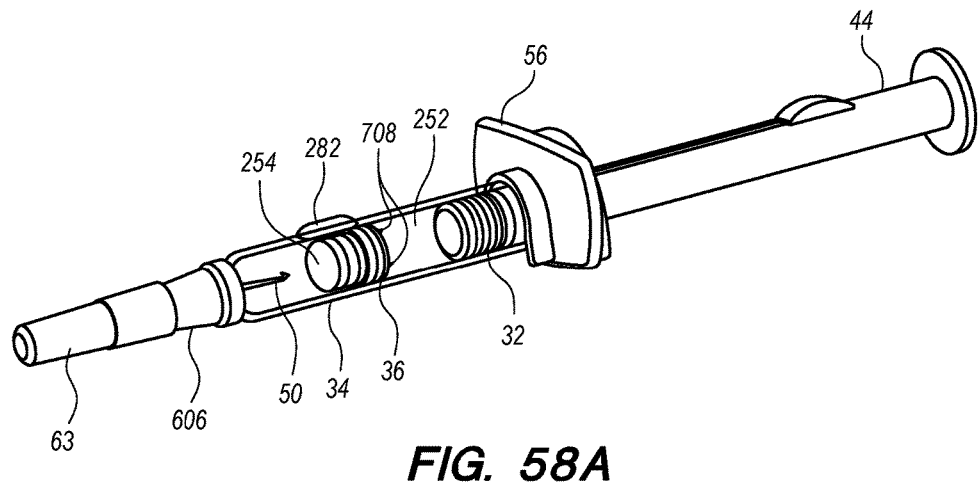
Figure 58B:
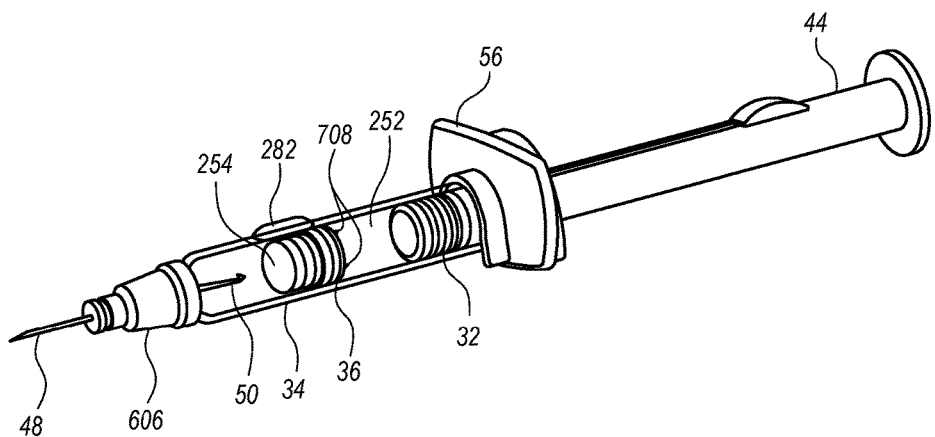
Figure 58C:
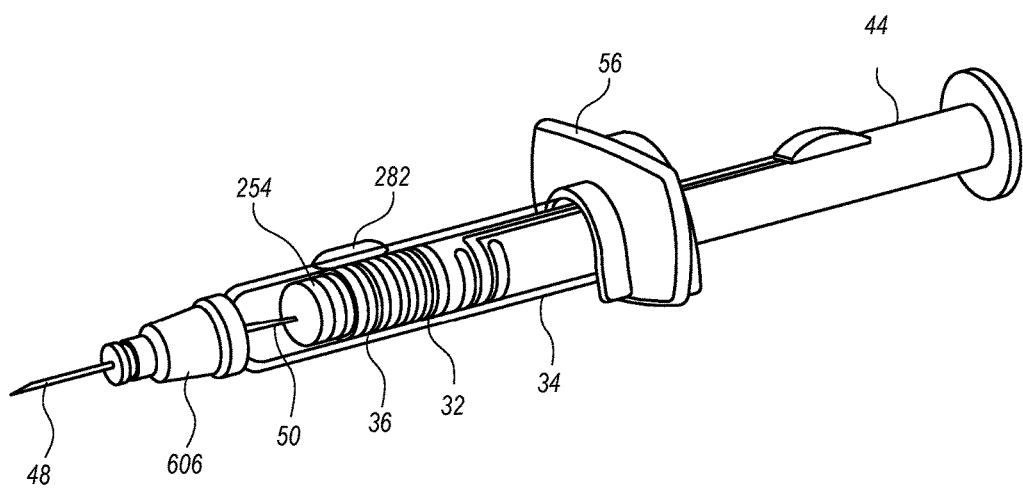
Figure 58D:
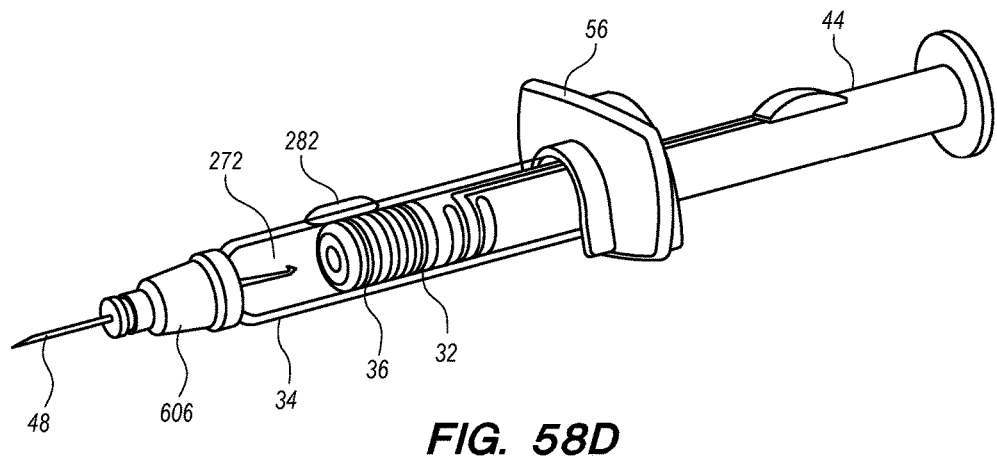
Figure 58E:
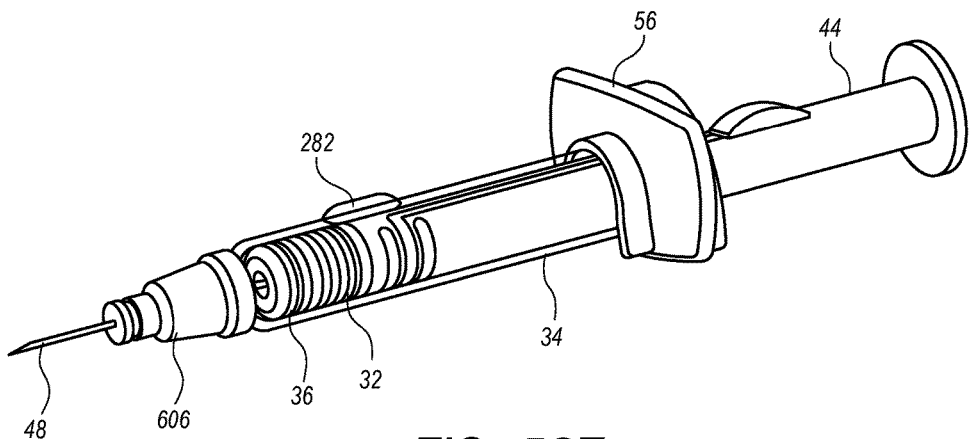
Figure 58F:
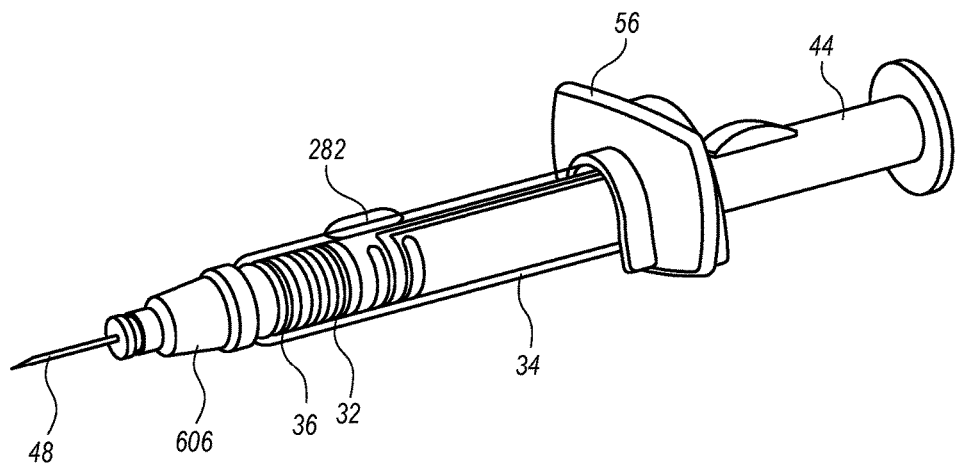
Figure 58G:
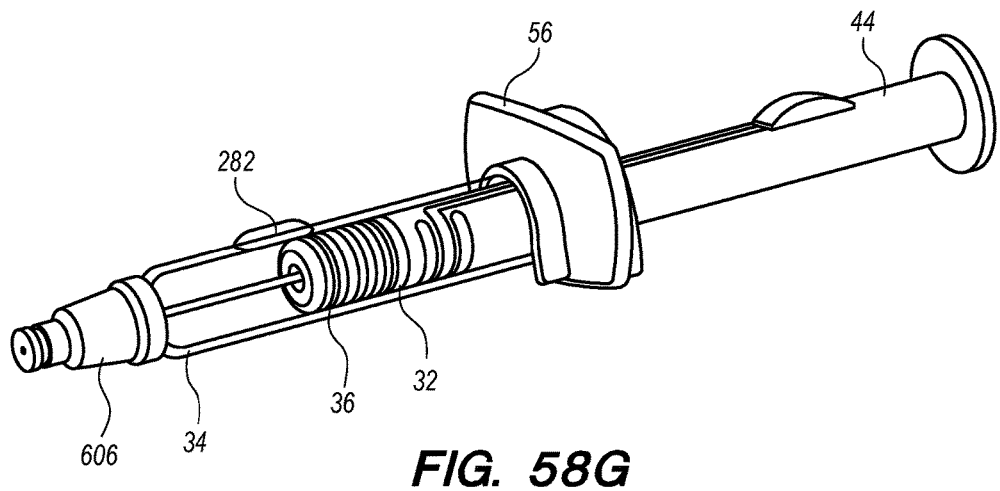

Referring to FIGS. 58A-58G, another dual-chamber embodiment is illustrated wherein rather than allowing for selective fluid passage through a portion of the needle to facilitate mixing, as in the embodiment of FIGS. 54A-54P, a syringe body (34) configuration features a bypass passageway (282) formed into the particular syringe body configuration and positioned such that upon insertion of the distal stopper member (36) to a position such as that shown in FIG. 58C, the bypass passageway (282) allows for pressurized fluid to bypass the distal stopper member (36) and gain access to the previously isolated other medical component (274) to form a mixed medication solution (272) which may be injected using further insertion of the plunger assembly (44) and associated stopper assembly (36, 32), as shown in FIGS. 58D-58F. As described above in reference to the embodiment of FIG. 55G, for example, it may be desirable to have the stoppers (32, 36) become coupled to one another to facilitate automatic withdrawal of not only the proximal stopper member (32) which is directly coupled to the automatically retracting plunger assembly (44), but also distal stopper member (36), to ensure that the needle assembly, which may be coupled to the distal stopper member (36), or both stopper members (36, 32) is withdrawn into a safe position at least partially within the syringe body at the appropriate time. Referring to FIGS. 58A and 58B, the depicted distal stopper member (36) features proximal harpoon-like coupling members (708) configured to stab into and couple to the proximal stopper member (32) when the two stopper members (36, 32) are urged against each other, such as during the injection as shown in FIG. 58F. As shown in FIG. 58G, after full depression/insertion of the plunger assembly (44) and associated stopper assembly (36, 32) to expel the medication solution (272) into the patient, the needle may be retracted to a safe position within the syringe body (34), as described above.

Figure 59A:
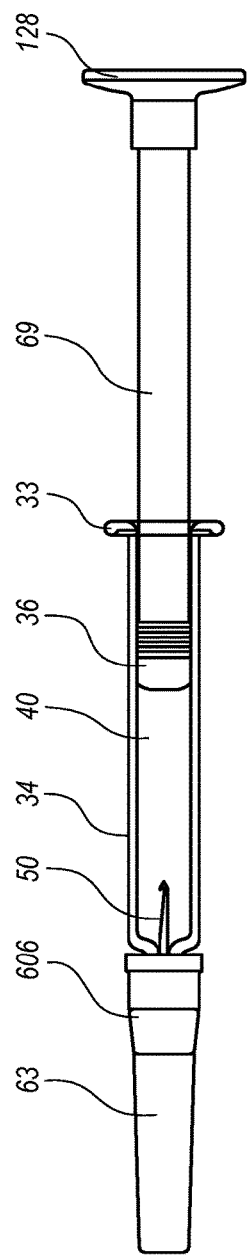
FIGS. 59A-61S illustrate various aspects of safe injection configurations, including but not limited to configurations wherein a needle retraction mechanism may be substantially housed within a plunger housing.
Figure 59B:
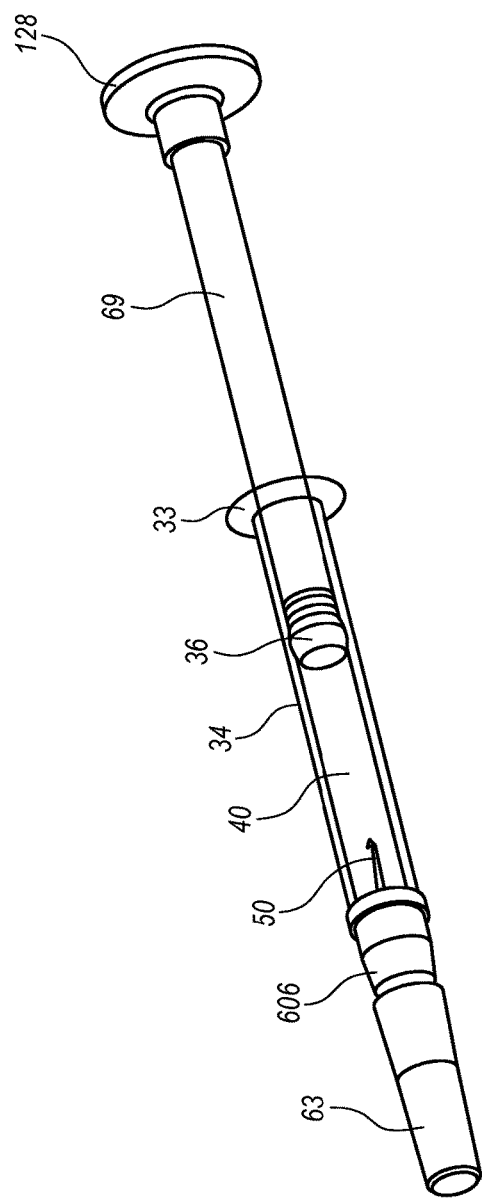

Referring to FIGS. 59A-61S, various embodiments are illustrated wherein a significant portion of the safe needle retraction hardware resides within a plunger housing. Referring to the embodiment of FIGS. 59A-59L, for example, a safe injection configuration comprises a conventional syringe body (34), fitted with a plunger tip (36) configured to be pierced by proximal needle end (50) at an appropriate time to assist with needle retraction; this plunger tip (36) is coupled to a plunger manipulation interface (128) by a plunger housing member (69) defining an inner volume occupied by various other portions of the assembly, as described below, which are configured to retract the needle at an appropriate time in the sequence of use. A needle coupling assembly (606) similar to those described above in reference to staked needle latching configurations is included in the illustrated embodiment; other embodiments may comprise Luer type needle assembly coupling to the syringe body (34), also as described above. The depicted version of the syringe body (34) comprises a conventional small-diameter flange (33) geometry which may be manipulated or interfaced between the index and middle fingers of the operator, for example, while a thumb of the operator is interfaced with the plunger manipulation interface (128). FIGS. 59A and 59B illustrate pre-utilization assemblies with a needle cover (63) in place to mechanically isolate the distal needle tip (48). Referring to FIG. 59C, the needle cover (63) has been removed and the assembly is readied for injection into a patient. Referring to FIG. 59D, after the distal needle end (48) has been inserted or stabbed into a tissue structure of a patient, the plunger manipulation interface (128) may be briefly pulled away from the syringe body (34) to "aspirate" or check to confirm that the needle distal tip (48) has not come to rest within an unwanted tissue structure portion, such as a vessel. For example, if the distal needle tip (48) has come to rest within a vessel, upon slightly pulling out the plunger tip (36), a small marking of blood of the patient is likely to appear within the medicine chamber (40), and the operator can see this and reposition the distal needle tip (48).

Referring to FIG. 59E, with the desired distal needle tip position confirmed, the plunger manipulation interface (128) is inserted relative to the syringe body (34) and the medicine is expelled out of the medicine chamber (40), through the needle tip (48), and into the patient. FIG. 59F illustrates a cross sectional view of the configuration of FIG. 59E. Referring to FIG. 59G, with complete seating of the plunger tip (36) into the syringe body (34), the proximal needle end (50) is stabbed through the plunger tip (36), while elastic deformation of the material comprising the plunger tip (36) allows the plunger tip to reach the bottom of the syringe body to expel all of the medicine, and trigger the spring to retract the needle while accounting for geometric variation of syringe body and other components due to manufacturing and assembly tolerances. Referring to FIG. 59H, needle retention features (712) similar to those (684, 686) described in reference to FIG. 53B are configured to prevent pull-out of the proximal needle tip (50) once it has been stabbed into and captured by the plunger tip (36). With complete insertion of the plunger tip (36), the needle latch (616) is configured to become unseated from its previous interface position (111) against the needle body, as shown in FIG. 59H, to allow for retraction of the needle; concomitantly, as is shown in the progression from FIGS. 59G/59H to FIGS. 59I/59J, the proximal needle end (50) is configured to directly abut or compress against an unlatching member (710) or rod that is configured to allow a rotatable latching member (714) to be positioned or configured into either of two states. The first configuration of the rotatable latching member (714), shown in FIG. 59G and associated cross section FIG. 59H, is the "latched" condition, where the rotatable latching member (714) is retained in the position shown in FIG. 59H by a proximal feature comprising the proximal aspect of the unlatching member (710). In this latched condition, a load generated by a compressed energy-storing member (718), such as a spring, is reacted by the geometric state of the latching member (714), maintaining the compressed state of the energy-storing member (718). The second configuration of the rotatable latching member (714), shown in FIG. 59I and associated cross section FIG. 59J, may be termed the "unlatched" condition wherein the unlatching member (710) has been moved more proximally with loading from the needle proximal end (50) to cause the rotatable latching member (714) to be free to rotate.

Figure 59I:
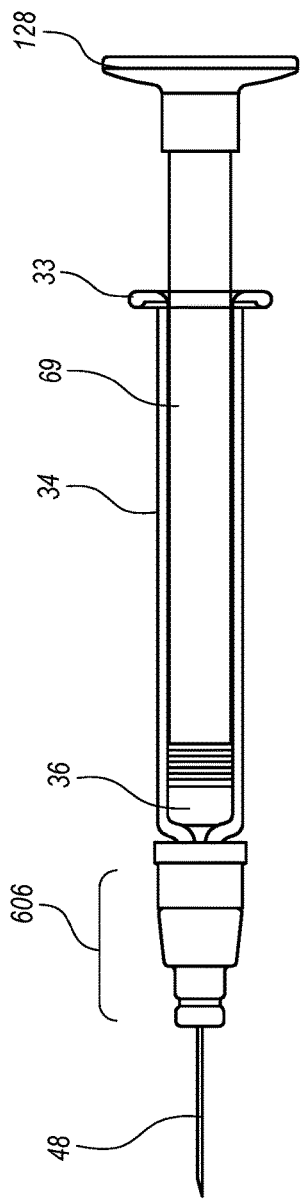
Figure 59J:
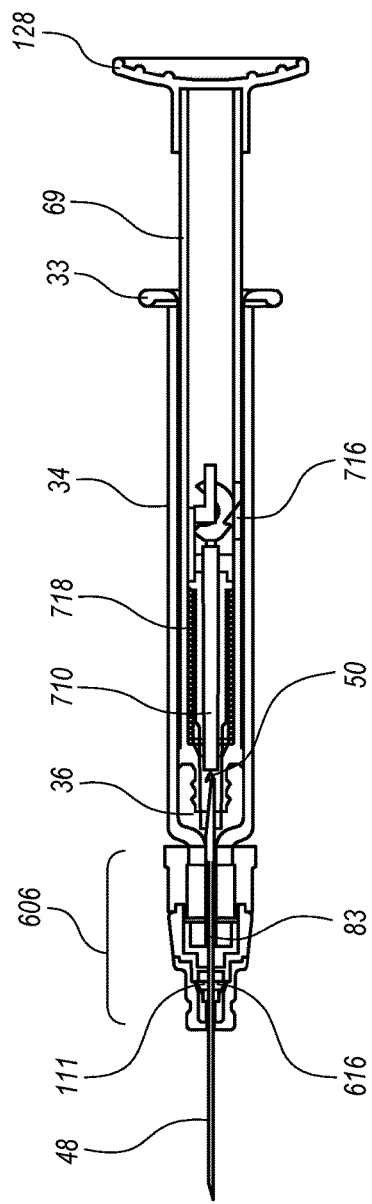

In this second configuration, with rotation of the rotatable latching member (714) out of the lock interface window (716) as shown in FIG. 59J, the load generated by the compressed energy-storing member (718) is not reacted by the rotatable latching member (714), and the energy-storing member (718) is free to expand longitudinally, as shown in FIG. 59K and associated cross section FIG. 59L, thereby pulling the unlatching member (710) and intercoupled retention features (712) proximally, which retracts the needle. Thus referring to FIG. 59J, in the unlatched configuration, the unlatching member (710) is moved proximally and the rotatable latching member (714) is configured to rotate from a latched position, wherein the rotatable latching member (714) is seated within a lock interface window (716), and wherein this interfacing of the latch position maintains the energy storage member (718), which may comprise a spring, in a stored configuration, to an unlatched position, wherein the rotatable latching member (714) is rotated slightly out of the lock interface window, as shown in FIG. 59I, and the cross sectional view of FIG. 59J, to free the energy storage member (718) to accelerate and move the unlatching member (710) and intercoupled retention features (712) to the right as the potential energy stored in the energy storage member (718) is released, thereby pulling the intercoupled proximal needle tip (50) along with it, as shown in FIG. 59K and the cross sectional view of FIG. 59L, such that the needle distal tip (48) becomes safely encapsulated within the syringe body (34). As described above, once in this configuration, the needle assembly (606) preferably is configured to prevent any further re-insertion of the distal needle tip (48) relative to the syringe body (34); in other words, needle tip re-exposure is prevented with such a safety configuration. Referring to FIG. 59M, in one embodiment the plunger tip (36) may be solid, not having any pre-formed through-holes to facilitate transection of the needle proximal end (50). As shown, for example, in FIG. 59L, complete retraction of the needle through the plunger tip (36) requires the needle to penetrate the plunger tip. To pull the needle through the plunger tip (36) without losing "grip" on the needle proximal end (50), the penetration force of the needle through the plunger tip (36) generally must be low enough so as not to exceed the "gripping load" provided by the interface that has been formed between the proximal needle tip (50) and the needle retention features (712) with stabbing of the proximal needle tip (50) through the plunger tip (36). With one embodiment, experimentation has shown that the penetration force between the needle assembly and the plunger tip is between about 1 and about 4 lbf, depending upon the rubber or elastomeric material used to manufacture the plunger tip (36). To further minimize resistance as the needle is pulled through the elastomeric plunger tip (36), in one embodiment it is desirable to create a chamfered geometry (734) on the proximal geometric aspects of the needle joining member (83), as shown in FIG. 59M.

Figure 60K:
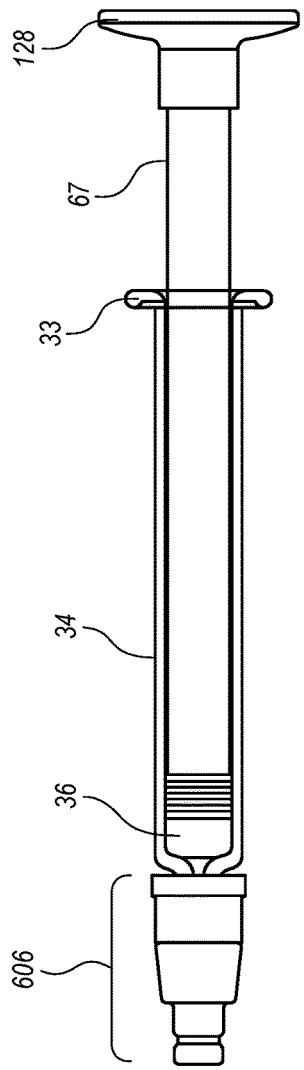

As was discussed above in reference to FIGS. 59G and 59H, in the embodiment of FIGS. 59A-59M, the elastomeric material comprising the plunger tip (36) is utilized to assist in dealing with slight geometric tolerances which may be present due to manufacturing, assembly, temperature, or other factors. In use, the operator feels the full insertion position of the plunger tip (36) relative to the syringe body (34) coming by an increased insertion load required to continue inserting the plunger tip (36). The operator may be trained to continue such insertion against such increasing insertion resistance load until a "click" sound is heard, which signifies that the needle latching mechanism has been triggered, thereby releasing the needle longitudinally relative to the syringe body so that it may be retracted. Referring to the embodiment of FIGS. 60A-60L, rather than solely relying upon the elastomeric compliance of the plunger tip (36) for such geometric tolerance accommodation, a coupling member (722) may be movably intercoupled between the plunger tip (36) and the plunger housing (67) such that a gap (720, as shown, for example, in FIG. 60F) is retained until a certain insertional load is obtained, after which this gap (720) is closed by virtue of the proximal end of the coupling member (722) sliding to the right relative to plunger housing (67), to eliminate the gap, as shown in FIG. 60G and associated cross sectional view, FIG. 60H. FIGS. 60A and 60B illustrate such an injection assembly ready to use with a protective cap (63) isolating the distal needle tip (48). FIG. 60C illustrates the protective cap (63) removed, ready for injection. FIG. 60D illustrates an aspiration step, as described above, wherein the plunger may be pulled backwards relative to the patient to confirm needle location.

Figure 60L:
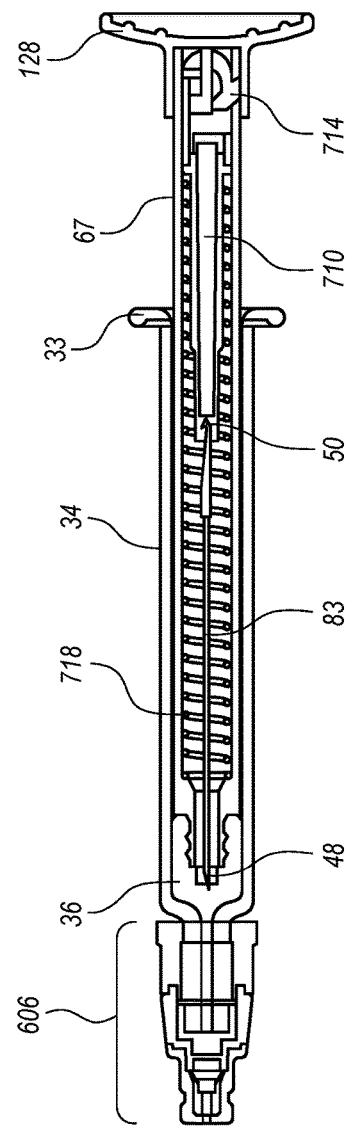

Thus in operation, upon full insertion of the plunger tip (36) relative to the syringe body (34), several things happen: the needle latching (616) mechanism becomes unlatched, allowing for retraction of the needle; the insertional load threshold is passed, causing the coupling member (722) to collapse the gap (720) and allow for full capture of the needle proximal end (50) by the capturing features (712), and compressive loads from the needle proximal end (50) abutting the unlatching member (710) cause the rotatable latching member (714) to be free to rotate out of the latched position relative to the lock interface window (716) defined into the plunger housing member (67), as shown in FIG. 60I and associated cross sectional view FIG. 60J; FIG. 60K and associated cross sectional view FIG. 60L illustrate the condition of the assembly after the needle has been retracted such that the distal needle tip (48) is housed within the syringe body (34).

Figure 61C:
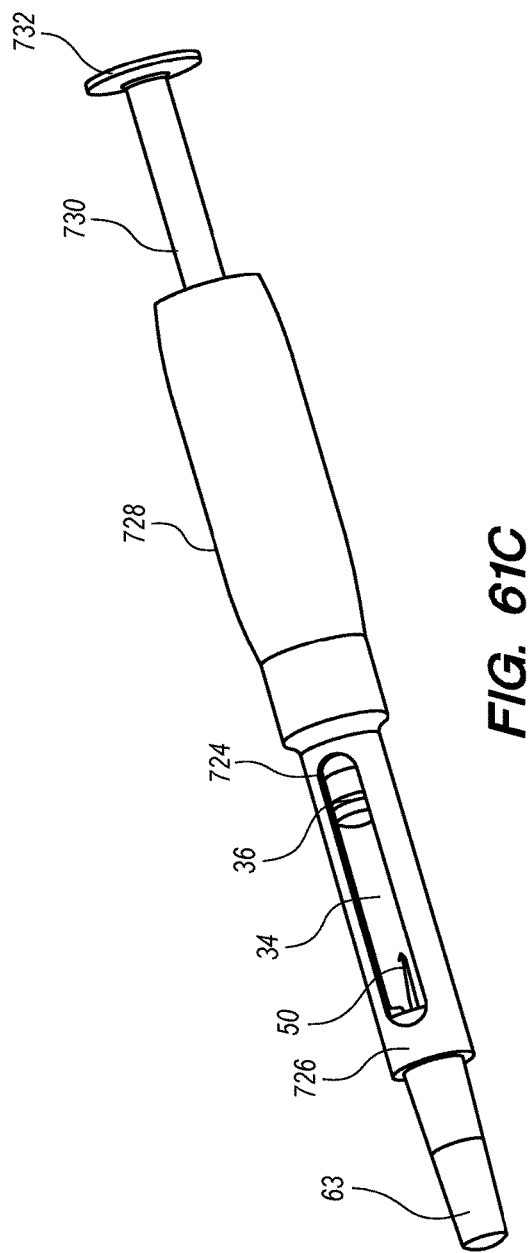
Figure 61D:
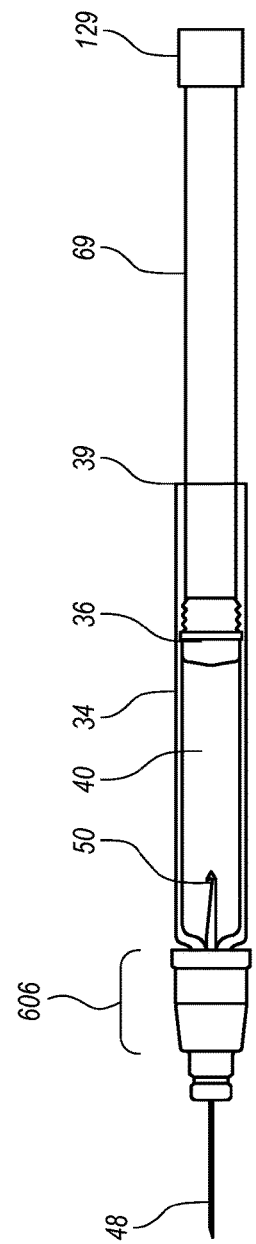
Figure 61O:
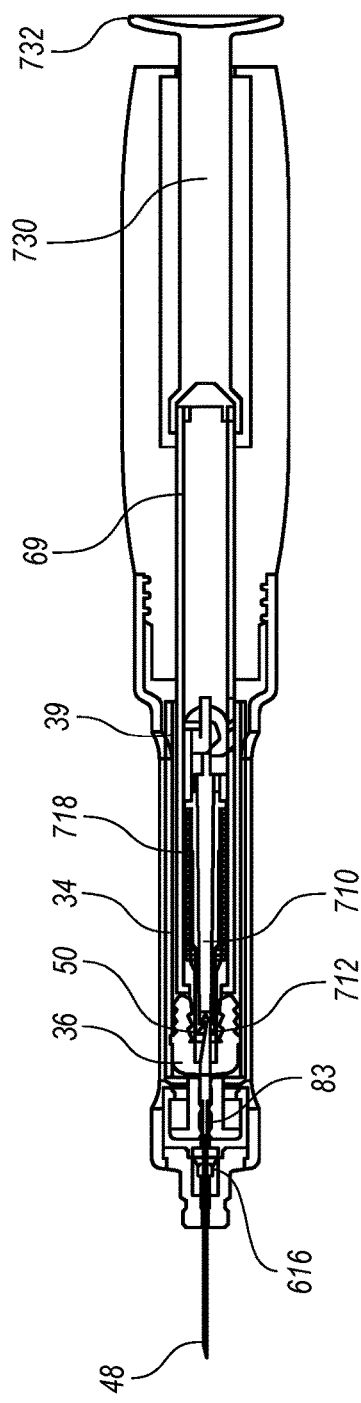
Figure 61P:
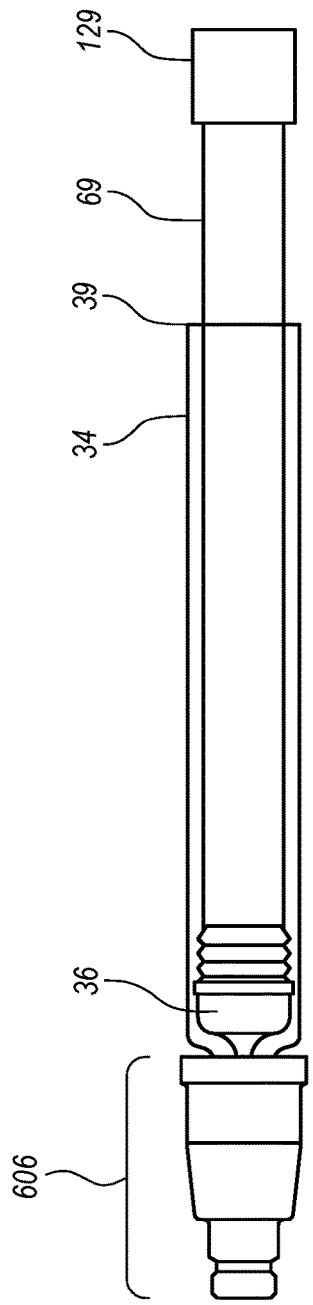
Figure 61S:
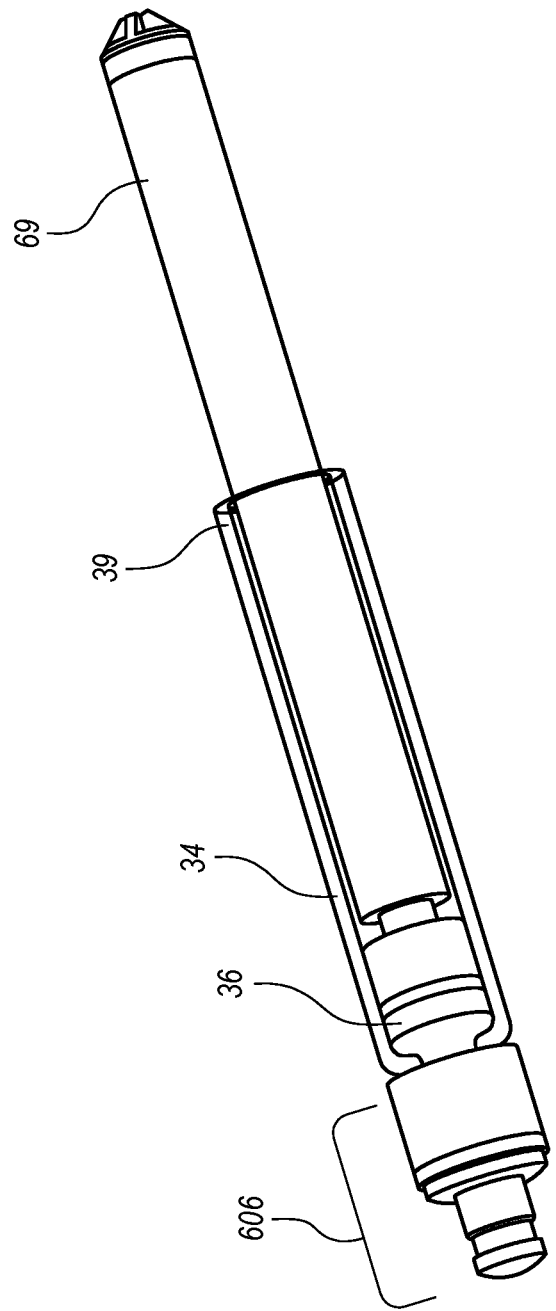

Referring to FIGS. 61A-61S, in another embodiment, configurations similar to those of FIGS. 59A-59L, or 60A-60A, but without the syringe body flange (33), may be utilized with "pen" or "re-use" housing interfaces, such as those depicted in FIGS. 61C, 61F, 61I, 61L, 61O, and 61R. Referring to FIG. 61A, a safe injection configuration similar to that of FIG. 59A is depicted, with the exceptions that the embodiment of FIG. 61A has a syringe body (34) that does not incorporate a proximal flange (element 33 of FIG. 59A), and has a plunger housing (69) without a manual manipulation interface (element 128 of FIG. 59A)—and rather has a proximal end (129) configured to be interfaced with a plunger coupling member (730) distal end of a pen or re-use housing configuration. FIG. 61B illustrates a cross sectional view of the configuration of FIG. 61A. As shown in the assembly view of FIG. 61C, the configuration of FIG. 61A may be at least temporarily housed within the pen or re-use housing assembly; the depicted pen or re-use housing assembly comprises a distal housing portion (726) defining a window (724) therethrough to visualize the injection components therein; a proximal housing portion (728) is movably coupled to a plunger coupling member (730), the distal portion of which is removably coupleable to the plunger housing (69) proximal end (129); a plunger manipulation interface (732) is coupled to the proximal end of the plunger coupling member (730). FIGS. 61D, 61E, and 61F illustrate similar configurations as those of FIGS. 61A, 61B, and 61C, respectively, with the protective needle cap (63) removed, and the needle distal tip (48) ready for injection. Referring to FIGS. 61G, 61J, and 61M (and, respectively, injection assembly cross sections 61H, 61K, and 61N, and pen or re-use housing assembly integration cross sections 61I, 61L, and 61O), the injection assembly is operated as described in relation to FIGS. 59E/59F, 59G/59H, and 59I/59J, with exception that the manual manipulation by the user is not direct to the injection assembly, but is rather to the pen or re-use housing, which is at least temporarily coupled to the injection assembly. Upon full insertion of the plunger tip (36), the needle becomes unlatched and is captured proximally by the plunger tip (36), and loading of the proximal rotatable latch member (714) causes retraction of the needle, as shown in FIGS. 61P, 61Q, and 61R, leaving a safely used and disposable injection assembly cartridge, as shown in FIG. 61S. Referring back to FIGS. 61H and 61I, the syringe body (34), such as one constructed from a glass material, may comprise a Luer taper on one end for attachment of the staked needle assembly, such as the staked needle assembly (606) described above. In an alternate embodiment, cartridge syringe body may be utilized which has a glass flange configuration, similar to that on a medicine vial, which consists of a rubber seal and an aluminum crimp to seal the medicine inside the glass cartridge. With such an embodiment, a needle configuration similar to that shown in FIG. 61I may be snapped over the glass flange to seal the medicine in the cartridge; the aluminum crimp may be replaced with a plastic needle housing.

As noted above, while the configurations of FIGS. 59A-61S are illustrated using a staked needle needle housing/ latch configuration as described in detail here, such configurations may also utilize Luer type coupling and associated hardware, also as described in detail here. In certain circumstances, the staked needle configurations may be desired for properties such as glue/adhesive free nature of the described embodiments, silicone films which may be "baked on" due to the fact that adhesive-free staked coupling configurations may not be as limiting on temperatures during processing, and also the tungsten-free nature of the aforementioned staked needle coupling configurations, wherein preferably there is no tungsten pin exposure for forming a needle aperture, as the aforementioned staked coupling configurations utilize Luer-style syringe bodies even for staked coupling, and may be completed using tungsten-free rods.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed:

1. A system for injecting medicine into a patient, comprising:
   a syringe body defining an interior medicine chamber having a proximal end and a distal end;
   a stopper member configured to be inserted into the interior medicine chamber to contain medicine within the interior medicine chamber;
   a plunger member having a plunger housing, and configured to be manually manipulated to insert the stopper member relative to the syringe body, the plunger member comprising an energy storage member having a first stored mode and a second released mode;
   a needle having proximal and distal ends, the proximal end comprising an anchoring geometry configured to at least partially penetrate the stopper member such that inserting the stopper member to the distal end of the interior medicine chamber causes the needle to be pulled proximally through the stopper member to be at least partially contained within the interior medicine chamber; and an unlatching member configured such that the needle proximal end moving the unlatching member causes the energy storage member to move from the first mode to the second mode.

2. The system of claim 1, further comprising a latching member having a latched mode and an unlatched mode respectively corresponding to the first and second modes of the energy storage member, wherein triggering the latching member from the latched mode to the unlatched mode results in an audible cue that signifies the latching member has been triggered and the needle has been retracted.

3. The system of claim 1, further comprising a latching member having a latched mode and an unlatched mode respectively corresponding to the first and second modes of the energy storage member,
   wherein inserting the stopper member to the distal end of the interior medicine chamber transforms the latching member from the latched mode to the unlatched mode, thereby allowing the energy-storing member to release energy stored by the energy-storing member,
   wherein the proximal end of the needle moving the unlatching member causes the latching member to move from the latched mode to the unlatched mode, and
   wherein the latching member is substantially disposed within a lumen defined by the plunger member.

4. A system for injecting medicine into a patient, comprising:
   a syringe body defining an interior medicine chamber having a proximal end and a distal end;
   a stopper member configured to be inserted into the interior medicine chamber to contain medicine within the interior medicine chamber;
   a plunger member having a plunger housing, and configured to be manually manipulated to insert the stopper member relative to the syringe body, the plunger member comprising an energy storage member having a first stored mode and a second released mode;
   a needle having proximal and distal ends, the proximal end comprising an anchoring geometry configured to at least partially penetrate the stopper member such that inserting the stopper member to the distal end of the interior medicine chamber causes the needle to be pulled proximally through the stopper member to be at least partially contained within the interior medicine chamber; and
   a needle retention feature configured to selectively couple the needle proximal end and the energy storage member such that inserting the stopper member to the distal end of the interior medicine chamber causes the needle to be pulled proximally through the stopper member.

5. The system of claim 4, the plunger member comprising an energy storage member having a first stored mode and a second released mode.

6. The system of claim 4, further comprising a coupling member disposed between the stopper member and the plunger housing, wherein the coupling member is configured to collapse when the stopper member is inserted to the distal end of the interior medicine chamber, thereby allowing the needle to be pulled proximally through the stopper member.

7. The system of claim 4, wherein the syringe body comprises a distal outer geometry configured to be mechanically coupled to a needle coupling assembly.

8. The system of claim 7, wherein the syringe body distal outer geometry comprises a Luer lock interface or a Luer taper interface.

9. The system of claim 4, further comprising a needle latch having a latched configuration wherein the needle cannot move proximally relative to the syringe body and an unlatched configuration wherein the needle is free to move proximally relative to the syringe body.

10. The system of claim 9, wherein inserting the stopper member to the distal end of the interior medicine chamber causes the needle latch to move from the latched configuration to the unlatched configuration.

11. The system of claim 10, the plunger member comprising an energy storage member having a first stored mode and a second released mode,
    wherein the energy storage member moves from a first stored mode to a second released mode to pull the needle proximally after the needle latch moves from the latched configuration to the unlatched configuration.

12. The system of claim 10, further comprising a needle unlatching member configured to move the needle latch from the latched configuration to the unlatch configuration when the needle unlatching member is moved distally relative to the needle latch in the latched configuration,
    wherein the needle and the needle unlatching member are configured such that moving the needle distally causes the needle to apply a distally directed force to the needle unlatching member, causing the needle unlatching member to move distally relative to the needle latch, thereby moving the needle latch from the latched configuration to the unlatched configuration.

13. The system of claim 4, wherein the syringe body defines a distal medicine port.

14. The system of claim 13, wherein the needle has a maximum outside diameter selected to be insertable through the distal medicine port of the syringe body.

15. The system of claim 13, further comprising a sealing member configured to seal an annular space defined by the needle in the distal medicine port.

16. The system of claim 4, wherein a distal portion of the stopper member comprises a conventional off-the-shelf compliant stopper.

17. The system of claim 16, wherein the stopper member comprises an unmodified solid compliant member with no recesses or projections for coupling to a needle.

18. The system of claim 4, wherein the syringe body comprises an unmodified off-the-shelf syringe body.

19. The system of claim 4, wherein the needle proximal end comprises at least one piercing element located proximally relative to at least one anchoring element.

20. The system of claim 19, wherein the piercing element comprises a solid construction without a lumen or aperture defined therethrough.

21. The system of claim 4, wherein the needle comprises a cannula member, a hub member, and a proximal member.

22. The system of claim 21, wherein the proximal member has a proximal coupling interface and comprises a piece of flat sheet metal material, a piece of flat plastic material, a piece of solid metal material, or a piece of solid plastic material.

* * * * *